United States Patent [19]
Birdsall et al.

[11] Patent Number: 5,877,199
[45] Date of Patent: Mar. 2, 1999

[54] HETEROCYCLIC COMPOUNDS, THEIR PREPARATION AND THEIR THERAPEUTIC USE

[75] Inventors: Nigel Birdsall, London; Sebastian Lazareno, Ware, both of United Kingdom; Syunji Naruto, Yokohama, Japan; Masahiko Sugimoto, Misato, Japan; Kazuo Koyama, Kawaguchi, Japan; Shinji Marumoto, Kita-ward, Japan

[73] Assignee: Sankyo Company, Limited, Tokyo, Japan

[21] Appl. No.: 791,499

[22] Filed: Jan. 27, 1997

Related U.S. Application Data

[63] Continuation of PCT/JP95/01494 Jul. 27, 1995, published as WO96/03377 Feb. 8, 1996.

[30] Foreign Application Priority Data

Jul. 27, 1994 [GB] United Kingdom .................... 9415175
Nov. 25, 1994 [GB] United Kingdom .................... 9423948

[51] Int. Cl.$^6$ .......................... A61K 31/40; C07D 209/88
[52] U.S. Cl. .......................... 514/411; 548/441; 548/443; 548/444
[58] Field of Search ............................ 514/411; 548/441, 548/443, 444

[56] References Cited

U.S. PATENT DOCUMENTS

| 1,675,478 | 7/1928 | Ballauf et al. ............................ 548/441 |
| 3,905,998 | 9/1975 | Alexander et al. ...................... 548/448 |
| 3,956,295 | 5/1976 | Birere et al. .......................... 548/441 X |
| 4,178,289 | 12/1979 | Berger et al. ............................ 548/441 |
| 4,988,820 | 1/1991 | Boshagen et al. .................... 548/448 X |
| 5,200,419 | 4/1993 | Hobbs et al. ............................ 514/323 |

FOREIGN PATENT DOCUMENTS 0 548 664  6/1993  European Pat. Off. .

OTHER PUBLICATIONS

Oikawa et al., Heterocycles, 1977, 8, 307–12.
Oikawa et al., J. Chem. Soc., Perkin Trans. 1, 1976, (13), 1479–1484.
Tucek et al., J. Neurochem., (1993), 61, Suppl. S19.
Riker and Wescoe, Ann. N.Y. Acad. Sci., 54, 373–394, (1951).
Waelbroek et al., J. Recep. Res., 8, 787–808 (1988).
Birdsall et al., Pierre Fabre Monograph Series, 1 "New Concepts in Alzheimer's Disease", Ed's Bailey, M., et al., Chapter 9, 103–121, 1986.
SKUP et al, "In Vitro Studies on the Effect of β–Carbolines on the Activities of Acetylcholinesterase and Choline Acetyltransferase and on the Muscarinin Receptor Binding of the Rat Brain", Journal of Neurochemistry, vol. 41, No. 1, 1983, pp. 62–68.
SKUP et al, Chemical Abstracts, vol. 99, No. 13, 26 Sep. 1983, Columbus, Ohio, abstract No. 99889a.
Dekhane et al, "N–e Methylated Quaternary Derivatives of β–Carbolline–3–Carboxylates Inhibit Acetylcholinesterase In Vitro", Biooragnic and Medicinal Chemistry Letters, vol. 3, No. 12, 1993, Oxford, pp. 2831–2836.
Dekhane et al, Chemical Abstracts, vol. 121, No. 9, 29 Aug. 1994, Columbus, Ohio, abstract No. 99051u.
Patent Abstracts of Japan, vol. 940, No. 10 (0–00000) of JP–A–06 298 732 (Taisho Pharmaceutical Co., Ltd.) 25 Oct. 1994.

Primary Examiner—Fiona T. Powers
Attorney, Agent, or Firm—Frishauf, Holtz, Goodman, Langer & Chick, P.C.

[57] ABSTRACT

A compound of formula (I):

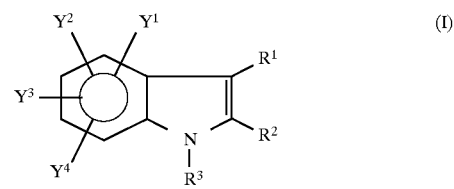

wherein
$Y^1$, $Y^2$, $Y^3$ and $Y^4$ are each hydrogen, halogen, nitro, cyano, hydroxyl, thiol, amino, alkyl, haloalkyl, alkylthio, a protected or unprotected carboxyl, a protected or unprotected sulfonamide, or tetrazol; one of $R^1$ and $R^2$ is hydrogen, alkyl, aryl, aralkyl, oxazolyl, or a protected or unprotected carboxyl and the other of $R^1$ and $R^2$ is hydrogen, alkyl, aryl or aralkyl; and $R^3$ is hydrogen or an amino protecting group, and pharmaceutically acceptable salts or esters thereof. The compounds are effective for treating dementia, Alzheimer's disease and delirium and are effective as sedatives.

18 Claims, 6 Drawing Sheets

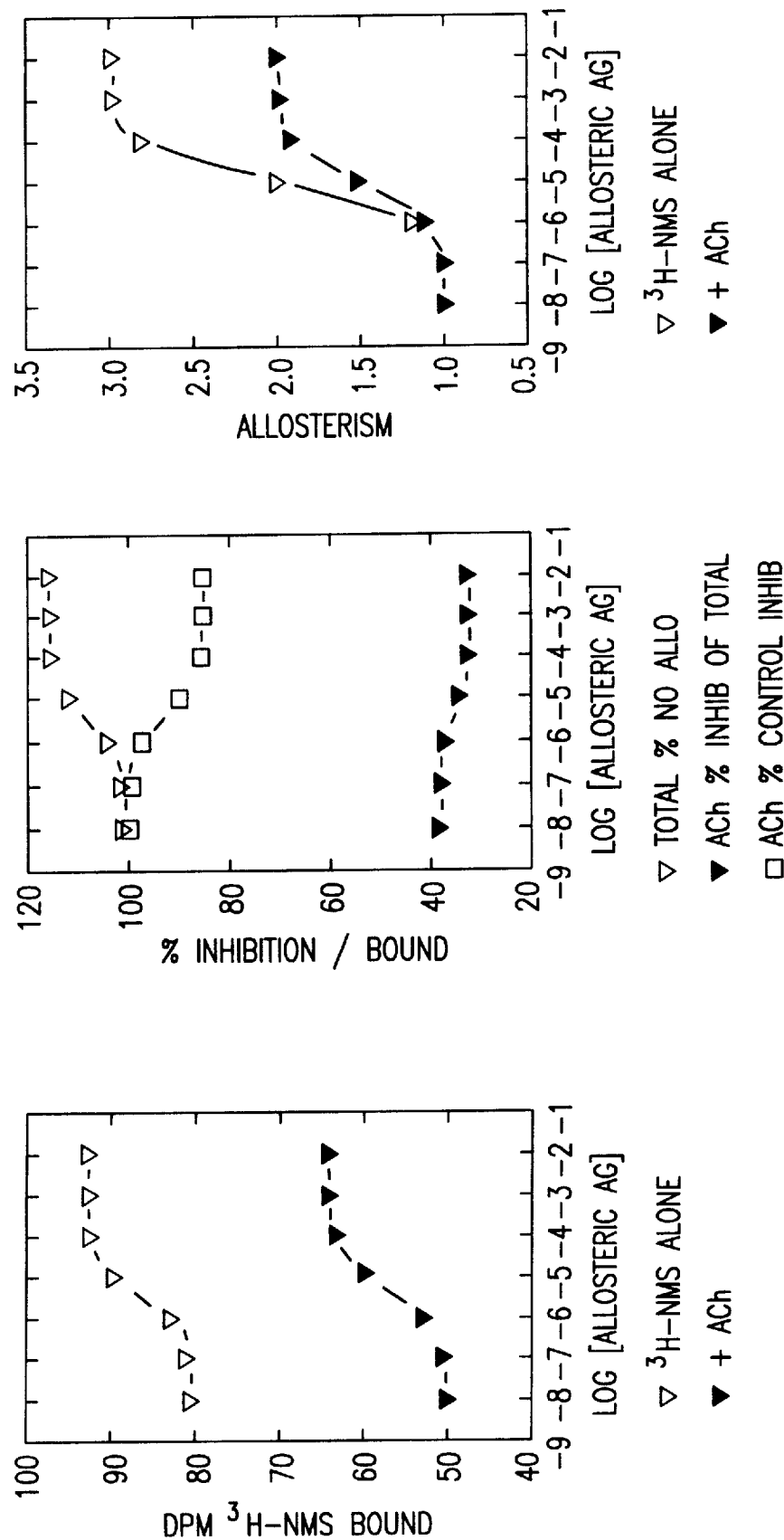

HETEROCYCLIC COMPOUNDS, THEIR PREPARATION AND THEIR THERAPEUTIC USE

This application is a continuation application of International Application PCT/JP95/01494 filed Jul. 27, 1995, published as WO96/03377 Feb. 8, 1996 (Chapter II).

1. Field of the Invention

The present invention relates to compounds useful as allosteric effectors at muscarinic receptors, to uses of such compounds and to the synthesis of such compounds.

2. Prior Art

Acetylcholine is known to be associated with memory, and it is also known that there are decreased levels of acetylcholine in the brain in sufferers of Alzheimer's Disease.

In an attempt to provide a cure for Alzheimer's Disease, various groups have endeavoured to alleviate the cholinergic deficit in vivo. This has been done, for example, by using cholinesterase inhibitors (to reduce the rate of acetylcholine breakdown) or by using alternative agonists to serve as a supplement to acetylcholine.

Neither course of action has proved successful, as the effect of each is generalised, so that acetylcholine throughout the body and at all receptors is prevented from breaking down, or supplemented (or both), without specifically targetting those receptors involved in Alzheimer's disease. Enhancing the effect of acetylcholine at some receptors can cause depression, for example, so that these courses of action are not being pursued.

More specifically, acetylcholine acts at receptors which fall into two classes; muscarinic and nicotinic. It is believed that the muscarinic receptors are involved in Alzheimer's disease.

The muscarinic receptors belong to the family of G-protein coupling receptors, and have been classified into three subtypes on the basis of their pharmacological properties and into five subtypes from their molecular structures. The nomenclature of muscarinic receptor subtypes has been confused, and, at the Fourth International Symposium on Muscarinic Receptors, it was recommended that subtypes based on the antagonist binding properties be referred to as $M_1$, $M_2$, $M_3$, $M_4$ and that those based on molecular structure be called m1–m5 (see below). This nomenclature is used hereinafter.

| Muscarinic receptor nomenclature | | | | |
|---|---|---|---|---|
| Pharmacological characterization | | | | |
| Subtype | $M_1$ | $M_2$ | $M_3$ | $M_4$ |
| Selective antagonists | pzpine (+)-tzpne | AF-DX 116, himbacine, m/tramine, gallamine* | p-fluoro-hexahydro-siladifenidol, hexahydro-siladifenidol | tropicamide |
| Molecular characterization | | | | |
| Sequences | m1 | m2 | m3 | m4 | m5 |
| Numbers of amino acids | 460 | 466 | 589/590 | 478/479 | 531/532 | pzpine = pirenzepine;
tzpne = telenzepine;
m/tramine = methoctramine;
*not competitive;

Recently, it has been possible to use cells expressing m1–m5 receptors. These cells are pure preparations of each receptor subtype and are very useful for characterizing each subtype and for screening for subtype specific agents.

Studies have been performed on muscarinic receptors in the heart (M2) using the antagonist N-methyl-scopolamine (NMS), and these have established that the binding of this antagonist can be affected by other agents, but that these agents do not necessarily act at the NMS binding site. Such action at a different binding site is known as allosteric action, or allosterism. Tucek et al. [J. Neurochem. (1993), 61, Suppl., S19] have shown that the neuromuscular blocking drug, alcuronium, allosterically increases the affinity of M2 muscarinic receptors in the heart for NMS.

It was reported by Riker and Wescoe in 1951 that gallamine had a negative action on heart receptors [Ann. N. Y. Acad. Sci., 54, 373–94 (1951)]. It was subsequently established that gallamine was not a competitive antagonist for acetylcholine.

Waelbroeck et al. [J. Recep. Res., 8, 787–808 (1988)] reported that curare acts allosterically against muscarinic receptors in the brain, but these results cannot be repeated.

Tubocurarine and batrachotoxin have also been reported to have negative allosteric effects on antagonist binding.

Birdsall et al. [Pierre Fabre Monograph Series, 1, New Concepts in Alzheimer's Disease, Ed's Briley, M., et al., Macmillan Press, Chapter 9, 103–121] speculate that "the muscarinic receptor sub-types exhibit a selectivity in their binding profile for allosteric agents, and it may hence be possible to selectively 'tune up' muscarinic responses". In this respect, the authors were referring to the difference between the receptors found in the CNS and those in other parts of the body.

In fact, we have now found that certain compounds are capable of action at the m1 receptor. In addition, certain compounds are capable of selectively acting as positive allosteric effectors for acetylcholine at the m1 receptors, but not at other receptors.

OBJECTS OF THE INVENTION

A first object of the invention is to provide compounds which will have an allosteric effect at any of the muscarinic receptors described above.

A second object of the invention is to provide compounds which will have an effect on muscarinic receptors in such a manner as to assist in the prophylaxis and/or treatment of any of the conditions described above, or any condition associated in any way with muscarinic receptors.

Thus, the present invention provides, in a first aspect, a method of regulating m1 receptor response in vivo in a mammalian subject, comprising the step of administering to said subject an effective amount of a selective allosteric effector to regulate said receptor. In a preferred embodiment, the allosteric effector exhibits positive cooperativity with acetylcholine at said receptor.

One class of compounds of the present invention are those compounds of formula (I):

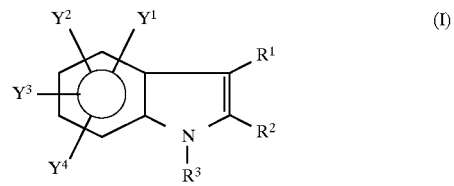

wherein:

$Y^1$, $Y^2$, $Y^3$, and $Y^4$ are the same or different and each represents a hydrogen atom, a halogen atom, a nitro group, a cyano group, a hydroxyl group, a thiol group, an amino group, an alkyl group having from 1 to 6 carbon atoms, an alkyl group having from 1 to 6 carbon atoms and substituted with a keto group or at least one substituent α defined below, a haloalkyl group having from 1 to 6 carbon atoms, an alkylthio group having from 1 to 6 carbon atoms, a carboxyl group, a protected carboxyl group, a sulfonamide group, a protected sulfonamide group or a group of formula

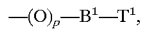

wherein $T^1$ represents a carboxyl group, a thiocarboxy group, a dithiocarboxy group, a protected carboxyl group, a protected thiocarboxy group, a protected dithiocarboxy group, a sulfonamide group, a protected sulfonamide group or a tetrazolyl group, $B^1$ represents an alkylene group which has from 1 to 4 carbon atoms and which is unsubstituted or is substituted by at least one of substituents α, defined below, and p is 0 or 1;

one of $R^1$ and $R^2$ represents a hydrogen atom, an alkyl group having from 1 to 6 carbon atoms, an aryl group, a substituted aryl group, an aralkyl group, a substituted aralkyl group, an oxazolyl group, a substituted oxazolyl group, a carboxyl group, a protected carboxyl group, a sulfonamide group, a protected sulfonamide group, or a group of formula $—(A)_p—B^2—T^2$, wherein A represents an oxygen atom or a sulfur atom, $T^2$ represents a carboxyl group, a protected carboxyl group, a sulfonamide group, a protected sulfonamide group, or a tetrazolyl group, $B^2$ represents an alkylene group which has from 1 to 6 carbon atoms and which is unsubstituted or has one or more substituents selected from amino groups, protected amino groups, hydroxyl groups, protected hydroxyl groups, oxazolyl groups and substituted oxazolyl groups, and p is as defined above;

and the other of $R^1$ and $R^2$ represents a hydrogen atom, an alkyl group having from 1 to 6 carbon atoms, an aryl group, a substituted aryl group, an aralkyl group or a substituted aralkyl group; or $R^1$ and $R^2$ together represent a group of formula (Ia):

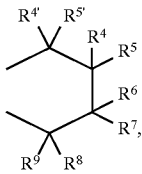

[in which $R^4$ and $R^{4'}$ are the same or different and each represents a hydrogen atom or an alkyl group having from 1 to 6 carbon atoms;

$R^5$ and $R^{5'}$ are the same or different and each represents a hydrogen atom or a group of formula $—(O)_p—(CH_2)_n—T^3$ in which $T^3$ represents a carboxyl group, a Protected carboxyl group, a sulfonamide group, a protected sulfonamide group, or a tetrazolyl group and n=0, 1 or 2, and p is as defined above;

$R^6$ represents a hydrogen atom or a hydroxyl group;

$R^7$ represents a hydrogen atom, a carboxyl group, a protected carboxyl group, a sulfonamide group, a protected sulfonamide group, or a group of formula $—(O)_p—B^3—T^4$ in which $T^4$ represents a carboxyl group, a protected carboxyl group, a sulfonamide group, a protected sulfonamide group, or a tetrazolyl group and $B^3$ represents an alkylene group which has from 1 to 4 carbon atoms and which is unsubstituted or is substituted by at least one of substituents α, and p is as defined above;

$R^8$ represents a hydrogen atom; or when $R^9$ represents an alkylthio group having from 1 to 6 carbon atoms, $R^7$ and $R^8$ together represent a lactone group;

$R^9$ represents a hydrogen atom or an alkylthio group having from 1 to 6 carbon atoms; or $R^8$ and $R^9$ together represent an oxo group]; or $R^1$ and $R^2$ together represent a group of formula (Ib):

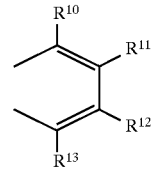

[in which $R^{10}$, $R^{11}$, $R^{12}$ and $R^{13}$ are the same or different and each represents a hydrogen atom, an alkyl group having from 1 to 6 carbon atoms, a hydroxyalkyl group having from 1 to 6 carbon atoms, an alkylthio group having from 1 to 6 carbon atoms, a hydroxyl group, a carboxyl group, a protected carboxyl group, a sulfonamide group, a protected sulfonamide group, or a group of formula

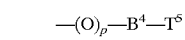

in which $T^5$ represents a carboxyl group, a protected carboxyl group, a sulfonamide group, a protected sulfonamide group or a tetrazolyl group, $B^4$ represents an alkylene group which has from 1 to 4 carbon atoms and which is unsubstituted or is substituted by at least one of substituents α, and, and p is as defined above]; or $R^1$ and $R^2$ together represent a group of formula (Ic):

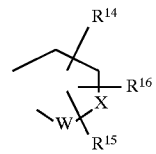

[in which $R^{14}$ represents a hydrogen atom, an alkyl group having from 1 to 6 carbon atoms, a hydroxyalkyl group having from 1 to 6 carbon atoms, a hydroxyl group, a carboxyl group, a protected carboxyl group, a sulfonamide group, a protected sulfonamide group, or a group of formula $—(O)_p—B^4—T^5$ in which $T^5$, $B^4$ and p are as defined above; $R^{15}$ and $R^{16}$ are the same or different, and each represents a hydrogen atom, an alkyl group having from 1 to 6 carbon atoms or an aryl group; Z is a methylene group, a group of formula >NH or a group of formula >N—, and W is a methylene group, a sulfur atom or a group of formula $>S—(O)_q$, where q is 0, 1 or 2, preferably 1 or 2, provided that at least one of W and Z is a methylene group];

$R^3$ represents a hydrogen atom or an amino protecting group; and said substituents α are hydroxyl groups, aryl groups, aralkyl groups and substituted aralkyl groups;

and pharmaceutically acceptable salts and esters thereof.

In a preferred embodiment, there is provided a compound of formula (I):

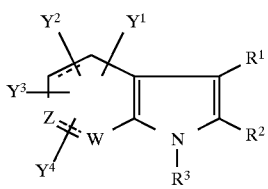

(I)

wherein:
Z represents a methylene group, a methine group, a group of formula >NH or a group of formula =N—, and W represents a methylene group, a methine group, a sulfur atom or a group of formula >S—(O)$_v$, where v is 1 or 2, provided that Z does not represent a group of formula >NH when W represents a group of formula >S—(O)$_v$;

each ... represents a single bond or a double bond, provided that when W represents a sulfur atom or a group of formula >S—(O)$_v$, then the ... bond between W and Z represents a single bond;

at least one of $Y^1$, $Y^2$, $Y^3$ and $Y^4$ represents a carboxyl group, a protected carboxyl group, a sulfonamide group, a protected sulfonamide group or a group of formula —(A)$_p$—$B^1$—$T^1$, wherein A represents an oxygen atom or a sulfur atom, $T^1$ represents a carboxyl group, a thiocarboxy group, a dithiocarboxy group, a protected carboxyl group, a protected thiocarboxy group, a protected dithiocarboxy group, a sulfonamide group, a protected sulfonamide group or a tetrazolyl group, $B^1$ represents a direct bond, an alkylene group which has from 1 to 4 carbon atoms, or an alkylene group which has from 1 to 4 carbon atoms and which is substituted by at least one substituent selected from substituents α, defined below, and p is 0 or 1;

any members of the group $Y^1$, $Y^2$, $Y^3$ and $Y^4$ which are not as defined above may be the same or different and each represents a hydrogen atom, a halogen atom, a nitro group, a hydroxyl group, a thiol group, an amino group, an alkyl group having from 1 to 6 carbon atoms, an alkyl group having from 1 to 6 carbon atoms and which is substituted with a keto group or at least one substituent γ defined below, an alkoxy group having from 1 to 6 carbon atoms, an alkylthio group having from 1 to 6 carbon atoms, an alkylsulfinyl group having from 1 to 6 carbon atoms, an alkylsulfonyl group having from 1 to 6 carbon atoms, an aryl group, an aralkyloxy group, an aralkylthio group, and $Y^1$, together with $Y^2$, may represent a lactone group or a keto group;

one of $R^1$ and $R^2$ represents a hydrogen atom, an alkyl group having from 1 to 6 carbon atoms, an alkanoyl group having from 1 to 6 carbon atoms, an aryl group, an arylcarbonyl group having from 7 to 15 carbon atoms, an aralkyl group, a carboxyl group, a protected carboxyl group, a sulfonamide group, a protected sulfonamide group, or a group of formula —(O)$_q$—$B^2$—$T^2$, wherein $T^2$ represents a carboxyl group, a protected carboxyl group, a sulfonamide group, a protected sulfonamide group or a tetrazolyl group, $B^2$ represents an alkylene group which has from 1 to 6 carbon atoms or an alkylene group which has from 1 to 6 carbon atoms and which has one or more substituents selected from amino groups, protected amino groups, hydroxyl groups and protected hydroxyl groups, and q is 0 or 1;

the other of $R^1$ and $R^2$ representing a hydrogen atom, an alkyl group having from 1 to 6 carbon atoms, an aryl group or an aralkyl group, or $R^1$ and $R^2$ together represent a group of formula (Ib'):

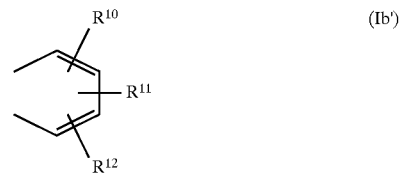

[in which $R^{10}$, $R^{11}$ and $R^{12}$ are the same or different and each represents a hydrogen atom, a hydroxy group, a halogen atom, a haloalkyl group, an alkyl group having from 1 to 6 carbon atoms, an alkyl group having from 1 to 6 carbon atoms and having at least one substituent γ defined below, an alkoxy group having from 1 to 6 carbon atoms, an alkylthio group having from 1 to 6 carbon atoms, an alkylsulfinyl group having from 1 to 6 carbon atoms or an alkylsulfonyl group having from 1 to 6 carbon atoms];

$R^3$ represents a hydrogen atom or an amino protecting group;

said aryl groups being carbocyclic aromatic groups having from 6 to 14 carbon atoms, which may be unsubstituted or substituted with at least one substituent selected from substituents β defined below;

the alkyl parts of said aralkyl groups having from 1 to 3 carbon atoms, the aryl part being as defined above;

substituents α
hydroxyl groups, alkyl groups having from 1 to 6 carbon atoms, alkoxy groups having from 1 to 6 carbon atoms, alkylthio groups having from 1 to 6 carbon atoms, aryl groups as defined above and aralkyl groups as defined above;

substituents β
halogen atoms, nitro groups, hydroxyl groups, amino groups, protected amino groups, alkyl groups having from 1 to 6 carbon atoms, alkoxycarbonyl groups having from 2 to 7 carbon atoms, carboxyl groups, carboxamide groups and aralkoxy groups wherein the aralkyl part is as defined above;

substituents γ
hydroxyl groups, halogen atoms and aryl groups as defined above;

and pharmaceutically acceptable salts and esters thereof.

Other aims, objects, aspects and embodiments of the present invention will become clear as the description progresses.

BRIEF DESCRIPTION OF THE DRAWINGS

FIGS. 1a-1, 1a-2 and 1a-3 represent negative allosterism (of 0.15) at $^3$H-NMS and ACh. FIGS. 1a-4, 1a-5 and 1a-6 represent −ve allosterism (0.15) at $^3$H-NMS. +ve (2) at ACh. For FIGS. 1a-1, 1a-2, 1a-3, 1a-4, 1a-5 and 1a-6, the following applies: $K^3{}_{H\text{-}NMS}=10^{10}$.$K_{ACh}=10^5$.both at the KD concentration, $K_{allosteric\ ag}=10^5$. FIGS. 1b-1, 1b-2 and 1b-3 represent positive allosterism (2) at $^3$H-NMS, −ve (0.15) at ACh. FIGS. 1b-4, 1b-5 and 1b-6 represent positive allosterism (2) at $^3$H-NMS and at ACh. For FIGS. 1b-1, 1b-2, 1b-3, 1b-4, 1b-5 and 1b-6, the following applies: $K^3_{H\text{-}NMS}$= $10^{10}.K_{ACh}=10^5$, both at the Kd concentration, $K_{allosteric\ ag}=10^5$. FIGS. 1c-1, 1c-2 and 1c-3 represent positive allosterism (3) at $^3$H-NMS, neutral at ACh. FIGS. 1c-4, 1c-5 and 1c-6 represent positive allosterism at $_3$H-NMS (3) and at ACh (2). For FIGS. 1c-1, 1c-2, 1c-3, 1c-4, 1c-5 and 1c-6, the following applies: $K^3_{H\text{-}NMS}=10^{10}.K_{ACh}=10^5$.[$^3$H-NMS]=0.4 nM, [ACh]=30 μm, $K_{allosteric\ ag}=10^5$.

DETAILED DESCRIPTION OF THE INVENTION

Figures 1, 1A, 2, 3:
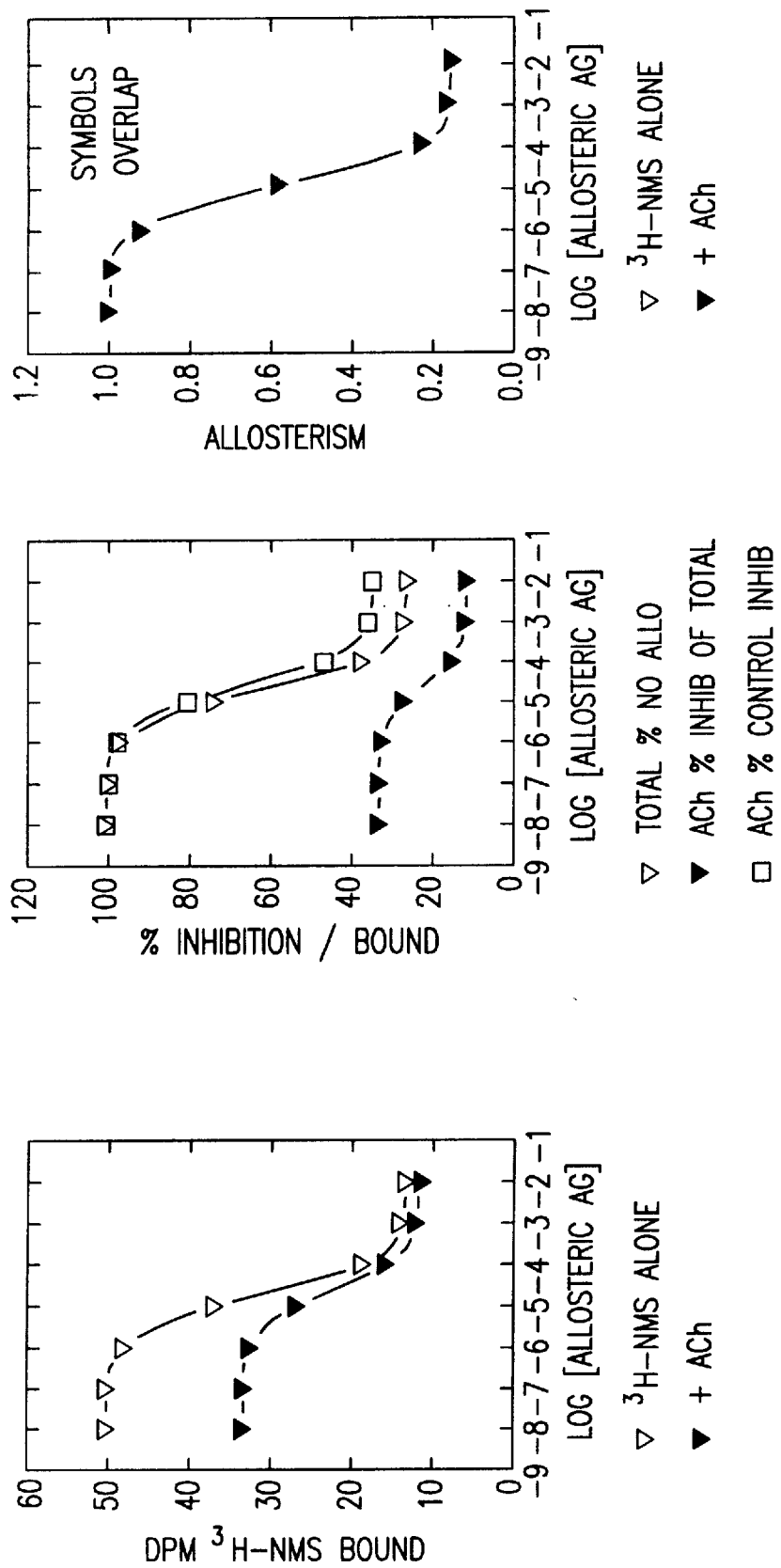
FIGS. 1a-1, 1a-2, 1a-3, 1a-4, 1a-5, 1a-6, 1b-1, 1b-2, 1b-3, 1b-4, 1b-5, 1b-6, 1c-1, 1c-2, 1c-3, 1c-4, 1c-5 and 1c-6 depict graphs (theoretical curves) showing the effect of allosteric agent on the binding of $^3$H-NMS alone and with ACh.
Figures 1, 1A, 2, 3, 4, 5, 6:
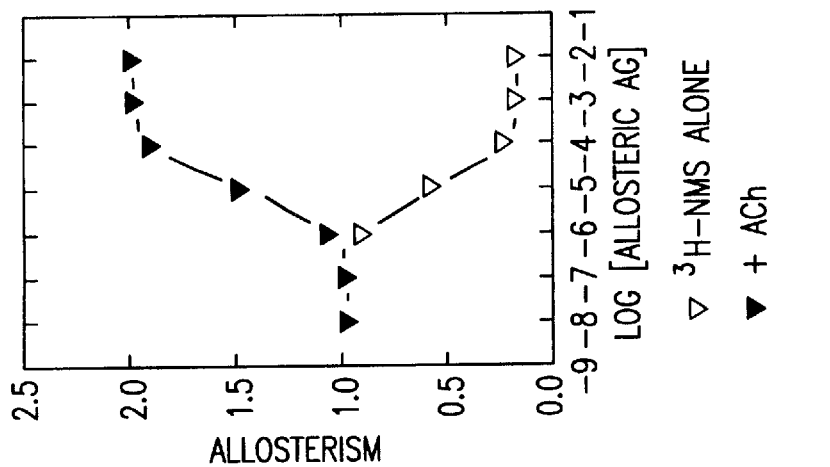
Figures 1, 1A, 2, 3, 4, 5:
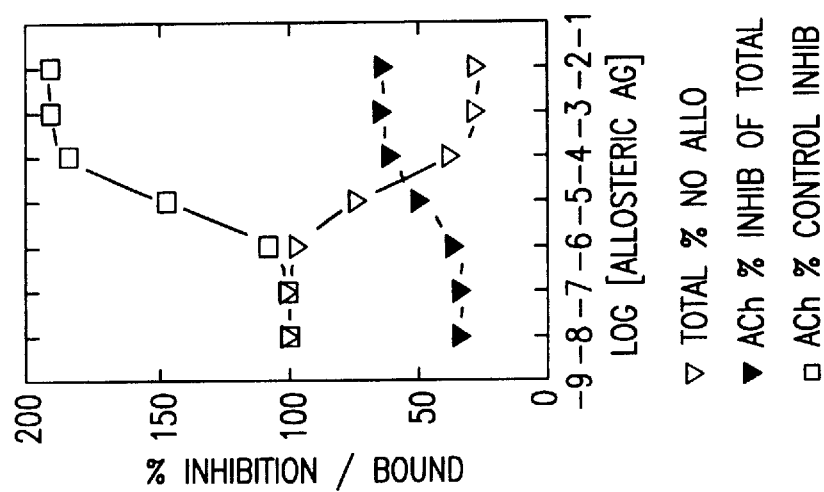
Figures 1, 1A, 2, 3, 4:
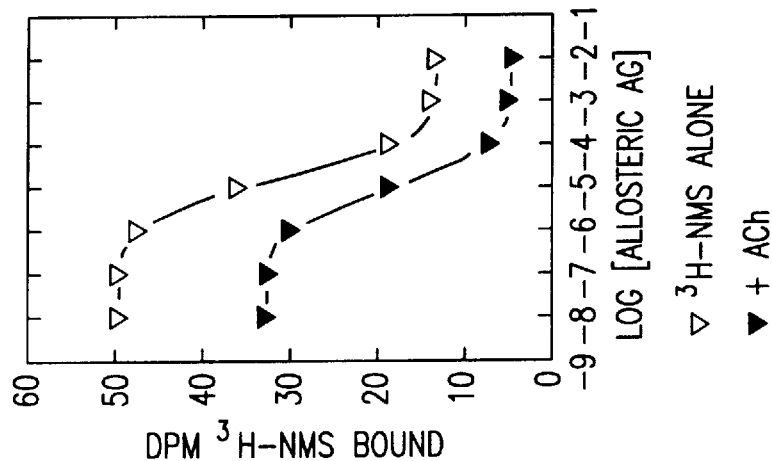

We prefer that W is a methine group, a methylene group or a sulfur atom, preferably a methine group.

In the compounds of the invention, we prefer that the bonds represented by ... are preferably double bonds.

Preferably, at least one of $Y^1$, $Y^2$, $Y^3$ and $Y^4$ represents a carboxyl group, a sulfonamide group or, preferably, a group of formula —(A)$_p$—B$^1$—T$^1$.

A preferably represents an oxygen atom, where it exists.

$T^1$ preferably represents a carboxyl group, a thiocarboxy group, a dithiocarboxy group or a tetrazolyl group, preferably a carboxyl group or a tetrazolyl group.

$B^1$ preferably represents an alkylene group which has from 1 to 4 carbon atoms or an alkylene group which has from 1 to 4 carbon atoms and which is substituted by at least one aralkyl group, although we prefer the alkylene group to have 1 or 2 carbon atoms.

We prefer p to be 0.

Where any members of the group $Y^1$, $Y^2$, $Y^3$ and $Y^4$ are not defined above, then we prefer them to be the same or different with each representing a hydrogen atom, a hydroxyl group, a thiol group, an alkyl group having from 1 to 6 carbon atoms, an alkoxy group having from 1 to 6 carbon atoms, an alkylthio group having from 1 to 6 carbon atoms, an alkylsulfinyl group having from 1 to 6 carbon atoms, an alkylsulfonyl group having from 1 to 6 carbon atoms, an aralkyloxy group, an aralkylthio group, $Y^1$, together with $Y^2$, optionally representing a keto group. Particularly preferably, the others of the group $Y^1$, $Y^2$, $Y^3$ and $Y^4$ are the same or different with each representing a hydrogen atom, an alkyl group having from 1 to 6 carbon atoms, an alkoxy group having from 1 to 6 carbon atoms or an alkylthio group having from 1 to 6 carbon atoms.

One of $R^1$ and $R^2$ preferably represents a hydrogen atom, an alkyl group having from 1 to 6 carbon atoms or an aryl group, particularly preferably a hydrogen atom or an alkyl group having from 1 to 4 carbon atoms.

The other of $R^1$ and $R^2$ preferably represents a hydrogen atom, an alkyl group having from 1 to 6 carbon atoms or an aryl group, particularly preferably a hydrogen atom or an alkyl group having from 1 to 4 carbon atoms.

We particularly prefer that $R^1$ and $R^2$ together represent a group of formula (Ia). We also prefer that $R^{10}$, $R^{11}$ and $R^{12}$ are the same or different and each represents a hydrogen atom, a halogen atom, an alkyl group having from 1 to 6 carbon atoms, an alkoxy group having from 1 to 6 carbon atoms or an alkylthio group having from 1 to 6 carbon atoms.

$R^3$ preferably represents an aralkyl group, particularly a benzyl or phenethyl group, or a benzyl or phenethyl group substituted with at least one substituent selected from the group consisting of halogen atoms and nitro groups. We especially prefer that $R^3$ represents an unsubstituted benzyl group.

In the compounds of the present invention, we prefer that any aryl groups are selected from carbocyclic aromatic groups having from 6 to 10 carbon atoms and carbocyclic aromatic groups having from 6 to 10 carbon atoms and which have at least one substituent selected from substituents β, above.

In the compounds of the present invention, we prefer that any aralkyl groups are unsubstituted or substituted with at least one substituent selected from the group consisting of halogen atoms and nitro groups.

In the compounds which follow, it will be appreciated that, as in the compounds above, any preferred restrictions on substituent groups are generally applicable to any compounds of the present invention.

Preferred compounds have the formula (I):

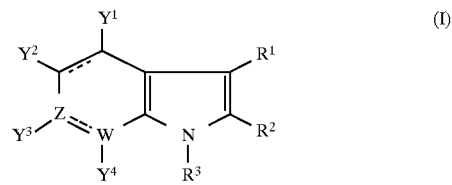

(I)

wherein W is —S—, —C--- or is a group of Formula >S—(O)$_v$, where v is 1 or 2;

Z is —C---, >N— or =N—;

the dotted lines individually indicate that the bond to which they are adjacent is a single or a double bond;

$Y^1$ represents a hydrogen atom, a thiol group, a hydroxy group, a cyano group, an acetyl group, an alkyl group having from 1 to 6 carbon atoms, a perhaloalkyl group having 1 or 2 carbon atoms, an alkylthio group having from 1 to 6 carbon atoms, an alkyl group having 1 or 2 substituents selected from substituents g below, an aralkyl group or an aralkyl group substituted with one or more substituents selected from substituents f below;

$Y^2$ and $Y^3$ are the same or different, and each represents a hydrogen atom, an alkyl group having from 1 to 6 carbon atoms, a carboxyl group, an alkylcarbonyl group having from 1 to 6 carbon atoms, a hydroxyl group, an alkoxy group having from 1 to 6 carbon atoms, an alkoxy group substituted with one or more substituents selected from substituents g below, a cyano group, a carbamoyl group, a group of Formula —CONR$^{30}$R$^{31}$, wherein R$^{30}$ and R$^{31}$ are as defined below, an alkylthio group having from 1 to 6 carbon atoms, an alkylthio group substituted with one or more substituents selected from substituents f below or an alkyl group substituted with one or more substituents selected from substituents h below;

$Y^4$ represents a hydrogen atom, an alkyl group having from 1 to 6 carbon atoms, an alkoxy group having from 1 to 6 carbon atoms, an aryloxy group, an alkylthio group having from 1 to 6 carbon atoms, a hydroxyl group, a thiol group, a methylsulfonyl group, a methylsulfinyl or an arylthio group;

$R^3$ represents an alkylcarbonyl group having from 1 to 6 carbon atoms, a hydrogen atom, a methylsulfonyl group, an alkyl group having from 1 to 6 carbon atoms, a benzoyl group, a benzoyl group substituted with one or more substituents selected from substituents f below, an aryl group, an aryl group substituted with one or more substituents selected from substituents f below, an alkyl group having from 1 to 6 carbon atoms and substituted with one or more substituents selected from substituents h below, an aralkyl group wherein the alkyl part has from 1 to 6 carbon atoms or an aralkyl group wherein the alkyl group has from 1 to 6 carbon atoms and the aryl part is substituted with one or more substituents selected from substituents f below;

$R^2$ and $R^1$ are the same or different, and each represents a hydrogen atom or an alkyl group having from 1 to 6 carbon atoms, or together, $R^1$ and $R^2$ form a phenyl group fused at the bond joining $R^2$ and $R^1$, said phenyl group optionally being substituted with one or more of substituents f below, one of the ring carbon atoms optionally being replaced by a nitrogen atom;

said aryl groups and aryl parts of said aralkyl groups being carbocyclic aromatic groups having from 6 to 14 carbon atoms, which may be unsubstituted or substituted with at least one substituent selected from substituents f defined below;

substituents f aryloxy groups, nitro groups, halogen atoms, carbamoyl groups, hydroxy groups, alkoxy groups having 1 to 6 carbon atoms, tetrazolyl groups, carboxyl groups and aryl groups;

substituents g aryl groups, carboxyl groups, cyano groups, hydroxy groups, halogen atoms, thiol groups, amino groups and mono- or di-alkyl amino groups wherein said alkyl groups each have from 1 to 6 carbon atoms, groups of formula $CONR^{30}R^{31}$ wherein $R^{30}$ and $R^{31}$ each represents an alkyl group having from 1 to 6 carbon atoms or, together with the nitrogen to which they are joined form a cyclic or heterocyclic group, or a group of formula $CSNR^{30}R^{31}$ where $R^{30}$ and $R^{31}$ are as defined above;

substituents h tetrazolyl groups, carboxyl groups, phenyl groups, phenyl substituted with one or more substituents selected from substituents f above, carbamoyl groups, sulfonamide groups, protected sulfonamide groups, carbonylsulfonamide groups, hydroxyl groups, alkoxy groups having 1 to 6 carbon atoms, thiol groups, alkylthio groups having from 1 to 6 carbon atoms, aryl groups, heterocyclic groups, carbonyl groups, thiocarbonyl groups, groups of Formula $CONR^{30}R^{31}$ wherein $R^{30}$ and $R^{31}$ each represents an alkyl group having from 1 to 6 carbon atoms or, together with the nitrogen to which they are joined form a cyclic or heterocyclic group, or a group of Formula $CSNR^{30}R^{31}$ where $R^{30}$ and $R^{31}$ are as defined above;

PROVIDED THAT not all of $Y^1$, $Y^2$, $Y^3$, $Y^4$ and $R^3$ are hydrogen atoms and, when the dotted lines represent single bonds, then any of $Y^1$, $Y^2$, $Y^3$ and $Y^4$ may also represent a keto group and/or any of $Y^1$, $Y^2$, $Y^3$ and $Y^4$ may also represent two such groups $Y^1$, $Y^2$, $Y^3$ and $Y^4$, and pharmaceutically acceptable salts and esters thereof.

In the above formula, it will be appreciated that the substituents $Y^1$, $Y^2$, $Y^3$ and $Y^4$ have been allocated particular positions, which are preferred positions.

Another class of compounds of the present invention are those compounds of formula (II):

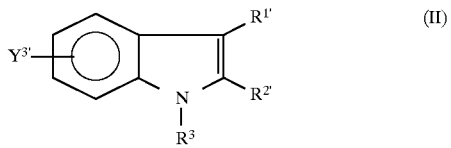

wherein:

$Y^{3'}$ represents a hydrogen atom, a halogen atom, a nitro group, a hydroxyl group, an amino group, an alkyl group having from 1 to 6 carbon atoms, an aryl group, a substituted aryl group, an aralkyl group, a substituted aralkyl group, or, when both $R^{1'}$ and $R^{2'}$ are hydrogen atoms, a group of formula —B—T, wherein T represents a carboxyl group, a sulfonamide group, a protected sulfonamide group or a tetrazolyl group and B represents an alkylene group having from 1 to 4 carbon atoms and being optionally substituted by a phenyl or benzyl group, said phenyl or benzyl group being optionally substituted by one or more substituents selected from halogen atoms, nitro groups, hydroxyl groups, amino groups and methyl groups;

$R^{1'}$ represents a hydrogen atom or a group of formula —B'—T', wherein T' represents a carboxyl group, a sulfonamide group, a protected sulfonamide group, or a tetrazolyl group and B' represents an alkylene group having from 1 to 4 carbon atoms and being optionally substituted by an amino group;

$R^{2'}$ represents a hydrogen atom; or $R^{1'}$ and $R^{2'}$ together represent a group of formula (Ia):

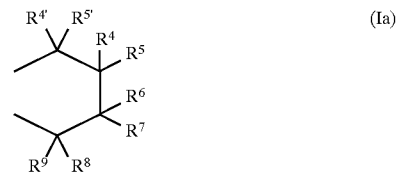

[in which $R^4$ and $R^{4'}$ are the same or different and each represents a hydrogen atom or an alkyl group having from 1 to 6 carbon atoms;

$R^5$ and $R^{5'}$ are the same or different and each represents a hydrogen atom or a group of formula $—(CH_2)_n—T''$ in which T'' represents a carboxyl group, a sulfonamide group, a protected sulfonamide group, or a tetrazolyl group and n=0, 1 or 2;

$R^6$ represents a hydrogen atom or a hydroxyl group;

$R^7$ represents a hydrogen atom or a group of formula $—(CH_2)_m—T'''$ in which T''' represents a carboxyl group, a sulfonamide group, a protected sulfonamide group, or a tetrazolyl group and m=0, 1 or 2;

$R^8$ represents a hydrogen atom or, together with $R^6$, represents a lactone group;

$R^9$ represents a hydrogen atom, a keto group or a methylthio group]; or $R^{1'}$ and $R^{2'}$ together represent a group of formula (Ib''):

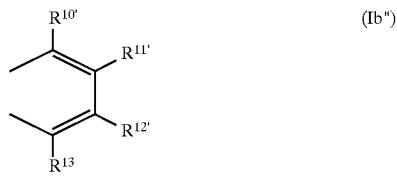

[in which $R^{10'}$ represents a hydrogen atom or an alkyl group having from 1 to 6 carbon atoms;

$R^{11'}$ represents a hydrogen atom or a group of formula $—(CH_2)_nT''''$ in which T'''' represents a carboxyl group, a sulfonamide group, a protected sulfonamide group, or a tetrazolyl group and n is as defined above;

$R^{12'}$ represents a hydrogen atom, a hydroxyl group, a carboxyl group, a sulfonamide group, a protected sulfonamide group, or a group of formula $—(O)_p—B''—$ T"'" in which T"'" represents a carboxyl group, a sulfonamide group, a protected sulfonamide group, or a tetrazolyl group, p=0 or 1 and B" represents an alkylene group having from 1 to 4 carbon atoms and being optionally substituted by a hydroxyl group, a phenyl group or a benzyl group, said phenyl or benzyl group being optionally substituted by one or more substituents selected from halogen atoms, nitro groups, hydroxyl groups, amino groups and methyl groups;

$R^{13}$ represents a hydrogen atom, an alkyl group having from 1 to 6 carbon atoms, or a methylthio group]; and $R^3$ represents a hydrogen atom or an alkyl group having from 1 to 6 carbon atoms substituted with a keto group and/or a phenyl group, said phenyl group being optionally substituted with one or more substituents selected from halogen atoms, nitro groups, hydroxyl groups, amino groups and methyl groups;

and pharmaceutically acceptable salts and esters thereof.

Another class of compounds of the present invention are those compounds of formula (II):

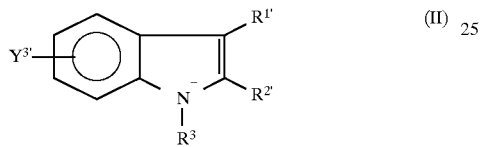

wherein:

one of $R^{1'}$ and $R^{2'}$ represents a hydrogen atom, an alkyl group having from 1 to 6 carbon atoms, an aryl group, a substituted aryl group, an aralkyl group, a substituted aralkyl group, an oxazolyl group, a substituted oxazolyl group which is substituted by at least one of substituents β, defined below, a group of formula —(A)$_p$—B$^5$—COOH, where A represents an oxygen atom or a sulfur atom, p is 0 or 1, B$^5$ represents an alkylene group which has from 1 to 6 carbon atoms and which is unsubstituted or is substituted by at least one substituent selected from amino groups, protected amino groups, hydroxyl groups, protected hydroxyl groups, oxazolyl groups and substituted oxazolyl groups;

and the other of $R^{1'}$ and $R^{2'}$ represents a hydrogen atom, an alkyl group having from 1 to 6 carbon atoms, an aryl group, a substituted aryl group, an aralkyl group or a substituted aralkyl group; or $R^{1'}$ and $R^{2'}$ together represent a group of formula (Id), (Ie) or (Ic):

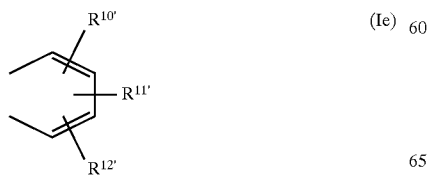

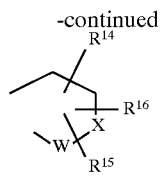

$R^{14}$ and $R^{10'}$ are the same or different and each represents a hydroxy group, a haloalkyl group having from 1 to 6 carbon atoms, a hydroxyalkyl group having from 1 to 6 carbon atoms, a carboxyl group, a protected carboxyl group, a sulfonamide group, a protected sulfonamide group, or a group of formula

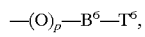

where $B^6$ represents an alkylene group which has from 1 to 4 carbon atoms and which is unsubstituted or is substituted by at least one of substituents γ, defined below, $T^6$ represents a carboxyl group, a protected carboxyl group, a sulfonamide group, a protected sulfonamide group, or a tetrazolyl group, and p is as defined above;

$R^{15}$ and $R^{12'}$ are the same or different and each represents a hydrogen atom, an alkyl group having from 1 to 6 carbon atoms, a haloalkyl group having from 1 to 6 carbon atoms, or an aryl group;

Z represents a methylene group, a group of formula >NH or a group of formula >N—;

W represents a methylene group, a sulfur atom or a group of formula >S—(O)$_q$, wherein q is as defined above;

provided that at least one of W and Z is a methylene group;

$R^{11'}$ represents a hydrogen atom, a haloalkyl group having from 1 to 6 carbon atoms, or an alkylthio group having from 1 to 6 carbon atoms;

$R^6$ represents a hydroxy group;

$R^7$ represents a carboxyl group, a protected carboxyl group, a sulfonamide group, a protected sulfonamide group, or a group of formula —B$^7$—T$^7$, where $B^7$ represents an alkylene group which has from 1 to 4 carbon atoms and which is unsubstituted or is substituted by at least one of substituents γ, defined below, and $T^7$ represents a carboxyl group, a protected carboxyl group, a sulfonamide group, a protected sulfonamide group, or a tetrazolyl group;

$R^9$ represents a hydrogen atom or an alkylthio group having from 1 to 6 carbon atoms; or $R^7$ and $R^8$ together represent a lactone group, when $R^9$ represents an alkylthio group having from 1 to 6 carbon atoms; or $R^9$ and $R^8$ together represent a oxo group;

$R^3$ represents a hydrogen atom or an amino-protecting group;

$Y^{3'}$ represents a hydrogen atom, a halogen atom, a carboxyl group, a protected carboxyl group, a sulfonamide group, a protected sulfonamide group, or a group of formula —B$^8$—T$^8$, where $B^8$ represents an alkylene group which has from 1 to 4 carbon atoms and which is unsubstituted or is substituted by at least one of substituents γ, defined below, and $T^8$ represents a carboxyl group, a protected carboxyl group, a sulfonamide group, a protected sulfonamide group, or a tetrazolyl group;

said substituents β are selected from alkyl groups having from 1 to 6 carbon atoms, aralkyl groups, substituted aralkyl groups, carboxyl groups, nitro groups, halogen atoms and cyano groups;

said substituents γ are selected from hydroxy groups, aralkyl groups, and substituted aralkyl groups;

and pharmaceutically acceptable salts and esters thereof.

Another class of compounds of the present invention are those compounds of formula (I):

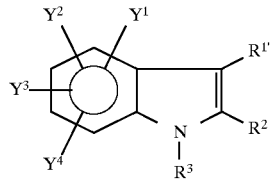

wherein:

$R^{1'}$ represents a hydrogen atom;

$R^{2'}$ represents a hydrogen atom; or $R^{1'}$ and $R^{2'}$ together represent a group of formula (If):

$R^3$ represents a hydrogen atom, an aralkyl group, an aralkyl group which is substituted by at least one of substituents ε, defined below, or an aromatic acyl group;

$Y^1$ represents a hydrogen atom, a thiol group, an alkyl group having from 1 to 6 carbon atoms, a haloalkyl group having from 1 to 6 carbon atoms, a sulfonamide group, a protected sulfonamide group, or a group of formula —E—COOH;

$Y^2$ represents a hydrogen atom, an alkyl group having from 1 to 6 carbon atoms, an alkylthio group having from 1 to 6 carbon atoms, a haloalkyl group having from 1 to 6 carbon atoms, a sulfonamide group, a protected sulfonamide group, or a group of formula —E—COOH or —E—Tet, where Tet represents a tetrazolyl group;

$Y^3$ represents a haloalkyl group having from 1 to 6 carbon atoms, a sulfonamide group, a protected sulfonamide group, a group of formula —E—COOH or —E—Tet, where Tet is as defined above;

$Y^4$ represents a hydrogen atom, an alkyl group having from 1 to 6 carbon atoms, a haloalkyl group having from 1 to 6 carbon atoms or a halogen atom; and E represents an alkylene group which has from 1 to 4 carbon atoms and which is unsubstituted or is substituted by at least one of substituents γ, defined below, or an oxyalkylene group which has from 1 to 3 carbon atoms and which is unsubstituted or is substituted by at least one of substituents γ, defined below;

PROVIDED that (1) when $R^{1'}$ and $R^{2'}$ both represent hydrogen atoms, at least one of $Y^1$, $Y^2$ and $Y^3$ represents a group of formula —E—COCH and $R^3$ does not represent a hydrogen atom;

(2) when $R^{1'}$ and $R^{2'}$ together represent a group of formula (If), $Y^3$ represents a carboxy group and $R^3$ represents a hydrogen atom, $Y^1$, $Y^2$ and $Y^4$ do not all represent hydrogen atoms;

(3) when $R^{1'}$ and $R^{2'}$ together represent a group of formula (If), $Y^3$ represents a carboxy group, $Y^2$ represents a hydrogen atom, and one of $Y^1$ and $Y^4$ represents a carboxy group, $R^3$ does not represent a hydrogen atom;

(4) when $R^{1'}$ and $R^{2'}$ together represent a group of formula (If), $Y^3$ represents a carboxy group, and at least one of $Y^1$, $Y^2$ and $Y^4$ represents an alkyl group, $R^3$ does not represent a hydrogen atom;

(5) when $R^{1'}$ and $R^{2'}$ together represent a group of formula (If), $Y^3$ represents a carboxy group and $Y^4$ represents a halogen atom, $Y^1$ and $Y^2$ do not both represent hydrogen atoms;

said substituents γ are selected from alkyl groups having from 1 to 6 carbon atoms, aralkyl groups, and aralkyl groups substituted by at least one of substituents ε, defined below;

said substituents ε are selected from halogen atoms and nitro groups.

A most preferred class of compounds of the present invention are those compounds of formula (III):

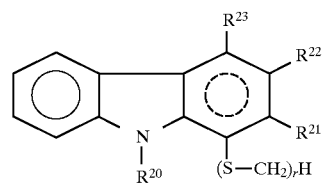

wherein:

the dotted circle indicates that the ring in which it is present is fully unsaturated;

$R^{20}$ represents a benzyl group optionally substituted with one or more substituents selected from halogen atoms, amino groups, nitro groups and hydroxy groups;

$R^{21}$ represents a group of formula —Q-Alk-COOH wherein Q represents an oxygen atom or a direct bond and Alk represents a lower alkylene group, Alk optionally being substituted with a benzyl group optionally further substituted with one or more substituents selected from halogen atoms, amino groups, nitro groups and hydroxy groups;

$R^{22}$ represents a hydrogen atom;

$R^{23}$ represents a hydrogen atom or a lower alkyl group; and r=0 or 1; OR the dotted circle indicates that the core triple ring structure is a 1,2,3,4-tetrahydrocarbazole;

$R^{20}$, $R^{21}$ and $R^{23}$ all represent hydrogen atoms and $R^{22}$ represents a lower alkyl group substituted with a carboxyl group; and r=1.

In the compounds of formula (III), when the dotted circle indicates that the core triple ring structure is a 1,2,3,4-tetrahydrocarbazole, then we also prefer those compounds wherein r=0 for use in the therapeutic indications of the present invention.

In the compounds of formula (III), when $R^{20}$ represents a substituted benzyl group, or Alk is substituted with a substituted benzyl group, then the preferred substituents on said benzyl group are halogen atoms, particularly preferably chlorine, fluorine and bromine atoms, or nitro groups, the preferred number of substituents being 0 or 1.

In the compounds of formula (III), Alk is preferably a methylene, ethylene or propylene group, particularly preferably an ethylene group, and Z is preferably a carbon-carbon single bond.

In the compounds of formula (III), $R^{23}$ preferably represents a hydrogen atom or a methyl group, preferably a hydrogen atom.

The present invention also provides the above classes of compounds for use in the treatment of dementia.

The present invention also provides the above classes of compounds for use in the treatment of Alzheimer's disease and delirium and as sedatives for the central nervous system.

The present invention still further provides the above classes of compounds for use in the manufacture of a medicament for the treatment of Alzheimer's disease.

The invention also embraces those compounds among those described above which are novel.

In the compounds of the present invention, where $Y^1$, $Y^2$, $Y^3$, $Y^4$, $Y$, $R^3$, $R^{12}$, B, B", substituent ε or substituent β represents a halogen atom, this may be a fluorine, chlorine, bromine or iodine atom and is preferably a fluorine or chlorine atom.

Where $Y^1$, $Y^2$, $Y^3$, $Y^4$, $Y$, $R^1$, $R^2$, $R^3$, $R^4$, $R^{4'}$, $R^{10}$, $R^{11}$, $R^{12}$, $R^{13}$, $R^{14}$, $R^{15}$, substituent β or substituent γ represents an alkyl group having from 1 to 6 carbon atoms, this may be a straight or branched chain group having from 1 to 6, preferably from 1 to 4, carbon atoms, and examples include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alkyl groups having from 1 to 4 carbon atoms, preferably the methyl, ethyl, propyl, isopropyl, butyl and isobutyl groups, and most preferably the methyl group.

Where $Y^1$, $Y^2$, $Y^3$, $Y^4$, $Y$, $R^9$, $R^{10}$, $R^{11}$, $R^{12}$ or $R^{13}$ represents an alkylthio group having from 1 to 6 carbon atoms, this may be a straight or branched chain group having from 1 to 6, preferably from 1 to 4, carbon atoms, and examples include the methylthio, ethylthio, propylthio, isopropylthio, butylthio, isobutylthio, sec-butylthio, t-butylthio, pentylthio, isopentylthio, neopentylthio, 2-methylbutylthio, 1-ethylpropylthio, 4-methylpentylthio, 3-methylpentylthio, 2-methylpentylthio, 1-methylpentylthio, 3,3-dimethylbutylthio, 2,2-dimethylbutylthio, 1,1-dimethylbutylthio, 1,2-dimethylbutylthio, 1,3-dimethylbutylthio, 2,3-dimethylbutylthio, 2-ethylbutylthio, hexylthio and isohexylthio groups. Of these, we prefer those alkylthio groups having from 1 to 4 carbon atoms, preferably the methylthio, ethylthio, propylthio, isopropylthio, butylthio and isobutylthio groups, and most preferably the methylthio group.

Where $Y^1$, $Y^2$, $Y^3$, $Y^4$, $T$, $T^1$, $T^2$, $T^3$, $T^4$, $T^5$, $T^6$, $T^7$, $T^8$, $R^1$, $R^7$, $R^{10}$, $R^{11}$, $R^{12}$, $R^{13}$, $R^{14}$ represents a protected carboxy group, there is no particular restriction on the nature of the carboxy-protecting group used, and any carboxy-protecting group known in the art may equally be used in this reaction. Non-limiting examples of such groups include:

alkyl groups having from 1 to 25 carbon atoms, more preferably from 1 to 6 carbon atoms, such as the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl, isohexyl, heptyl, octyl, nonyl, decyl, dodecyl, tridecyl, pentadecyl, octadecyl, nonadecyl, icosyl, henicosyl, docosyl, tricosyl, tetracosyl and pentacosyl groups, but most preferably the methyl, ethyl and t-butyl groups;

cycloalkyl groups having from 3 to 7 carbon atoms, for example the cyclopropyl, cyclobutyl, cyclopentyl, cyclohexyl and cycloheptyl groups;

aralkyl groups, in which the alkyl part has from 1 to 3 carbon atoms and the aryl part is a carbocyclic aromatic group having from 6 to 14 carbon atoms, which may be substituted or unsubstituted and, if substituted, has at least one of substituents β defined and exemplified above, although the unsubstituted groups are preferred; examples of such aralkyl groups include the benzyl, phenethyl, 1-phenylethyl, 3-phenylpropyl, 2-phenylpropyl, 1-naphthylmethyl, 2-naphthylmethyl, 2-(1-naphthyl)ethyl, 2-(2-naphthyl)ethyl, benzhydryl (i.e. diphenylmethyl), triphenylmethyl, bis(o-nitrophenyl)methyl, 9-anthrylmethyl, 2,4,6-trimethylbenzyl, 4-bromobenzyl, 2-nitrobenzyl, 4-nitrobenzyl, 3-nitrobenzyl, 4-methoxybenzyl and piperonyl groups;

alkenyl groups having from 2 to 6 carbon atoms, such as the the vinyl, allyl, 2-methylallyl, 1-propenyl, isopropenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl and 5-hexenyl groups, of which the vinyl, allyl, 2-methylallyl, 1-propenyl, isopropenyl and butenyl groups are preferred, the allyl and 2-methylallyl groups being most preferred, haloalkyl groups having from 1 to 6, preferably from 1 to 4, carbon atoms, in which the alkyl part is as defined and exemplified in relation to the alkyl groups above, and the halogen atom is chlorine, fluorine, bromine or iodine, such as the 2,2,2-trichloroethyl, 2-haloethyl (e.g. 2-chloroethyl, 2-fluoroethyl, 2-bromoethyl or 2-iodoethyl), 2,2-dibromoethyl and 2,2,2-tribromoethyl groups;

substituted silylalkyl groups, in which the alkyl part is as defined and exemplified above, and the silyl group has up to 3 substituents selected from alkyl groups having from 1 to 6 carbon atoms and phenyl groups which are unsubstituted or have at least one substituent selected from substituents β defined and exemplified above, for example a 2-trimethylsilylethyl group;

phenyl groups, in which the phenyl group is unsubstituted or substituted, preferably with at least one alkyl group having from 1 to 4 carbon atoms or acylamino group, for example the phenyl, tolyl and benzamidophenyl groups;

phenacyl groups, which may be unsubstituted or have at least one of substituents β defined and exemplified above, for example the phenacyl group itself or the p-bromophenacyl group;

cyclic and acyclic terpenyl groups, for example the geranyl, neryl, linalyl, phytyl, menthyl (especially m- and p-menthyl), thujyl, caryl, pinanyl, bornyl, norcaryl, norpinanyl, norbornyl, menthenyl, camphenyl and nor-bornenyl groups;

alkoxymethyl groups, in which the alkoxy part has from 1 to 6, preferably from 1 to 4, carbon atoms and may itself be substituted by a single unsubstituted alkoxy group, such as the methoxymethyl, ethoxymethyl, propoxymethyl, isopropoxymethyl, butoxymethyl and methoxyethoxymethyl groups;

aliphatic acyloxyalkyl groups, in which the acyl group is preferably an alkanoyl group and is more preferably an alkanoyl group having from 2 to 6 carbon atoms, and the alkyl part has from 1 to 6, and preferably from 1 to 4, carbon atoms such as the acetoxymethyl, propionyloxymethyl, butyryloxymethyl, isobutyryloxymethyl, pivaloyloxymethyl, 1-pivaloyloxyethyl, 1-acetoxyethyl, 1-isobutyryloxyethyl, 1-pivaloyloxypropyl, 2-methyl-1-pivaloyloxypropyl, 2-pivaloyloxypropyl, 1-isobutyryloxyethyl, 1-isobutyryloxypropyl, 1-acetoxypropyl, 1-acetoxy-2-methylpropyl, 1-propionyloxyethyl, 1-propionyloxypropyl, 2-acetoxypropyl and 1-butyryloxyethyl groups;

cycloalkyl-substituted aliphatic acyloxyalkyl groups, in which the acyl group is preferably an alkanoyl group and is more preferably an alkanoyl group having from 2 to 6 carbon atoms, the cycloalkyl substituent has from 3 to 7 carbon atoms, and the alkyl part has from 1 to 6, preferably from 1 to 4, carbon atoms, such as the (cyclohexylacetoxy)methyl, 1-(cyclohexylacetoxy) ethyl, 1-(cyclohexylacetoxy)propyl, 2-methyl-1-(cyclohexylacetoxy)propyl, (cyclopentylacetoxy)methyl, 1-(cyclopentylacetoxy)ethyl, 1-(cyclopentylacetoxy)propyl and 2-methyl-1-(cyclopentylacetoxy)propyl, groups;

alkoxycarbonyloxyalkyl groups, especially 1-(alkoxycarbonyloxy)ethyl groups, in which the alkoxy part has from 1 to 10, preferably from 1 to 6, and more preferably from 1 to 4, carbon atoms, and the alkyl part has from 1 to 6, preferably from 1 to 4, carbon atoms, such as the 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl, 1-isobutoxycarbonyloxyethyl, 1-sec-butoxycarbonyloxyethyl, 1-t-butoxycarbonyloxyethyl, 1-(1-ethylpropoxycarbonyloxy)ethyl and 1-(1,1-dipropylbutoxycarbonyloxy)ethyl groups, and other alkoxycarbonylalkyl groups, in which both the alkoxy and alkyl groups have from 1 to 6, preferably from 1 to 4, carbon atoms, such as the 2-methyl-1-(isopropoxycarbonyloxy) propyl, 2-(isopropoxycarbonyloxy)propyl, isopropoxycarbonyloxymethyl, t-butoxycarbonyloxymethyl, methoxycarbonyloxymethyl and ethoxycarbonyloxymethyl groups;

cycloalkylcarbonyloxyalkyl and cycloalkyloxycarbonyloxyalkyl groups, in which the cycloalkyl group has from 3 to 10, preferably from 3 to 7, carbon atoms, is mono- or poly-cyclic and is optionally substituted by at least one (and preferably only one) alkyl group having from 1 to 4 carbon atoms (e.g. selected from those alkyl groups exemplified above) and the alkyl part has from 1 to 6, more preferably from 1 to 4, carbon atoms (e.g. selected from those alkyl groups exemplified above) and is most preferably methyl, ethyl or propyl, for example the 1-methylcyclohexylcarbonyloxymethyl, 1-methylcyclohexyloxycarbonyloxymethyl, cyclopentyloxycarbonyloxymethyl, cyclopentylcarbonyloxymethyl, 1-cyclohexyloxycarbonyloxyethyl, 1-cyclohexylcarbonyloxyethyl, 1-cyclopentyloxycarbonyloxyethyl, 1-cyclopentylcarbonyloxyethyl, 1-cycloheptyloxycarbonyloxyethyl, 1-cycloheptylcarbonyloxyethyl, 1-methylcyclopentylcarbonyloxymethyl, 1-methylcyclopentyloxycarbonyloxymethyl, 2-methyl-1-(1-methylcyclohexylcarbonyloxy)propyl, 1-(1-methylcyclohexylcarbonyloxy)propyl, 2-(1-methylcyclohexylcarbonyloxy)propyl, 1-(cyclohexylcarbonyloxy)propyl, 2-(cyclohexylcarbonyloxy)propyl, 2-methyl-1-(1-methylcyclopentylcarbonyloxy)propyl, 1-(1-methylcyclopentylcarbonyloxy)propyl, 2-(1-methylcyclopentylcarbonyloxy)propyl, 1-(cyclopentylcarbonyloxy)propyl, 2-(cyclopentylcarbonyloxy)propyl, 1-(1-methylcyclopentylcarbonyloxy)ethyl, 1-(1-methylcyclopentylcarbonyloxy)propyl, adamantyloxycarbonyloxymethyl, adamantylcarbonyloxymethyl, 1-adamantyloxycarbonyloxyethyl and 1-adamantylcarbonyloxyethyl groups;

cycloalkylalkoxycarbonyloxyalkyl groups in which the alkoxy group has a single cycloalkyl substituent, the cycloalkyl substituent having from 3 to 10, preferably from 3 to 7, carbon atoms and mono- or poly-cyclic, for example the cyclopropylmethoxycarbonyloxy-methyl, cyclobutylmethoxycarbonyloxymethyl, cyclopentylmethoxycarbonyloxymethyl, cyclohexylmethoxycarbonyloxymethyl, 1-(cyclopropylmethoxycarbonyloxy)ethyl, 1-(cyclobutylmethoxycarbonyloxy)ethyl, 1-(cyclopentylmethoxycarbonyloxy)ethyl and 1-(cyclohexylmethoxycarbonyloxy)ethyl groups;

terpenylcarbonyloxyalkyl and terpenyloxycarbonyloxyalkyl groups, in which the terpenyl group is as exemplified above, and is preferably a cyclic terpenyl group, for example the 1-(menthyloxycarbonyloxy)ethyl, 1-(menthylcarbonyloxy)ethyl, menthyloxycarbonyloxymethyl, menthylcarbonyloxymethyl, 1-(3-pinanyloxycarbonyloxy)ethyl, 1-(3-pinanylcarbonyloxy)ethyl, 3-pinanyloxycarbonyloxymethyl and 3-pinanylcarbonyloxymethyl groups;

5-alkyl or 5-phenyl [which may be substituted by at least one of substituents β, defined and exemplified above] (2-oxo-1,3-dioxolen-4-yl)alkyl groups in which each alkyl group (which may be the same or different) has from 1 to 6, preferably from 1 to 4, carbon atoms, for example the (5-methyl-2-oxo-1,3-dioxolen-4-yl) methyl, (5-phenyl-2-oxo-1,3-dioxolen-4-yl)methyl, (5-isopropyl-2-oxo-1,3-dioxolen-4-yl)methyl, (5-t-butyl-2-oxo-1,3-dioxolen-4-yl)methyl and 1-(5-methyl-2-oxo-1,3-dioxolen-4-yl)ethyl groups; and other groups, such as the phthalidyl, indanyl and 2-oxo-4,5,6,7-tetrahydro-1,3-benzodioxolen-4-yl groups.

Where T, $T^1$, $T^2$, $T^3$, $T^4$, $T^5$, $T^6$, $T^7$, $T^8$, T', T'', T''', T'''', T''''' or Tet represents a tetrazolyl group, this is preferably a tetrazol-5-yl group.

Where $R^1$, $B^2$ or $B^5$ represents an oxazolyl group, this is preferably an oxazol-5-yl group, which may be substituted or unsubstituted. In the case of substituents on the carbon atom, these may be selected from alkyl groups having from 1 to 6 carbon atoms (such as those exemplified above), and aralkyl and acyl groups (such as those exemplified below), as well as nitro groups, halogen atoms and cyano groups.

Where $B^1$ $B^2$ $B^3$ $B^4$, $B^5$ $B^6$ $B^7$ $B^8$, B, B', B" or E represents an alkylene group, this may be a straight or branched chain alkylene group having from 1 to 3 or from 1 to 4 carbon atoms. Examples of such groups include the methylene, ethylene, ethylidene, trimethylene, propylene, propylidene, isopropylidene, tetramethylene, butylidene, 1-methylethylene, 2-methylethylene, 1-methyltrimethylene, 2-methyltrimethylene, 3-methyltrimethylene, pentamethylene and hexamethylene groups, of which the methylene and ethylene groups are preferred.

Where E represents an oxyalkylene group, this may be a straight or branched chain oxyalkylene group having from 1 to 3 or from 1 to 4 carbon atoms. Examples of such groups include the oxymethylene, oxyethylene, oxytrimethylene, oxypropylene, oxytetramethylene, 1-methyloxyethylene, 2-methyloxyethylene, 1-methyloxytrimethylene, 2-methyloxytrimethylene and 3-methyloxytrimethylene groups, of which the oxymethylene and oxyethylene groups are preferred.

Where the alkylene group represented by $B^2$ or $B^5$ is substituted by a protected amino group or where $R^3$ or $R^{13}$ represents an amino-protecting group, the protecting group used is not critical to the present invention, and any protecting group used in compounds of this type may equally be used here. Examples of suitable protecting groups include: acyl groups, such as the lower aliphatic carboxylic acyl, preferably alkanoyl and particularly alkanoyl groups having from 1 to 6 carbon atoms; or aromatic carboxylic acyl groups, preferably arylcarbonyl groups in which the aryl moiety is as defined and exemplified below in relation to $R^1$, $R^2$, $R^{12}$, $R^{15}$, Y or substituent α, for example: aliphatic lower acyl groups such as the formyl, acetyl, propionyl, butyryl, isobutyryl, valeryl, isovaleryl and pivaloyl groups; and aromatic acyl groups, such as the benzoyl, 4-acetoxybenzoyl, 4-methoxybenzoyl, 3-methoxybenzoyl, 2-methoxybenzoyl, 4-methylbenzoyl, 3-fluorobenzoyl, 4-fluorobenzoyl, 3-chlorobenzoyl, 4-chlorobenzoyl, 3,4-dichlorobenzoyl, 3,4-difluorobenzoyl, 3,4-dimethoxybenzoyl, 4-nitrobenzoyl, 4-aminobenzoyl, 4-acetamidobenzoyl and 1-naphthoyl groups. Of these, we prefer the acetyl, benzoyl and isobutyryl groups.

The aromatic acyl groups represented by $R^3$ in one embodiment of the present invention may also be as defined and exemplified above.

Where $R^1$, $R^2$, $R^{12}$, $R^{15}$, Y or substituent a is an aryl group, this has from 6 to 14 carbon atoms, more preferably from 6 to 10, and most preferably 6 or 10, carbon atoms, in one or more, preferably one, two or three, and more preferably one, carbocyclic ring, and examples of the unsubstituted groups include the phenyl, 1-naphthyl, 2-naphthyl, indenyl, acenaphthenyl, anthryl and phenanthryl groups, preferably the phenyl or naphthyl (1- or 2-naphthyl) group, and more preferably the phenyl group. Such groups may be unsubstituted or they may have on the ring at least one substituent, preferably from 1 to 3 substituents, selected from the group consisting of substituents ψ, defined and exemplified below. Examples of such substituted groups include the phenyl, 2-methylphenyl, 3-methylphenyl, 4-methylphenyl, 2-methoxyphenyl, 3-methoxyphenyl, 4-methoxyphenyl, 2-nitrophenyl, 3-nitrophenyl, 4-nitrophenyl, 2-fluorophenyl, 3-fluorophenyl, 4-fluorophenyl, 2-chlorophenyl, 3-chlorophenyl and 4-chlorophenyl groups. However, the unsubstituted groups, especially the phenyl group, are preferred.

Examples of substituents ψ include:

alkyl groups having from 1 to 4 carbon atoms, such as the methyl, ethyl, propyl, isopropyl, butyl, isobutyl, sec-butyl and t-butyl groups, of which the methyl, ethyl, propyl and isopropyl groups are preferred;

alkoxy groups having from 1 to 4 carbon atoms, such as the methoxy, ethoxy, propoxy, isopropoxy, butoxy, isobutoxy, sec-butoxy and t-butoxy groups, of which the methoxy and ethoxy groups are preferred; and halogen atoms, such as the fluorine, chlorine, bromine and iodine atoms, of which the fluorine, chlorine and bromine atoms are preferred; and nitro groups.

Where $R^1$, $R^2$, $R^3$, Y, substituent α, substituent β or substituent γ is an aralkyl group, this may be an alkyl group having from 1 to 4 carbon atoms which is substituted by at least one, and preferably from 1 to 3, more preferably 1 or 2, and most preferably one, aryl group, which may be any of the aryl groups defined and exemplified above. Examples of the alkyl groups so substituted include the methyl, ethyl, propyl, isopropyl, butyl, isobutyl and sec-butyl groups. Examples of preferred aralkyl groups include the benzyl, 1-phenylethyl, 2-phenylethyl (=phenethyl), 1-phenylpropyl, 2-phenylpropyl, 3-phenylpropyl, 4-phenylbutyl, 2-methyl-2-phenylethyl, 1-methyl-2-phenylethyl, 1-naphthylmethyl, 2-naphthylmethyl, indenylmethyl, acenaphthenylmethyl, anthrylmethyl, phenanthrylmethyl, benzhydryl and trityl (=triphenylmethyl) groups, preferably the benzyl or naphthylmethyl (1- or 2-naphthylmethyl) group, and more preferably the benzyl group. Such groups may be unsubstituted or they may have on the ring at least one substituent, preferably 1 to 3 substituents, selected from the group consisting of substituents ψ, defined and exemplified above. Examples of such substituted groups include the benzyl, 2-methylbenzyl, 3-methylbenzyl, 4-methylbenzyl, 2-methoxybenzyl, 3-methoxybenzyl, 4-methoxybenzyl, 2-nitrobenzyl, 3-nitrobenzyl, 4-nitrobenzyl, 2-fluorobenzyl, 3-fluorobenzyl, 4-fluorobenzyl, 2-chlorobenzyl, 3-chlorobenzyl and 4-chlorobenzyl groups. However, the unsubstituted groups, especially the benzyl group, are preferred.

Where $R^7$ and $R^8$ or $R^8$ and $R^6$ represents a lactone group, this is a group containing —O—C(O)—, and optionally one or more methylene groups, i.e. —$(CH_2)_s$—O—C(O)—$(CH_2)_t$—, where s and t are the same or different and each is 0 or an integer from 1 to 3, preferably 1 or 2, provided that (s+t) is not greater than 5.

Where $R^{10}$, $R^{11}$, $R^{12}$, $R^{13}$ or $R^{14}$ represents a hydroxyalkyl group having from 1 to 6 carbon atoms, this may be a straight or branched chain group having from 1 to 6, preferably from 1 to 4, carbon atoms, and examples include the hydroxymethyl, 1- or 2-hydroxyethyl, 1-, 2- or 3-hydroxypropyl, 1- or 2-hydroxy-2-methylethyl, 1-, 2-, 3- or 4-hydroxybutyl, 1-, 2-, 3-, 4- or 5-hydroxypentyl or 1-, 2-, 3-, 4-, 5- or 6-hydroxyhexyl groups. Of these, we prefer those hydroxyalkyl groups having from 1 to 4 carbon atoms, preferably the hydroxymethyl, 2-hydroxyethyl, 3-hydroxypropyl and 4-hydroxybutyl groups, and most preferably the hydroxymethyl group.

Where $Y^1$, $Y^2$, $Y^3$, $Y^4$, $R^{10}$, $R^{11}$, $R^{12}$, $R^{14}$ or $R^{15}$ represents a haloalkyl group, this may be a straight or branched chain group having from 1 to 6, preferably from 1 to 4, carbon atoms, in which the alkyl part is as defined and exemplified in relation to the alkyl groups above, and the halogen atom is chlorine, fluorine, bromine or iodine, such as the trifluoromethyl, trichloromethyl, tribromomethyl, triiodomethyl, difluoromethyl, dichloromethyl, dibromomethyl, diiodomethyl, fluoromethyl, chloromethyl, bromomethyl, iodomethyl, 2,2,2-trichloroethyl, 2,2,2-trifluoroethyl, pentafluoroethyl, 2-haloethyl (e.g. 2-chloroethyl, 2-fluoroethyl, 2-bromoethyl or 2-iodoethyl), 2,2-dibromoethyl, 2,2,2-tribromoethyl, 3-fluoropropyl, 4-fluorobutyl, 5-fluoropentyl, 6-fluorohexyl, 3-chloropropyl, 4-chlorobutyl, 5-chloropentyl, 6-chlorohexyl and groups;

Where $B^2$ or $B^5$ is substituted by a protected hydroxyl group, then there is no particular restriction on the nature of the hydroxy-protecting group used, and any hydroxy-protecting group known in the art may be employed. Suitable groups include protecting groups capable of being cleaved by chemical methods (such as hydrogenolysis, hydrolysis, electrolysis or photolysis) to generate a free hydroxy group, and protecting groups capable of being cleaved in vivo by biological methods such as hydrolysis.

Suitable examples of hydroxy-protecting groups which may be cleaved by chemical means include: aliphatic acyl groups, preferably alkanoyl groups having from 1 to 25 carbon atoms, more preferably from 1 to 20 carbon atoms, still more preferably from 1 to 6 carbon atoms, and most preferably from 1 to 4 carbon atoms (such as formyl, acetyl, propionyl, butyryl, isobutyryl, pivaloyl, valeryl, isovaleryl, hexanoyl, heptanoyl, octanoyl, lauroyl, myristoyl, tridecanoyl, palmitoyl and stearoyl groups, of which the acetyl group is most preferred);

- halogenated alkanoyl groups having from 2 to 6 carbon atoms, especially halogenated acetyl groups (such as the chloroacetyl, dichloroacetyl, trichloroacetyl and trifluoroacetyl groups);
- lower alkoxyalkanoyl groups in which the alkoxy part has from 1 to 6, preferably from 1 to 3, carbon atoms and the alkanoyl part has from 2 to 6 carbon atoms and is preferably an acetyl group (such as the methoxyacetyl group);
- unsaturated analogues of the above groups, especially alkenoyl or alkynoyl groups having from 3 to 6 carbon atoms [such as the acryloyl, methacryloyl, propioloyl, crotonoyl, isocrotonoyl and (E)-2-methyl-2-butenoyl groups];
- aromatic acyl groups, preferably arylcarbonyl groups, in which the aryl part has from 6 to 14, more preferably from 6 to 10, and most preferably 6, ring carbon atoms and is a carbocyclic group, which is unsubstituted or has from 1 to 5, preferably from 1 to 3 substituents, selected from the group consisting of substituents ψ, defined and exemplified above, said aromatic acyl groups including, for example,
  - unsubstituted groups (such as the benzoyl, α-naphthoyl and β-naphthoyl groups); halogenated arylcarbonyl groups (such as the 2-bromobenzoyl and 4-chlorobenzoyl groups); lower alkyl-substituted arylcarbonyl groups, in which the or each alkyl substituent has from 1 to 6, preferably from 1 to 4, carbon atoms (such as the 2,4,6-trimethylbenzoyl and 4-toluoyl groups); lower alkoxy-substituted arylcarbonyl groups, in which the or each alkoxy substituent preferably has from 1 to 6, more preferably from 1 to 4, carbon atoms (such as the 4-anisoyl group); carboxy-substituted arylcarbonyl groups (such as the 2-carboxybenzoyl, 3-carboxybenzoyl and 4-carboxybenzoyl groups); nitro-substituted arylcarbonyl groups (such as the 4-nitrobenzoyl and 2-nitrobenzoyl groups); lower alkoxycarbonyl-substituted arylcarbonyl groups, in which the or each alkoxycarbonyl substituent preferably has from 2 to 6 carbon atoms [such as the 2-(methoxycarbonyl) benzoyl group]; and aryl-substituted arylcarbonyl groups, in which the aryl substituent is as defined above, except that, if it is substituted by a further aryl group, that aryl group is not itself substituted by an aryl group (such as the 4-phenylbenzoyl group);
- heterocyclic groups having 5 or 6 ring atoms, of which 1 or 2 are hetero-atoms selected from the group consisting of oxygen, sulfur and nitrogen atoms, preferably oxygen or sulfur atoms, which groups may be unsubstituted or may have at least one substituent selected from the group consisting of substituents ψ and oxygen atoms, preferably halogen atoms and alkoxy groups, and wherein suitable examples of said heterocyclic groups include:
  - the tetrahydropyranyl groups, which may be substituted or unsubstituted, such as the tetrahydropyran-2-yl, 3-bromotetrahydropyran-2-yl and 4-methoxytetrahydropyran-4-yl groups, tetrahydrothiopyranyl groups, which may be substituted or unsubstituted, such as the tetrahydrothiopyran-2-yl and 4-methoxytetrahydrothiopyran-4-yl groups; tetrahydrofuranyl groups and tetrahydrothienyl groups, which may be substituted or unsubstituted, such as the tetrahydrofuran-2-yl group and tetrahydrothien-2-yl group;
- tri-substituted silyl groups, in which all three or two or one of the substituents are alkyl groups having from 1 to 5, preferably from 1 to 4, carbon atoms, and none, one or two of the substituents are aryl groups, as defined above, but preferably phenyl or substituted phenyl groups, preferably: tri(loweralkyl)silyl groups, such as the trimethylsilyl, triethylsilyl, isopropyldimethylsilyl, t-butyldimethylsilyl, methyldiisopropylsilyl, methyldi-t-butylsilyl and triisopropylsilyl groups; and tri(lower alkyl)silyl groups in which one or two of the alkyl groups have been replaced by aryl groups, such as the diphenylmethylsilyl, diphenylbutylsilyl, diphenyl-t-butylsilyl, diphenylisopropylsilyl and phenyldiisopropylsilyl groups;
- alkoxyalkyl groups, in which the alkoxy and alkyl parts each have from 1 to 6, preferably from 1 to 4, carbon atoms, especially alkoxymethyl groups, and such groups which have at least one, preferably from 1 to 5, more preferably from 1 to 3, and most preferably 1, substituents, preferably: lower alkoxymethyl groups and other alkoxyalkyl groups (such as the methoxymethyl, ethoxymethyl, propoxymethyl, isopropoxymethyl, butoxymethyl and t-butoxymethyl groups); lower alkoxy-substituted lower alkoxymethyl groups (such as the 2-methoxyethoxymethyl group); halogenated lower alkoxymethyl groups [such as the 2,2,2-trichloroethoxymethyl and bis(2-chloroethoxy) methyl groups] and lower alkoxysubstituted ethyl groups (such as the 1-ethoxyethyl, 1-methyl-1-methoxyethyl and 1-isopropoxyethyl groups);
- other substituted ethyl groups, preferably: halogenated ethyl groups (such as the 2,2,2-trichloroethyl group); and arylselenyl-substituted ethyl groups, in which the aryl part is as defined above, such as the 2-(phenylselenyl)ethyl group;
- aralkyl groups, preferably alkyl groups having from 1 to 4, more preferably from 1 to 3, and most preferably 1 or 2, carbon atoms which are substituted with from 1 to 3 aryl groups, as defined and exemplified above, which may be unsubstituted (such as the benzyl, phenethyl, 1-phenylethyl, 3-phenylpropyl, α-naphthylmethyl, β-naphthylmethyl, diphenylmethyl, triphenylmethyl, α-naphthyldiphenylmethyl and 9-anthrylmethyl groups) or substituted on the aryl part with a lower alkyl group, a lower alkoxy group, a nitro group, a halogen atom, a cyano group, or an alkylenedioxy group having from 1 to 3 carbon atoms, preferably a methylenedioxy group, examples including:
  - the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzoyl, 4-bromobenzyl, 4-cyanobenzyl, 4-cyanobenzyldiphenylmethyl, bis(2-nitrophenyl)methyl and piperonyl groups;

alkoxycarbonyl groups, especially such groups having from 2 to 7, more preferably 2 to 5, carbon atoms and which may be unsubstituted (such as the methoxycarbonyl, ethoxycarbonyl, t-butoxycarbonyl and isobutoxycarbonyl groups) or substituted with a halogen atom or a tri-substituted silyl group, for example, a tri(lower alkylsilyl) group (such as the 2,2,2-trichloroethoxycarbonyl and 2-trimethylsilylethoxycarbonyl groups); alkenyloxycarbonyl groups in which the alkenyl part has from 2 to 6, preferably from 2 to 4, carbon atoms (such as the vinyloxycarbonyl and allyloxycarbonyl groups); sulfo groups; and aralkyloxycarbonyl groups, in which the aralkyl part is as defined and exemplified above, and in which the aryl ring, if substituted, is substituted by at least one substituent selected from the group consisting of substituents ψ, defined and exemplified above, one or two lower alkoxy or nitro substituents, such as one of the benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups.

Examples of hydroxy-protecting groups which are capable of being cleaved in vivo by biological methods such as enzymatic hydrolysis include:

acyloxyalkyl groups, in which the alkyl part has from 1 to 6 carbon atoms, such as the acetoxymethyl, dimethylaminoacetoxymethyl, propionyloxymethyl, butyryloxymethyl, pivaloyloxymethyl and 1-acetoxyethyl groups;

1-(alkoxycarbonyloxy)alkyl groups, in which each of the alkoxy and alkyl parts has from 1 to 6 carbon atoms, such as the methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, cyclohexyloxycarbonyloxymethyl, cyclohexyloxycarbonyloxycyclohexylmethyl, 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl, 1-isobutoxycarbonyloxyethyl, 1-t-butoxycarbonyloxyethyl, 1-cyclohexyloxycarbonyloxyethyl and 1-ethoxycarbonyloxypropyl groups;

carbonyloxyalkyl groups, including oxodioxolenylmethyl groups, such as the 4-methyloxodioxolenylmethyl, 4-phenyl-4-oxodioxolenylmethyl and oxodioxolenylmethyl groups;

dioxolenylalkyl groups, aliphatic acyl groups and aromatic acyl groups;

any residue which forms a salt of a half-ester of a dicarboxylic acid, such as succinic acid;

any residue which forms a salt of a phosphate;

a residue of an ester of an amino acid; and carbonyloxyalkyloxycarbonyl groups, such as the pivaloyloxymethoxycarbonyl group.

Of the above, we prefer the aliphatic acyl groups, tri-substituted silyl groups, and most preferably the tri-substituted silyl groups.

Where $Y^1$, $Y^2$, $Y^3$, $Y^4$, $T^1$, $T^2$, $T^3$, $T^4$, $T^5$, $T^6$, $T^7$, $T^8$, $R^1$, $R^2$, $R^7$, $R^{10}$, $R^{11}$, $R^{12}$, $R^{13}$, $R^{14}$, T, T', T'', T''', T'''' or T''''' represents a protected sulfonamide group, there is no particular restriction on the nature of the sulfonamide-protecting group used, and any sulfonamide protecting group known in the art may equally be used here.

Non-limiting examples of suitable protecting groups for sulfonamides include: acyl groups, which may be unsubstituted or substituted by at least one (and preferably only one) aryl groups having from 6 to 14 carbon atoms (most preferably phenyl), such as the lower aliphatic acyl or aromatic acyl groups, for example;

aliphatic lower acyl groups such as the formyl, acetyl, phenylacetyl, diphenylacetyl, propyonyl, 3-phenylpropionyl, butyryl, isobutyryl, valeryl, isovaleryl and pivaloyl groups; and aromatic acyl groups, such as the benzoyl, 4-acetoxybenzoyl, 4-methoxybenzoyl, 3-methoxybenzoyl, 2-methoxybenzoyl, 4-methylbenzoyl, 3-fluorobenzoyl, 4-fluorobenzoyl, 3-chlorobenzoyl, 4-chlorobenzoyl, 3,4-dichlorobenzoyl, 3,4-difluorobenzoyl, 3,4-dimethylbenzoyl, 4-nitrobenzoyl, 4-aminobenzoyl, 4-acetamidobenzoyl, 4-phenylbenzoyl and 1-naphthoyl groups. Of these, we prefer the acetyl, phenylacetyl, benzoyl and isobutyryl groups, most preferably the phenylacetyl group.

Where the compound of the present invention contains a carboxyl group, it may form esters. Examples of groups with which such compounds may form esters include the carboxy-protecting groups listed above. In most cases, we prefer to administer the compound as the free acid; however, where the compound is to be administered as an ester, we prefer that the ester group should be one of those groups which can be removed easily in vivo, and most preferably the aliphatic acyloxyalkyl groups, alkoxycarbonyloxyalkyl groups, cycloalkylcarbonyloxyalkyl groups, phthalidyl groups and (5-substituted 2-oxo-1,3-dioxolen-4-yl)methyl groups.

Those compounds of the present invention which contain a carboxyl group can form salts. Examples of such salts include: salts with an alkali metal, such as sodium, potassium or lithium; salts with an alkaline earth metal, such as barium or calcium; salts with another metal, such as magnesium or aluminum; ammonium salts; organic base salts, such as a salt with triethylamine, diisopropylamine, cyclohexylamine or dicyclohexylamine; and salts with a basic amino acid, such as lysine or arginine. Also, where the compound of the present invention contains a basic group in its molecule, it can form acid addition salts. Examples of such acid addition salts include: salts with mineral acids, especially hydrohalic acids (such as hydrofluoric acid, hydrobromic acid, hydroiodic acid or hydrochloric acid), nitric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid, benzoic acid, mandelic acid, ascorbic acid, lactic acid, gluconic acid or citric acid; and salts with amino acids, such as glutamic acid or aspartic acid.

A preferred class of compounds of the present invention are those compounds of formula (I), in which:

$Y^1$, $Y^2$ and $Y^4$ each represents a hydrogen atom;

$Y^3$ represents a hydrogen atom, a halogen atom, a nitro group, a hydroxyl group, an amino group, an alkyl group having from 1 to 6 carbon atoms, an alkylthio group having from 1 to 6 carbon atoms, a carboxyl group, a protected carboxyl group or a group of formula $$—(O)_p—B^1—T^1,$$

wherein $T^1$ represents a carboxyl group, a protected carboxyl group or a tetrazolyl group, $B^1$ represents an alkylene group which has from 1 to 3 carbon atoms and which is unsubstituted or is substituted by at least one of substituents α, defined below, and p is 0 or 1;

$R^{1'}$ represents a hydrogen atom, a carboxyl group, a protected carboxyl group, an alkyl group having from 1 to 6 carbon atoms, an aryl group, a substituted aryl group, an aralkyl group, a substituted aralkyl group or a group of formula —$B^2$—COOH, wherein $T^2$ represents a carboxyl group, a protected carboxyl group or a tetrazolyl group, $B^2$ represents an alkylene group which has from 1 to 4 carbon atoms and which is unsubstituted or is substituted by an amino group or a protected amino group;

$R^{2'}$ represents a hydrogen atom, an alkyl group having from 1 to 6 carbon atoms, an aryl group, a substituted aryl group, an aralkyl group or a substituted aralkyl group; or $R^{1'}$ and $R^{2'}$ together represent a group of formula (Id):

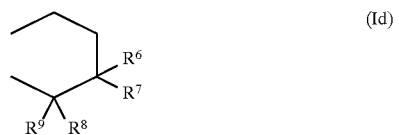

[in which $R^6$ represents a hydrogen atom or a hydroxyl group;

$R^7$ represents a hydrogen atom, a carboxyl group, a protected carboxyl group, or a group of formula —$B^3$—$T^4$ in which $T^4$ represents a carboxyl group, a protected carboxyl group or a tetrazolyl group and $B^3$ represents an alkylene group which has from 1 to 4 carbon atoms and which is unsubstituted or is substituted by at least one of substituents γ;

$R^9$ represents a hydrogen atom or an alkylthio group having from 1 to 6 carbon atoms;

when $R^9$ represents an alkylthio group, $R^7$ and $R^8$ together represent a lactone group; or $R^8$ and $R^9$ together represent an oxo group]; or $R^{1'}$ and $R^{2'}$ together represent a group of formula (Ie):

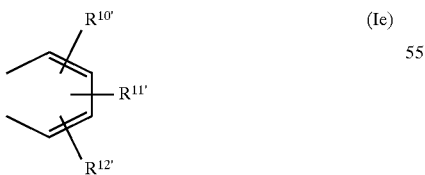

[in which $R^{10'}$ represents a hydroxyalkyl group having from 1 to 6 carbon atoms, a hydroxyl group, a carboxyl group, a protected carboxyl group, or a group of formula —$(O)_p$—$B^4$—$T^5$ in which $T^5$ represents a carboxyl group, a protected carboxyl group or a tetrazolyl group, $B^4$ represents an alkylene group which has from 1 to 4 carbon atoms and which is unsubstituted or is substituted by at least one of substituents γ, and, and p is as defined above]; or $R^{1'}$ and $R^{2'}$ together represent a group of formula (Ic):

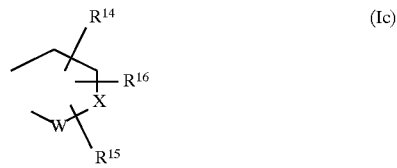

[in which $R^{14}$ represents a hydroxyalkyl group having from 1 to 6 carbon atoms, a hydroxyl group, a carboxyl group, a protected carboxyl group or a group of formula —$(O)_p$—$B^4$—$T^5$ in which $T^5$, $B^4$ and p are as defined above; $R^{15}$ and $R^{16}$ are the same or different, and each represents a hydrogen atom, an alkyl group having from 1 to 6 carbon atoms or an aryl group; and Z is a methylene group, a group of formula >NH or a group of formula >N—];

$R^3$ represents a hydrogen atom or an amino protecting group; and said substituents a are hydroxyl groups, aryl groups and aralkyl groups;

and pharmaceutically acceptable salts and esters thereof.

A further preferred class of compounds of the present invention are those compounds of formula (I) in which:

$R^{1'}$ represents a hydrogen atom;

$R^{2'}$ represents a hydrogen atom; or $R^{1'}$ and $R^{2'}$ together represent a group of formula (If):

$R^3$ represents a hydrogen atom, an aralkyl group, an aralkyl group which is substituted by at least one of substituents ε, defined below, or an aromatic acyl group;

$Y^1$ represents a hydrogen atom, an alkyl group having from 1 to 3 carbon atoms or a group of formula —E'—COOH;

$Y^2$ represents a hydrogen atom, an alkyl group having from 1 to 3 carbon atoms, an alkylthio group having from 1 to 3 carbon atoms or a group of formula —E'—COOH or —E'—Tet, where Tet represents a tetrazolyl group;

$Y^3$ represents a group of formula —E'—COCH or a group —E'—Tet, where Tet is as defined above;

$Y^4$ represents a hydrogen atom, an alkyl group having from 1 to 3 carbon atoms or a halogen atom; and E' represents a direct bond, an alkylene group which has from 1 to 3 carbon atoms and which is unsubstituted or is substituted by at least one of substituents γ, defined below, or an oxyalkylene group which has from 1 to 3 carbon atoms and which is unsubstituted or is substituted by at least one of substituents γ, defined below;

and pharmaceutically acceptable salts and esters thereof.

Particularly preferred classes of compounds of the present invention are those compounds as defined above in which any one or any combination of two or more of the following restrictions also applies:

(1) $R^{1'}$ and $R^{2'}$ together represent a group of formula (If), as shown above.

(2) $R^3$ represents an aralkyl group, an aralkyl group having one or more substituents β or an aromatic acyl group.

(3) $R^3$ represents an aralkyl group or an aralkyl group having one or more of substituents β.

(4) $R^3$ represents a benzyl group or a benzyl group having one or more of substituents β.

(5) $Y^1$ represents a hydrogen atom, a group of formula —E'—COOH, or a group of formula —E'—Tet, where E' and Tet are as defined above.

(6) $Y^1$ represents a hydrogen atom.

(7) $Y^2$ represents a hydrogen atom, an alkylthio group having from 1 to 6, preferably from 1 to 3, carbon atoms, a group of formula —E'—COOH, or a group of formula —E'—Tet, where E' and Tet are as defined above.

(8) $Y^2$ represents an alkylthio group having from 1 to 6, preferably from 1 to 3, carbon atoms.

(9) $Y^4$ represents an alkyl group having from 1 to 6, preferably from 1 to 3, carbon atoms or a halogen atom.

(10) $Y^4$ represents an alkyl group having from 1 to 6, preferably from 1 to 3, carbon atoms.

(11) E' represents a direct bond, an alkylene group having from 1 to 3 carbon atoms, a substituted alkylene group which has from 1 to 3 carbon atoms and is substituted by at least one of substituents α, defined above, an oxyalkylene group having from 1 to 3 carbon atoms or a substituted oxyalkylene group which has from 1 to 3 carbon atoms and is substituted by at least one of substituents α, defined above.

(12) E' represents a direct bond, an alkylene group having from 1 to 3 carbon atoms, a substituted alkylene group which has from 1 to 3 carbon atoms and is substituted by at least one of substituents α, defined above, or an oxyalkylene group having from 1 to 3 carbon atoms.

(13) E' represents a direct bond, an alkylene group having from 1 to 3 carbon atoms, a substituted alkylene group which has from 1 to 3 carbon atoms and is substituted by at least one of substituents α', defined below, an oxyalkylene group having from 1 to 3 carbon atoms or a substituted oxyalkylene group which has from 1 to 3 carbon atoms and is substituted by at least one of substituents α', defined below.

(14) E' represents a direct bond, an alkylene group having from 1 to 3 carbon atoms, a substituted alkylene group which has from 1 to 3 carbon atoms and is substituted by at least one of substituents α', defined below, or an oxyalkylene group having from 1 to 3 carbon atoms.

Substituents α', referred to in (13) and (14) above are aralkyl groups and substituted aralkyl groups which are substituted by at least one of substituents β, defined above.

Examples of specific compounds of the present invention are the indole derivatives indicated by formula (I-1):

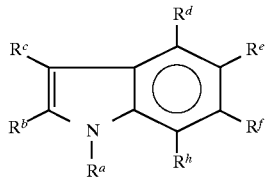

(I-1)

in which all substituent groups are as defined below, those not mentioned being hydrogen:

1-1. $R^a$=CH$_3$; $R^f$=CH$_2$COOH;
1-2. $R^a$=Et; $R^e$=COOH;
1-3. $R^a$=Et; $R^f$=CH$_2$COOH;
1-4. $R^a$=Et; $R^e$=CH$_2$CH$_2$COCH;
1-5. $R^a$=iBu; $R^e$=CH$_2$COOH;
1-6. $R^a$=Bz; $R^d$=CH$_2$COOH;
1-7. $R^a$=Bz; $R^d$=CH$_2$COOH; $R^h$=CH$_3$;
1-8. $R^a$=Bz; $R^d$=CH$_2$CCCH; $R^h$=SCH$_3$;
1-9. $R^a$=Bz; $R^e$=CH$_2$COOH;
1-10. $R^a$=Bz; $R^f$=CH$_2$COOH;
1-11. $R^a$=Bz; $R^f$=CH$_2$COOH; $R^h$=CH$_3$;
1-12. $R^a$=Bz; $R^f$=CH$_2$COOH; $R^h$=SCH$_3$;
1-13. $R^a$=Bz; $R^h$=CH$_2$COOH;
1-14. $R^a$=2-ClBz; $R^e$=CH$_2$COOH; $R^h$=Et;
1-15. $R^a$=4-ClBz; $R^f$=CH$_2$COOH;
1-16. $R^a$=Bz; $R^f$=CH$_2$COOH; $R^h$=Ph;
1-17. $R^a$=3-FBz; $R^f$=CH$_2$COOH;
1-18. $R^a$=4-FBz; $R^f$=CH$_2$COOH; $R^h$=SCH$_3$;
1-19. $R^a$=3-MeOBz; $R^e$=CH$_2$COOH;
1-20. $R^a$=4-MeOBz; $R^e$=CH$_2$COOH; $R^h$=SCH$_3$;
1-21. $R^a$=3,4-diMeOBz; $R^f$=CH$_2$COOH;
1-22. $R^a$=Bz; $R^f$=CH(CH$_3$)COOH;
1-23. $R^a$=Bz; $R^d$=CH(Bz)COOH; $R^h$=SCH$_3$;
1-24. $R^a$=Bz; $R^e$=CH(Bz)COOH;
1-25. $R^a$=Bz; $R^d$=Cl; $R^f$=CH(Bz)COOH;
1-26. $R^a$=Bz; $R^d$=Cl; $R^h$=CH(Bz)COOH;
1-27. $R^a$=Bz; $R^e$=CH(3-ClBz)COOH; $R^h$=SCH$_3$;
1-28. $R^a$=Bz; $R^d$=CH$_3$; $R^f$=CH(4-FBz)COOH;
1-29. $R^a$=Bz; $R^d$=Ph; $R^e$=CH(3-MeOBz)COOH;
1-30. $R^a$=Bz; $R^e$=Cl; $R^f$=CH(3,4-diMeOBz)COOH;
1-31. $R^a$=3-ClBz; $R^e$=CH(3-ClBz)COOH;
1-32. $R^a$=3-ClBz; $R^e$=CH(3-FBz)COOH; $R^h$=SCH$_3$;
1-33. $R^a$=3-ClBz; $R^e$=CH(3,4-diMeOBz)COOH;
1-34. $R^a$=4-ClBz; $R^f$=CH(4-ClBz)COOH; $R^h$=SCH$_3$;
1-35. $R^a$=3-FBz; $R^e$=CH(3-ClBz)COOH;
1-36. $R^a$=3-FBz; $R^f$=CH(4-MeOBz)COOH; $R^h$=CH$_3$;
1-37. $R^a$=4-FBz; $R^f$=CH(4-FBz)COOH; $R^h$=SCH$_3$;
1-38. $R^a$=4-FBz; $R^f$=CH(4-MeOBz)COOH;
1-39. $R^a$=4-MeOBz; $R^d$=CH$_3$; $R^e$=CH(3-ClBz)COOH;
1-40. $R^a$=4-MeOBz; $R^d$=F; $R^e$=CH(3-FBz)COOH;
1-41. $R^a$=4-MeOBz; $R^e$=CH(3-MeOBz)COOH;
1-42. $R^a$=3-ClBz; $R^d$=CH$_3$; $R^f$=CH(Bz)COOH;
1-43. $R^a$=4-ClBz; $R^f$=CH(Bz)COOH;
1-44. $R^a$=2-FBz; $R^d$=CH$_3$; $R^e$=CH(Bz)COOH;
1-45. $R^a$=2-FBz; $R^e$=CH(Bz)COOH;
1-46. $R^a$=3-FBz; $R^f$=CH(Bz)COOH;
1-47. $R^a$=3-FBz; $R^d$=CH$_3$; $R^f$=CH(Bz)COOH;
1-48. $R^a$=4-FBz; $R^e$=CH(Bz)COOH;
1-49. $R^a$=4-MeOBz; $R^f$=CH(Bz)COOH;
1-50. $R^a$=4-MeOBz; $R^f$=CH(Bz)COOH; $R^h$=SCH$_3$;
1-51. $R^a$=3,4-diMeOBz; $R^e$=CH(Bz)COOH;
1-52. $R^a$=3,4-diMeOBz; $R^d$=CH$_3$; $R^e$=CH(Bz)COOH;
1-53. $R^a$=3,4-diMeOBz; $R^f$=CH(Bz)COOH;
1-54. $R^a$=3,4-diMeOBz; $R^d$=CH$_3$; $R^f$=CH(Bz)COOH; $R^h$=SCH$_3$;
1-55. $R^a$=4-NH$_2$Bz; $R^f$=CH(Bz)COOH; $R^h$=SCH$_3$;
1-56. $R^a$=Bz; $R^f$=CH(2-PhEt)COOH; $R^h$=SCH$_3$;
1-57. $R^a$=Bz; $R^f$=CH$_2$CH$_2$COOH;
1-58. $R^a$=2-ClBz; $R^e$=CH$_2$CH$_2$COOH; $R^h$=SCH$_3$;
1-59. $R^a$=3-ClBz; $R^f$=CH$_2$CH$_2$COOH;
1-60. $R^a$=4-ClBz; $R^f$=CH$_2$CH$_2$COOH; $R^e$=CH$_3$;
1-61. $R^a$=2-FBz; $R^f$=CH$_2$CH$_2$COOH;
1-62. $R^a$=4-FBz; $R^e$=CH$_2$CH$_2$COOH; $R^h$=SCH$_3$;
1-63. $R^a$=2-MeOBz; $R^e$=CH$_2$CH$_2$COOH;
1-64. $R^a$=4-MeOBz; $R^d$=CH$_3$; $R^f$=CH$_2$CH$_2$COOH; $R^h$=SCH$_3$;
1-65. $R^a$=3,4-di-MeOBz; $R^e$=CH$_2$CH$_2$COOH; $R^h$=Pr;
1-66. $R^a$=4-NH$_2$Bz; $R^e$=CH$_2$CH$_2$COOH;
1-67. $R^a$=Bz; $R^e$=CH$_2$CH$_2$CH$_2$COOH;
1-68. $R^a$=Bz; $R^b$=CH$_3$; $R^e$=CH$_2$COOH; $R^h$=SCH$_3$;
1-69. $R^a$=Bz; $R^b$=CH$_3$; $R^d$=CH$_3$; $R^e$=CH(3-MeOBz)COOH;

1-70. $R^a$=Bz; $R^b$=CH$_3$; $R^f$=CH(2-PhEt)COOH;
1-71. $R^a$=Bz; $R^b$=Ph; $R^e$=CH$_2$COOH; $R^h$=SCH$_3$;
1-72. $R^a$=Bz; $R^b$=Ph; $R^d$=CH$_3$; $R^e$=CH(3-MeOBz)COOH;
1-73. $R^a$=Bz; $R^b$=Ph; $R^f$=CH(2-PhEt)COOH;
1-74. $R^a$=Bz; $R^c$=Ph; $R^e$=CH$_2$COOH; $R^h$=SCH$_3$;
1-75. $R^a$=Bz; $R^c$=Ph; $R^d$=CH$_3$; $R^e$=CH(3-MeOBz)COOH;
1-76. $R^a$=Bz; $R^c$=Ph; $R^f$=CH(2-PhEt)COOH;
1-77. $R^a$=4-FBz; $R^c$=Bz; $R^f$=CH$_2$COOH; $R^h$=SCH$_3$;
1-78. $R^a$=3-MeOBz; $R^c$=Bz; $R^d$=CH$_3$; $R^e$=CH$_2$COOH;
1-79. $R^a$=4-ClBz; $R^c$=Bz; $R^e$=CH(3-MeOBz)COOH; $R^h$=CH$_3$;
1-80. $R^a$=4-FBz; $R^b$=CH$_3$; $R^c$=Ph; $R^f$=CH$_2$COOH;
1-81. $R^a$=Bz; $R^b$=CH$_3$; $R^c$=Ph; $R^e$=CH(Bz)COOH; $R^h$=SCH$_3$;
1-82. $R^a$=3-ClBz; $R^b$=CH$_3$; $R^c$=Ph; $R^e$=CH(3-FBz)COOH;
1-83. $R^a$=Bz; $R^b$=CH; $R^c$=Ph; $R^e$=CH(2-PhEt)COOH; $R^h$=CH$_3$;
1-84. $R^a$=Bz; $R^b$=CH$_3$; $R^c$=Ph; $R^f$=CH$_2$CH$_2$COOH;
1-85. $R^a$=Bz; $R^b$=CH$_3$; $R^c$=Bz; $R^e$=CH$_2$COOH; $R^h$=SCH$_3$;
1-86. $R^a$=Bz; $R^b$=CH$_3$; $R^c$=Bz; $R^e$=CH(3-MeOBz)COOH;
1-87. $R^a$=3-FBz; $R^b$=CH$_3$; $R^c$=Bz; $R^e$=CH(3-ClBz)COOH;
1-88. $R^a$=4-NH$_2$Bz; $R^b$=CH$_3$; $R^c$=Bz; $R^d$=CH$_3$; $R^f$=CH(Bz)COOH;
1-89. $R^a$=4-FBz; $R^b$=CH$_3$; $R^c$=2-PhEt; $R^d$=CH$_3$; $R^f$=CH$_2$COOH;
1-90. $R^a$=Bz; $R^b$=CH$_3$; $R^c$=2-PhEt; $R^e$=CH(3-MeOBz)COOH; $R^h$=SCH$_3$;
1-91. $R^a$=4-FBz; $R^b$=CH$_3$; $R^c$=2-PhEt; $R^e$=CH(3-MeOBz)COOH;
1-92. $R^a$=4-ClBz; $R^b$=CH$_3$; $R^c$=2-PhEt; $R^f$=CH(Bz)COOH;
1-93. $R^a$=4-ClBz; $R^b$=Ph; $R^c$=2-PhEt; $R^f$=CH$_2$COOH;
1-94. $R^a$=3-ClBz; $R^b$=Ph; $R^c$=2-PhEt; $R^e$=CH(3-FBz)COOH;
1-95. $R^a$=3,4-diMeOBz; $R^b$=Ph; $R^c$=2-PhEt; $R^f$=CH(Bz)COOH; $R^h$=CH$_3$;
1-96. $R^a$=4-ClBz; $R^b$=Ph; $R^c$=Pr; $R^f$=CH$_2$COOH; $R^h$=CH$_3$;
1-97. $R^a$=Bz; $R^b$=Ph; $R^c$=Pr; $R^e$=CH(Bz)COOH; $R^h$=SCH$_3$;
1-98. $R^a$=3-ClBz; $R^b$=Ph; $R^c$=Pr; $R^e$=CH(3-FBz)COOH;
1-99. $R^a$=4-ClBz; $R^b$=Et; $R^c$=Pr; $R^d$=SCH$_3$; $R^f$=CH$_2$COOH;
1-100. $R^a$=Bz; $R^b$=Et; $R^c$=Pr; $R^e$=CH(Bz)COOH; $R^h$=Ph
1-101. $R^a$=3-ClBz; $R^b$=Et; $R^c$=Pr; $R^e$=CH(3-FBz)COOH; $R^h$=SCH$_3$;
1-102. $R^a$=4-FBz; $R^b$=Bz; $R^c$=2-PhEt; $R^f$=CH$_2$COOH; $R^h$=Et;
1-103. $R^a$=Bz; $R^b$=Bz; $R^c$=2-PhEt; $R^e$=CH(3-MeOBz)COOH;
1-104. $R^a$=3-FBz; $R^b$=Bz; $R^c$=2-PhEt; $R^e$=CH(3-ClBz)COOH;
1-105. $R^a$=Bz; $R^b$=4-FBz; $R^c$=2-PhEt; $R^e$=CH$_2$COOH;
1-106. $R^a$=Bz; $R^b$=Bz; $R^c$=2-PhEt; $R^e$=CH(3-MeOBz)COOH; $R^h$=CH$_3$;
1-107. $R^a$=3-FBz; $R^b$=Bz; $R^c$=3-FPhEt; $R^e$=CH(3-ClBz)COOH;
1-108. $R^a$=Bz; $R^b$=4-FBz; $R^c$=Bz; $R^e$=CH$_2$COOH; $R^h$=SCH$_3$;
1-109. $R^a$=Bz; $R^b$=Bz; $R^c$=Bz; $R^e$=CH(3-MeOBz)COOH;
1-110. $R^a$=3-ClBz; $R^b$=3-MeOBz; $R^c$=Bz; $R^e$=CH(3-FBz)COOH;
1-111. $R^a$=4-FBz; $R_f$=CH$_2$COOH; $R^h$=SCH$_3$;
1-112. $R^a$=Bz; $R^d$=CH$_3$; $R^f$=CH(4-FBz)COOH;
1-113. $R^a$=3-ClBz; $R^e$=CH(3-FBz)COOH;
1-114. $R^a$=4-MeOBz; $R^e$=CH(3-ClBz)COOH;
1-115. $R^a$=Bz; $R^f$=CH(2-PhEt)COOH; $R^h$=CH$_3$;
1-116. $R^a$=4-ClBz; $R^f$=CH$_2$CH$_2$COOH; $R^h$=F;
1-117. $R^a$=4-FBz; $R^f$=CH$_2$COOCH$_2$OCOC(CH$_3$)$_3$; $R^h$=SCH$_3$;
1-118. $R^a$=Bz; $R^f$=CH(4-FBz)COOCH$_2$OCOC(CH$_3$)$_3$;
1-119. $R^a$=3-ClBz; $R^d$=CH$_3$; $R^e$=CH(3-FBz)COOCH$_2$OCOC(CH$_3$)$_3$;
1-120. $R^a$=4-MeOBz; $R^e$=CH(3-ClBz)COOCH$_2$OCOC(CH$_3$)$_3$;
1-121. $R^a$=Bz; $R^f$=CH(2-PhEt)COOCH$_2$OCOC(CH$_3$)$_3$; $R^h$=SCH$_3$;
1-122. $R^a$=4-ClBz; $R^f$=CH$_2$CH$_2$COOCH$_2$OCOC(CH$_3$)$_3$;
1-123. $R^a$=3-ClBz; $R^f$=CH$_2$COOCH$_3$; $R^h$=SCH$_3$;
1-124. $R^a$=Bz; $R^f$=CH(4-FBz)COOCH$_3$;
1-125. $R^a$=3-FBz; $R^d$=CH$_3$; $R^f$=CH(4-FBz)COOCH$_3$;
1-126. $R^a$=Bz; $R^f$=CH(2-PhEt)COOCH$_3$;
1-127. $R^a$=3-ClBz; $R^f$=CH$_2$COOEt;
1-128. $R^a$=3-ClBz; $R^f$=CH$_2$COOEt; $R^h$=SCH$_3$;
1-129. $R^a$=3-ClBz; $R^e$=CH(3-FBz)COOEt;
1-130. $R^a$=3-FBz; $R^f$=CH(4-FBz)COOEt;
1-131. $R^a$=Bz; $R^d$=CH$_3$; $R^f$=CH(2-PhEt)COOEt;
1-132. $R^a$=Bz; $R^f$=CH(2-PhEt)COOEt;
1-133. $R^a$=3-ClBz; $R^f$=CH$_2$COOCH$_2$CH$_2$OCOCH$_3$;
1-134. $R^a$=3-ClBz; $R^f$=CH$_2$COOCH$_2$CH$_2$OCOCH$_3$; $R^h$=SCH$_3$;
1-135. $R^a$=3-ClBz; $R^e$=CH(3-FBz)COOCH$_2$CH$_2$OCOCH$_3$;
1-136. $R^a$=4-MeOBz; $R^e$=CH(3-ClBz)COOCH$_2$CH$_2$OCOCH$_3$; $R^h$=CH$_3$;
1-137. $R^a$=3-ClBz; $R^f$=CH$_2$COOCH$_2$CH$_2$N(CH$_3$)$_2$;
1-138. $R^a$=3-ClBz; $R^f$=CH$_2$COOCH$_2$CH$_2$N(CH$_3$)$_2$; $R^h$=SCH$_3$;
1-139. $R^a$=3-ClBz; $R^e$=CH(3-FBz)COOCH$_2$CH$_2$N(CH$_3$)$_2$;
1-140. $R^a$=4-MeOBz; $R^e$=CH(3-ClBz)COOCH$_2$CH$_2$N(CH$_3$)$_2$;
1-141. $R^a$=3-ClBz; $R^f$=CH$_2$CONHCH$_3$;
1-142. $R^a$=Bz; $R^f$=CH(4-FBz)CONHCH$_3$;
1-143. $R^a$=Bz; $R^f$=CH(4-FBz)CONHCH$_3$; $R^h$=SCH$_3$;
1-144. $R^a$=3-FBz; $R^f$=CH(4-FBz)CONHCH$_3$;
1-145. $R^a$=Bz; $R^f$=CH(2-PhEt)CONHCH$_3$;
1-146. $R^a$=3-ClBz; $R^f$=CH$_2$CONHCH$_2$CH$_2$OH;
1-147. $R^a$=Bz; $R^f$=CH(4-FBz)CONHCH$_2$CH$_2$OH;
1-148. $R^a$=Bz; $R^f$=CH(4-FBz)CONHCH$_2$CH$_2$OH; $R^h$=CH$_3$;
1-149. $R^a$=4-MeOBz; $R^e$=CH(3-ClBz)CONHCH$_2$CH$_2$OH;
1-150. $R^a$=4-ClBz; $R^f$=CH$_2$CH$_2$CONHCH$_2$CH$_2$OH;
1-151. $R^a$=3-ClBz; $R^f$=CH$_2$CONHCH$_2$CH$_2$N(CH$_3$)$_2$;
1-152. $R^a$=3-ClBz; $R^f$=CH$_2$CONHCH$_2$CH$_2$N(CH$_3$)$_2$; $R^h$=CH$_3$;
1-153. $R^a$=Bz; $R^f$=CH(4-FBz)CONHCH$_2$CH$_2$N(CH$_3$)$_2$;
1-154. $R^a$=4-MeOBz; $R^e$=CH(3-ClBz)CONHCH$_2$CH$_2$N(CH$_3$)$_2$;
1-155. $R^a$=4-ClBz; $R^f$=CH$_2$CH$_2$CONHCH$_2$CH$_2$N(CH$_3$)$_2$;
1-156. $R^a$=Bz; $R^b$=CH$_3$; $R^f$=OCH$_2$COOH; $R^h$=SCH$_3$;

1-157. $R^a$=3-FBz; $R^b$=CH$_3$; $R^d$=CH$_3$; $R^f$=OCH$_2$COOH;
1-158. $R^a$=3,4-diMeOBz; $R^b$=CH$_3$; $R^f$=OCH$_2$COOH;
1-159. $R^a$=Bz; $R^b$=CH$_3$; $R^f$=OCH(4-FBz)COOH; $R^h$=SCH$_3$;
1-160. $R^a$=3-ClBz; $R^b$=CH$_3$; $R^e$=OCH(3,4-diMeOBz)COOH;
1-161. $R^a$=4-MeOBz; $R^b$=CH$_3$; $R^e$=OCH(3-ClBz)COOH;
1-162. $R^a$=2-FBz; $R^b$=CH$_3$; $R^e$=OCH(Bz)COOH; $R^h$=CH$_3$;
1-163. $R^a$=2-FBz; $R^b$=CH$_3$; $R^e$=OCH(Bz)COOCH$_2$OCOC(CH$_3$)$_3$; $R^h$=CH$_3$;
1-164. $R^a$=Bz; $R^b$=CH$_3$; $R^f$=OCH(4-FBz)COOCH$_2$CH$_2$N(CH$_3$)$_2$; $R^h$=SCH$_3$;
1-165. $R^a$=Bz; $R^b$=CH$_3$; $R^f$=OCH$_2$CH$_2$COOH; $R^h$=SCH$_3$;
1-166. $R^a$=3-FBz; $R^b$=CH$_3$; $R^d$=CH$_3$; $R^f$=OCH$_2$CH$_2$COOH;
1-167. $R^a$=3,4-diMeOBz; $R^b$=CH$_3$; $R^f$=OCH$_2$CH$_2$COOH;
1-168. $R^a$=Bz; $R^b$=CH$_3$; $R^f$=OCH$_2$CH(4-FBz)COOH; $R^h$=SCH$_3$;
1-169. $R^a$=3-ClBz; $R^b$=CH$_3$; $R^e$=OCH$_2$CH(3,4-diMeOBz)COOH;
1-170. $R^a$=4-MeOBz; $R^b$=CH$_3$; $R^e$=OCH$_2$CH(3-ClBz)COOH;
1-171. $R^a$=2-FBz; $R^b$=CH$_3$; $R^e$=OCH$_2$CH(Bz)COOCH$_2$OCOC(CH$_3$)$_3$; $R^h$=CH$_3$;
1-172. $R^a$=2-FBz; $R^b$=CH$_3$; $R^e$=OCH$_2$CH(Bz)COOCH$_2$CH$_2$N(CH$_3$)$_2$; $R^h$=SCH$_3$;
1-173. $R^a$=COPh; $R^f$=CH(Bz)COOH; $R^h$=SCH$_3$;
1-174. $R^a$=COPh; $R^f$=CH$_2$COOH;
1-175. $R^a$=CO(2-Cl—Ph); $R^e$=CH(3-MeOBz)COOH; $R^h$=SCH$_3$;
1-176. $R^a$=CO(3-Cl—Ph); $R^f$=CH$_2$COOH;
1-177. $R^a$=CO(4-Cl—Ph); $R^f$=CH$_2$COOH; $R^e$=CH$_3$;
1-178. $R^a$=CO(2-F—Ph); $R^f$=CH(3-F—Ph)COOH;
1-179. $R^a$=CO(4-F—Ph); $R^e$=CH$_2$COOH; $R^h$=SCH$_3$;
1-180. $R^a$=CO(2-MeO—Ph); $R^e$=CH(4-FBz)COOH;
1-181. $R^a$=CO(4-MeO—Ph); $R^d$=CH$_3$; $R^f$=CH$_2$COOH; $R^h$=SCH$_3$;
1-182. $R^a$=CO(3,4-MeO—Ph); $R^e$=CH(3-ClBz)COOH; $R^h$=Pr;
1-183. $R^a$=CO(4-NH2-Ph); $R^e$=CH$_2$COOH;
1-184. $R^a$=CO(4-F—Ph); $R^e$=CH$_2$COOCH$_2$CH$_2$N(CH$_3$)$_2$; $R^h$=SCH$_3$;
1-185. $R^a$=CO(4-F—Ph); $R^e$=CH(Bz)COOCH$_2$CH$_2$N(CH$_3$)$_2$; $R^h$=SCH$_3$;
1-186. $R^a$=CO(2-MeO—Ph); $R^e$=CH(Bz)COOCH$_2$OCOC(CH$_3$)$_3$;
1-187. $R^a$=COCH$_3$; $R^f$=CH(Bz)COOH; $R^h$=SCH$_3$;
1-188. $R^a$=COCH$_3$; $R^f$=CH$_2$COOH;
1-189. $R^a$=COCH(CH$_3$)$_2$; $R^e$=CH$_2$COOH;
1-190. $R^a$=COCH(CH$_3$)$_2$; $R^f$=CH(Bz)COOH; $R^h$=SCH$_3$;
1-191. $R^a$=COCH(CH$_3$)$_2$; $R^e$=CH(Bz)COOCH$_2$CH$_2$N(CH$_3$)$_2$; $R^h$=SCH$_3$;
1-192. $R^a$=COCH(CH$_3$)$_2$; $R^e$=CH(Bz)COOCH$_2$OCOC(CH$_3$)$_3$;
1-193. $R^a$=COCHEt; $R^e$=CH$_2$COOH;
1-194. $R^a$=COCHEt; $R^e$=CH(Bz)COOH;
1-195. $R^a$=COCHCH$_2$(CH$_3$)$_2$; $R^e$=CH$_2$COOH;
1-196. $R^a$=COCHCH$_2$(CH$_3$)$_2$; $R^f$=CH(Bz)COOH; $R^h$=SCH$_3$;
1-197. $R^a$=COCHCH$_2$(CH$_3$)$_2$; $R^e$=CH$_2$COOCH$_2$CH$_2$N(CH$_3$)$_2$; $R^h$=SCH$_3$;
1-198. $R^a$=COCHCH$_2$(CH$_3$)$_2$; $R^e$=CH(Bz)COOCH$_2$CH$_2$N(CH$_3$)$_2$; $R^h$=SCH$_3$;
1-199. $R^a$=COCHCH$_2$(CH$_3$)$_2$; $R^e$=CH(Bz)COOCH$_2$OCOC(CH$_3$)$_3$;
1-200. $R^a$=COCHCH$_2$(CH$_3$)$_2$; $R^e$=CH(Bz)COOCH$_2$OCOC(CH$_3$)$_3$; $R^h$=SCH$_3$;
1-201. $R^a$=Bz; $R^e$=CH$_2$Tet;
1-202. $R^a$=Bz; $R^f$=CH$_2$Tet;
1-203. $R^a$=Bz; $R^f$=CH$_2$CH$_2$Tet;
1-204. $R^a$=4-FBz; $R^f$=CH$_2$CH$_2$CH$_2$Tet;
1-205. $R^a$=Bz; $R^e$=CH$_2$CH$_2$Tet;
1-206. $R^a$=Bz; $R^d$=Tet;
1-207. $R^a$=(3-MeO)PhCH$_2$; $R^h$=Tet;
1-208. $R^a$=Bz; $R^d$=CH$_2$Tet;
1-209. $R^a$=Bz; $R^h$=CH$_2$Tet;
1-210. $R^a$=(4-F)PhCH$_2$; $R^d$=SO$_2$NHCOCH$_3$;
1-211. $R^a$=Bz; $R^e$=SO$_2$NHCOCH$_3$;
1-212. $R^a$=Bz; $R^f$=SO$_2$NHCOCH$_3$;
1-213. $R^a$=(4-NO$_2$)PhCH$_2$; $R^h$=SO$_2$NHCOCH$_3$;
1-214. $R^a$=Bz; $R^d$=SO$_2$NHCOCH$_2$CH$_3$;
1-215. $R^a$=Bz; $R^e$=SO$_2$NHCOCH$_2$CH$_3$;
1-216. $R^a$=Bz; $R^f$=SO$_2$NHCOCH$_2$CH$_3$;
1-217. $R^a$=Bz; $R^h$=SO$_2$NHCOCH$_2$CH$_3$;
1-218. $R^a$=Bz; $R^d$=SO$_2$NHCOCH$_2$Ph;
1-219. $R^a$=(4-Cl)PhCH$_2$; $R^e$=SO$_2$NHCOCH$_2$Ph;
1-220. $R^a$=Bz; $R^f$=SO$_2$NHCOCH$_2$Ph;
1-221. $R^a$=Bz; $R^h$=SO$_2$NHCOCH$_2$Ph;
1-222. $R^a$=Bz; $R^d$=CH$_2$SO$_2$NHCOCH$_3$;
1-223. $R^a$=Bz; $R^e$=CH$_2$SO$_2$NHCOCH$_3$;
1-224. $R^a$=4-(CF$_3$)PhCH$_2$; $R^f$=CH$_2$SO$_2$NHCOCH$_3$;
1-225. $R^a$=Bz; $R^h$=CH$_2$SO$_2$NHCOCH$_3$;
1-226. $R^a$=Bz; $R^d$=CH$_2$SO$_2$NHCOCH$_2$CH$_3$;
1-227. $R^a$=Bz; $R^e$=CH$_2$SO$_2$NHCOCH$_2$CH$_3$;
1-228. $R^a$=Bz; $R^f$=CH$_2$SO$_2$NHCOCH$_2$CH$_3$;
1-229. $R^a$=(4-MeO)PhCH$_2$; $R^h$=CH$_2$SO$_2$NHCOCH$_2$CH$_3$;
1-230. $R^a$=Bz; $R^d$=CH$_2$SO$_2$NHCOCH$_2$Ph;
1-231. $R^a$=Bz; $R^e$=CH$_2$SO$_2$NHCOCH$_2$Ph;
1-232. $R^a$=Bz; $R^f$=CH$_2$SO$_2$NHCOCH$_2$Ph;
1-233. $R^a$=Bz; $R^h$=CH$_2$SO$_2$NHCOCH$_2$Ph;
1-234. $R^a$=Bz; $R^d$=Tet;
1-235. $R^a$=4-(MeO$_2$C)Bz;
1-236. $R^a$=4-(HOOC)Bz;
1-237. $R^a$=4-Tet—Bz;
1-238. $R^a$=4-Ph—Bz; $R^d$=CN;
1-239. $R^a$=4-Ph—Bz; $R^d$=CH$_2$COOH;
1-240. $R^a$=Bz; $R^b$=Me; $R^e$=Me; $R^f$=CH$_2$COOH;
1-241. $R^a$=Bz; $R^b$=Me; $R^e$=Me; $R^f$=CH$_2$Tet.

Of these, the preferred compounds are Nos. 1-12, 1-23, 1-33, 1-34, 1-37, 1-51, 1-54, 1-68, 1-71, 1-74, 1-77, 1-81, 1-93, 1-99, 1-111, 1-117, 1-123, 1-134, 1-138, 1-148, 1-159, 1-168, 1-173, 1-197, 1-202, 1-208, 1-212, 1-219, 1-223, 1-239 and 1-241 and the most preferred are Nos. 1-12, 1-34, 1-37, 1-77, 1-93, 1-202, 1-208, 1-219 and 1-239.

Further examples of specific compounds of the present invention are the tetrahydrocarbazole derivatives indicated by formula (I-2):

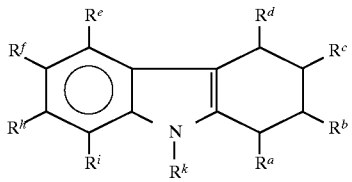

(I-2)

in which all substituent groups are as defined below, those not mentioned being hydrogen:

2-1. $R^b$=CH$_2$COOH; $R^k$=CH$_3$;
2-2. $R^c$=COOH; $R^k$=Et;
2-3. $R^b$=CH$_2$COOH; $R^k$=Et;
2-4. $R^c$=CH$_2$CH$_2$COOH; $R^k$=Et;
2-5. $R^c$=CH$_2$COOH; $R^k$=iBu;
2-6. $R^a$=CH$_2$COOH; $R^k$=Bz;
2-7. $R^b$=CH$_2$COOH; $R^k$=Bz;
2-8. $R^c$=CH$_2$COOH; $R^k$=Bz;
2-9. $R^d$=CH$_2$COOH; $R^k$=Bz;
2-10. $R^a$=SCH$_3$; $R^b$=CH$_2$COOH; $R^k$=Bz;
2-11. $R^c$=CH$_2$COOH; $R^k$=Bz;
2-12. $R^a$=SCH$_3$; $R^b$=CH$_2$COOH; $R^k$=Bz;
2-13. $R^a$=SCH$_3$; $R^c$=CH$_2$COOH; $R^k$=Bz;
2-14. $R^a$=SCH$_3$; $R^b$=CH$_2$COOH; $R^d$=SCH$_3$; $R^k$=Bz;
2-15. $R^a$=Et; $R^c$=CH$_2$COOH; $R^k$=2-ClBz;
2-16. $R^b$=CH$_2$COOH; $R^k$=4-ClBz;
2-17. $R^a$=Ph; $R^b$=CH$_2$COOH; $R^k$=Bz;
2-18. $R^b$=CH$_2$COOH; $R^k$=-FBz;
2-19. $R^a$=SCH$_3$; $R^b$=CH$_2$COOH; $R^k$=4-FBz;
2-20. $R^c$=CH$_2$COOH; $R^k$=3-MeOBz;
2-21. $R^a$=SCH$_3$; $R^c$=CH$_2$COOH; $R^k$=4-MeOBz;
2-22. $R^b$=CH$_2$COOH; $R^k$=3,4-diMeOBz;
2-23. $R^b$=C(CH$_3$)COOH; $R^k$=Bz;
2-24. $R^a$=SCH$_3$; $R^d$=CH(Bz)COOH; $R^k$=Bz;
2-25. $R^c$=CH(Bz)COOH; $R^k$=Bz;
2-26. $R^b$=CH(Bz)COOH; $R^e$=Cl $R^k$=Bz;
2-27. $R^b$=CH(Bz)COOH; $R^h$=Cl $R^k$=Bz;
2-28. $R^a$=SCH$_3$; $R^c$=CH(3-ClBz)COOH; $R^k$=Bz;
2-29. $R^b$=CH(4-FBz)COOH; $R^d$=CH$_3$; $R^e$=OH; $R^k$=Bz;
2-30. $R^c$=CH(3-MeOBz)COOH; $R^d$=Ph; $R^e$=OCH$_3$; $R^k$=Bz;
2-31. $R^b$=CH(3,4-diMeOBz)COOH; $R^e$=Cl; $R^k$=Bz;
2-32. $R^c$=CH(3-ClBz)COOH; $R^f$=F $R^k$=3-ClBz;
2-33. $R^a$=SCH$_3$; $R^c$=CH(3-FBz)COOH; $R^k$=3-ClBz;
2-34. $R^c$=CH(3,4-diMeOBz)COOH; $R^k$=3-ClBz;
2-35. $R^a$=SCH$_3$; $R^b$=CH(4-ClBz)COOH; $R^k$=4-ClBz;
2-36. $R^c$=CH(3-ClBz)COOH; $R^k$=3-FBz;
2-37. $R^a$=CH$_3$; $R^b$=CH(4-MeOBz)COOH; $R^k$=3-FBz;
2-38. $R^a$=SCH$_3$; $R^b$=CH(4-FBz)COOH; $R^d$=CH$_3$; $R^k$=4-FBz;
2-39. $R^b$=CH(4-MeOBz)COOH; $R^k$=4-FBz;
2-40. $R^c$=CH(3-ClBz)COOH; $R^d$=CH$_3$; $R^k$=4-MeOBz;
2-41. $R^c$=CH(3 FBz)COOH; $R^e$OH; $R^k$=4-MeOBz;
2-42. $R^c$=CH(3-MeOBz)COOH; $R^f$=OH; $R^k$=4-MeOBz;
2-43. $R^b$=CH(Bz)COOH; $R^d$=CH$_3$; $R^k$=3-ClBz;
2-44. $R^b$=CH(Bz)COOH; $R^k$=4-ClBz;
2-45. $R^c$=CH(Bz)COOH; $R^d$=CH$_3$; $R^k$=2-FBz;
2-46. $R^c$=CH(Bz)COOH; $R^k$=2-FBz;
2-47. $R^b$=CH(Bz)COOH; $R^f$=Cl; $R^k$=3-FBz;
2-48. $R^b$=CH(Bz)COOH; $R^d$=CH$_3$; $R^k$=3-FBz;
2-49. $R^c$=CH(Bz)COOH; $R^k$=4-FBz;
2-50. $R^b$=CH(Bz)COOH; $R^e$=F; $R^k$=4-MeOBz;
2-51. $R^a$=SCH$_3$; $R^b$=CH(Bz)COOH; $R^k$=4-MeOBz;
2-52. $R^c$=CH(Bz)COOH; $R^k$=3,4-diMeOBz;
2-53. $R^c$=CH(Bz)COOH; $R^d$=CH$_3$; $R^k$=3,4-di-MeOBz;
2-54. $R^b$=CH(Bz)COOH; $R^k$=3,4-diMeOBz;
2-55. $R^a$=SCH$_3$; $R^b$=CH(Bz)COOH; $R^d$=CH$_3$; $R^k$=3,4-diMeOBz;
2-56. $R^a$=SCH$_3$; $R^b$=CH(Bz)COOH; $R^k$=4-NH$_2$Bz;
2-57. $R^a$=SCH$_3$; $R^b$=CH(2-PhEt)COOH; $R^k$=Bz;
2-58. $R^b$=CH$_2$CH$_2$COOH; $R^f$=OH; $R^k$=Bz;
2-59. $R^a$=SCH$_3$; $R^c$=CH$_2$CH$_2$COOH; $R^k$=2-ClBz;
2-60. $R^b$=CH$_2$CH$_2$COOH; $R^k$=3-ClBz;
2-61. $R^c$=CH$_3$; $R^b$=CH$_2$CH$_2$COOH; $R^f$=F; $R^k$=4-ClBz;
2-62. $R^b$=CH$_2$CH$_2$COOH; $R^k$=2-FBz;
2-63. $R^a$=SH$_3$; $R^c$=CH$_2$CH$_2$COOH; $R^k$=4-FBz;
2-64. $R^c$=CH$_2$CH$_2$COOH; $R^k$=2-MeOBz;
2-65. $R^a$=SCH$_3$; $R^b$=CH$_2$CH$_2$COOH; $R^d$=CH$_3$; $R^k$=4-MeOBz;
2-66. $R^a$=Pr; $R^c$=CH$_2$CH$_2$COOH; $R^k$=3,4-diMeOBz;
2-67. $R^c$=CH$_2$CH$_2$COOH; $R^e$=OCH$^3$; $R^k$=4-NH$_2$Bz;
2-68. $R^a$=SCH$_3$; $R^b$=CH$_2$COOH; $R^e$=CH$_3$; $R^k$=Bz;
2-69. $R^b$=CH$_2$COOH; $R^d$=CH$_3$; $R^f$=CH$_3$; $R^k$=3-FBz;
2-70. $R^a$=CH$_3$; $R^b$=CH$_2$COOH; $R^k$=3,4-diMeOBz;
2-71. $R^a$=SCH$_3$; $R^b$=CH(4-FBz)COOH; $R^d$=CH$^3$; $R^k$=Bz;
2-72. $R^c$=CH(3,4-diMeOBz)COOH; $R^d$=CH$_3$; $R^k$=3-ClBz;
2-73. $R^c$=CH(3-ClBz)COOH; $R^e$=OH; $R^k$=4-MeOBz;
2-74. $R^a$=CH$_3$; $R^c$=CH(Bz)COOH; $R^f$=F; $R^k$=2-FBz;
2-75. $R^a$=SCH$_3$; $R^c$=CH$_2$COOH; $R^f$=Ph; $R^k$=Bz;
2-76. $R^a$=CH$_3$; $R^c$=CH(3-MeOBz)COOH; $R^k$=Bz;
2-77. $R^b$=CH(2-PhEt)COOH; $R^d$=Ph; $R^k$=Bz;
2-78. $R^a$=SCH$_3$; $R^b$=CH$_2$COOH; $R^f$=Bz; $R^k$=4-FBz;
2-79. $R^c$=CH$_2$COOH; $R^d$=CH$_3$; $R^h$=CH$_3$; $R^k$=3-MeOBz;
2-80. $R^a$=CH$_3$; $R^c$=CH(3-MeOBz)COOH; $R^h$=Bz; $R^k$=4-ClBz;
2-81. $R^b$=CH$_2$COOH; $R^d$=CH$_3$; R8=CH$_3$; $R^k$=4-FBz;
2-82. $R^a$=SCH$_3$; $R^c$=CH(Bz)COOH; $R^e$=OCH$_3$; $R^k$=Bz;
2-83. $R^a$=CH$_3$; $R^c$=CH(3-FBz)COOH; $R^k$=3-ClBz;
2-84. $R^a$=CH$_3$; $R^b$=CH$_3$; $R^c$=CH(2-PhEt)COOH; $R^f$=F; $R^k$=Bz;
2-85. $R^a$=CH$_3$; $R^b$=CH$_2$CH$_2$COOH; $R^h$=OH; $R^k$=Bz;
2-86. $R^a$=SCH$_3$; $R^b$=CH$_3$; $R^c$=CH$_2$COOH; $R^e$=OH; $R^k$=Bz;
2-87. $R^a$=CH$_3$; $R^c$=CH(3-MeOBz)COOH; $R^k$=Bz;
2-88. $R^a$=CH$_3$; $R^c$=CH(3-ClBz)COOH; $R^h$=CH$_3$; $R^k$=3-FBz;
2-89. $R^b$=CH(Bz)COOH; $R^d$=CH$_3$; $R^f$=CH$_3$; $R^k$=4-NH$_2$Bz;
2-90. $R^a$=SCH$_3$; $R^b$=4-FBz; $R^c$=CH$_2$COOH; $R^k$=Bz;
2-91. $R^a$=CH$_3$; $R^b$=CH(2-PhEt)COOH; $R^f$=OH; $R^k$=Bz;
2-92. $R^a$=F; $R^b$=CH$_2$CH$_2$COOH; $R^e$=OH; $R^k$=4-ClBz;
2-93. $R^c$=CH(3-ClBz)COOCH$_2$OCOC(CH$_3$)$_3$; $R^k$=4-MeOBz;
2-94. $R^a$=SCH$_3$; $R^b$=CH(2-PhEt)COOCH$_2$OCOC(CH$_3$)$_3$; $R^k$=Bz;
2-95. $R^b$=CH(4-FBz)COOCH$_3$; $R^d$=CH$_3$; $R^k$=3-FBz;
2-96. $R^a$=SCH$_3$; $R^b$=CH$_2$COOEt; $R^k$=3-ClBz;
2-97. $R^b$=CH(2-PhEt)COOEt; $R^k$=Bz;
2-98. $R^a$=SCH$_3$; $R^b$=CH$_2$COOCH$_2$CH$_2$OCOCH$_3$; $R^k$=3-ClBz;
2-99. $R^a$=SCH$_3$; $R^b$=CH$_2$COOCH$_2$CH$_2$N(CH$_3$)$_2$; $R^k$=3-ClBz;
2-100. $R^c$=CH(3-ClBz)COOCH$_2$CH$_2$N(CH$_3$)$_2$; $R^k$=4-MeOBz;
2-101. $R^b$=CH(4-FBz)CONHCH$_3$; $R^k$=Bz;
2-102. $R^a$=CH$_3$; $R^b$=CH(4-FBz)CONHCH$_2$CH$_2$OH; $R^k$=Bz;
2-103. $R^b$=CH$_2$CONHCH$_2$CH$_2$N(CH$_3$)$_2$; $R^k$=3-ClBz;
2-104. $R^a$=SCH$_3$; $R^b$=OCH$_2$COOH; $R^e$=CH$_3$; $R^k$=Bz;
2-105. $R^b$=OCH$_2$COOH $R^d$=CH$_3$; $R^f$=CH$_3$; $R^k$=3-FBz;

2-106. $R^a$=SCH$_3$; $R^b$=OCH(4-FBz)COOCH$_2$CH$_2$N(CH$_3$)$_2$; $R^d$=CH$_3$; $R^k$=Bz
2-107. $R^b$=OCH$_2$CH$_2$COOH; $R^d$=CH$_3$; $R^f$=CH$_3$; $R^k$=3-FBz;
2-108. $R^a$=CH$_3$; $R^b$=OCH$_2$CH$_2$COOH; $R^k$=3,4-diMeOBz;
2-109. $R^b$=CH$_2$COOH; $R^k$=CO(4-Cl—Ph);
2-110. $R^c$=CH(4-MeOBz)COOH; $R^k$=CO(2-F—Ph);
2-111. $R^b$=CH(Ph)COOH; $R^d$=CH$_3$; $R^k$=COCH$_3$;
2-112. $R^b$=CH(CH$_2$COOH; $R^d$=CH$_3$; $R^k$=COEt;
2-113. $R^a$=SCH$_3$; $R^b$=CH$_2$COOH; $R^k$=COEt;
2-114. $R^b$=CH$_2$COOH; $R^d$=CH$_3$; $R^k$=CH$_2$(thiophen-2-yl);
2-115. $R^b$=CH$_2$COOH; $R^k$=CH$_2$(thiophen-2-yl);
2-116. $R^b$=CH$_2$COOH; $R^d$=CH$_3$; $R^k$=CH$_2$(pyridin-3-yl);
2-117. $R^a$=COOH; $R^k$=Bz;
2-118. $R^b$=COOH; $R^k$=Bz;
2-119. $R^c$=COOH; $R^k$=Bz;
2-120. $R^d$=COOH; $R^k$=Bz;
2-121. $R^a$=CH$_3$; $R^b$=COOH; $R^k$=Bz;
2-122. $R^a$=CH$_3$; $R^c$=COOH; $R^k$=Bz;
2-123. $R^a$=CH$_3$; $R^d$=COOH; $R^k$=Bz;
2-124. $R^b$=CH$_2$Tet; $R^k$=Bz;
2-125. $R^a$=SCH$_3$; $R^b$=CH$_2$Tet; $R^k$=Bz;
2-126. $R^a$=SCH$_3$; $R^b$=CH$_2$CH$_2$Tet; $R^k$=4-FBz;
2-127. $R^a$=SCH$_3$; $R^b$=CH$_2$CH$_2$CH$_2$Tet; $R^k$=4-FBz;
2-128. $R^a$=CH$_3$; $R^b$=CH$_2$Tet; $R^k$=Bz;
2-129. $R^c$=CH$_2$COOH; $R^d$=O; $R^k$=Bz;
2-130. $R^c$=CH$_2$COOH; $R^d$=O;
2-131. $R^b$=CH$_2$COOH; $R^k$=Bz;
2-132. $R^b$=CH(COOH)$_2$; $R^k$=Bz.

Of these, the preferred compounds are Nos. 2-10, 2-13, 2-14, 2-19, 2-32, 2-36, 2-46, 2-57, 2-68, 2-80, 2-94, 2-100, 2-122, 2-125, 2-126 and 2-128, and the most preferred are Nos. 2-10, 2-94, 2-122.

Further examples of specific compounds of the present invention are the carbazole derivatives indicated by formula (I-3):

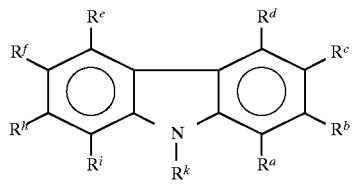

in which all substituent groups are as defined below, those not mentioned being hydrogen:

3-1. $R^b$=CH$_2$COOH; $R^k$=CH$_3$;
3-2. $R^c$=COOH; $R^k$=Et;
3-3. $R^b$=CH$_2$H COOH; $R^k$=Et;
3-4. $R^c$=CH$_2$CH$_2$COOH; $R^k$=Et;
3-5. $R^c$=CH$_2$COOH; $R^k$=iBu;
3-6. $R^a$=CH$_2$COOH; $R^k$=Bz;
3-7. $R^b$=CH$_2$COOH; $R^k$=Bz;
3-8. $R^c$=CH$_2$COOH; $R^k$=Bz;
3-9. $R^d$=CH$_2$COOH; $R^k$=Bz;
3-10. $R^a$=SCH$_3$; $R^b$=CH$_2$COOH; $R^k$=Bz;
3-11. $R^c$=CH$_2$COOH; $R^k$=Bz;
3-12. $R^a$=SCH$_3$; $R^b$=CH$_2$COOH; $R^k$=Bz;
3-13. $R^a$=SCH$_3$; $R^c$=CH$_2$COOH; $R^k$=Bz;
3-14. $R^a$=SCH$_3$; $R^b$=CH$_2$COOH; $R^d$=SCH$_3$; $R^k$=Bz;
3-15. $R^a$=Et; $R^c$=CH$_2$COOH; $R^k$=3-ClBz;
3-16. $R^b$=CH$_2$COOH; $R^k$=4-ClBz;
3-17. $R^a$=Ph; $R^b$=CH$_2$COOH; $R^k$=Bz;
3-18. $R^b$=CH$_2$H COOH; $R^k$=3-FBz;
3-19. $R^a$=SCH$_3$; $R^b$=COOH; $R^k$=4-FBz;
3-20. $R^c$=CH$_2$COOH; $R^k$=3-MeOBz;
3-21. $R^a$=SCH$_3$; $R^c$=CH$_2$COOH; $R^k$=4-MeOBz;
3-22. $R^b$=CH$_2$COOH; $R^k$=3,4-diMeOBz;
3-23. $R^b$=CH(CH$_3$)COOH; $R^k$=Bz;
3-24. $R^a$=SCH$_3$; $R^d$=CH(Bz)COOH; $R^k$=Bz;
3-25. $R^c$=CH(Bz)COOH; $R^k$=Bz;
3-26. $R^b$=CH(Bz)COOH; $R^e$=Cl $R^k$=Bz;
3-27. $R^a$=CH(Bz)COOH; $R^h$=Cl $R^k$=Bz;
3-28. $R^a$=SCH$_3$; $R^c$=CH(3-ClBz)COOH; $R^k$=Bz;
3-29. $R^b$=CH(4-FBz)COOH; $R^d$=CH$_3$; $R^e$=OH; $R^k$=Bz;
3-30. $R^c$=CH(3-MeOBz)COOH; $R^d$=Ph; $R^e$=OCH$_3$; $R^k$=Bz;
3-31. $R^b$=CH(3,4-diMeOBz)COOH; $R^e$=Cl; $R^k$=Bz;
3-32. $R^c$=CH(3-ClBz)COOH; $R^f$=F $R^k$=3-ClBz;
3-33. $R^a$=SCH$_3$; $R^c$=CH(3-FBz)COOH; $R^k$=3-ClBz;
3-34. $R^c$=CH(3,4-diMeOBz)COOH; $R^k$=3-ClBz;
3-35. $R^a$=SCH$_3$; $R^b$=CH(4-ClBz)COOH; $R^k$=4-ClBz;
3-36. $R^c$=CH(3-ClBz)COOH; $R^k$=3-FBz;
3-37. $R^a$=CH$_3$; $R^b$=CH(4-MeOBz)COOH; $R^k$=3-FBz;
3-38. $R^a$=SCH$_3$; $R^b$=CH(4-FBz)COOH; $R^d$=CH$_3$; $R^k$=4-FBz;
3-39. $R^b$=CH(4-MeOBz)COOH; $R^k$=4-FBz;
3-40. $R^c$=CH(3-ClBz)COOH; $R^d$=CH$_3$; $R^k$=4-MeOBz;
3-41. $R^c$=CH(3-FBz)COOH; $R^e$=OH; $R^k$=4-MeOBz;
3-42. $R^c$=CH(3-MeOBz)COOH; $R^f$=OH; $R^k$=4-MeOBz;
3-43. $R^b$=CH(Bz)COOH; $R^d$=CH$_3$; $R^k$=3-ClBz;
3-44. $R^b$=CH(Bz)COOH; $R^k$=4-ClBz;
3-45. $R^c$=CH(Bz)COOH; $R^d$=CH$_3$; $R^k$=3-FBz;
3-46. $R^c$=CH(Bz)COOH; $R^k$=3-FBz;
3-47. $R^b$=CH(Bz)COOH; $R^f$=Cl; $R^k$=3-FBz;
3-48. $R^b$=CH(Bz)COOH; $R^d$=CH$_3$; $R^k$=3-FBz;
3-49. $R^c$=CH(Bz)COOH; $R^k$=4-FBz;
3-50. $R^b$=CH(Bz)COOH; $R^e$=F; $R^k$=4-MeOBz;
3-51. $R^a$=SCH$_3$; $R^b$=CH(Bz)COOH; $R^k$=4-MeOBz;
3-52. $R^c$=CH(Bz)COOH; $R^k$=3,4-diMeOBz;
3-53. $R^c$=CH(Bz)COOH; $R^d$=CH$_3$; $R^k$=3,4-diMeOBz;
3-54. $R^b$=CH(Bz)COOH; $R^k$=3,4-diMeOBz;
3-55. $R^a$=SCH$_3$; $R^b$=CH(Bz)COOH; $R^d$=CH$_3$; $R^k$=3,4-diMeOBz;
3-56. $R^a$=SCH$_3$; $R^b$=CH(Bz)COOH; $R^k$=4-NH$_2$Bz;
3-57. $R^a$=SCH$_3$; $R^b$=CH(3-PhEt)COOH; $R^k$=Bz;
3-58. $R^b$=CH$_2$CH$_2$COOH; $R^f$=OH; $R^k$=Bz;
3-59. $R^a$=SCH$_3$; $R^c$=CH$_2$CH$_2$COOH; $R^k$=3-ClBz;
3-60. $R^b$=CH$_2$CH$_2$COOH; $R^k$=3-ClBz;
3-61. $R^c$=CH$_3$; $R^b$=CH$_2$CH$_2$COOH; $R^f$=F; $R^k$=4-ClBz;
3-62. $R^b$=CH$_2$CH$_2$COOH; $R^k$=3-FBz;
3-63. $R^a$=SCH$_3$; $R^c$=CH$_2$CH$_2$COOH; $R^k$=4-FBz;
3-64. $R^c$=CH$_2$CH$_2$COOH; $R^k$=3-MeOBz;
3-65. $R^a$=SCH$_3$; $R^b$=CH$_2$CH$_2$COOH; $R^d$=CH$_3$; $R^k$=4-MeOBz;
3-66. $R^a$=Pr; $R^c$=CH$_2$CH$_2$COOH; $R^k$=3,4-diMeOBz;
3-67. $R^c$=CH$_2$CH$_2$COOH; $R^e$=OCH$_3$; $R^k$=4-NH$_2$Bz;
3-68. $R^a$=SCH$_3$; $R^b$=CH$_2$COOH; $R^e$=CH$_3$; $R^k$=Bz;
3-69. $R^b$=CH$_2$COOH; $R^d$=CH$_3$; $R^f$=CH$_3$; $R^k$=3-FBz;
3-70. $R^a$=CH$_3$; $R^b$=CH$_2$COOH; $R^k$=3,4-diMeOBz;
3-71. $R^a$=SCH$_3$; $R^b$=CH(4-FBz)COOH; $R^d$=CH3; $R^k$=Bz;
3-72. $R^c$=CH(3,4-diMeOBz)COOH; $R^d$=CH$_3$; $R^k$=3-ClBz;
3-73. $R^c$=CH(3-ClBz)COOH; $R^e$=OH; $R^k$=4-MeOBz;
3-74. $R^a$=CH$_3$; $R^c$=CH(Bz)COOH; $R^f$=F; $R^k$=3-FBz;
3-75. $R^a$=SCH$_3$; $R^c$=CH$_2$COOH; $R^f$=Ph; $R^k$=Bz;
3-76. $R^a$=CH$_3$; $R^c$=CH(3-MeOBz)COOH; $R^k$=Bz;
3-77. $R^b$=CH(3-PhEt)COOH; $R^d$=Ph; $R^k$=Bz;
3-78. $R^a$=SCH$_3$; $R^b$=CH$_2$COOH; $R^f$=Bz; $R^k$=4-FBz;
3-79. $R^c$=CH$_2$COOH; $R^d$=CH$_3$; $R^h$=CH$_3$; $R^k$=3-MeOBz;

3-80. $R^a$=$CH_3$; $R^c$=CH(3-MeOBz)COOH; $R^h$=Bz; $R^k$=4-ClBz;
3-81. $R^b$=$CH_2$COOH; $R^d$=$CH_3$; $R^g$=$CH_3$; $R^k$=4-FBz;
3-82. $R^a$=$SCH_3$; $R^c$=CH(Bz)COOH; $R^e$=$OCH_3$; $R^k$=Bz;
3-83. $R^a$=$CH_3$; $R^c$=CH(3-FBz)COOH; $R^k$=3-ClBz;
3-84. $R^a$=$CH_3$; $R^b$=$CH_3$; $R^c$=CH(3-PhEt)COOH; $R^f$=F; $R^k$=Bz;
3-85. $R^a$=$CH_3$; $R^b$=$CH_2CH_2$COOH; $R^h$=OH; $R^k$=Bz;
3-86. $R^a$=$SCH_3$; $R^b$=$CH_3$; $R^c$=$CH_2$COOH; $R^e$=OH; $R^k$=Bz;
3-87. $R^a$=$CH_3$; $R^c$=H(3-MeOBz)COOH; $R^k$=Bz;
3-88. $R^a$=$CH_3$; $R^c$=CH(3-ClBz)COOH; $R^h$=$CH_3$; $R^k$=3-FBz;
3-89. $R^b$=CH(Bz)COOH; $R^d$=$CH_3$; $R^f$=$CH_3$; $R^k$=4-$NH_2$Bz;
3-90. $R^a$=$SCH_3$; $R^b$=4-FBz; $R^c$=$CH_2$COOH; $R^k$=Bz;
3-91. $R^c$=CH(3-MeOBz)COOH; $R^d$=$CH_3$; $R^f$=$CH_3$; $R^b$=Bz;
3-92. $R^c$=CH(4-FBz)COOH; $R^d$=F; $R^f$=OH; $R^b$=Bz;
3-93. $R^a$=$SCH_3$; $R^b$=$CH_2CH_2$COOH; $R^k$=4-FBz;
3-94. $R^b$=CH($CH_2$4-FBz)COOH; $R^d$=$CH_3$; $R^k$=Bz;
3-95. $R^c$=CH($CH_2$3-FBz)COOH; $R^e$=Cl; $R^k$=3-ClBz;
3-96. $R^c$=CH($CH_2$3-ClBz)COOH; $R^h$=$CH_3$; $R^k$=4-MeOBz;
3-97. $R^a$=$CH_3$; $R^b$=CHCH$_2$(3-PhEt)COOH; $R^f$=OH; $R^k$=Bz;
3-98. $R^a$=F; $R^b$=$CH_2CH_2$COOH; $R^e$=OH; $R^k$=4-ClBz;
3-99. $R^a$=$SCH_3$; $R^b$=$CH_2$COOCH$_2$OCOC($CH_3$)$_3$; $R^k$=4-FBz;
3-100. $R^b$=CH(4-FBZ)COOCH$_2$OCOC($CH_3$)$_3$; $R^k$=Bz;
3-101. $R^c$=CH(3-FBz)COOCH$_2$OCOC($CH_3$)$_3$; $R^d$=$CH_3$; $R^k$=3-ClBz;
3-102. $R^c$=CH(3-ClBz)COOCH$_2$OCOC($CH_3$)$_3$; $R^k$=4-MeOBz;
3-103. $R^a$=$SCH_3$; $R^b$=CH(3-PhEt)COOCH$_2$OCOC($CH_3$)$_3$; $R^k$=Bz;
3-104. $R^b$=$CH_2CH_2$COOCH$_2$OCOC($CH_3$)$_3$; $R^k$=4-ClBz;
3-105. $R^a$=$SCH_3$; $R^b$=$CH_2$COOCH$_3$; $R^k$=3-ClBz;
3-106. $R^b$=CH(4-FBz)COOCH$_3$; $R^k$=Bz;
3-107. $R^b$=CH(4-FBz)COOCH$_3$; $R^d$=$CH_3$; $R^k$=3-FBz;
3-108. $R^b$=CH(3-PhEt)COOCH$_3$; $R^k$=Bz;
3-109. $R^b$=$CH_2$COOEt; $R^k$=3-ClBz;
3-110. $R^a$=$SCH_3$; $R^b$=$CH_2$COOEt; $R^k$=3-ClBz;
3-111. $R^c$=CH(3-FBz)COOEt; $R^k$=3-ClBz;
3-112. $R^b$=CH(4-FBz)COOEt; $R^k$=3-FBz;
3-113. $R^b$=CH(3-PhEt)COOEt; $R^d$=$CH_3$; $R^k$=Bz;
3-114. $R^b$=CH(3-PhEt)COOEt; $R^k$=Bz;
3-115. $R^b$=$CH_2$COOCH$_2$CH$_2$OCOCH$_3$; $R^k$=3-ClBz;
3-116. $R^a$=$SCH_3$; $R^b$=$CH_2$COOCH$_2$CH$_2$OCOCH$_3$; $R^k$=3-ClBz;
3-117. $R^c$=CH(3-FBz)COOCH$_2$CH$_2$OCOCH$_3$; $R^k$=3-ClBz;
3-118. $R^a$=$CH_3$; $R^c$=CH(3-ClBz)COOCH$_2$CH$_2$OCOCH$_3$; $R^k$=4-MeOBz;
3-119. $R^b$=$CH_2$COOCH$_2$CH$_2$N($CH_3$)$_2$; $R^k$=3-ClBz;
3-120. $R^a$=$SCH_3$; $R^b$=$CH_2$COOCH$_2$CH$_2$N($CH_3$)$_2$; $R^k$=3-ClBz;
3-121. $R^c$=CH(3-FBz)COOCH$_2$CH$_2$N($CH_3$)$_2$; $R^k$=3-ClBz;
3-122. $R^c$=CH(3-ClBz)COOCH$_2$CH$_2$N($CH_3$)$_2$; $R^k$=4-MeOBz;
3-123. $R^b$=$CH_2$CONHCH$_3$; $R^k$=3-ClBz;
3-124. $R^b$=CH(4-FBz)CONHCH$_3$; $R^k$=Bz;
3-125. $R^a$=$SCH_3$; $R^b$=CH(4-FBz)CONHCH$_3$; $R^k$=Bz;
3-126. $R^b$=CH(4-FBz)CONHCH$_3$; $R^k$=3-FBz;
3-127. $R^b$=CH(3-PhEt)CONHCH$_3$; $R^k$=Bz;
3-128. $R^b$=$CH_2$CONHCH$_2$CH$_2$OH; $R^k$=3-ClBz;
3-129. $R^b$=CH(4-FBz)CONHCH$_2$CH$_2$OH; $R^k$=Bz;
3-130. $R^a$=$CH_3$; $R^b$=CH(4-FBz)CONHCH$_2$CH$_2$OH; $R^k$=Bz;
3-131. $R^c$=CH(3-ClBz)CONHCH$_2$CH$_2$OH; $R^k$=4-MeOBz;
3-132. $R^b$=$CH_2CH_2$CONHCH$_2$CH$_2$OH; $R^k$=4-ClBz;
3-133. $R^b$=$CH_2$CONHCH$_2$CH$_2$N($CH_3$)$_2$; $R^k$=3-ClBz;
3-134. $R^a$=$CH_3$; $R^b$=$CH_2$CONHCH$_2$CH$_2$N($CH_3$)$_2$; $R^k$=3-ClBz;
3-135. $R^b$=CH(4-FBz)CONHCH$_2$CH$_2$N($CH_3$)$_2$; $R^k$=Bz;
3-136. $R^c$=CH(3-ClBz)CONHCH$_2$CH$_2$N($CH_3$)$_2$; $R^k$=4-MeOBz;
3-137. $R^b$=$CH_2CH_2$CONHCH$_2$CH$_2$N($CH_3$)$_2$; $R^k$=4-ClBz;
3-138. $R^a$=$SCH_3$; $R^b$=OCH$_2$COOH; $R^e$=$CH_3$; $R^k$=Bz;
3-139. $R^b$=OCH$_2$COOH $R^d$=$CH_3$; $R^f$=$CH_3$; $R^k$=3-FBz;
3-140. $R^a$=$CH_3$; $R^b$=OCH$_2$COOH; $R^k$=3,4-diMeOBz;
3-141. $R^a$=$SCH_3$; $R^b$=OCH(4-FBz)COOH; $R^d$=$CH_3$; $R^k$=Bz;
3-142. $R^c$=OCH(3,4-diMeOBz)COOH $R^d$=$CH_3$; $R^k$=3-ClBz;
3-143. $R^c$=OCH(3-ClBz)COOH; $R^e$=OH; $R^k$=4-MeOBz;
3-144. $R^a$=$CH_3$; $R^c$=OCH(Bz)COOCH$_2$OCOC($CH_3$)$_3$; $R^f$=F; $R^k$=3-FBz
3-145. $R^a$=$SCH_3$; $R^b$=OCH(4-FBz)COOCH$_2$CH$_2$N($CH_3$)$_2$; $R^d$=$CH_3$; $R^k$=Bz;
3-146. $R^a$=$SCH_3$; $R^b$=OCH$_2$CH$_2$COOH; $R^e$=$CH_3$; $R^k$=Bz;
3-147. $R^b$=OCH$_2$CH$_2$COOH; $R^d$=$CH_3$; $R^f$=$CH_3$; $R^k$=3-FBz;
3-148. $R^a$=$CH_3$; $R^b$=OCH$_2$CH$_2$COOH; $R^k$=3,4-diMeOBz;
3-149. $R^a$=$SCH_3$; $R^b$=OCH$_2$CH(4-FBz)COOH; $R^d$=$CH_3$; $R^k$=Bz;
3-150. $R^c$=OCH(3,4-diMeOBz)CH$_2$COOH; $R^d$=$CH_3$; $R^k$=3-ClBz;
3-151. $R^c$=OCH(3-ClBz)CH$_2$COOH $R^e$=OH; $R^k$=4-MeOBz;
3-152. $R^a$=$CH_3$; $R^c$=OCH$_2$CH(Bz)COOCH$_2$OCOC($CH_3$)$_3$; $R^f$=F $R^k$=3-FBz
3-153. $R^a$=$SCH_3$; $R^b$=OCH$_2$CH(4-FBz)COOCH$_2$CH$_2$N($CH_3$)$_2$; $R^d$=$CH_3$; $R^k$=Bz;
3-154. $R^b$=$CH_2$COOH; $R^d$=$CH_3$; $R^k$=COPh
3-155. $R^b$=$CH_2$COOH; $R^k$=CO(4-Cl—Ph);
3-156. $R^c$=CH(3-FBz)COOH; $R^d$=$CH_3$; $R^k$=CO(3-F—Ph);
3-157. $R^c$=CH(4-MeOBz)COOH; $R^k$=CO(3-F—Ph);
3-158. $R^b$=CH(3-PhEt)COOH; $R^f$=Cl; $R^k$=CO(3-F—Ph);
3-159. $R^b$=CH(Bz)COOH; $R^d$=$CH_3$; $R^k$=CO(3-F—Ph);
3-160. $R^c$=CH(Bz)COOH; $R^k$=CO(4-F—Ph);
3-161. $R^b$=CH(Bz)COOH; $R^e$=F; $R^k$=CO(4-MeO—Ph)
3-162. $R^a$=$SCH_3$; $R^b$=CH(Bz)COOH; $R^k$=COPh;
3-163. $R^c$=CH(Bz)COOH; $R^k$=CO(3,4-MeO—Ph);
3-164. $R^c$=CH(Bz)COOH; $R^d$=$CH_3$; $R^k$=CO(3,4-MeO—Ph);
3-165. $R^b$=CH(Bz)COOH; $R^k$=CO(3,4-MeO—Ph);
3-166. $R^b$=$CH_2$COOH; $R^d$=$CH_3$; $R^k$=COCH$_3$;
3-167. $R^b$=CH(Ph)COOH; $R^d$=$CH_3$; $R^k$=COCH$_3$;
3-168. $R^a$=$SCH_3$; $R^b$=$CH_2$COOH; $R^k$=COCH$_3$;
3-169. $R^a$=$SCH_3$; $R^b$=CH(Bz)COOH; $R^k$=COCH$_3$;

3-170. $R^b$=CH$_2$COOH; $R^d$=CH$_3$; $R^k$=COCH(CH$_3$)$_2$;
3-171. $R^b$=CH(Ph)COOH; $R^d$=CH$_3$; $R^k$=COCH(CH$_3$)$_2$;
3-172. $R^a$=SCH$_3$; $R^b$=CH$_2$COOH; $R^k$=COCH(CH$_3$)$_2$;
3-173. $R^a$=SCH$_3$; $R^b$=CH(Bz)COOH; $R^k$=COCH(CH$_3$)$_2$;
3-174. $R^b$=CH$_2$COOH; $R^d$=CH$_3$; $R^k$=COCH(CH$_3$)$_2$;
3-175. $R^b$=CH$_2$CH$_2$COOH; $R^d$=CH$_3$; $R^k$=COEt;
3-176. $R^a$=SCH$_3$; $R^b$=CH$_2$COOH; $R^k$=COEt;
3-177. $R^b$=CH$_2$COOH; $R^d$=CH$_3$; $R^k$=CH$_2$(thiophen-3-yl);
3-178. $R^b$=CH$_2$COOH; $R^k$=CH$_2$(thiophen-3-yl);
3-179. $R^c$=CH(3-FBz)COOH; $R^d$=CH$_3$; $R^k$=CH$_2$(thiophen-3-yl);
3-180. $R^c$=CH(4-MeOBz)COOH; $R^k$=CH$_2$(thiophen-3-yl);
3-181. $R^c$=CH(4-MeOBz)COOCH$_2$OCOC(CH$_3$)$_3$; $R^k$=CH$_2$(thiophen-3-yl);
3-182. $R^b$=CH$_2$COOH; $R^d$=CH$_3$; $R^k$=CH$_2$(thiophen-3-yl);
3-183. $R^b$=CH$_2$COOH; $R^k$=CH$_2$(thiophen-3-yl);
3-184. $R^c$=CH(3-FBz)COOH; $R^d$=CH$_3$; $R^k$=CH$_2$(thiophen-3-yl);
3-185. $R^c$=CH(4-MeOBz)COOH; $R^k$=CH$_2$(thiophen-3-yl);
3-186. $R^c$=CH(4-MeOBz)COOCH$_2$OCOC(CH$_3$)$_3$; $R^k$=CH$_2$(thiophen-3-yl);
3-187. $R^b$=CH$_2$COOH; $R^d$=CH$_3$; $R^k$=CH$_2$(pyridin-3-yl);
3-188. $R^b$=CH$_2$COOH; $R^k$=CH$_2$(pyridin-3-yl);
3-189. $R^c$=CH(3-FBz)COOH; $R^d$=CH$_3$; $R^k$=CH$_2$(pyridin-3-yl);
3-190. $R^c$=CH(4-MeOBz)COOH; $R^k$=CH$_2$(pyridin-3-yl);
3-191. $R^c$=CH(4-MeOBz)COOCH$_2$OCOC(CH$_3$)$_3$; $R^k$=CH$_2$(pyridin-3-yl);
3-192. $R^b$=CH$_2$COOH; $R^d$=CH$_3$; $R^k$=CH$_2$(pyridin-3-yl);
3-193. $R^b$=CH$_2$COOH; $R^k$=CH$_2$(pyridn-3-yl);
3-194. $R^c$=CH(3-FBz)COOH; $R^d$=CH$_3$; $R^k$=CH$_2$(pyridin-3-yl);
3-195. $R^c$=CH(4-MeOBz)COOH; $R^k$=CH$_2$(pyridin-3-yl);
3-196. $R^c$=CH(4-MeOBz)COOCH$_2$OCOC(CH$_3$)$_3$; $R^k$=CH$_2$(pyridin-3-yl);
3-197. $R^b$=CH$_2$COOH; $R^d$=CH$_3$; $R^k$=CH$_2$(pyridin-4-yl);
3-198. $R^b$=CH$_2$COOH; $R^k$=CH$_2$(pyridin-4-yl);
3-199. $R^c$=CH(3-FBz)COOH; $R^d$=CH$_3$; $R^k$=CH$_2$(pyridin-4-yl);
3-200. $R^c$=CH(4-MeOBz)COOH; $R^k$=CH$_2$(pyridin-4-yl);
3-201. $R^b$=CH$_2$Tet; $R^k$=Bz;
3-202. $R^a$=SCH$_3$; $R^b$=CH$_2$Tet; $R^k$=Bz;
3-203. $R^a$=SCH$_3$; $R^b$=CH$_2$CH$_2$Tet; $R^k$=4-FBz;
3-204. $R^a$=SCH$_3$; $R^b$=CH$_2$CH$_2$CH$_2$Tet; $R^k$=4-FBz;
3-205. $R^a$=CH$_3$; $R^b$=CH$_2$Tet; $R^k$=Bz;
3-206. $R^a$=SCH$_3$; $R^c$=Tet; $R^k$=Bz;
3-207. $R^a$=SCH$_3$; $R^d$=Tet; $R^k$=(3-MeO)PhCH$_2$;
3-208. $R^a$=SCH$_3$; $R^c$=CH$_2$Tet; $R^k$=Bz;
3-209. $R^a$=SCH$_3$; $R^d$=CH$_2$Tet; $R^k$=(4-F)PhCH$_2$;
3-210. $R^a$=CH$_3$; $R^b$=SO$_2$NHCOCH$_3$; $R^k$=(4-F)PhCH$_2$;
3-211. $R^a$=SCH$_3$; $R^b$=SO$_2$NHCOCH$_3$; $R^k$=Bz;
3-212. $R^a$=CH$_3$; $R^c$=SO$_2$NHCOCH$_3$; $R^k$=CH$_2$CH$_2$CH$_3$;
3-213. $R^a$=SCH$_3$; $R^d$=SO$_2$NHCOCH$_3$; $R^k$=(4-Cl)PhCH$_2$;
3-214. $R^a$=SCH$_3$; $R^b$=SO$_2$NHCOCH$_2$CH$_3$; $R^k$=Bz;
3-215. $R^a$=CH$_3$; $R^b$=SO$_2$NHCOCH$_2$CH$_3$; $R^k$=(4-F)PhCH$_2$;
3-216. $R^a$=SCH$_3$; $R^c$=SO$_2$NHCOCH$_2$CH$_3$; $R^k$=CH$_3$;
3-217. $R^a$=CH$_3$; $R^d$=SO$_2$NHCOCH$_2$CH$_3$; $R^k$=Bz;
3-218. $R^a$=CH$_3$; $R^b$=SO$_2$NHCOCH$_2$Ph; $R^k$=(3,4-MeO)PhCH$_2$;
3-219. $R^a$=SCH$_3$; $R^b$=SO$_2$NHCOCH$_2$Ph; $R^k$=Bz;
3-220. $R^a$=CH$_3$; $R^c$=SO$_2$NHCOCH$_2$Ph; $R^k$=Bz;
3-221. $R^a$=SCH$_3$; $R^d$=SO$_2$NHCOCH$_2$Ph; $R^k$=(4-Cl)PhCH$_2$;
3-222. $R^a$=SCH$_3$; $R^b$=CH$_2$SO$_2$NHCOCH$_3$; $R^k$=Bz;
3-223. $R^a$=CH$_3$; $R^b$=CH$_2$SO$_2$NHCOCH$_3$; $R^k$=Bz;
3-224. $R^a$=SCH$_3$; $R^c$=CH$_2$SO$_2$NHCOCH$_3$; $R^k$=(4-F)PhCH$_2$;
3-225. $R^a$=CH$_3$; $R^d$=CH$_2$SO$_2$NHCOCH$_3$; $R^k$=(4-CF$_3$)PhCH$_2$;
3-226. $R^a$=CH$_3$; $R^b$=CH$_2$SO$_2$NHCOCH$_2$CH$_3$; $R^k$=Bz;
3-227. $R^a$=SCH$_3$; $R^b$=CH$_2$SO$_2$NHCOCH$_2$CH$_3$; $R^k$=Bz;
3-228. $R^a$=CH$_3$; $R^c$=CH$_2$SO$_2$NHCOCH$_2$CH$_3$; $R^k$=(4-NO$_2$)PhCH$_2$;
3-229. $R^a$=SCH$_3$; $R^d$=CH$_2$SO$_2$NHCOCH$_2$CH$_3$; $R^k$=Bz;
3-230. $R^a$=SCH$_3$; $R^b$=CH$_2$SO$_2$NHCOCH$_2$Ph; $R^k$=(4-F)PhCH$_2$;
3-231. $R^a$=CH$_3$; $R^b$=CH$_2$SO$_2$NHCOCH$_2$Ph; $R^k$=Bz;
3-232. $R^a$=SCH$_3$; $R^c$=CH$_2$SO$_2$NHCOCH$_2$Ph; $R^k$=Bz;
3-233. $R^a$=CH$_3$; $R^d$=CH$_2$SO$_2$NHCOCH$_2$Ph; $R^k$=(4-F)PhCH$_2$;
3-234. $R^b$=C(CH$_3$)$_2$COOH; $R^k$=Bz;
3-235. $R^a$=SMe; $R^b$=CH$_2$COOH; $R^d$=n-Pr; $R^k$=Bz;
3-236. $R^a$=SMe; $R^b$=CH$_2$Tet; $R^d$=n-Pr; $R^k$=Bz;
3-237. $R^a$=SMe; $R^b$=OCH$_2$COOH; $R^d$=n-Pr; $R^k$=Bz;
3-238. $R^a$=SMe; $R^b$=CH(CH$_2$Ph)COOH; $R^d$=n-Pr; $R^k$=Bz.

Of these, the preferred compounds are Nos. 3-12, 3-13, 3-19, 3-32, 3-38, 3-41, 3-42, 3-57, 3-63, 3-73, 3-82, 3-86,93, 3-101, 3-105, 3-116, 3-120, 3-140, 3-153, 3-161, 3-169, 3-179, 3-202, 3-203, 3-205, 3-212, 3-219, 3-223, 3-235, and 3-236 and the most preferred are Nos. 3-12, 3-19, 3-38, 3-73, 3-202, 3-219 and 3-236

Further examples of specific compounds of the present invention are the thiopyranoindole derivatives indicated by formula (I-4):

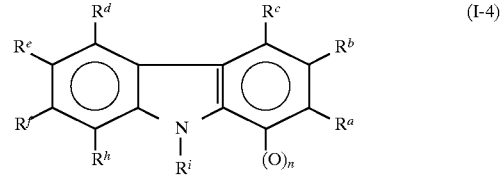

in which all substituent groups are as defined below, those not mentioned being hydrogen:
4-1. $R^a$=COOH; n=0;
4-2. $R^c$=COOH; $R^e$=CH$_3$; n=0;
4-3. $R^e$=COOH; n=0;
4-4. $R^f$=CCOH; n=0;
4-5. $R^a$=CH$_2$COOH; n=0;
4-6. $R^b$=CH$_2$COOH; n=0;
4-7. $R^d$=CH$_2$COOH; n=0;
4-8. $R^a$=CH$_2$CH$_2$COOH; n=0;
4-9. $R^b$=CH$_2$CH$_2$COOH; n=0;
4-10. $R^c$=CH$_2$CH$_2$COOH; n=0;
4-11. $R^a$=Tet; n=0;
4-12. $R^b$=Tet; n=0;
4-13. $R^c$=Tet; n=0;
4-14. $R^a$=CH$_2$Tet; n=0;
4-15. $R^c$=CH$_2$Tet; n=0;
4-16. $R^a$CH$_2$CH$_2$Tet; n=0;
4-17. $R^b$=CH$_2$CH$_2$Tet; $R^f$=Cl; n=0;
4-18. $R^b$=SO$_2$NHCOCH$_3$; n=0;
4-19. $R^c$=SO$_2$NHCOCH$_3$; n=0;
4-20. $R^a$=CH$_2$SO$_2$NHCOCH$_3$; n=0;
4-21. $R^a$=COOH; $R^c$=CH$_3$; n=0;
4-22. $R^b$=COOH; $R^c$=CH$_2$CH$_3$; n=0;

4-23. $R^a$=CH$_3$; $R^c$=COOH; n=0;
4-24. $R^a$=CH$_2$COOH; $R^c$=CH$_2$CH$_3$; n=0;
4-25. $R^b$=CH$_2$COOH; $R^c$=CH$_3$; $R^f$=MeO; n=0;
4-26. $R^b$=CH$_3$; $R^c$=CH$_2$COOH; n=0;
4-27. $R^a$=CH$_2$CH$_2$COOH; $R^c$=CH$_3$; n=0;
4-28. $R^b$=CH$_2$CH$_2$COOH; $R^c$=CH$_3$; n=0;
4-29. $R^a$=CH$_2$CH$_3$; $R^c$=CH$_2$CH$_2$COOH; n=0;
4-30. $R^a$=Tet; $R^c$=CH$_3$; n=0;
4-31. $R^b$=Tet; $R^c$=CH$_2$Ph; n=0;
4-32. $R^a$=CH$_3$; $R^b$=CH$_3$; $R^c$=Tet; n=0;
4-33. $R^a$=CH$_2$Tet; $R^c$=Ph; n=0;
4-34. $R^b$=CH$_2$Tet; $R^c$=CH$_3$; n=0;
4-35. $R^a$=CH$_2$CH$_2$Ph; $R^b$=CH$_3$; $R^c$=CH$_2$Tet; $R^h$=CH$_3$; n=0;
4-36. $R^b$=CH$_2$CH$_2$Tet; $R^c$=CH$_3$; n=0;
4-37. $R^a$=CH$_3$; $R^c$=CH$_2$CH$_2$Tet; n=0;
4-38. $R^a$=SO$_2$NHCOCH$_3$; $R^c$=CH$_3$; $R^d$=Cl; n=0;
4-39. $R^b$=CH$_3$; $R^c$=SO$_2$NHCOCH$_3$; n=0;
4-40. $R^a$=CH$_2$SO$_2$NHCOCH$_3$; $R^c$=CH$_3$; n=0;
4-41. $R^a$=COOH; $R^c$=(4-F)Ph; n=0;
4-42. $R^b$=COOH; $R^c$=(3-MeO)Ph; n=0;
4-43. $R^b$=CH$_2$COOH; $R^c$=Ph; n=0;
4-44. $R^a$=CH$_2$CH$_2$COOH; $R^c$=(4-MeO)Ph; n=0;
4-45. $R^a$=Ph; $R^c$=CH$_2$CH$_2$COOH; n=0;
4-46. $R^a$=Tet; $R^c$=Ph; n=0;
4-47. $R^a$=CH$_2$Tet; $R^c$=(3-F)Ph; n=0;
4-48. $R^b$=CH$_2$CH$_2$CH$_3$; $R^c$=CH$_2$Tet; n=0;
4-49. $R^a$=CH$_2$CH$_2$Tet; $R^c$=(3-NO$_2$)Ph; n=0;
4-50. $R^b$=SO$_2$NHCOPh; $R^c$=Ph; n=0;
4-51. $R^b$=CH$_2$SO$_2$NHCOPh; $R^c$=(4-NH$_2$)Ph; n=0;
4-52. $R^a$=Ph; $R^c$=CH$_2$SO$_2$NHCOPh; n=0;
4-53. $R^a$=COOH; $R^c$=Ph; $R^i$=CH$_2$-(4-F)Ph; n=0;
4-54. $R^b$=COOH; $R^c$=(4-Cl)Ph; $R^i$=CH$_2$Ph; n=0;
4-55. $R^a$=Ph; $R^b$=CH$_3$; $R^c$=COOH; $R^i$=CH$_2$Ph; n=0;
4-56. $R^a$=CH$_2$COOH; $R^c$=Ph; $R^i$=CH$_2$Ph; n=0;
4-57. $R^b$=CH$_2$COOH; $R^c$=Ph; $R^i$=CH$_2$-(4-NH$_2$)Ph; n=0;
4-58. $R^b$=(3-F)Ph; $R^c$=CH$_2$COOH; $R^i$=CH$_2$Ph; n=0;
4-59. $R^a$=CH$_2$CH$_2$COOH; $R^c$=Ph; $R^i$=CH$_2$-(4-MeO)Ph; n=0;
4-60. $R^b$=CH$_2$CH$_2$COOH; $R^c$=(3-CH$_3$CO)Ph; $R^i$=CH$_2$Ph; n=0;
4-61. $R^a$=Tet; $R^c$=Ph; $R^i$=CH$_2$-(4-Cl)Ph; n=0;
4-62. $R^b$=Tet; $R^c$=Ph; $R^i$=CH$_2$Ph; $R^e$=F; n=0;
4-63. $R^a$=Ph; $R^c$=Tet; $R^i$=CH$_2$-(3,4-DiMeO)Ph; n=0;
4-64. $R^a$=CH$_2$Tet; $R^i$=CH$_2$Ph; n=0;
4-65. $R^a$=CH$_2$CH$_2$Tet; $R^c$=Ph; $R^i$=CH$_2$-(4-F)Ph; n=0;
4-66. $R^a$=Ph; $R^c$=CH$_2$CH$_2$Tet; $R^i$=CH$_2$Ph; n=0;
4-67. $R^a$=SO$_2$NHCOPh; $R^c$=(3-NO$_2$)Ph; $R^h$=NO$_2$; $R^i$=CH$_2$Ph; n=0;
4-68. $R^b$=CH$_2$SO$_2$NHCOPh; $R^c$=Ph; $R^i$=CH$_2$-(4-Cl)Ph; n=0;
4-69. $R^a$=COOH; $R^b$=(3-F)Ph; $R^i$=CH$_2$Ph; n=0;
4-70. $R^b$=COOH; $R^c$=Ph; $R^i$=CH$_2$-(4-NO$_2$)Ph; n=0;
4-71. $R^a$=CH$_3$; $R^b$=Ph; $R^c$=COOH; $R^i$=CH$_2$-(3-F)Ph; n=0;
4-72. $R^a$=CH$_2$COOH; $R^b$=(4-CH$_3$CONH)Ph; $R^i$=CH$_2$Ph; n=0;
4-73. $R^a$=(3-F)Ph; $R^b$=CH$_2$COOH; $R^i$=CH$_2$-(4-F)Ph; n=0;
4-74. $R^a$=CH$_2$Ph; $R^b$=CH$_2$COOH; $R^i$=CH$_2$-(3,4-DiMeO)Ph; n=0;
4-75. $R^a$=CH$_2$CH$_2$COOH; $R^b$=Ph; $R^i$=CH$_2$Ph; n=0;
4-76. $R^a$=(4-MeO)Ph; $R^b$=CH$_2$CH$_2$COOH; $R^i$=CH$_2$Ph; n=0;
4-77. $R^a$=Tet; $R^b$=Ph; $R^i$=CH$_2$-(4-F)Ph; n=0;
4-78. $R^a$=CH$_3$; $R^b$=Tet; $R^i$=CH$_2$-(3-MeO)Ph; n=0;

4-79. $R^a$=(4-F)Ph; $R^b$=Tet; $R^i$=CH$_2$Ph; n=0;
4-80. $R^a$=CH$_2$Tet; $R^b$=(4-MeO)Ph; $R^i$=CH$_2$-(4-F)Ph; n=0;
4-81. $R^a$=CH$_2$CH$_2$Tet; $R^b$=Ph; $R^i$=CH$_2$-(3-MeO)Ph; n=0;
4-82. $R^b$=CH$_2$CH$_2$Tet; $R^c$=(4-F)Ph; $R^i$=CH$_2$Ph; n=0;
4-83. $R^a$=SO$_2$NHCOPh; $R^b$=Ph; $R^i$=CH$_2$-(2-F)Ph; n=0;
4-84. $R^b$=CH$_2$SO$_2$NHCOPh; $R^c$=(3-Cl)Ph; $R^i$=CH$_2$Ph; n=0;
4-85. $R^a$=COOH; $R^b$=(3-F)Ph; $R^i$=CH$_2$Ph; n=0;
4-86. $R^a$=Ph; $R^b$=COOH; $R^i$=CH$_2$-(4-MeO)Ph; n=0;
4-87. $R^a$=CH$_3$; $R^b$=COOH; $R^c$=CH$_2$CH$_2$CH$_3$; $R^i$=CH$_2$-(3-F)Ph; n
4-88. $R^a$=CH$_2$COOH; $R^b$=(2-Cl)Ph; $R^i$=CH$_2$-(4-Cl)Ph; n=0;
4-89. $R^a$=(4-MeO)Ph; $R^b$=CH$_2$COOH; $R^i$=CH$_2$Ph; n=0;
4-90. $R^a$=Ph; $R^b$=CH$_2$COOH; $R^c$=CH$_3$; $R^i$=CH$_2$-(3-NH$_2$)Ph; n=0;
4-91. $R^a$=CH$_2$CH$_2$COOH; $R^b$=(3,4-DiMeO)Ph; $R^f$=NH$_2$; $R^i$=CH$_2$Ph; n=0;
4-92. $R^a$=CH$_2$CH$_3$; $R^b$=CH$_2$CH$_2$COOH; $R^i$=CH$_2$-(4-F)Ph; n=0;
4-93. $R^a$=Tet; $R^b$=(4-NO$_2$)Ph; $R^i$=CH$_2$Ph; n=0;
4-94. $R^a$=Ph; $R^b$=Tet; $R^i$=CH$_2$-(4-MeO)Ph; n=0;
4-95. $R^a$=Tet; $R^b$=(3-Cl)Ph; $R^i$=CH$_2$Ph; n=0;
4-96. $R^a$=CH$_2$Tet; $R^b$=Ph; $R^i$=CH$_2$-(4-F)Ph; n=0;
4-97. $R^a$=CH$_2$CH$_2$Tet; $R^b$=Ph; $R^i$=CH$_2$-(3-F)Ph; n=0;
4-98. $R^b$=CH$_2$CH$_2$Tet; $R^c$=(4-F)Ph; $R^i$=CH$_2$-(4-F)Ph; n=0;
4-99. $R^a$=SO$_2$NHCOPh; $R^b$=Ph; $R^i$=CH$_2$Ph; n=0;
4-100. $R^b$=CH$_2$SO$_2$NHCOPh; $R^c$=Ph; $R^i$=CH$_2$-(3,4-DiMeO)Ph; n=0;
4-101. $R^a$=COOH; $R^b$=CH$_3$; $R^i$=CH$_2$-(3,4-DiMeO)Ph; n=0;
4-102. $R^b$=COCH; $R^c$=CH$_3$; $R^i$=CH$_2$Ph; n=0;
4-103. $R^a$=CH$_2$COOH; $R^b$=CH$_3$; $R^i$=CH$_2$Ph; n=0;
4-104. $R^b$=CH$_2$COOH; $R^c$=CH$_3$; $R^i$=CH$_2$Ph; n=0;
4-105. $R^a$=CH$_3$; $R^b$=CH$_2$COOH; $R^c$=CH$_3$; $R^i$=CH$_2$-(3,4-DiMeO)Ph; n=0;
4-106. $R^a$=CH$_2$CH$_2$COOH; $R^b$=CH$_3$; $R^i$=CH$_2$Ph; n=0;
4-107. $R^b$=CH$_2$CH$_2$COOH; $R^c$=CH$_3$; $R^i$=CH$_2$Ph; n=0;
4-108. $R^a$=Tet; $R^b$=CH$_3$; $R^i$=CH$_2$Ph; n=0;
4-109. $R^a$=CH$_3$; $R^b$=Tet; $R^i$=CH$_2$Ph; n=0;
4-110. $R^a$=CH$_3$; $R^c$=Tet; $R^i$=CH$_2$Ph; n=0;
4-111. $R^a$=CH$_2$Tet; $R^b$=CH$_3$; $R^i$=CH$_2$Ph; n=0;
4-112. $R^a$=CH$_2$CH$_2$Tet; $R^b$=CH$_3$; $R^i$=CH$_2$Ph; n=0;
4-113. $R^b$=CH$_2$CH$_2$Tet; $R^c$=CH$_3$; $R^i$=CH$_2$Ph; n=0;
4-114. $R^a$=SO$_2$NHCOCH$_3$; $R^b$=CH$_3$; $R^i$=CH$_2$Ph; n=0;
4-115. $R^a$=CH$_3$; $R^b$=CH$_2$SO$_2$NHCOCH$_3$; $R^z$=CH$_2$Ph; n=0;
4-116. $R^a$=COOH; $R^b$=CH$_3$; $R^c$=CH$_3$; $R^i$=CH$_2$Ph; n=0;
4-117. $R^a$=CH$_3$; $R^b$=COOH; $R^c$=CH$_3$; $R^i$=CH$_2$-(3,4-DiMeO)Ph; n=0;
4-118. $R^a$=CH$_3$; $R^b$=CH$_3$; $R^c$=COOH; $R^i$=CH$_2$Ph; n=0;
4-119. $R^a$=CH$_2$COOH; $R^b$=CH$_3$; $R^c$=CH$_3$; $R^i$=CH$_2$Ph; n=0;
4-120. $R^a$=CH$_3$; $R^b$=CH$_2$COOH; $R^c$=CH$_3$; $R^i$=CH$_2$Ph; n=0;
4-121. $R^a$=CH$_3$; $R^b$=CH$_3$; $R^c$=CH$_2$COOH; $R^i$=CH$_2$-(3,4-DiMeO)Ph; n=0;
4-122. $R^a$=CH$_2$CH$_2$COOH; $R^b$=CH$_3$; $R^c$=CH$_3$; $R^i$=CH$_2$Ph; n=0;
4-123. $R^a$=CH$_3$; $R^b$=CH$_2$CH$_2$COOH; $R^c$=CH$_3$; $R^i$=CH$_2$Ph; n=0;

4-124. $R^a$=Tet; $R^b$=CH$_3$; $R^c$=CH$_3$; $R^i$=CH$_2$Ph; n=0;
4-125. $R^a$=CH$_3$; $R^b$=Tet; $R^c$=CH$_3$;
  $R^i$=CH$_2$-(3,4-DiMeO)Ph; n=0;
4-126. $R^a$=CH$_3$; $R^b$=CH$_3$; $R^c$=Tet; $R^i$=CH$_2$Ph; n=0;
4-127. $R^a$=CH$_2$Tet; $R^b$=CH$_3$; $R^c$=CH$_3$; $R^i$=CH$_2$Ph; n=0;
4-128. $R^a$=CH$_2$CH$_2$Tet; $R^b$=CH$_3$; $R^c$=CH$_3$; $R^i$=CH$_2$Ph; n=0;
4-129. $R^a$=CH$_3$; $R^b$=CH$_2$CH$_2$Tet; $R^c$=CH$_3$;
  $R^i$=CH$_2$-(3,4-DiMeO)Ph; n=0;
4-130. $R^a$=SO$_2$NHCOCH$_3$; $R^b$=CH$_3$; $R^c$=CH$_3$;
  $R^i$=CH$_2$Ph; n=0;
4-131. $R^a$=CH$_3$; $R^b$=CH$_2$SO$_2$NHCOCH$_3$; $R^c$=CH$_3$;
  $R^i$=CH$_2$Ph; n=0;
4-132. $R^a$=COOH; $R^b$=CH$_3$; $R^c$=CH$_3$; $R^i$=(3,4-DiMeO)Ph; n=0
4-133. $R^a$=CH$_3$; $R^b$=COOH; $R^c$=CH$_3$; $R^i$=Ph; n=0;
4-134. $R^a$=CH$_3$; $R^b$=CH$_3$; $R^c$=COOH; $R^i$=Ph; n=0;
4-135. $R^a$=CH$_2$COOH; $R^b$=CH$_3$; $R^c$=CH$_3$; $R^i$=Ph; n=0;
4-136. $R^a$=CH$_3$; $R^b$=CH$_2$COOH; $R^c$=CH$_3$; $R^i$=Ph; n=0;
4-137. $R^a$=CH$_3$; $R^b$=CH$_3$; $R^c$=CH$_2$COOH; $R^i$=Ph; n=0;
4-138. $R^a$=CH$_2$CH$_2$COOH; $R^b$=CH$_3$; $R^c$=CH$_3$; $R^i$=Ph; n=0;
4-139. $R^a$=CH$_3$; $R^b$=CH$_2$CH$_2$COOH; $R^c$=CH$_3$; $R^i$=Ph; n=0;
4-140. $R^a$=Tet; $R^b$=CH$_3$; $R^c$=CH$_3$; $R^i$=Ph; n=0;
4-141. $R^a$=CH$_2$CH$_3$; $R^b$=Tet; $R^c$=CH$_3$; $R^i$=Ph; n=0;
4-142. $R^a$=CH$_3$; $R^b$=CH$_3$; $R^c$=Tet; $R^i$=Ph; n=0;
4-143. $R^a$=CH$_2$Tet; $R^b$=CH$_3$; $R^c$=CH$_3$; $R^i$=Ph; n=0;
4-144. $R^a$=CH$_2$CH$_2$Tet; $R^b$=CH$_3$; $R^c$=CH$_3$;
  $R^i$=(3,4-DiMeO)Ph; n=0;
4-145. $R^a$=CH$_3$; $R^b$=CH$_2$CH$_2$Tet; $R^c$=CH$_3$; $R^i$=Ph; n=0;
4-146. $R^a$=SO$_2$NHCOCH$_3$; $R^b$=CH$_3$; $R^c$=CH$_3$;
  $R^i$=(3,4-DiMeO)Ph; n=0;
4-147. $R^a$=CH$_2$CH$_3$; $R^b$=CH$_2$SO$_2$NHCOCH$_3$; $R^c$=CH$_3$;
  $R^i$=Ph; n=0;
4-148. $R^a$=COOH; $R^b$=CH$_3$; $R^c$=CH$_3$;
  $R^i$=CH$_2$CH$_2$CH$_3$; n=0;
4-149. $R^a$=CH$_2$CH$_3$; $R^b$=COOH; $R^c$=CH$_3$;
  $R^i$=CH$_2$CH$_2$CH$_2$Ph; n=0;
4-150. $R^a$=CH$_3$; $R^b$=COOH; $R^c$=CH$_3$;
  $R^i$=CH$_2$CH$_2$CH$_2$CH$_3$; n=0;
4-151. $R^a$=CH$_2$COOH; $R^b$=CH$_3$; $R^c$=CH$_3$;
  $R^i$=CH$_2$CH$_2$CH$_2$CH$_3$; n=0;
4-152. $R^a$=CH$_3$; $R^b$=CH$_2$COOH; $R^c$=CH$_2$CH$_3$;
  $R^i$=CH$_2$CH$_2$CH$_3$; n=0;
4-153. $R^a$=CH$_2$CH$_3$; $R^b$=CH$_3$; $R^c$=CH$_2$COOH;
  $R^i$=CH$_2$CH$_2$CH$_3$; n=0;
4-154. $R^a$=CH$_2$CH$_2$COOH; $R^b$=CH$_2$CH$_3$; $R^c$=CH$_3$;
  $R^i$=CH$_2$CH$_2$CH$_3$; n=0;
4-155. $R^a$=CH$_3$; $R^b$=CH$_2$CH$_2$COOH; $R^c$=CH$_3$;
  $R^i$=CH$_2$CH$_2$CH$_3$; n=0;
4-156. $R^a$=Tet; $R^b$=CH$_3$; $R^c$=CH$_2$-(3-MeO)Ph;
  $R^i$=CH$_2$CH$_2$CH$_3$; n=0;
4-157. $R^a$=CH$_3$; $R^b$=Tet; $R^c$=CH$_3$; $R^i$=CH$_2$CH$_2$CH$_2$Ph; n=0;
4-158. $R^a$=CH$_2$Ph; $R^b$=Tet; $R^c$=CH$_3$; $R^i$=CH$_2$CH$_2$CH$_3$; n=0;
4-159. $R^a$=CH$_2$Tet; $R^b$=CH$_2$CH$_3$; $R^c$=CH$_3$;
  $R^i$=CH$_2$CH$_2$CH$_2$Ph; n=0;
4-160. $R^a$=CH$_2$CH$_2$Tet; $R^b$=CH$_3$; $R^c$=CH$_2$CH$_3$;
  $R^i$=CH$_2$CH$_2$CH$_3$; n=0;
4-161. $R^a$=CH$_3$; $R^b$=CH$_2$CH$_2$Tet; $R^c$=CH$_2$Ph;
  $R^i$=CH$_2$CH$_2$CH$_3$; n=0;
4-162. $R^a$=SO$_2$NHCOCH$_3$; $R^b$=CH$_3$; $R^c$=CH$_3$;
  $R^i$=CH$_2$CH$_2$-(4-Cl)Ph; n=0;
4-163. $R^a$=CH$_2$Ph; $R^b$=CH$_2$SO$_2$NHCOCH$_3$; $R^c$=CH$_3$;
  $R^i$=CH$_2$CH$_2$CH$_3$; n=0;
4-164. $R^a$=COOH; $R^b$=CH$_3$; $R^c$=CH$_3$; $R^i$=CH$_2$Ph; n=1;
4-165. $R^a$=CH$_3$; $R^b$=COOH; $R^i$=CH$_2$Ph; n=1;
4-166. $R^a$=CH$_2$CH$_3$; $R^b$=COOH; $R^i$=CH$_2$CH$_3$; n=1;
4-167. $R^a$=CH$_2$COOH; $R^b$=CH$_2$CH$_3$; $R^c$=CH$_3$;
  $R^i$=CH$_2$Ph; n=1;
4-168. $R^b$=CH$_2$COOH; $R^c$=CH$_3$; $R^i$=CH$_2$CH$_2$CH$_3$; n=1;
4-169. $R^a$=CH$_3$; $R^b$=CH$_2$COOH; $R^c$=CH$_3$;
  $R^i$=CH$_2$CH$_2$Ph; n=1;
4-170. $R^a$=CH$_2$CH$_2$COOH; $R^b$=CH$_3$; $R^c$=CH$_3$;
  $R^i$=CH$_2$Ph; n=1;
4-171. $R^a$=CH$_3$; $R^b$=CH$_2$CH$_2$COOH; $R^c$=CH$_3$;
  $R^i$=CH$_2$CH$_2$CH$_3$; n=1;
4-172. $R^a$=Tet; $R^b$=CH$_3$; $R^c$=CH$_3$;
  $R^i$=CH$_2$CH$_2$-(4-F)Ph; n=1;
4-173. $R^a$=CH$_3$; $R^b$=Tet; $R^c$=CH$_3$;
  $R^i$=CH$_2$-(3,4-DiMeO)Ph; n=1;
4-174. $R^a$=CH$_3$; $R^b$=CH$_3$; $R^c$=Tet;
  $R^i$=CH$_2$CH$_2$CH$_3$; n=1;
4-175. $R^a$=CH$_2$Tet; $R^c$=CH$_3$; $R^1$=CH$_2$Ph; n=1;
4-176. $R^b$=CH$_2$Tet; $R^c$=CH$_3$; $R^i$=CH$_2$Ph; n=1;
4-177. $R^a$=CH$_2$Tet; $R^i$=CH$_2$Ph; n=1;
4-178. $R^a$=CH$_2$CH$_2$Tet; $R^b$=CH$_3$; $R^c$=CH$_3$;
  $R^i$=CH$_2$CH$_2$CH$_3$; n=1;
4-179. $R^b$=CH$_2$CH$_2$Tet; $R^c$=CH$_3$; $R^i$=CH$_2$Ph; n=1;
4-180. $R^a$=SO$_2$NHCOCH$_3$; $R^b$=CH$_3$; $R^c$=CH$_3$;
  $R^i$=CH$_2$-(3-MeO)Ph; n=1;
4-181. $R^b$=CH$_2$SO$_2$NHCOCH$_3$; $R^c$=CH$_3$; $R^i$=CH$_2$CH$_3$; n=1;
4-182. $R^a$=COOH; $R^b$=CH$_3$; $R^c$=CH$_3$; $R^i$=CH$_2$Ph; n=2;
4-183. $R^a$=CH$_3$; $R^b$=COOH; $R^i$=CH$_2$Ph; n=2;
4-184. $R^a$=CH$_2$CH$_3$; $R^c$=COOH; $R^i$=CH$_2$CH$_3$; n=2;
4-185. $R^a$=CH$_2$COOH; $R^b$=CH$_2$CH$_3$; $R^c$=CH$_3$;
  $R^i$=CH$_2$Ph; n=2;
4-186. $R^b$=CH$_2$COOH; $R^c$=CH$_3$; $R^i$=CH$_2$CH$_2$CH$_3$; n=2;
4-187. $R^a$=CH$_3$; $R^b$=CH$_2$COOH; $R^c$=CH$_3$;
  $R^i$=CH$_2$CH$_2$Ph; n=2;
4-188. $R^a$=CH$_2$CH$_2$COOH; $R^b$=CH$_3$; $R^c$=CH$_3$;
  $R^i$=CH$_2$Ph; n=2;
4-189. $R^a$=CH$_3$; $R^b$=CH$_2$CH$_2$COOH; $R^c$=CH$_3$;
  $R^i$=CH$_2$CH$_2$CH$_3$; n=2;
4-190. $R^a$=Tet; $R^b$=CH$_3$; $R^c$=CH$_3$;
  $R^i$=CH$_2$CH$_2$-(4-F)Ph; n=2;
4-191. $R^a$=CH$_3$; $R^b$=Tet; $R^c$=CH$_3$;
  $R^i$=CH$_2$-(3,4-DiMeO)Ph; n=2;
4-192. $R^a$=CH$_3$; $R^b$=CH$_3$; $R^c$=Tet;
  $R^i$=CH$_2$CH$_2$CH$_3$; n=2;
4-193. $R^a$=CH$_2$Tet; $R^c$=CH$_3$; $R^i$=CH$_2$Ph; n=2;
4-194. $R^b$=CH$_2$Tet; $R^c$=CH$_3$; $R^i$=CH$_2$Ph; n=2;
4-195. $R^a$=CH$_2$Tet; $R^i$=CH$_2$Ph; n=2;
4-196. $R^a$=CH$_2$CH$_2$Tet; $R^b$=CH$_3$; $R^c$=CH$_3$;
  $R^i$=CH$_2$CH$_2$CH$_3$; n=2;
4-197. $R^b$=CH$_2$CH$_2$Tet; $R^c$=CH$_3$; $R^i$=CH$_2$Ph; n=2;
4-198. $R^a$=SO$_2$NHCOCH$_3$; $R^b$=CH$_3$; $R^c$=CH$_3$;
  $R^i$=CH$_2$-(3-MeO)Ph; n=2;
4-199. $R^b$=CH$_2$SO$_2$NHCOCH$_3$; $R^c$=CH$_3$; $R^i$=CH$_2$CH$_3$; n=2;

Of these, the preferred compounds are Nos. 4-5, 4-15, 4-35, 4-56, 4-57, 4-64, 4-68, 4-73, 4-89, 4-103, 4-104, 4-120, 4-135, 4-136, 4-143, 4-152, 4-168 and 4-193, and the most preferred are Nos. 4-56, 4-57, 4-64, 4-103, 4-135 and 4-143.

In the above, the following abbreviations are used:

iBu isobutyl;

Bz benzyl;

Et ethyl;

Me methyl;

Ph phenyl;

Pr propyl;

Tet tetrazolyl.

In general, preferred compounds of the present invention are those compounds of Examples 5, 7, 9, 14, 15, 17, 19, 21, 23, 25, 29, 31, 33, 37, 42, 46, 52, 61, 72, 83, 84, 86, 87, 97, 102, 103, 104, 106, 111, 114, 116, 118, 120, 130, 132, 134, 136, 137, 141, 143, 145, 149, 152, 157, 161, 163, 165, 167, 170, 172, 174, 176, 178, 180, 182, 184, 190, 200, 202, 204, 212, 214, 217, 218, 221, 222, 228, 229, 233 and 235, while the most preferred compounds are those compounds of Examples 5, 7, 9, 14, 17, 19, 21, 25, 83, 84, 86, 87, 97, 103, 116, 118, 132, 136, 137, 141, 149, 152, 161, 165, 180, 190, 200, 204, 212, 218 and 233.

Other preferred compounds are:

(9-Benzyl-1-isopropyl-4-methylcarbazol-2-yl)acetic acid;
(9-Benzyl-1-methylthio-4-trifluoromethylcarbazol-2-yl) acetic acid;
(9-Benzyl-4-methylthiocarbazol-3-yl)acetic acid;
(9-Benzyl-4-methyl-1-methylthiocarbazol-2-yl)acetic acid;
(9-Benzyl-3-methyl-1-methylthiocarbazol-2-yl)acetic acid;
(9-Benzyl-4-methyl-1-methoxycarbazol-2-yl)acetic acid;
(9-Benzyl-1-methyl-4-methylthiocarbazol-3-yl)acetic acid;
(9-Benzyl-1-methyl-4-methylthiocarbazol-3-yl)acetic acid;
(8-Aza-9-benzyl-4-methyl-1-methylthiocarbazol-2-yl) acetic acid;

and pharmaceutically acceptable salts and esters thereof.

The compounds of the present invention may be prepared by a variety of methods well known per se for the preparation of compounds of this type. For example, they may be prepared as illustrated in the following Reaction Schemes A to K.

Reaction Scheme A

Compounds of formula (I) in which $R^3$ represents a hydrogen atom and $Y^3$ represents a carboxymethyl group, that is to say compounds of formula (XIII), may be prepared as shown in the following Reaction Scheme:

In this scheme, the starting material, the compound of formula (XI), may have been prepared following the procedure described in Chem. Ber., 95, 2205 (1962).

In the above formulae, $R^1$, $R^2$, $R^3$, $Y^1$, $Y^2$ and $Y^4$ are as defined above.

Step A1

In this step, a carboxylic acid compound of formula (XII) is prepared by the hydrolysis of a cyano compound of formula (XI).

This reaction is normally and preferably effected in the presence of a solvent, preferably an aqueous solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran, dioxane or dimethoxyethane; alcohols, such as methanol or ethanol; and mixtures of alcohols and water. Of these, we prefer the alcohols or a mixture of an alcohol and water.

There is likewise no particular restriction upon the nature of the base used, and any base commonly used in conventional hydrolysis reactions may equally be used here. Examples of suitable bases include: alkali metal carbonates, such as sodium carbonate, potassium carbonate or lithium carbonate; alkali metal hydroxides, such as lithium hydroxide, sodium hydroxide or potassium hydroxide; and alkaline earth metal hydroxides, such as barium hydroxide. Of these, we prefer sodium hydroxide or potassium hydroxide.

The reaction with the base can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 150° C., more preferably from 25° to 100° C. or at the reflux temperature of the reaction medium. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 10 hours will usually suffice.

After completion of the reaction, the desired compound can be recovered from the reaction mixture by conventional means. For example, one suitable method comprises: washing the organic phase with water; separating the organic phase containing the desired compound; drying the resulting solution over a drying agent, such as anhydrous magnesium sulfate; and distilling off the solvent. The desired compound thus obtained can, if required, be further purified by such conventional means as recrystallization, reprecipitation or the various chromatography techniques, notably column chromatography.

Step A2

In this step, the carboxylic acid compound of formula (XII), prepared as described in Step A1, is subjected to an Arndt-Eistert synthesis, to introduce A methylene group attached to the carboxyl group and produce a compound of formula (XIII), which may be a compound of the present invention.

In the first reaction of this step, the carboxylic acid compound of formula (XII) is first converted to its acid halide, preferably acid chloride, by reaction with a halogenating, preferably chlorinating, agent, such as oxalyl chloride, carbonyl chloride, phosphorus oxychloride or phosphorus pentachloride, preferably oxalyl chloride. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride, chloroform or dichloroethane; ethers, such as diethyl ether, tetrahydrofuran, dioxane or dimethoxyethane; and amides, such as formamide, dimethylformamide or dimethylacetamide. Of these, we prefer the halogenated hydrocarbons (particularly methylene chloride) or amides (particularly dimethylformamide).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 50° C., more preferably at about room temperature. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 12 hours will usually suffice.

In the next reaction of this step, the acid halide, preferably acid chloride, prepared as described above, is converted to the corresponding diazoketone by reaction with diazomethane. The reaction is normally and preferably effected in the Presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran, dioxane or dimethoxyethane; alcohols, such as methanol or ethanol; ketones, such as acetone or methyl ethyl ketone; and water. Of these, we prefer the alcohols (particularly methanol) or ethers (particularly diethyl ether).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 50° C., more preferably at about room temperature. The time required for the reaction may also vary widely, depending on many factors, notably the reaction temperature and the nature of the reagents and solvent employed. However, provided that the reaction is effected under the preferred conditions outlined above, a period of from 5 to 30 hours, more preferably from 10 to 24 hours will usually suffice.

In the final reaction of this step, the diazoketone is converted to the desired compound of formula (XIII) by reaction with water in the presence of a catalyst, preferably a heavy metal catalyst, such as silver or silver oxide. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran, dioxane or dimethoxyethane; alcohols, such as methanol or ethanol; ketones, such as acetone or methyl ethyl ketone; and water. Of these, we prefer the alcohols (particularly methanol).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 10° to 150° C., more preferably at the reflux temperature of the reaction medium. The time required for the reaction may also vary widely, depending on many factors, notably the reaction temperature and the nature of the reagents and solvent employed. However, provided that the reaction is effected under the preferred conditions outlined above, a period of from 1 to 20 hours, more preferably from 3 to 10 hours will usually suffice.

After completion of any or all of the above reactions, the desired compound can be recovered from the reaction mixture by conventional means. For example, one suitable method comprises: washing the organic phase with water; separating the organic phase containing the desired compound; drying the resulting solution over a drying agent, such as anhydrous magnesium sulfate; and distilling off the solvent. The desired compound thus obtained can, if required, be further purified by such conventional means as recrystallization, reprecipitation or the various chromatography techniques, notably column chromatography.

Reaction Scheme B

Compounds of formula (I) in which $R^3$ preferably represents a hydrogen atom and $Y^3$ represents a 2-carboxyethyl group, that is to say compounds of formula (XVIII), may be prepared as shown in the following Reaction Scheme:

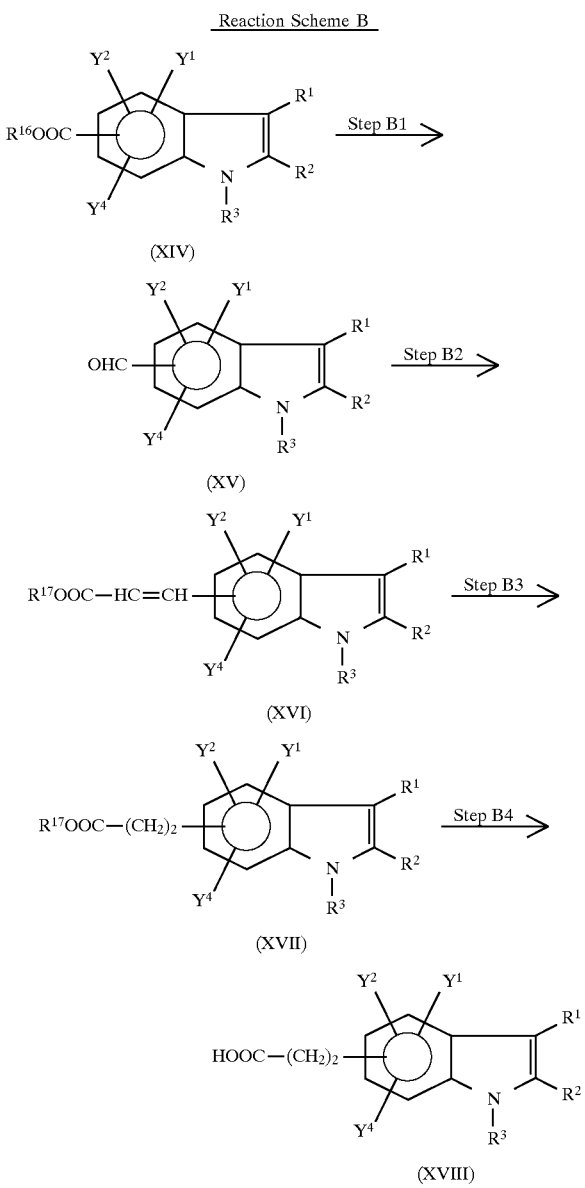

In the above formulae, $R^1$, $R^2$, $R^3$, $Y^1$, $Y^2$ and $Y^4$ are as defined above, and $R^{16}$ and $R^{17}$ are the same or different and each represents a carboxy-protecting group.

There is no particular restriction on the nature of the carboxy-protecting group represented by $R^{16}$ and $R^{17}$, and any carboxy-protecting group known in the art may equally be used in this reaction. Examples of such groups which may be used in this reaction include those protecting groups defined and exemplified above in relation to the carboxy-protecting groups which may be represented by $Y^1$, etc.

Step B1

In this step, the compound of formula (XIV) is reduced to a formyl compound of formula (XV).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Preferred solvents are non-polar. Examples of suitable solvents include: aliphatic hydrocarbons, such as hexane; aromatic hydrocarbons, such as benzene, toluene or xylene; ethers, such as diethyl ether, tetrahydrofuran, dioxane or dimethoxyethane; halogenated hydrocarbons, such as methylene chloride, chloroform or dichloroethane; and alcohols, such as methanol or ethanol. Of these, we prefer the alcohols (particularly methanol), halogenated hydrocarbons (particularly methylene chloride) and the ethers (particularly tetrahydrofuran).

There is likewise no particular restriction upon the nature of the reducing agent used, and any reducing agent commonly used in conventional reactions may equally be used here. Examples of suitable reducing agents include sodium borohydride, lithium aluminum hydride, diisobutylaluminum hydride, lithium aluminum tri-t-butoxyhydride and lithium aluminum trimethoxy-hydride.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from $-78°$ to $50°$ C., more preferably from $-60°$ to $25°$ C. and most preferably at about room temperature. The time required for the reaction may also vary widely, depending on many factors, notably the reaction temperature and the nature of the reagents and solvent employed. However, provided that the reaction is effected under the preferred conditions outlined above, a period of from 5 minutes to 24 hours, preferably 10 minutes to 12 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible organic solvent, such as ethyl acetate; washing the organic phase with water; separating the organic phase containing the desired compound; drying the extract over a drying agent, such as anhydrous magnesium sulfate; and distilling off the solvent. The desired compound thus obtained can, if required, be further purified by such conventional means as recrystallization, reprecipitation or the various chromatography techniques, notably column chromatography.

Step B2

In this step, a compound of formula (XVI) is prepared by a Wittig reaction from a compound of formula (XV), which may have been prepared by the procedure described in step B1.

The compound of formula (XV) is reacted with a Wittig reagent, in this case preferably an alkyl or aralkyl di(alkyl or aryl)phosphonoacetate under conditions conventional for this type of reaction. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; halogenated hydrocarbons, such as methylene chloride, chloroform or dichloroethane; ethers, such as diethyl ether, tetrahydrofuran, dioxane or dimethoxyethane; nitriles, such as acetonitrile or isobutyronitrile; amides, such as formamide, dimethylformamide, dimethylacetamide or hexamethylphosphoric triamide; and sulfoxides, such as dimethyl sulfoxide or sulfolane. Of these, we prefer tetrahydrofuran.

The reaction can take place over a wide range of temperatures, and the precise reaction temperature is not critical to the invention. In general, we find it convenient to carry out the reaction at a temperature of from $0°$ to $80°$ C., more preferably from $0°$ to $20°$ C. The time required for the reaction may also vary widely, depending on many factors, notably the reaction temperature and the nature of the reagents and solvent employed. However, provided that the reaction is effected under the preferred conditions outlined above, a period of from 5 minutes to 5 hours, more preferably from 10 minutes to 30 minutes, will usually suffice.

After completion of the reaction, the desired compound can be recovered from the reaction mixture by conventional means. For example, one suitable method comprises: filtering off insoluble materials, if any; adding water and a water-immiscible organic solvent, such as ethyl acetate; washing the organic phase with water or an aqueous solution; separating the organic phase containing the desired compound; drying the extract over a drying agent, such as anhydrous magnesium sulfate; and distilling off the solvent. The desired compound thus obtained can, if required, be further purified by such conventional means as recrystallization, reprecipitation or the various chromatography techniques, notably column chromatography.

Step B3

In this step, the carbon-carbon double bond in the compound of formula (XVI), which may have been prepared as described in Step B2, is reduced to a carbon-carbon single bond, to produce the compound of formula (XVII).

Any reduction process commonly used for this type of reaction may be employed here, although a catalytic reduction process is preferred. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; ethers, such as diethyl ether, tetrahydrofuran, dioxane or dimethoxyethane; and alcohols, such as methanol or ethanol. Of these, we prefer the alcohols (particularly methanol) and the ethers (particularly tetrahydrofuran).

There is likewise no particular restriction upon the nature of the catalyst used, and any catalyst commonly used in conventional reactions may equally be used here. Examples of suitable catalysts include palladium, palladium-on-charcoal, platinum or Raney nickel.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from $-20°$ to $40°$ C., more preferably from $0°$ to 25° C., most preferably about room temperature. The time required for the reaction may also vary widely, depending on many factors, notably the reaction temperature and the nature of the reagents and solvent employed. However, provided that the reaction is effected under the preferred conditions outlined above, a period of from 5 minutes to 24 hours, more preferably from 10 minutes to 12 hours will usually suffice.

After completion of the reaction, the desired compound can be recovered from the reaction mixture by conventional means. For example, one suitable method comprises: filtering off the catalyst employed and then distilling off the solvent. The desired compound thus obtained can, if required, be further purified by such conventional means as recrystallization, reprecipitation or the various chromatography techniques, notably column chromatography.

Step B4

In this step, the compound of formula (XVII) is hydrolysed to remove the carboxy-protecting group $R^{17}$ and give the desired compound of formula (XVIII). The reaction is normally and preferably effected in the presence of a base.

This reaction is also normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as tetrahydrofuran, dioxane or dimethoxyethane; alcohols, such as methanol or ethanol; and mixtures of alcohols and water. Of these, we prefer the alcohols or a mixture of an alcohol and water.

There is likewise no particular restriction upon the nature of the base used, and any base commonly used in conventional reactions of this type may equally be used here. Examples of suitable bases include: alkali metal carbonates, such as sodium carbonate, potassium carbonate or lithium carbonate; and alkali metal hydroxides, such as sodium hydroxide, potassium hydroxide or lithium hydroxide, or alkaline earth metal hydroxides, such as barium hydroxide. Of these, we prefer sodium hydroxide or potassium hydroxide.

The reaction with the base can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° to 150° C., more preferably from 10° to 50° C., and most preferably about room temperature. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 10 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible organic solvent, such as ethyl acetate; washing the organic phase with water or with an appropriate aqueous solution; separating the organic phase containing the desired compound; drying the extract over a drying agent, such as anhydrous magnesium sulfate; and distilling off the solvent. The desired product thus obtained can, if required, be further purified by such conventional means as recrystallization, reprecicitation or the various chromatography techniques, notably column chromatography.

Reaction Scheme C

In this reaction scheme, a compound of formula (XXIV) or (XXV) is prepared.

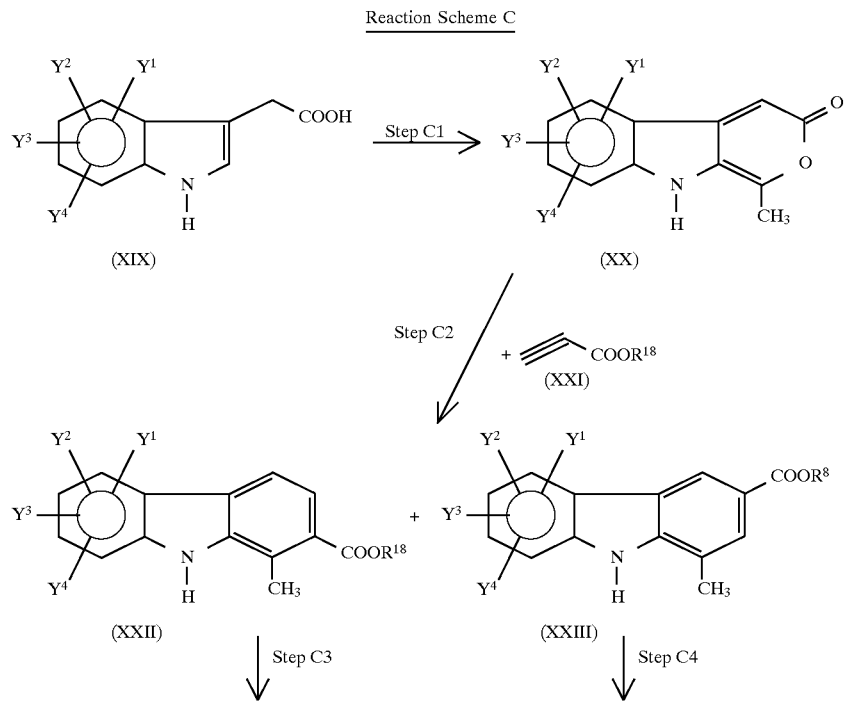

-continued
Reaction Scheme C

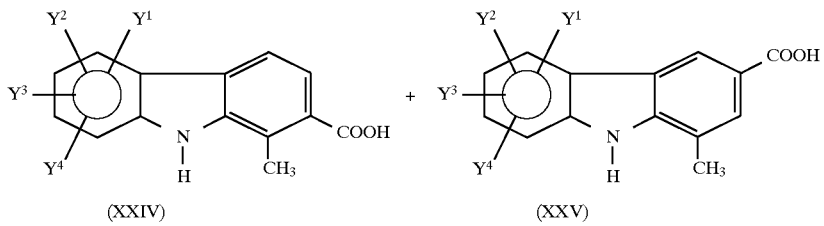

In the above formulae, $Y^1$, $Y^2$, $Y^3$ and $Y^4$ are as defined above, and $R^{18}$ represents a carboxy-protecting group, for example as defined and exemplified above.

Step C1

In this step, the compound of formula (XIX) is reacted with acetic anhydride in the presence of a Lewis acid, to prepare a compound of formula (XX).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Non-polar solvents are preferred. Examples of suitable solvents include: aliphatic hydrocarbons, such as hexane; aromatic hydrocarbons, such as benzene, toluene or xylene; ethers, such as diethyl ether, tetrahydrofuran, dioxane or dimethoxyethane; halogenated hydrocarbons, such as methylene chloride, chloroform or dichloroethane; and alcohols, such as methanol or ethanol. Of these, we prefer the halogenated hydrocarbons (particularly methylene chloride) and the ethers (particularly diethyl ether).

There is likewise no particular restriction upon the nature of the Lewis acid used, and any Lewis acid commonly used in conventional reactions may equally be used here. Examples of suitable Lewis acids include boron trifluoride, boron trifluoride diethyl etherate, titanium tetrachloride and stannic chloride.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° C. to the boiling temperature of the reaction medium, more preferably from 30° C. to the boiling temperature of the reaction medium. The time required for the reaction may also vary widely, depending on many factors, notably the reaction temperature and the nature of the reagents and solvent employed. However, provided that the reaction is effected under the preferred conditions outlined above, a period of from 30 minutes to 10 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible organic solvent, such as ethyl acetate; washing the organic phase with water or with an appropriate aqueous solution; separating the organic phase containing the desired compound; drying the extract over a drying agent, such as anhydrous magnesium sulfate; and distilling off the solvent. The desired product thus obtained can, if required, be further purified by such conventional means as recrystallization, reprecipitation or the various chromatography techniques, notably column chromatography.

Step C2

In this step, the compound of formula (XX), which may have been prepared as described in Step C1, is reacted with a propiolate of formula (XXI) in a Diels-Alder reaction, to give a mixture of compounds of formulae (XXII) and (XXIII).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Non-polar solvents are preferred. Examples of suitable solvents include: aliphatic hydrocarbons, such as hexane; aromatic hydrocarbons, such as benzene, toluene or xylene; ethers, such as diethyl ether, tetrahydrofuran, dioxane or dimethoxyethane; halogenated hydrocarbons, such as methylene chloride, chloroform or dichloroethane; and alcohols, such as methanol or ethanol. Of these, we prefer the alcohols (particularly methanol), halogenated hydrocarbons (particularly methylene chloride), the ethers (particularly tetrahydrofuran) and the aromatic hydrocarbons (particularly xylene).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° C. to the boiling temperature of the reaction medium, more preferably from 30° C. to the boiling temperature of the reaction medium. The time required for the reaction may also vary widely, depending on many factors, notably the reaction temperature and the nature of the reagents and solvent employed. However, provided that the reaction is effected under the preferred conditions outlined above, a period of from 30 minutes to 10 hours will usually suffice.

After completion of the reaction, the desired compound can be recovered from the reaction mixture by conventional means. For example, one suitable method comprises removing the solvent by distillation, preferably in vacuo, to leave the desired product, which can, if required, be further purified by such conventional means as recrystallization, reprecipitation or the various chromatography techniques, notably column chromatography.

The compounds of formulae (XXII) and (XXIII) may be separated at this stage or they may be used as a mixture in steps C3 and C4.

Steps C3 and C4

In these steps the compounds of formulae (XXII) and (XXIII) are hydrolysed to give compounds of formulae (XXIV) and (XXV), respectively. The reaction involved in this Step is essentially the same as that involved in Step B4 of Reaction Scheme B, and may be carried out using the same reagents and reaction conditions.

Reaction Scheme D

In this scheme, a compound of formula (XXVI), which may have been prepared following the procedures described in Chem. Pharm. Bull., 29, 1601 (1981), is hydrolysed, to give a compound of formula (XXVII):

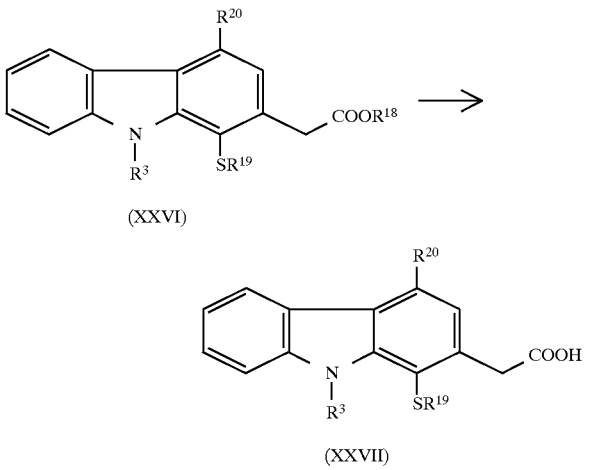

(XXVI)

(XXVII)

In the above formulae, $R^3$ and $R^{18}$ are as defined above; and $R^{19}$ and $R^{20}$ are the same or different and each represents an alkyl group having from 1 to 6 carbon atoms. Examples of such alkyl groups include the methyl, ethyl, propyl, isopropyl, butyl, isobutyl, sec-butyl, t-butyl, pentyl, isopentyl, neopentyl, 2-methylbutyl, 1-ethylpropyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl, 2-ethylbutyl, hexyl and isohexyl groups. Of these, we prefer those alkyl groups having from 1 to 4 carbon atoms, preferably the methyl, ethyl, propyl, isopropyl, butyl and isobutyl groups, and most preferably the methyl group.

The reaction involved in this Step is essentially the same as that involved in Step B4 of Reaction Scheme B, and may be carried out using the same reagents and reaction conditions.

Reaction Scheme E

In this scheme, a compound of formula (XXVIII), which is a compound of formula (I) in which $R^3$ represents a hydrogen atom, is converted to a compound of formula (XXIX), which is a compound of formula (I) in which $R^3$ represents an amino-protecting group, particularly an alkyl, aralkyl or acyl group:

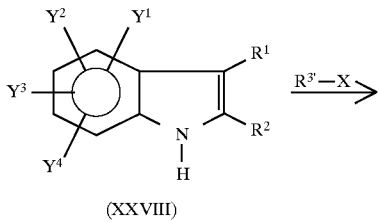

(XXVIII)

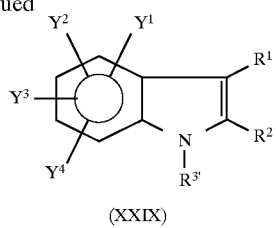

(XXIX)

In the above formulae, $R^1$, $R^2$, $Y^1$, $Y^2$, $Y^3$ and $Y^4$ are as defined above; $R^{3'}$ represents an alkyl, aralkyl or acyl group (as defined and exemplified above in relation to $R^3$); and X represents a leaving group.

This reaction involves reacting a compound of formula (XXVIII) with a suitable amount, for example from 1 to 4 equivalents (more preferably from 2 to 3 equivalents) of a compound of formula: $R^{3'}$—X (where $R^{3'}$ and X are as defined above) in a solvent in the presence or absence of a base, but preferably in the presence of a base.

There is no particular limitation upon the nature of the leaving group represented by X, provided that it is a group capable of leaving as a nucleophilic residue, such as are well known in the art. Examples of preferred leaving groups include: halogen atoms, such as the chlorine, bromine and iodine atoms; lower alkoxycarbonyloxy groups, such as the methoxycarbonyloxy and ethoxycarbonyloxy groups; halogenated alkylcarbonyloxy groups, such as the chloroacetoxy, dichloroacetoxy, trichloroacetoxy and trifluoroacetoxy groups; lower alkanesulfonyloxy groups, such as the methanesulfonyloxy and ethanesulfonyloxy groups; lower haloalkanesulfonyloxy groups, such as the trifluoromethanesulfonyloxy and pentafluoroethanesulfonyloxy groups; and arylsulfonyloxy groups, such as the benzenesulfonyloxy, P-toluenesulfonyloxy and D-nitrobenzenesulfonyloxy groups. Of these, we prefer the halogen atoms, lower haloalkanesulfonyloxy groups and arylsulfonyloxy groups.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; nitriles, such as acetonitrile and isobutyronitrile; and amides, such as formamide, dimethylformamide, dimethylacetamide, N-methyl-2-pyrrolidone, N-methylpyrrolidinone and hexamethylphosphoric triamide. Of these, we prefer the ethers (particularly dimethoxyethane or tetrahydrofuran) and the amides (particularly dimethylformamide).

There is likewise no particular restriction upon the nature of the base used, and any base commonly used in conventional reactions of this type may equally be used here. Examples of suitable bases include: alkali metal hydrides, such as lithium hydride, sodium hydride or potassium hydride; alkali metal alkoxides, such as sodium methoxide, sodium ethoxide, potassium t-butoxide or lithium methoxide; and organic metal bases, such as butyllithium or lithium diisopropylamide. Of these, we prefer the alkali metal hydrides (particularly lithium hydride or sodium hydride).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° to 60° C., more preferably from 0° C. to 20° C., for alkylation or aralkylation, and from −78° C. to room temperature, more preferably from −78° C. to 0° C., for acylation. The time required for the reaction may also vary widely, depending on many factors, notably the reaction temperature and the nature of the reagents and solvent employed. However, provided that the reaction is effected under the preferred conditions outlined above, a period of from 5 minutes to 24 hours, more preferably from 5 minutes to 6 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible organic solvent, such as ethyl acetate; washing the organic phase with water; separating the organic phase containing the desired compound; drying the extract over a drying agent, such as anhydrous magnesium sulfate; and distilling off the solvent. The desired compound thus obtained can, if required, be further purified by such conventional means as recrystallization, reprecipitation or the various chromatography techniques, notably column chromatography.

Alternatively, where $R^{3'}$ represents an acyl group, the compound of formula $R^{3'}$—X may be replaced by the corresponding anhydride of formula $R^{3''}$—O—$R^{3''}$ (where $R^{3''}$ represents an acyl group). This reaction may take place in the presence or absence of a base and is carried out under the same conditions, including solvent, temperatures and time, as described above.

Reaction Scheme F

In this scheme, an alkyl or aralkyl group, as defined and exemplified above in relation to substituents γ, is introduced into a compound of formula (XXX), to give a compound of formula (XXXI):

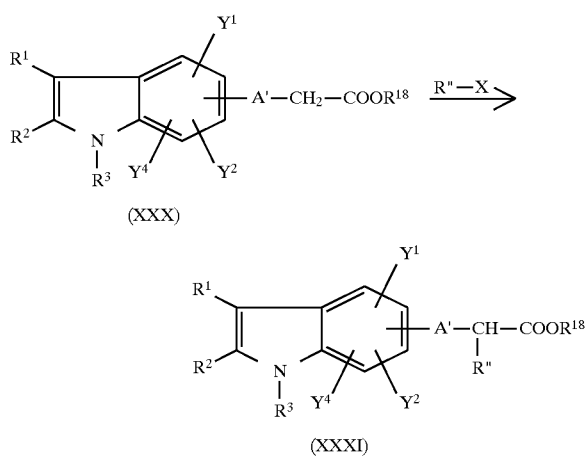

In the above formulae, $R^1$, $R^2$, $R^3$, $Y^1$, $Y^2$, and $Y^4$ are as defined above; R" represents an alkyl or aralkyl group, as defined and exemplified above in relation to substituents γ, A' represents an unsubstituted alkylene or oxyalkylene group having one fewer carbon atom than the corresponding group in the compound of formula (I); and $R^{18}$ and X are as defined and exemplified above. The reaction preferably takes place in the presence of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene or xylene; ethers, such as diethyl ether, tetrahydrofuran, dioxane or dimethoxyethane; amides, such as dimethylformamide, dimethylacetamide or hexamethylphosphoric triamide; and sulfoxides, such as dimethyl sulfoxide or sulfolane. Of these, we prefer the ethers (particularly tetrahydrofuran or dimethoxyethane) and the amides (particularly dimethylformamide).

There is likewise no particular restriction upon the nature of the base used, and any base commonly used in conventional reactions may equally be used here. Examples of suitable bases include: alkali metal hydrides, such as lithium hydride, sodium hydride or potassium hydride; alkali metal alkoxides, such as sodium methoxide, sodium ethoxide, potassium t-butoxide or lithium methoxide; and organic metal bases, such as butyllithium or lithium diisopropylamide. Of these, we prefer the alkali metal hydrides (particularly lithium hydride or sodium hydride).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° to 60° C., more preferably from 0° C. to 20° C. The time required for the reaction may also vary widely, depending on many factors, notably the reaction temperature and the nature of the reagents and solvent employed. However, provided that the reaction is effected under the preferred conditions outlined above, a period of from 5 minutes to 24 hours, more preferably from 5 minutes to 6 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible organic solvent, such as ethyl acetate; washing the organic phase with water; separating the organic phase containing the desired compound; drying the extract over a drying agent, such as anhydrous magnesium sulfate; and distilling off the solvent. The desired compound thus obtained can, if required, be further purified by such conventional means as recrystallization, reprecipitation or the various chromatography techniques, notably column chromatography.

Reaction Scheme G

This reaction scheme produces an indole derivative having two methylthio groups at the 4-position and an oxo group at the 5-position, which may be a useful starting material for the preparation of some of the compounds of the present invention:

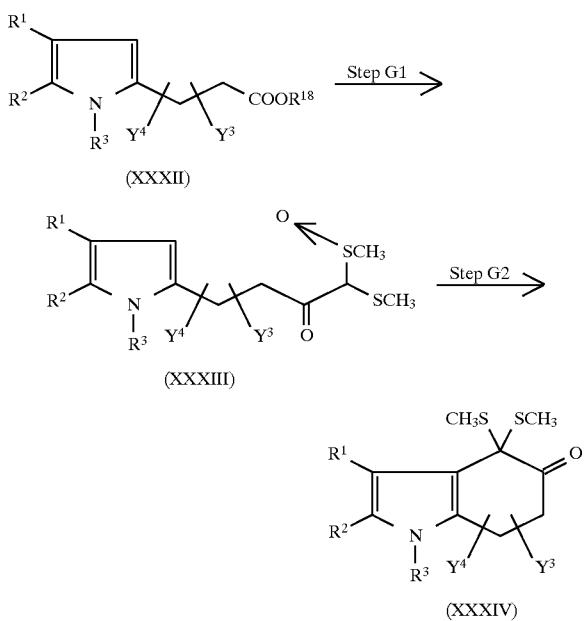

(XXXII)

(XXXIII)

(XXXIV)

In the above formulae, $R^1$, $R^2$, $R^3$, $Y^3$, and $Y^4$ are as defined above.

Step G1

In this step, a compound of formula (XXXII) is reacted with methyl methylsulfinylmethyl sulfide, to give a compound of formula (XXXIII).

This reaction preferably takes place in the presence of an acid. There is no particular restriction upon the nature of the acid used, and any acid commonly used in conventional reactions may equally be used here. Examples of suitable acids include: Lewis acids, such as boron trifluoride, boron trifluoride diethyl etherate, titanium tetrachloride and stannic chloride; mineral acids, especially hydrohalic acids (such as hydrofluoric acid, hydrobromic acid, hydroiodic acid or hydrochloric acid), nitric acid, carbonic acid, sulfuric acid or phosphoric acid; lower alkylsulfonic acids, such as methanesulfonic acid, trifluoromethanesulfonic acid or ethanesulfonic acid; arylsulfonic acids, such as benzenesulfonic acid or p-toluenesulfonic acid; and organic carboxylic acids, such as acetic acid or benzoic acid.

The reaction is normally and preferably effected in the presence of a solvent. There is no particular restriction on the nature of she solvent to be employed, provided that it has no adverse effect on the reaction or on the reagents involved and that it can dissolve the reagents, at least to some extent. Preferred solvents are non-polar. Examples of suitable solvents include: aromatic hydrocarbons, such as benzene, toluene or xylene; ethers, such as diethyl ether, tetrahydrofuran, dioxane or dimethoxyethane; amides, such as dimethylformamide, dimethylacetamide or hexamethylphosphoric triamide; and sulfoxides, such as dimethyl sulfoxide or sulfolane. Of these, we prefer the ethers (particularly tetrahydrofuran or dimethoxyethane) and the amides (particularly dimethylformamide).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −78° C. to the reflux temperature of the reaction medium, more preferably from 0° C. to the reflux temperature of the reaction medium. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 30 minutes to 6 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible organic solvent, such as ethyl acetate; washing the organic phase with water; separating the organic phase containing the desired compound; drying the extract over a drying agent, such as anhydrous magnesium sulfate; and distilling off the solvent. The desired compound thus obtained can, if required, be further purified by such conventional means as recrystallization, reprecipitation or the various chromatography techniques, notably column chromatography.

Step G2

In this step, a compound of formula (XXXIII) is cyclised by treatment with an acid, to give a compound of formula (XXXIV).

This reaction takes place in the presence of an acid. There is no particular restriction upon the nature of the acid used, and any acid commonly used in conventional reactions may equally be used here. Examples of suitable acids include: Lewis acids, such as boron trifluoride, boron trifluoride diethyl etherate, titanium tetrachloride and stannic chloride; mineral acids, especially hydrohalic acids (such as hydrofluoric acid, hydrobromic acid, hydroiodic acid or hydrochloric acid), nitric acid, carbonic acid, sulfuric acid or phosphoric acid; lower alkylsulfonic acids, such as methanesulfonic acid, trifluoromethanesulfonic acid or ethanesulfonic acid; arylsulfonic acids, such as benzenesulfonic acid or p-toluenesulfonic acid; and organic carboxylic acids, such as acetic acid or benzoic acid.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Preferred solvents are non-polar. Examples of suitable solvents include: aromatic hydrocarbons, such as benzene, toluene or xylene; ethers, such as diethyl ether, tetrahydrofuran, dioxane or dimethoxyethane; amides, such as dimethylformamide, dimethylacetamide or hexamethylphosphoric triamide; and sulfoxides, such as dimethyl sulfoxide or sulfolane. Of these, we prefer the ethers (particularly tetrahydrofuran or dimethoxyethane) and the amides (particularly dimethylformamide).

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from 0° C. to 200° C., more preferably from about room temperature to 150° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours, more preferably from 30 minutes to 6 hours will usually suffice.

After completion of the reaction, the desired compound can be recovered from the reaction mixture by conventional means. For example, one suitable method comprises: properly neutralizing the reaction mixture; filtering off insoluble materials, if any; adding water and a water-immiscible organic solvent, such as ethyl acetate; washing the organic phase with water; separating the organic phase containing the desired compound; drying the extract over a drying agent, such as anhydrous magnesium sulfate; and distilling off the solvent. The desired compound thus obtained can, if required, be further purified by such conventional means as recrystallization, reprecipitation or the various chromatography techniques, notably column chromatography.

Reaction Scheme H

Compounds containing a carboxyl group can be converted to the corresponding compounds containing a tetrazolylmethyl group by the following reactions:

Step H1

In this step, the carboxylic acid compound is reacted with a cyano compound (preferably an alkali metal cyanide, such as sodium cyanide or potassium cyanide, or a trialkylsilyl cyanide in which the alkyl parts have from 1 to 6 carbon atoms, such as trimethylsilyl cyanide) in an inert solvent. When the trialkylsilyl cyanide is employed, the O-trialkylsilyl derivative thus obtained is then treated with an acid, to give a desired cyanomethyl compound.

When an alkali metal cyanide is employed, it is preferably used in an amount of from 1 to 3 equivalents, more preferably from 1.2 to 2 equivalents per mole of the carboxylic acid compound. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran or dioxane; halogenated hydrocarbons, especially halogenated alipphatic hydrocarbons, such as methylene chloride or chloroform; alcohols, such as methanol or ethanol; water; or a mixture of water and one or more of these organic solvents. The reaction can take place over a wide range of temperatures, and the precise reaction temperature is not critical to the invention. In general, we find it convenient to carry out the reaction at a temperature of from $-10°$ C. to $80°$ C., more preferably from $0°$ C. to $30°$ C. The time required for the reaction may also vary widely, depending on many factors, notably the reaction temperature and the nature of the reagents and solvent employed. However, provided that the reaction is effected under the preferred conditions outlined above, a period of from 1 to 24 hours, more preferably from 2 to 16 hours, will usually suffice. This reaction can, if desired, be accelerated by adding sodium hydrogen sulfite. After completion of the reaction, the product can be recovered by conventional means, for example by extracting the reaction mixture with a water-immiscible organic solvent (such as ethyl acetate) and evaporating the solvent from the extract. If necessary, the resulting product can be further purified by conventional means, such as recrystallization or the various chromatography techniques, notably column chromatography.

If a trialkylsilyl cyanide is employed, it is preferably used in an amount of from 1 to 2 equivalents, more preferably from 1.05 to 1.2 equivalents, per mole of the carboxylic acid compound, and the reaction is preferably carried out in the presence of a catalytic amount of zinc iodide. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran or dioxane; and halogenated hydrocarbons, especially halogenated aliphatic hydrocarbons, such as methylene chloride and chloroform. The reaction can take place over a wide range of temperatures, and the precise reaction temperature is not critical to the invention. In general, we find it convenient to carry out the reaction at a temperature of from $-10°$ C. to $80°$ C., more preferably from $10°$ C. to $40°$ C. The time required for the reaction may also vary widely, depending on many factors, notably the reaction temperature and the nature of the reagents and solvent employed. However, provided that the reaction is effected under the preferred conditions outlined above, a period of from 30 minutes to 24 hours, more preferably from 1 to 16 hours, will usually suffice. After completion of the reaction, the desired cyano compound, in the form of its O-trialkylsilyl derivative, can be obtained by concentrating the reaction mixture, extracting the concentrate with a water-immiscible organic solvent, washing the extract with a weakly alkaline aqueous solution, such as aqueous sodium hydrogencarbonate, and evaporating off the solvent. If necessary, the resulting product can be further purified by conventional means, such as recrystallization or the various chromatography techniques, notably column chromatography.

The O-trialkylsilyl group is then removed. This reaction can be carried out by treatment with a catalytic amount of an acid (for example p-toluenesulfonic acid, methanesulfonic acid or hydrochloric acid) in a suitable solvent, the nature of which is not critical, provided that it has no adverse effect on the reaction or on the reagents involved and that it can dissolve the reagents, at least to some extent. Examples of suitable solvents include alcohols, such as methanol or ethanol. The reaction can take place over a wide range of temperatures, and the precise reaction temperature is not critical to the invention. In general, we find it convenient to carry out the reaction at a temperature of from $-20°$ C. to $60°$ C., more preferably around room temperature. The time required for the reaction may also vary widely, depending on many factors, notably the reaction temperature and the nature of the reagents and solvent employed. However, provided that the reaction is effected under the preferred conditions outlined above, a period of from 10 minutes to 5 hours, more preferably from 30 minutes to 2 hours, will usually suffice.

The product of this step is a compound in which the carboxyl group of the original compound has been replaced by a cyanomethyl group, i.e. it contains one more carbon atom than the original compound.

After completion of the reaction, the product can be recovered from the reaction mixture by conventional means, for example: by concentrating the reaction mixture, extracting the concentrate with a water-immiscible organic solvent, such as ethyl acetate, washing with a weakly alkaline aqueous solution, such as aqueous sodium hydrogencarbonate, and evaporating off the solvent. If necessary, the resulting product can be further purified by conventional means, such as recrystallization or the various chromatography techniques, notably column chromatography.

Step H2

This step is an alternative to step Hi and produces a cyano compound containing the same number of carbon atoms as the original carboxylic acid compound.

In the first part of this step, the carboxylic acid compound is converted to a corresponding carbamoyl compound by reaction of the carboxylic acid compound (or an active derivative thereof, for example a lower alkyl ester, e.g. methyl ester, acid halide, e.g. chloride, or acid anhydride, which can be prepared by well known methods) with ammonia.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, tetrahydrofuran, dioxane or dimethoxyethane; alcohols, such as methanol or ethanol; ketones, such as acetone or methyl ethyl ketone; and water. Of these, we prefer the alcohols (particularly methanol).

The reaction can take place over a wide range of temperatures, and the precise reaction temperature is not critical to the invention. In general, we find it convenient to carry out the reaction at a temperature of from 10° C. to 50° C., more preferably at about room temperature. The time required for the reaction may also vary widely, depending on many factors, notably the reaction temperature and the nature of the reagents and solvent employed. However, provided that the reaction is effected under the preferred conditions outlined above, a period of from 1 hour to 10 days, more preferably from 10 hours to 8 days, will usually suffice.

The resulting carbamoyl compound is then dehydrated, to give a cyano compound.

This reaction may be conducted by reacting the corresponding carbamoyl compound with a dehydrating agent, preferably an acid anhydride, such as acetic anhydride, trifluoroacetic anhydride, methanesulfonic anhydride or trifluoromethanesulfonic anhydride, or thionyl chloride. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene and heptane; halogenated hydrocarbons, especially halogenated aliphatic hydrocarbons, such as methylene chloride and chloroform; ethers, such as diethyl ether, tetrahydrofuran and dioxane; and esters, such as ethyl acetate and butyl acetate. The reaction is effected in the presence of an organic amine, preferably triethylamine, pyridine or N-methylmorpholine.

The reaction can take place over a wide range of temperatures, and the precise reaction temperature is not critical to the invention. In general, we find it convenient to carry out the reaction at a temperature of from –10° C. to 100° C., more preferably from 0° C. to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 16 hours, more preferably from 30 minutes to 6 hours, will usually suffice.

After completion of the reaction, the product can be recovered by adding a weakly basic aqueous solution (such as an aqueous solution of sodium hydrogencarbonate) and a water-immiscible organic solvent, such as ethyl acetate, to the reaction mixture, separating the resulting organic solvent layer and distilling off the solvent. The product may then, if necessary, be further purified by conventional means, for example, by recrystallization, or by the various chromatography techniques, notably by column chromatography.

Step H3

In this step, a tetrazolylmethyl or tetrazolyl compound is prepared by converting the cyano group contained in the cyanomethyl compound, obtained as described in step H1, or the cyano compound, obtained as described in step H2, to a tetrazolyl group. This step can be carried out using any of the following three reactions.

Reaction (a): Reaction with an alkali metal azide

This reaction is carried out by reacting the corresponding cyanomethyl or cyano compound with a suitable amount, for example from 1 to 5 equivalents, more preferably from 1 to 3 equivalents, of an alkali metal azide, such as lithium azide, sodium azide or potassium azide, preferably sodium azide, in the presence of an ammonium halide. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as dioxane or 1,2-dimethoxyethane; alcohols, such as methanol or ethanol; amides, such as dimethylformamide or dimethylacetamide; and sulfoxides, such as dimethyl sulfoxide. The amount of ammonium halide is preferably from 0.5 to 2 equivalents, more preferably from 1 to 1.2 equivalents, per mole of the cyanomethyl or cyano compound. Examples of suitable ammonium halides include ammonium fluoride, ammonium chloride and ammonium bromide, preferably ammonium chloride.

The reaction can take place over a wide range of temperatures, and the precise reaction temperature is not critical to the invention. In general, we find it convenient to carry out the reaction at a temperature of from 70° C. to 150° C., more preferably from 90° C. to 120° C. The time required for the reaction may also vary widely, depending on many factors, notably the reaction temperature and the nature of the reagents and solvent employed. However, provided that the reaction is effected under the preferred conditions outlined above, a period of from 10 hours to 7 days, more preferably from 1 to 5 days will usually suffice.

After completion of the reaction, the product may be recovered from the reaction mixture by conventional means. For example, water and a water-immiscible organic solvent, such as ethyl acetate, are added to the reaction mixture, and the organic solvent layer is separated, after which the solvent is evaporated off, to give the product. If necessary, the resulting product can be further purified by conventional means, such as recrystallization or the various chromatography techniques, notably column chromatography.

Reaction (b): Reaction with a trialkyl or triaryltin azide

This reaction is carried out by reacting the cyano cyano compound with a suitable amount, for example from 1 to 3 equivalents, more preferably from 1 to 2 equivalents, of a trialkyltin azide or a triaryltin azide. Examples of trialkyltin azides include those in which each alkyl group has from 1 to 6 carbon atoms, such as trimethyltin azide, triethyltin azide or tributyltin azide. Examples of triaryltin azides include triphenyltin azide and tritolyltin azide. The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: hydrocarbons, such as benzene, toluene, xylene or heptane; halogenated hydrocarbons, such as dichloroethane or chloroform; ethers, such as dioxane or 1,2-dimethoxyethane; esters, such as ethyl acetate or butyl acetate; amides, such as dimethylformamide or dimethylacetamide; and sulfoxides, such as dimethyl sulfoxide. The resulting tin adduct is then treated with an acid (preferably hydrochloric acid or sulfuric acid), a base (preferably an alkali metal hydroxide, such as sodium hydroxide or potassium hydroxide, an alkali metal carbonate, such as sodium carbonate or potassium carbonate, or an alkali metal hydrogencarbonate, such as sodium hydrogencarbonate or potassium hydrogencarbonate) or an alkali metal fluoride (preferably sodium fluoride or potassium fluoride). The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: those solvents described above; alcohols, such as methanol or ethanol; water; and aqueous alcohols.

The reaction can take place over a wide range of temperatures, and the precise reaction temperature is not critical to the invention. In general, we find it convenient to carry out the reaction with the tin compound at a temperature of from 60° C. to 150° C., more preferably from 80° C. to 120° C., and the treatment with the acid, base or fluoride at around room temperature. The time required for the reaction may also vary widely, depending on many factors, notably the reaction temperature and the nature of the reagents and solvent employed. However, provided that the reaction is effected under the preferred conditions outlined above, a period of from 8 hours to 7 days, more preferably from 1 to 5 days will usually suffice for the reaction with the tin compound, whilst the treatment with the acid, base or fluoride will normally require from 30 minutes to 24 hours, more preferably from 1 to 6 hours.

After completion of the reaction, the product may be recovered from the reaction mixture by conventional means. For example, water and a water-immiscible organic solvent, such as ethyl acetate, are added to the reaction mixture, and the organic solvent layer is separated, after which the solvent is evaporated off, to give the product. If necessary, the resulting product can be further purified by conventional means, such as recrystallization or the various chromatography techniques, notably column chromatography.

Reaction (c): Reaction with a trialkyl or triaryltin halide and an alkali metal azide This reaction is carried out in the same manner as in Reaction (b), except that a suitable amount, for example from 1 to 3 equivalents, more preferably from 1 to 2 equivalents, of a trialkyl or triaryltin halide (for example trimethyltin chloride, triethyltin chloride, tributyltin chloride or triphenyltin chloride) and a suitable amount, for example from 1 to 3 equivalents, more preferably from 1 to 2 equivalents, of an alkali metal azide (preferably sodium azide or potassium azide) are used in place of the trialkyl or triaryltin azide.

After completion of the reaction, the product may be recovered from the reaction mixture by conventional means. For example, water and a water-immiscible organic solvent, such as ethyl acetate, are added to the reaction mixture, and the organic solvent layer is separated, after which the solvent is evaporated off, to give the product. If necessary, the resulting product can be further purified by conventional means, such as recrystallization or the various chromatography techniques, notably column chromatography.

Reaction Scheme I

Compounds containing a carboxyalkyl group can be converted to the corresponding α-hydroxycarbonyl compounds by α-hydroxylation of the carboxyl moiety by reacting the carboxyalkyl containing compound with a base and, subsequently, molecular oxygen (preferably oxygen gas).

There is no particular restriction upon the nature of the base used, and any base commonly used in conventional α-hydroxylation reactions may be used. Examples of suitable bases include the organic metal bases, such as butyllithium, lithium diisopropylamide, sodium hexamethyldisilazide and lithium hexamethyldisilazide (which may be prepared following the procedures described in U.S. Pat. No. 4,347,375). Of these, we prefer sodium hexamethyldisilazide or lithium hexamethyldisilazide (particularly lithium hexamethyldisilazide).

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Preferred solvents are non-polar. Example of suitable solvents include: aromatic hydrocarbons, such as benzene, toluene or xylene; ethers, such as diethyl ether, tetrahydrofuran, dioxane or dimethoxyethane. Of these, we prefer the ethers, particularly tetrahydrofuran.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −20° C. to 100° C., more preferably from about 0° C. to 50° C.

The time required for the reaction may also vary widely, depending on many factors, notably the reaction temperature and the nature of the reagents and solvent employed. However, provided that the reaction is effected under the preferred conditions outlined above, a period from 10 minutes to 24 hours, more preferably from 30 minutes to 60 hours, will usually suffice.

After completion of the reaction, the desired compound can be recovered from the reaction mixture by conventional means. For example, one suitable method comprises: adding water and a water-immiscible organic solvent, such as ethyl acetate; washing the organic phase with water; separating the organic phase containing the desired compound; drying the resulting solution over a drying agent, such as anhydrous magnesium sulfate; and distilling off the solvent. The desired compound thus obtained can, if required, be further purified by such conventional means as recrystallisation, reprecipitation or one of the various chromatography techniques, notably column chromatography.

Reaction Scheme J

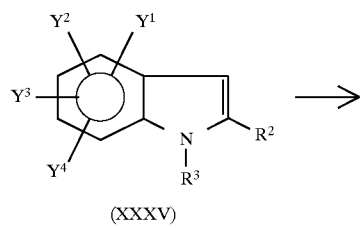

(XXXV)

-continued
Reaction Scheme J

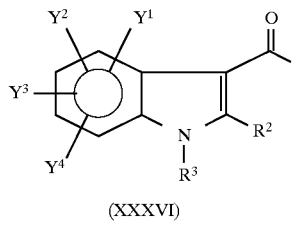

(XXXVI)

In the above formulae, $R^2$, $R^3$, $Y^1$, $Y^2$, $Y^3$ and $Y^4$ are as defined above, and $R^{51}$ represents a methyl group or a hydrogen atom.

Step J

In this step, an acetyl compound of formula (XXXVI) is prepared from an indole compound of formula (XXXV) by a Vilsmeier reaction using oxyphosphorylchloride and dimethylformamide or dimethylacetamide.

The reaction is normally and preferably effected in the presence of a solvent. There is no particular restriction on the nature of the solvent to be employed, provided that it has no adverse effect either on the reaction or on the reagents involved, and that it can dissolve the reagents, at least to some extent. Examples of suitable solvents include: aliphatic hydrocarbons, such as hexane; halogenated hydrocarbons, such as methylene chloride, chloroform or dichloroethane; ethers, such as diethyl ether, tetrahydrofuran, dioxane or dimethoxyethane; and amides, such as formamide, dimethylformamide or dimethylacetamide. We prefer to use dimethylformamide or dimethylacetamide as the solvent, especially as these compounds are also reactants.

The reaction can take place over a wide range of temperatures, and the precise reaction temperature is not critical to the invention. The preferred reaction temperature will depend upon such factors as the nature of the solvent and the starting materials. However, in general, we find it convenient to carry out the reaction at a temperature of from −20° C. to 200° C., more preferably from 0° C. to 100° C., and most preferably at about 5° to 10° C. The time required for the reaction may also vary widely, depending on many factors, notably the reaction temperature and the nature of the reagents and solvent employed. However, where the reaction is effected under the preferred conditions outlined above, a period of from 5 minutes to 24 hours, preferably 10 minutes to 12 hours, is usually sufficient.

After completion of the reaction, the desired compound can be recovered from the reaction mixture by conventional means. For example, one suitable method comprises: properly neutralizing the reaction mixture; filtering off insoluble materials, if any; adding water and a water-immiscible organic solvent, such as ethyl acetate; washing the organic phase with water; separating the organic phase containing the desired compound; drying the extract over a drying agent, such as anhydrous magnesium sulfate; and removing the solvent by evaporation under reduced pressure. The thus obtained compound can, if required, be further purified by such conventional means as recrystallization, reprecipitation or any of the various chromatography techniques, especially column chromatography.

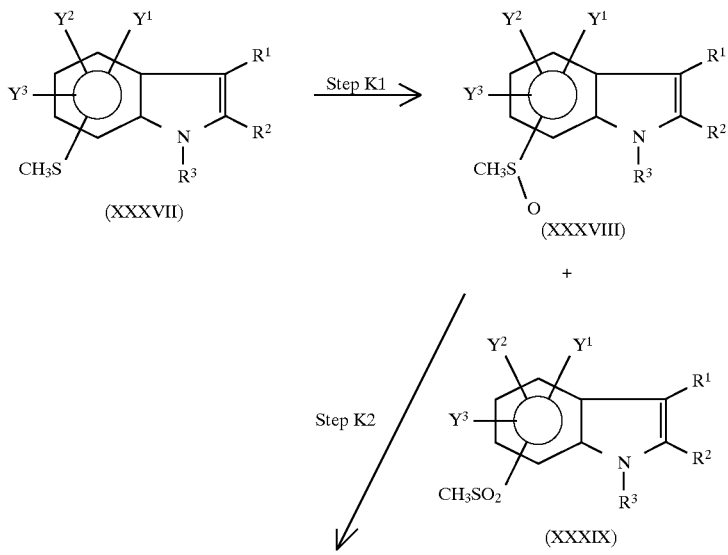

-continued
Reaction Scheme K

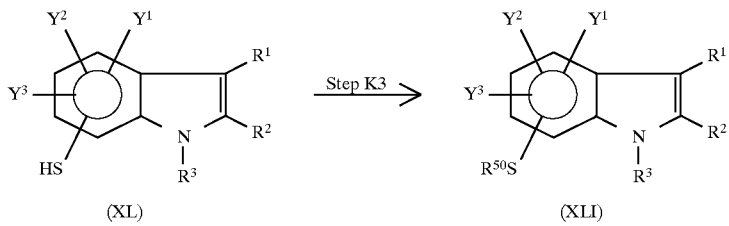

In the above formulae, $R^1$, $R^2$, $R^3$, $Y^1$, $Y^2$ and $Y^3$ are as defined above, $R^{50}$ represents an alkyl group having from 1 to 6 carbon atoms, and X represents a leaving group.

Step K1

In this step, the methylthio group of the compound of formula (XXXVII) is oxidized to a sulfinyl or sulfuryl group of a compound of formula (XXXVIII) or (XXXIX), respectively.

Any oxidation process commonly used for this type of reaction may be employed here, although a catalytic oxidation process is preferred.

The reaction is normally and preferably effected in the presence of a solvent. There is no particular restriction on the nature of the solvent to be employed, provided that it has no adverse effect either on the reaction or on the reagents involved and that it can dissolve the reagents, at least to some extent. Preferred solvents are non-polar, and examples of suitable solvents include: aliphatic hydrocarbons, such as hexane; aromatic hydrocarbons, such as benzene, toluene or xylene; ethers, such as diethyl ether, tetrahydrofuran, dioxane or dimethoxyethane; halogenated hydrocarbons, such as methylene chloride, chloroform or dichloroethane; and alcohols, such as methanol or ethanol. We prefer to use halogenated hydrocarbons or ethers as solvents, particularly methylene chloride or tetrahydrofuran.

There is likewise no particular restriction upon the nature of the catalyst used, and any catalyst commonly used in conventional reactions may equally be used here. An example of a suitable catalyst is m-chloroperbenzoic acid.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out the reaction at a temperature of from −78° to 80° C., more preferably from 0° to 50° C., and most preferably at about room temperature. The time required for the reaction may also vary widely, depending on many factors, notably the reaction temperature and the nature of the reagents and solvent employed. However, where the reaction is effected under the preferred conditions outlined above, a period of From 5 minutes to 24 hours, preferably about 10 minutes to 12 hours, is usually sufficient.

After the reaction has been allowed to go to completion, the target compound can be recovered from the reaction mixture by conventional means. For example, one suitable method comprises: properly neutralizing the reaction mixture; filtering off insoluble materials, if any; adding water and a water-immiscible organic solvent, such as ethyl acetate; washing the organic phase with water; separating the organic phase containing the desired compound; drying the extract over a drying agent, such as anhydrous magnesium sulfate; and removal of the solvent by evaporation under reduced pressure. The target compound can, if required, then be further purified by such conventional means as recrystallization, reprecipitation or any of the various chromatography techniques, especially column chromatography.

Step K2

In this step, a compound of formula (XL) is prepared from a compound of formula (XXXVIII) or (XXXIX) by a Pummerer rearrangement, as described in Tetrahedron Letters vol.25, No.17, 1753 (1984). The compound of formula (XXXVIII) or (XXXIX) may be prepared by the procedure described in step K1 above.

The compound of formula (XXXVIII) or (XXXIX) is reacted with a strong carboxylic acid anhydride, in this case preferably a trihalogenated acetic anhydride, such as trifluoroacetic anhydride, under conditions conventional for this type of reaction. The reaction mixture is then suitably dried, such as by treatment with anhydrous magnesium sulfate, and then hydrolyzed. Hydrolysis may be effected either with an with alcohol, such as methanol or ethanol, or with an acidic aqueous solution, such as an aqueous acetic acid.

The reaction is normally and preferably effected in the presence of a solvent. There is no particular restriction on the nature of the solvent to be employed, provided that it has no adverse effect either on the reaction or on the reagents involved, and that it can dissolve the reagents, at least to some extent. Examples of suitable solvents include: aromatic hydrocarbons, such as benzene, toluene or xylene; halogenated hydrocarbons, such as methylene chloride, chloroform or dichloroethane; ethers, such as diethyl ether, tetrahydrofuran, dioxane or dimethoxyethane; nitriles, such as acetonitrile or isobutyronitrile; amides, such as formamide, dimethylformamide, dimethylacetamide or hexamethylphosphoric triamide; and sulfoxides, such as dimethyl sulfoxide or sulfolane. Of these, we prefer the halogenated hydrocarbons, such as methylene chloride.

The reaction can take place over a wide range of temperatures, and the precise reaction temperature is not critical to the invention. In general, we find it convenient to carry out the reaction at a temperature of from −50° C. to 80° C., more preferably from 0° to 30° C., and most preferably at about room temperature. The time required for the reaction may also vary widely, depending on many factors, notably the reaction temperature and the nature of the reagents and solvent employed. However, where the reaction is effected under the preferred conditions outlined above, a period of from 5 minutes to 5 hours, more preferably from 10 minutes to 30 minutes, is usually sufficient.

After the reaction has been allowed to go to completion, the target compound can be recovered from the reaction mixture by conventional means. For example, one suitable method comprises: filtering off insoluble materials, if any; adding water and a water-immiscible organic solvent, such as ethyl acetate; washing the organic phase with water or an aqueous solution; separating the organic phase containing the target compound; drying the extract over a drying agent, such as anhydrous magnesium sulfate; and distilling off the solvent. The target compound can, if required, then be further purified by such conventional means as recrystallization, reprecipitation or any of the various chromatography techniques, especially column chromatography.

Step K3

This reaction involves reacting a compound of formula (XL) with a compound of formula $R^{50}$—X (where $R^{50}$ and X are as defined above) to obtain a compound of formula (XLI). A suitable amount of the compound of formula $R^{50}$X is, for example, from 1 to 4 equivalents (more preferably from 2 to 3 equivalents), and is preferably in a solvent in the presence or absence of a base, but preferably in the presence of a base.

There is no particular limitation upon the nature of the leaving group represented by X, provided that it is a group capable of leaving as a nucleophilic residue, such as are well known in the art. Examples of preferred leaving groups include: halogen atoms, such as chlorine, bromine and iodine atoms; lower alkoxycarbonyloxy groups, such as the methoxycarbonyloxy and ethoxycarbonyloxy groups; halogenated alkylcarbonyloxy groups, such as the chloroacetoxy, dichloroacetoxy, trichloroacetoxy and trifluoroacetoxy groups; lower alkanesulfonyloxy groups, such as the methanesulfonyloxy and ethanesulfonyloxy groups; lower haloalkanesulfonyloxy groups, such as the trifluoromethanesulfonyloxy and pentafluoroethanesulfonyloxy groups; and arylsulfonyloxy groups, such as the benzenesulfonyloxy, p-toluenesulfonyloxy and p-nitrobenzenesulfonyloxy groups. Of these, we prefer the halogen atoms, lower haloalkanesulfonyloxy groups and arylsulfonyloxy groups.

The reaction is normally and preferably effected in the presence of a solvent. There is no particular restriction on the nature of the solvent to be employed, provided that it has no adverse effect either on the reaction or on the reagents involved, and that it can dissolve the reagents, at least to some extent. Examples of suitable solvents include: aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; nitriles, such as acetonitrile and isobutyronitrile; and amides, such as formamide, dimethylformamide, dimethylacetamide, N-methyl-2-pyrrolidone, N-methylpyrrolidinone and hexamethylphosphoric triamide. We prefer to use ethers or amides as solvents, particularly dimethoxyethane, tetrahydrofuran or dimethylformamide.

There is no particular limitation upon the nature of the base used, and any base which can be used in conventional reactions of this type may equally be used here. Examples of preferred bases include organic bases, such as N-methylmorpholine, triethylamine, tributylamine, diisopropylethylamine, dicyclohexylamine, N-methylpiperidine, pyridine, 4-(1-pyrrolidinyl)pyridine, picoline, 4-(N,N-dimethylamino)pyridine, 2,6-di-t-butyl-4-methylpyridine, quinoline, N,N-dimethylaniline and N,N-diethylaniline. If desired, a catalytic amount of 4-(N,N-dimethylamino)pyridine, 4-(1-pyrrolidinyl)pyridine or a combination of other bases can be used. In order to promote the reaction, a quaternary ammonium salt (such as benzyltriethylammonium chloride or tetrabutylammonium chloride) or a crown ether (such as dibenzo-18-crown-6) may be added to the reaction system.

The reaction can take place over a wide range of temperatures, and the precise reaction temperature is not critical to the invention. The preferred reaction temperature will depend upon such factors as the nature of the solvent, and the starting material or reagent used. However, in general, we find it convenient to carry out any alkylation or aralkylation reaction at a temperature of from −20° to 60° C., more preferably from 0° C. to 20° C. We find it convenient to carry out any acylation reaction at a temperature of from −78° C. to room temperature, more preferably from −78° C. to 0° C. The time required for the reaction may also vary widely, depending on many factors, notably the reaction temperature and the nature of the reagents and solvent employed. However, where the reaction is effected under the preferred conditions outlined above, a period of from 5 minutes to 24 hours, more preferably from 5 minutes to 6 hours, is usually sufficient.

After the reaction has been allowed to go to completion, the target compound can be recovered from the reaction mixture by conventional means. For example, one suitable method comprises: properly neutralizing the reaction mixture; filtering off insoluble materials, if any; adding water and a water-immiscible organic solvent, such as ethyl acetate; washing the organic phase with water; separating the organic phase containing the target compound; drying the extract over a drying agent, such as anhydrous magnesium sulfate; and distilling off the solvent. The target compound can, if required, then be further purified by such conventional means as recrystallization, reprecipitation or any of the various chromatography techniques, especially column chromatography.

Alternatively, Steps K2 and K3 can be executed as a "one-pot" reaction. Thus, after the reaction with a strong carboxylic acid anhydride, a suitable hydrolyzing agent, $R^{50}$—X and base are all added to the reaction mixture at once. The reaction is carried out under similar conditions, including solvent, temperatures and time, to those described above.

The preparation of various of the compounds of the present invention is illustrated in the following non-limiting Examples.

EXAMPLE 1 tert-Butyl (2-hydroxy-1,1-bismethylthio-1,2,3,4-tetrahydrocarbazol-2-yl)acetate

1(a) Methyl 3-(indol-3-yl)propionate 36.2 g of powdered potassium carbonate was added, with ice-cooling, to a solution of 24.8 g of 3-(indol-3-yl) propionic acid in 500 ml of N,N-dimethylformamide, followed by the addition of a solution of 10.2 ml methyl iodide in 50 ml of N,N-dimethylformamide. The reaction mixture was then warmed to room temperature and stirred for 3 hours. After this time, ice water was added to the reaction mixture, and the aqueous layer was extracted with ethyl acetate. The organic extract was then washed with water, dried over anhydrous magnesium sulfate and concentrated by evaporation under reduced pressure. The resulting residue was subjected to column chromatography using 500 g of silica gel with a 4:1 v/v mixture of hexane and ethyl acetate as the eluent, to yield 25.8 g of the title compound as an amorphous solid.

1(b) 3-(4-Methylthio-4-methylsulfinyl-3-oxobuten-1-yl) indole

A solution of 11.2 g of methyl methylsulfinyl sulfide in tetrahydrofuran was added, with ice-cooling, to a suspension of 13.1 g of sodium hydride (55% w/w dispersion in mineral oil) in 100 ml of tetrahydrofuran. The reaction mixture was then heated to room temperature and stirred for 2 hours. A solution of 12.2 g of methyl 3-(indol-3-yl)propionate, as obtained in Example 1(a) above, in 50 ml of tetrahydrofuran was subsequently added to the reaction mixture, which was next refluxed for 2 hours, and then acidified by the addition of a 1N aqueous solution of hydrochloric acid. The aqueous layer was extracted with ethyl acetate, and the resulting organic extract was washed with water, dried over anhydrous magnesium sulfate and concentrated by evaporation under reduced pressure. The residue thus obtained was subjected to column chromatography using 400 g of silica gel with a 1:2 v/v mixture of hexane and ethyl acetate as the eluent, to yield 16.8 g of the title compound as an amorphous solid.

1(c) 1,1-Bismethylthio-1,2,3,4-tetrahydrocarbazol-3-one 680 mg of p-toluenesulfonic acid was added to a mixture of 10.6 g of 3-(4-methylthio-4-methylsulfinyl-3-oxobutene-1-yl)indole, as obtained in Example 1(b), in 150 ml of tetrahydrofuran and 40 ml of benzene. The reaction mixture was next refluxed for 3 hours and then neutralized by the addition of a saturated aqueous solution of sodium hydrogencarbonate. The solvent was removed from the resulting mixture by evaporation under reduced pressure and ethyl acetate was added to the residue. The aqueous layer was then extracted with ethyl acetate, and the organic extract was washed with a saturated aqueous solution of sodium chloride, dried over anhydrous magnesium sulfate and concentrated by evaporation under reduced pressure. The resulting residue was subjected to column chromatography using 300 g of silica gel with a 9:1 v/v mixture of hexane and ethyl acetate as the eluent, to yield 9.7 g of the title compound as an amorphous solid.

1(d) tert-Butyl (2-hydroxy-1,1-bismethylthio-1,2,3,4-tetrahydrocarbazol-2-yl)acetate 53 ml of a 1.7M solution of n-butyllithium in hexane was added at a temperature of −78° C. to a solution of 13.9 g of diisopropylamine in 50 ml of toluene. The reaction mixture was then warmed to 0° C. and stirred for 15 minutes. The reaction mixture was then cooled to −78° C., and a solution of 5.0 g of 1,1-bismethylthio-1,2,3,4-tetrahydrocarbazol-3-one, as obtained in Example 1(c), in 10 ml of toluene was added to the cooled solution. The reaction mixture was next stirred for 30 minutes and then heated to room temperature and stirred for 2 hours. After this time, a saturated aqueous solution of ammonium chloride was added to the reaction mixture. The aqueous layer was extracted with toluene, and the organic extract was washed with a saturated aqueous solution of sodium chloride, dried over anhydrous magnesium sulfate and concentrated by evaporation under reduced pressure. The resulting residue was subjected to column chromatography using 250 g of silica gel with benzene as the eluent, to yield 6.8 g of the title compound as an amorphous solid.

EXAMPLE 2 tert-Butyl (1-methylthiocarbazol-2-yl)acetate 2.5 ml of glacial acetic acid was added to a solution of 3.37 g of tert-butyl (2-hydroxy-1,1-bismethylthio-1,2,3,4-tetrahydrocarbazol-2-yl)acetate, as obtained in Example 1, in 40 ml of xylene. The reaction mixture was subsequently refluxed for 1 hour and then neutralized by the addition of a saturated aqueous solution of sodium hydrogencarbonate. The aqueous layer was extracted with ethyl acetate, and the organic extract was washed with a saturated aqueous solution of sodium chloride, dried over anhydrous magnesium sulfate and concentrated by evaporation under reduced pressure. The resulting residue was subjected to column chromatography using 80 g of silica gel with a 19:1 v/v mixture of benzene and ethyl acetate as the eluent, to yield 2.40 g of the title compound, melting at 137°–138° C., 50 mg of 2-hydroxy-1-methylthiocarbazole (melting at 138°–140° C.), 85 mg of tert-butyl (2-hydroxy-1-oxo-1,2,3,4-tetrahydrocarbazol-2-yl)acetate (melting at 156°–157° C.) and 125 mg of 3,3a,4,5,10,10b-hexahydro-3a-hydroxy-10b-methylthiofuro[2,3-a]carbazol-2-one (obtained as an amorphous solid).

The Nuclear Magnetic Resonance Spectrum [(CDCl$_3$, 270 MHz), δ ppm] results for each of the above compounds are as follows:

tert-Butyl (1-methylthiocarbazol-2-yl)acetate 1.46 (9H, singlet); 2.36 (3H, singlet); 4.05 (2H, singlet); 7.21 (1H, doublet, J=7.8 Hz); 7.24 (1H, triplet, J=7.9 Hz); 7.42 (1H, triplet, J=7.9 Hz); 7.49 (1H, doublet, J=7.9 Hz); 7.99 (1H, doublet, J=7.9 Hz); 8.04 (1H, doublet, J=7.8 Hz); 8.62 (1H, broad singlet).

2-Hydroxy-1-methylthiocarbazole 2.33 (3H, singlet); 6.77 (1H, singlet); 6.93 (1H, doublet, J=8.4 Hz); 7.22 (1H, triplet, J=7.7 Hz); 7.36 (1H, triplet, J=7.7 Hz); 7.45 (1H, doublet, J=7.7 Hz); 7.94 (1H, doublet, J=8.4 Hz); 7.96 (1H, doublet, J=7.7 Hz); 8.39 (1H, broad singlet).

tert-Butyl (2-hydroxy-1-oxo-1,2,3,4-tetrahydrocarbazol-2-yl)acetate 1.49 (9H, singlet); 2.3–2.5 (2H, multiplet); 2.60 (1H, doublet, J=14.6 Hz); 2.69 (1H, doublet, J=14.6 Hz); 3.02 (1H, doubled doublet of doublets, J=5.1, 8.7, 17.4 Hz); 3.23 (1H, triplet of doublets, J=5.1, 17.4 Hz); 4.59 (1H, singlet); 7.1–7.2 (1H, multiplet); 7.3–7.5 (2H, multiplet); 7.66 (1H, doublet, J=7.9 Hz); 8.81 (1H, broad singlet).

3,3a,4,5,10,10b-Hexahydro-3a-hydroxy-10b-methylthiofuro[2,3-a]carbazol-2-one 2.08 (3H, singlet); 2.12 (1H, doubled doublet of doublets, J=5.9, 9.9, 13.9 Hz); 2.27 (1H, doubled doublet of doublets, J=3.3, 5.9, 13.9 Hz); 2.70 (1H, doublet, J=16.8 Hz); 2.74 (1H, doubled doublet of doublets, J=5.9, 9.9, 17.2 Hz); 2.78 (1H, doublet, J=16.8 Hz); 3.02 (1H, doubled doublet of doublets, J=3.3, 5.9, 17.2 Hz); 3.17 (1H, singlet); 7.14 (1H, triplet, J=7.6 Hz); 7.28 (1H, triplet, J=7.6 Hz); 7.38 (1H, doublet, J=7.6 Hz); 7.53 (1H, doublet, J=7.6 Hz); 8.40 (1H, broad singlet).

EXAMPLE 3

(1-Methylthiocarbazol-2-yl)acetic acid 5 ml of formic acid was added to 51 mg of tert-butyl (1-methylthiocarbazol-2-yl)acetate, as obtained in Example 2. The reaction mixture was then warmed to room temperature and stirred for 4 hours. Formic acid was next removed under reduced pressure, and the residue was recrystallized from ethyl acetate and hexane, to yield 44 mg of the title compound, melting at 210°–212° C.

Nuclear Magnetic Resonance Spectrum (CDCl$_3$, 270 MHz), δ ppm: 2.36 (3H, singlet); 4.20 (2H, singlet); 7.22 (1H, doublet, J=7.9 Hz); 7.2–7.3 (1H, multiplet); 7.44 (1H, triplet, J=7.6 Hz); 7.48 (1H, triplet, J=7.6 Hz); 8.01 (1H, doublet, J=7.9 Hz); 8.04 (1H, doublet, J=7.6 Hz); 8.63 (1H, broad singlet).

EXAMPLE 4 tert-Butyl (9-benzyl-1-methylthiocarbazol-2-yl) acetate

A solution of 98 mg of tert-butyl (1-methylthiocarbazol-2-yl)acetate, as obtained in Example 2, in 1 ml of N,N- dimethylformamide was added, with ice-cooling, to a suspension of 13 mg of sodium hydride (55% w/w dispersion in mineral oil) in 2 ml of N,N-dimethylformamide. 51 mg of benzyl bromide was added to the reaction mixture which was then stirred for 1 hour. After this time, a saturated aqueous solution of ammonium chloride was added to the reaction mixture. The aqueous layer was extracted with ethyl acetate and the organic extract was washed with water, dried over anhydrous magnesium sulfate and concentrated by evaporation under reduced pressure. The resulting residue was subjected to column chromatography using 4 g of silica gel with a 1:2 v/v mixture of hexane and benzene as the eluent, to yield 120 mg of the title compound as an oil.

Nuclear Magnetic Resonance Spectrum ($CDCl_3$, 270 MHz), δ ppm: 1.43 (9H, singlet); 1.98 (3H, singlet); 4.09 (2H, singlet); 6.35 (2H, singlet); 7.03 (2H, doublet, J=6.5 Hz); 7.1–7.5 (7H, multiplet); 8.08 (2H, doublet, J=7.9 Hz).

EXAMPLE 5

(9-Benzyl-1-methylthiocarbazol-2-yl)acetic acid

Following a procedure and using relative proportions of starting materials similar to those described in Example 3, but using tert-butyl (9-benzyl-1-methylthiocarbazol-2-yl) acetate, as obtained in Example 4, as starting material, the title compound was obtained in quantitative yield, melting at 182°–183° C.

Nuclear Magnetic Resonance Spectrum ($CDCl_3$, 270 MHz), δ ppm: 1.95 (3H, singlet); 4.22 (2H, singlet); 6.34 (2H, singlet); 7.03 (2H, doublet, J=7.7 Hz); 7.1–7.5 (7H, multiples); 8.0–8.2 (2H, multiplet).

EXAMPLE 6 tert-Butyl [9-(4-chlorobenzyl)-1-methylthiocarbazol-2-yl]acetate

Following a procedure and using relative proportions of starting materials similar to those described in Example 4, but using 4-chlorobenzyl chloride as starting material, the title compound was obtained as an oil in a yield of 96%.

EXAMPLE 7

[9-(4-Chlorobenzyl)-1-methylthiocarbazol-2-yl] acetic acid

Following a procedure and using relative proportions of starting materials similar to those described in Example 3, but using tert-butyl [9-(4-chlorobenzyl)-1-methylthiocarbazol-2-yl]acetate, as obtained in Example 6, as starting material, the title compound was obtained in quantitative yield, melting at 176°–178° C.

Nuclear Magnetic Resonance Spectrum ($CDCl_3$, 270 Hz), δ ppm: 2.01 (3H, singlet); 4.23 (2H, singlet); 6.30 (2H, singlet); 6.96 (2H, doublet, J=8.4 Hz); 7.1–7.4 (5H, multiplet); 7.43 (1H, triplet, J=7.6 Hz); 8.0–8.2 (2H, multiplet).

EXAMPLE 8 tert-Butyl [9-(4-fluorobenzyl)-1-methylthiocarbazol-2-yl]acetate

Following a procedure and using relative proportions of starting materials similar to those described in Example 4, but using 4-fluorobenzyl bromide as starting material, the title compound was obtained as an oil in a yield of 98%.

EXAMPLE 9

[9-(4-Fluorobenzyl)-1-methylthiocarbazol-2-yl] acetic acid

Following a procedure and using relative proportions of starting materials similar to those described in Example 3, but using tert-butyl [9-(4-fluorobenzyl)-1-methylthiocarbazol-2-yl]acetate, as obtained in Example 8, as starting material, the title compound was obtained in quantitative yield, melting at 156°–157° C.

Nuclear Magnetic Resonance Spectrum ($CDCl_3$, 270 MHz), δ ppm: 2.00 (3H, singlet); 4.22 (2H, singlet); 6.30 (2H, singlet); 6.8–7.1 (4H, multiplet); 7.2–7.4 (3H, multiplet); 7.43 (1H, triplet, J=8.0 Hz); 8.08 (1H, doublet, J=7.8 Hz); 8.10 (1H, doublet, J=7.9 Hz).

EXAMPLE 10 tert-Butyl [9-(4-nitrobenzyl)-1-methylthiocarbazol-2-yl]acetate

Following a procedure and using relative proportions of starting materials similar to those described in Example 4, but using 4-nitrobenzyl bromide as starting material, the title compound was obtained as an oil in a yield of 94%.

EXAMPLE 11

[9-(4-Nitrobenzyl)-1-methylthiocarbazol-2-yl]acetic acid

Following a procedure and using relative proportions of starting materials similar to those described in Example 3, but using tert-butyl [9-(4-nitrobenzyl)-1-methylthiocarbazol-2-yl]acetate, as obtained in Example 10, as starting material, the title compound was obtained in quantitative yield as an amorphous solid.

Nuclear Magnetic Resonance Spectrum ($CDCl_3$, 270 MHz), δ ppm: 2.02 (3H, singlet); 4.21 (2H, singlet); 6.41 (2H, singlet); 7.17 (2H, doublet, J=8.5 Hz); 7.2–7.4 (5H, multiplet); 7.44 (1H, triplet, J=7.5 Hz); 8.0–8.2 (4H, multiplet).

EXAMPLE 12 tert-Butyl (9-benzyl-1-methylthiocarbazol-2-yl) hydroxyacetate 0.47 ml of a 1.0M solution of lithium hexamethyldisilazide in tetrahydrofuran was added, with ice-cooling, to a solution of 65 mg of tert-butyl (9-benzyl-1-methylthiocarbazol-2-yl)acetate, as obtained in Example 4, in 5 ml of tetrahydrofuran. The reaction mixture was then stirred for 1 hour in the presence of atmospheric oxygen. After this time, a saturated aqueous solution of ammonium chloride was added to the reaction mixture. The aqueous layer was extracted with ethyl acetate and the organic extract was washed with a saturated aqueous solution of sodium chloride, dried over anhydrous magnesium sulfate and concentrated by evaporation under reduced pressure. The resulting residue was subjected to column chromatography using 1.5 g of silica gel with a 3:1 v/v mixture of hexane and ethyl acetate as the eluent, to yield 43 mg of the title compound as an oil.

Nuclear Magnetic Resonance Spectrum (CDCl3, 270 MHz), δ ppm: 1.34 (9H, singlet); 2.09 (3H, singlet); 3.69 (1H, broad singlet); 6.23 (1H, singlet); 6.37 (2H, singlet); 7.01 (2H, doublet, J=7.8 Hz); 7.1–7.5 (7H, multiplet); 8.09 (1H, doublet, J=7.9 Hz); 8.13 (1H, doublet, J=8.0 Hz).

EXAMPLE 13

Benzyl [9-benzyl-4-methyl-1-methylthiocarbazol-2-yl)acetate a) Following a procedure and using relative proportions of starting materials similar to those described in Examples 1 and 2, but using 3-(indol-3-yl)butyric acid as starting material, benzyl (4-methyl-1-methylthiocarbazol-2-yl) acetate was obtained, and was used without further purification in the next step.

b) A solution of 2.42 g of benzyl (4-methyl-1-methylthiocarbazol-2-yl)acetate, as obtained in a) above, in 40 ml of N,N-dimethylforamide was added, with ice-cooling, to a suspension of 280 mg of sodium hydride (55% w/w dispersion in mineral oil) in 30 ml of N,N-dimethylformamide. 1.1 g of benzyl bromide was next added to the reaction mixture which was then stirred for 1 hour. After this time, a saturated aqueous solution of ammonium chloride was added to the reaction mixture. The aqueous layer was extracted with ethyl acetate, and the organic extract was washed with water, dried over anhydrous magnesium sulfate and concentrated by evaporation under reduced pressure. The resulting residue was subjected to column chromatography using 80 g of silica gel with a 1:2 v/v mixture of hexane and benzene as the eluent, to yield 2.7 g of the title compound, as an oil, and 195 mg of benzyl 2-(4-methyl-1-methylthiocarbazol-2-yl)-3-phenylpropionate, also as an oil.

EXAMPLE 14

(9-Benzyl-4-methyl-1-methylthiocarbazol-2-yl) acetic acid 50 ml of ethanol and 50 ml of a 2N aqueous solution of sodium hydroxide was added to 1.16 g of benzyl (9-benzyl-4-methyl-1-methylthiocarbazol-2-yl)acetate, as obtained in Example 13a). The reaction mixture was stirred for 2 hours at room temperature, after which time it was acidified by adding a 1N aqueous solution of hydrochloric acid and then concentrated by evaporation under reduced pressure. Ethyl acetate was added to the residue thus obtained. The aqueous layer was extracted with ethyl acetate and the organic extract was washed with a saturated aqueous solution of sodium chloride, dried over anhydrous magnesium sulfate and concentrated by evaporation under reduced pressure. The resulting residue was subjected to column chromatography using 20 g of silica gel with a 1:1 v/v mixture of hexane and ethyl acetate as the eluent, and then recrystallized from ethyl acetate and hexane, to yield 0.90 g of the title compound, melting at 219°–220° C.

Nuclear Magnetic Resonance Spectrum (CDCl$_3$, 270 MHz), δ ppm: 1.96 (3H, singlet); 2.89 (3H, singlet); 4.15 (1H, singlet); 6.40 (2H, singlet); 7.0–7.5 (9H, multiplet); 8.19 (1H, doublet, J=7.9 Hz).

EXAMPLE 15

2-(4-Methyl-1-methylthiocarbazol-2-yl)-3-phenylpropionic acid

Following a procedure and using relative proportions of starting materials similar to those described in Example 14, but using benzyl 2-(4-methyl-1-methylthiocarbazol-2-yl)-3-phenylpropionate, as obtained in Example 13, as starting material, the title compound was obtained in a yield of 93%, melting at 186°–187° C.

Nuclear Magnetic Resonance Spectrum (CDCl$_3$, 270 MHz), δ ppm: 2.16 (3H, singlet); 2.91 (3H, singlet); 3.11 (1H, doublet of doublets, J=7.5, 13.7 Hz); 3.53 (1H, doublet of doublets, J=7.5, 13.7 Hz); 5.18 (1H, triplet, J=7.5 Hz); 7.1–7.6 (9H, multiplet); 8.17 (1H, doublet, J=7.9 Hz); 8.70 (1H, broad singlet).

EXAMPLE 16 tert-Butyl 2-(9-benzyl-1-methylthiocarbazol-2-yl)-3-phenylpropionate

A solution of 826 mg of tert-butyl (1-methylthiocarbazol-2-yl)acetate, as obtained in Example 2, in 5 ml of N,N-dimethylformamide was added, with ice-cooling, to a suspension of 220 mg of sodium hydride (55% w/w dispersion in mineral oil) in 10 ml of N,N-dimethylformamide. 855 mg of benzyl bromide was then added to the reaction mixture which was then warmed to room temperature and stirred for 1 hour. After this time, a saturated aqueous solution of ammonium chloride was added to the reaction mixture. The aqueous layer was extracted with ethyl acetate and the organic extract was washed with water, dried over anhydrous magnesium sulfate and concentrated by evaporation under reduced pressure. The resulting residue was subjected to column chromatography using 30 g of silica gel with a 1:2 v/v mixture of hexane and benzene as the eluent, to yield 1.21 g of the title compound as an oil.

Nuclear Magnetic Resonance Spectrum (CDCl$_3$, 270 MHz), δ ppm: 1.30 (9H, singlet); 1.89 (3H, singlet); 2.99 (1H, doublet of doublets, J=7.2, 13.7 Hz); 3.41 (1H, doublet of doublets, J=8.0, 13.7 Hz); 5.23 (1H, doublet of doublets, J=7.2, 8.0 Hz); 6.31 (2H, singlet); 6.9–7.5 (14H, multiplet); 8.07 (1H, doublet, J=7.7 Hz); 8.13 (1H, doublet, J=8.2 Hz).

EXAMPLE 17

2-(9-Benzyl-1-methylthiocarbazol-2-yl)-3-phenylpropionic acid

Following a procedure and using relative proportions of starting materials similar to those described in Example 3, but using tert-butyl 2-(9-benzyl-1-methylthiocarbazol-2-yl)-3-phenylpropionate, as obtained in Example 16, as starting material, the title compound was obtained in a yield of 99%, melting at 154°–156° C.

Nuclear Magnetic Resonance Spectrum (CDCl$_3$, 270 MHz), δ ppm: 1.86 (3H, singlet); 3.06 (1H, doublet of doublets, J=7.5, 13.7 Hz); 3.48 (1H, doublet of doublets, J=7.5, 13.7 Hz); 5.39 (1H, triplet, J=7.5 Hz); 6.32 (2H, singlet); 6.9–7.0 (2H, multiplet); 7.1–7.5 (12H, multiplet) 8.09 (1H, doublet, J=7.8 Hz); 8.15 (1H, doublet, J=8.2 Hz).

EXAMPLE 18 tert-Butyl 2-[9-(4-chlorobenzyl)-1-methylthiocarbazol-2-yl]-3-(4-chlorophenyl) propionate Following a procedure and using relative proportions of starting materials similar to those described in Example 16, but using 4-chlorobenzyl chloride as starting material, the title compound was obtained as an oil in a yield of 95%.

EXAMPLE 19

2-[9-(4-Chlorobenzyl)-1-methylthiocarbazol-2-yl]-3-(4-chlorophenyl)propionic acid Following a procedure and using relative proportions of starting materials similar to those described in Example 3, but using tert-butyl 2-(9-(4-chlorobenzyl)-1-methylthiocarbazol-2-yl)-3-(4-chlorophenyl)propionate, as obtained in Example 18 as starting material, the title compound was obtained in quantitative yield, melting at 104°–107° C.

Nuclear Magnetic Resonance Spectrum (CDCl$_3$, 270 MHz), δ ppm: 1.95 (3H, singlet); 3.02 (1H, doublet of doublets, J=7.5, 13.8 Hz); 3.43 (1H, doublet of doublets, J=7.5, 13.8 Hz); 5.35 (1H, triplet, J=7.5 Hz); 6.27 (2H, singlet); 6.8–7.5 (12H, multiplet); 8.0–8.2 (2H, multiplet).

EXAMPLE 20 tert-Butyl 2-[9-(4-fluorobenzyl)-1-methylthiocarbazol-2-yl]-3-(4-fluorophenyl)propionate Following a procedure and using relative proportions of starting materials similar to those described in Example 16, but using 4-fluorobenzyl bromide as starting material, the title compound was obtained as an oil in a yield of 97%.

EXAMPLE 21

2-[9-(4-Fluorobenzyl)-1-methylthiocarbazol-2-yl]-3-(4-fluorophenyl)propionic acid Following a procedure and using relative proportions of starting materials similar to those described in Example 3, but using tert-butyl 2-[9-(4-fluorobenzyl)-1-methylthiocarbazol-2-yl]-3-(4-fluorophenyl)propionate, as obtained in Example 20, as starting material, the title compound was obtained in quantitative yield, melting at 90°–94° C.

Nuclear Magnetic Resonance Spectrum (CDCl$_3$, 270 MHz), δ ppm: 1.93 (3H, singlet); 3.03 (1H, doublet of doublets, J=7.5, 13.7 Hz); 3.44 (1H, doublet of doublets, J=7.5, 13.7 Hz); 5.36 (1H, triplet, J=7.5 Hz); 6.25 (2H, singlet); 6.7–7.5 (12H, multiplet); 8.0–8.2 (2H, multiplet).

EXAMPLE 22 tert-Butyl 2-[9-(4-nitrobenzyl)-1-methylthiocarbazol-2-yl]-3-(4-nitrophenyl)propionate Following a procedure and using relative proportions of starting materials similar to those described in Example 16, but using 4-nitrobenzyl bromide as starting material, the title compound was obtained as an oil in a yield of 92%.

EXAMPLE 23

2-[9-(4-Nitrobenzyl)-1-methylthiocarbazol-2-yl]-3-(4-nitrophenyl)propionic acid

Following a procedure and using relative proportions of starting materials similar to those described in Example 3, but using tert-butyl 2-[(9-(4-nitrobenzyl)-1-methylthiocarbazol-2-yl]-3-(4-nitrophenyl)propionate, as obtained in Example 22, as starting material, the title compound was obtained in quantitative yield as an amorphous solid.

Nuclear Magnetic Resonance Spectrum (CDCl$_3$, 270 MHz), δ ppm: 1.96 (3H, singlet); 3.13 (1H, doublet of doublets, J=7.5, 13.7 Hz); 3.56 (1H, doublet of doublets, J=7.5, 13.7 Hz); 5.37 (1H, triplet, J=7.5 Hz); 6.28 (1H, doublet, J=17.8 Hz); 6.47 (1H, doublet, J=17.8 Hz); 7.12 (2H, doublet, J=8.7 Hz); 7.2–7.5 (6H, multiplet); 8.0–8.2 (6H, multiplet).

EXAMPLE 24

Benzyl 2-[9-benzyl-4-methyl-1-methylthiocarbazol-2-yl]-3-phenylpropionate

A solution of 100 mg of benzyl (9-benzyl-4-methyl-1-methylthiocarbazol-2-yl)acetate, as obtained in Example 13a), in 1 ml of N,N-dimethylformamide was added, with ice-cooling, to a suspension of 23 mg of sodium hydride (55% w/w dispersion in mineral oil) in 3 ml of N,N-dimethylformamide. 91 mg of benzyl bromide were then added to the reaction mixture which was then warmed to room temperature and stirred for 1 hour. After this time, a saturated aqueous solution of ammonium chloride was added to the reaction mixture. The aqueous layer was extracted with ethyl acetate and the organic extract was washed with water, dried over anhydrous magnesium sulfate and concentrated by evaporation under reduced pressure. The resulting residue was subjected to column chromatography using 3 g of silica gel with a 1:2 v/v mixture of hexane and benzene as the eluent, to yield 142 mg of the title compound as an oil.

EXAMPLE 25

2-(9-Benzyl-4-methyl-1-methylthiocarbazol-2-yl)-3-phenylpropionic acid

Following a procedure and using relative proportions of starting materials similar to those described in Example 14, but using benzyl 2-(9-benzyl-4-methyl-1-methylthiocarbazol-2-yl)-3-phenylpropionate, as obtained in Example 24, as starting material, the title compound was obtained in a yield of 91%, melting at 199°–200° C.

Nuclear Magnetic Resonance Spectrum (CDCl$_3$, 270 MHz), δ ppm: 1.85 (3H, singlet); 2.92 (3H, singlet); 3.03 (1H, doublet of doublets, J=7.4, 13.7 Hz); 3.46 (1H, doublet of doublets, J=7.4, 13.7 Hz); 5.38 (1H, triplet, J=7.4 Hz); 6.36 (2H, singlet); 6.99 (2H, doublet, J=7.9 Hz); 7.1–7.5 (12H, multiplet); 8.20 (1H, doublet, J=7.8 Hz).

EXAMPLE 26

1-Methylcarbazole-2-carboxylic acid 4 ml of ethanol and 4 ml of a 2N aqueous solution of potassium hydroxide were added to 100 mg of ethyl 1-methylcarbazole-2-carboxylate (obtained according to the procedures described in C. J. Moody and K. F. Rahimtoola, J. Chem. Soc. Parkin. Trans. I, 673 (1990)]. The reaction mixture was stirred for 2 hours at room temperature, and then acidified by the addition of a 1N aqueous solution of hydrochloric acid, after which it was concentrated by evaporation under reduced pressure. Ethyl acetate was added to the residue. The aqueous layer was extracted with ethyl acetate, and the organic extract was washed with a saturated aqueous solution of sodium chloride, dried over anhydrous magnesium sulfate and concentrated by evaporation under reduced pressure. The resulting residue was recrystallized from ethyl acetate and hexane, to yield 81 mg of the title compound, melting at >240° C.

Nuclear Magnetic Resonance Spectrum (CDCl$_3$, 270 MHz), δ ppm: 2.89 (3H, singlet); 7.24 (1H, triplet, J=8.0 Hz); 7.45 (1H, triplet, J=8.0 Hz); 7.52 (1H, doublet, J=8.0 Hz); 7.90 (1H, doublet, J=8.4 Hz); 7.94 (1H, doublet, J=8.4 Hz); 8.09 (1H, doublet, J=8.0 Hz); 8.89 (1H, broad singlet).

EXAMPLE 27

1-Methylcarbazole-3-carboxylic acid

Following a procedure and using relative proportions of starting materials similar to those described in Example 26, but using ethyl 1-methylcarbazole-3-carboxylate as starting material, the title compound was obtained in a yield of 92%, melting at >240° C.

Nuclear Magnetic Resonance Spectrum (CDCl$_3$, 270 MHz), δ ppm: 2.61 (3H, singlet); 7.26 (1H, triplet, J=7.8 Hz); 7.43 (1H, triplet, J=7.8 Hz); 7.51 (1H, doublet, J=7.8 Hz); 7.98 (1H, singlet); 8.10 (1H, doublet, J=7.8 Hz); 8.71 (1H, singlet); 9.20 (1H, broad singlet)

EXAMPLE 28

Ethyl 9-benzyl-1-methylcarbazole-2-carboxylate

A solution of 29 mg of ethyl 1-methylcarbazole-2-carboxylate in 1 ml of N,N-dimethylformamide was added, with ice-cooling, to a suspension of 10 mg of sodium hydride (55% w/w dispersion in mineral oil) in 2 ml of N,N-dimethylformamide. 29 mg of benzyl bromide was then added to the reaction mixture, which was then stirred for 1 hour, with ice-cooling. After this time, a saturated aqueous solution of ammonium chloride was added to the reaction mixture. The aqueous layer was extracted with ethyl acetate and the organic extract was washed with water, dried over anhydrous magnesium sulfate and concentrated by evaporation under reduced pressure. The resulting residue was subjected to column chromatography using 1 g of silica gel with a 9:1 v/v mixture of hexane and ethyl acetate as the eluent, to yield 38 mg of the title compound, melting at 79°–80° C.

Nuclear Magnetic Resonance Spectrum (CDCl$_3$, 270 MHz), δ ppm: 1.40 (3H, triplet, J=7.1 Hz); 2.80 (3H, singlet); 4.38 (2H, quartet, J=7.1 Hz); 5.79 (2H, singlet); 7.07 (2H, doublet, J=6.5 Hz); 7.2–7.5 (6H, multiplet); 7.66 (1H, doublet, J=8.2 Hz); 7.99 (1H, doublet, J=8.2 Hz); 8.12 (1H, doublet, J=8.0 Hz).

EXAMPLE 29

9-Benzyl-1-methylcarbazole-2-carboxylic acid

Following a procedure and using relative proportions of starting materials similar to those described in Example 26, but using ethyl 9-benzyl-1-methylcarbazole-2-carboxylate, as obtained in Example 28, as starting material, the title compound was obtained in a yield of 94%, melting at 215°–216° C.

Nuclear Magnetic Resonance Spectrum (CDCl$_3$, 270 MHz), δ ppm: 2.85 (3H, singlet); 5.80 (2H, singlet); 7.0–7.1 (2H, multiplet); 7.2–7.4 (5H, multiplet); 7.44 (1H, triplet, J=7.5 Hz); 7.76 (1H, doublet, J=8.1 Hz); 7.99 (1H, doublet, J=8.1 Hz); 8.12 (1H, doublet, J=7.5 Hz).

EXAMPLE 30

Ethyl 9-benzyl-1-methylcarbazole-3-carboxylate

Following a procedure and using relative proportions of starting materials similar to those described in Example 28, but using ethyl 1-methylcarbazole-3-carboxylate as starting material, the title compound was obtained in a yield of 96%, melting at 118°–119° C.

Nuclear Magnetic Resonance Spectrum (CDCl$_3$, 270 MHz), δ ppm: 1.44 (3H, triplet, J=7.1 Hz); 2.64 (3H, singlet); 4.43 (2H, quartet, J=7.1 Hz); 5.74 (2H, singlet); 6.9–7.0 (2H, multiplet); 7.2–7.5 (6H, multiplet); 7.87 (1H, singlet); 8.15 (1H, doublet, J=8.2 Hz); 8.72 (1H, singlet).

EXAMPLE 31

9-Benzyl-1-methylcarbazole-3-carboxylic acid

Following a procedure and using relative proportions of starting materials similar to those described in Example 26, but using ethyl 9-benzyl-1-methylcarbazole-3-carboxylate, as obtained in Example 30, as starting material, the title compound was obtained in a yield of 92%, melting at >240° C.

Nuclear Magnetic Resonance Spectrum (CDCl$_3$, 270 MHz), δ ppm: 2.70 (3H, singlet); 5.83 (2H, singlet); 7.0–7.1 (2H, multiplet); 7.2–7.4 (5H, multiplet); 7.46 (1H, triplet, J=7.6 Hz); 7.93 (1H, singlet); 8.18 (1H, doublet, J=7.6 Hz); 8.79 (1H, singlet).

EXAMPLE 32

Methyl (1-methylcarbazol-3-yl)acetate 73 mg of oxalyl chloride was added, with ice-cooling, to a solution of 92 mg of 1-methylcarbazole-3-carboxylic acid, as obtained in Example 27, in 5 ml of methylene chloride. One drop of N,N-dimethylformamide was then added to the reaction mixture, which was next warmed to room temperature, stirred for 2 hours, and then concentrated by evaporation under reduced pressure. 10 ml of diethyl ether and an excess of a solution of diazomethane in diethyl ether were added to the residue thus obtained, and the reaction mixture was stirred for one night at room temperature. Acetic acid and then a saturated aqueous solution of sodium hydrogencarbonate were added to the reaction mixture. The aqueous layer was extracted with ethyl acetate, and the organic extract was washed with water, dried over anhydrous magnesium sulfate and concentrated by evaporation under reduced pressure. The resulting residue was subjected to column chromatography using 2 g of silica gel with a 1:1 v/v mixture of hexane and ethyl acetate as the eluent. Subsequently, 6 mg of silver oxide was added to a solution of the eluted residue in 5 ml of methanol. The reaction mixture was refluxed for 5 hours, filtered to remove inorganic materials, and concentrated by evaporation under reduced pressure. The resulting residue was subjected to column chromatography using 2 g of silica gel with a 2:1 v/v mixture of hexane and ethyl acetate as the eluent, to yield 90 mg of the title compound as an oil.

EXAMPLE 33

(1-Methylcarbazol-3-yl)acetic acid

Following a procedure and using relative proportions of starting materials similar to those described in Example 26, but using methyl (1-methylcarbazol-3-yl)acetate, as obtained in Example 32, as starting material, the title compound was obtained in a yield of 93%, melting at 177°–179° C.

Nuclear Magnetic Resonance Spectrum (CDCl$_3$, 270 MHz), δ ppm: 2.56 (3H, singlet); 3.81 (2H, singlet); 7.1–7.5 (5H, multiplet); 7.85 (1H, singlet); 7.97 (1H, broad singlet); 8.04 (1H, doublet, J=7.9 Hz).

EXAMPLE 34

9-Benzyl-1-methylcarbazole-2-carbaldehyde 1.6 ml of a 1.5M solution of diisobutylaluminum hydride in hexane was added at −78° C. to a solution of 213 mg of ethyl 9-benzyl-1-methylcarbazole-2-carboxylate, as obtained in Example 28, in 5 ml of methylene chloride. The reaction mixture was stirred for 1 hour at this temperature, warmed to room temperature, and then stirred for a further 1 hour at room temperature. After this time, 0.1 ml of water, 0.1 ml of a 1N aqueous solution of sodium hydroxide and 0.3 ml of water were added successively to the reaction mixture. Precipitated crystals were filtered off and the filtrate was then concentrated by evaporation under reduced pressure. 187 mg of pyridinium dichromate and molecular sieve 4A, followed by 2 ml of methylene chloride, were added to 100 mg of the thus obtained residue. The resulting mixture was stirred for two hours at room temperature, filtered using Florisil (trade mark), and concentrated by evaporation under reduced pressure. The resulting residue was subjected to column chromatography using 2 g of silica gel with a 5:1 v/v mixture of hexane and ethyl acetate as the eluent, to yield 94 mg of the title compound as an amorphous solid.

EXAMPLE 35

Ethyl 3-(9-benzyl-1-methylcarbazol-2-yl)-3-propenoate 90 mg of ethyl diethylphosphonoacetate was added, with ice-cooling, to a suspension of 18 mg of sodium hydride (55% w/w dispersion in mineral oil) in 2 ml of tetrahydrofuran, and the reaction mixture was stirred for 15 minutes. A solution of 83 mg of 9-benzyl-1-methylcarbazole-2-carbaldehyde, as obtained in Example 34, in tetrahydrofuran was then added to the reaction mixture, which was then stirred for 15 minutes. After this time, a saturated aqueous solution of ammonium chloride was added to the reaction mixture. The aqueous layer was extracted with ethyl acetate, and the organic extract was washed with a saturated aqueous solution of sodium chloride, dried over anhydrous magnesium sulfate and concentrated by evaporation under reduced pressure. The resulting residue was subjected to column chromatography using 2 g of silica gel with a 5:1 v/v mixture of hexane and ethyl acetate as the eluent, to yield 97 mg of the title compound as an amorphous solid.

EXAMPLE 36

Ethyl 3-(9-benzyl-1-methylcarbazol-2-yl)propionate 10 mg of 10% w/w palladium on charcoal was added to a solution of 89 mg of ethyl 3-(9-benzyl-1-methylcarbazol-2-yl)-3-propenoate, as obtained in Example 35, in 1 ml each of methanol and of tetrahydrofuran. The reaction mixture was stirred for 1 hour under a stream of hydrogen gas at room temperature, filtered to remove the catalyst, and concentrated by evaporation under reduced pressure. The resulting residue was subjected to column chromatography using 2 g of silica gel with a 5:1 v/v mixture of hexane and ethyl acetate as the eluent, to yield 85 mg of the title compound, melting at 114°–115° C.

Nuclear Magnetic Resonance Spectrum (CDCl$_3$, 270 MHz), δ ppm: 1.24 (3H, triplet, J=7.2 Hz); 2.57 (3H, singlet); 2.59 (2H, triplet, J=8.2 Hz); 3.11 (2H, triplet, J=8.2 Hz); 4.13 (2H, quartet, J=7.2 Hz); 5.76 (2H, singlet); 7.0–7.4 (8H, multiplet); 7.37 (1H, triplet, J=7.0 Hz); 7.91 (1H, doublet, J=7.9 Hz); 8.06 (1H, doublet, J=7.8 Hz).

EXAMPLE 37

3-(9-Benzyl-1-methylcarbazol-2-yl)propionic acid

Following a procedure and using relative proportions of starting materials similar to those described in Example 26, but using ethyl 3-(9-benzyl-1-methylcarbazol-2-yl) propionate, as obtained in Example 36, as starting material, the title compound was obtained in a yield of 97%, melting at 160°–162° C.

Nuclear Magnetic Resonance Spectrum (CDCl$_3$, 270 MHz), δ ppm: 2.57 (3H, singlet); 2.66 (2H, triplet, J=8.1 Hz); 3.13 (2H, triplet, J=8.1 Hz); 5.77 (2H, singlet); 7.0–7.4 (9H, multiplet); 7.92 (1H, doublet, J=7.9 Hz); 8.07 (1H, doublet, J=7.7 Hz).

EXAMPLE 38

(Carbazol-2-yl)thioacetomorpholide 96 mg of morpholine and 18 mg of sulfur powder were added to 157 mg of 2-acetylcarbazole [obtained according to the procedures described by S. G. P. Plant and S. B. C. Williams, J. Chem. Soc., 1142 (1934)]. The reaction mixture was stirred for 5 hours at 80° C., and then acidified by the addition of a 0.5N aqueous solution of hydrochloric acid. The aqueous layer was extracted with ethyl acetate. The organic extract was washed with a saturated aqueous solution of sodium chloride, dried over anhydrous magnesium sulfate, and concentrated by evaporation under reduced pressure. The resulting residue was subjected to column chromatography using 5 g of silica gel with a 2:1 v/v mixture of hexane and ethyl acetate as the eluent, to yield 195 mg of the title compound as an amorphous solid.

EXAMPLE 39

(Carbazol-2-yl)acetic acid 1 ml of a 4N aqueous solution of potassium hydroxide was added to a solution of 100 mg of (carbazol-2-yl) thioacetomorpholide, as obtained in Example 38, in 2 ml of ethanol. The reaction mixture was refluxed for 10 hours, after which time it was acidified by the addition of a 1N aqueous solution of hydrochloric acid and was then concentrated by evaporation under reduced pressure. Ethyl acetate was added to the residue. The aqueous layer was extracted with ethyl acetate, and the organic extract was washed with a saturated aqueous solution of sodium chloride, dried over anhydrous magnesium sulfate and concentrated by evaporation under reduced pressure. The resulting residue was recrystallized from ethyl acetate and hexane, to yield 68 mg of the title compound, melting at 150°–152° C.

Nuclear Magnetic Resonance Spectrum (hexadeuterated dimethyl sulfoxide, 270 MHz), δ ppm: 3.76 (2H, singlet); 7.1–7.5 (5H, multiplet); 7.99 (1H, doublet, J=8.2 Hz); 8.02 (1H, doublet, J=9.2 Hz); 9.21 (1H, broad singlet).

EXAMPLE 40

2-Acetyl-9-benzylcarbazole

Following a procedure and using relative proportions of starting materials similar to those described in Example 28, but using 2-acetylcarbazole as starting material, the title compound was obtained in a yield of 95% as an amorphous solid.

EXAMPLE 41

(9-Benzylcarbazol-2-yl)acetomorpholide

Following a procedure and using relative proportions of starting materials similar to those described in Example 38, but using 2-acetyl-9-benzylcarbazole, as obtained in Example 40 as starting material, the title compound was obtained in a yield of 88% as an amorphous solid.

EXAMPLE 42

(9-Benzylcarbazol-2-yl)acetic acid

Following a procedure and using relative Proportions of starting materials similar to those described in Example 39, but using (9-benzylcarbazol-2-yl)acetomorpholide, as obtained in Example 41, as starting material, the title compound was obtained in a yield of 86%, melting at 149°–150° C.

Nuclear Magnetic Resonance Spectrum (CDCl$_3$, 270 MHz), δ ppm: 3.80 (2H, singlet); 5.50 (2H, singlet); 7.1–7.5 (10H, multiplet); 8.07 (1H, doublet, J=7.6 Hz); 8.10 (1H, doublet, J=6.6 Hz).

EXAMPLE 43 tert-Butyl (1-methylthiocarbazol-2-yloxy)acetate 135 mg of powdered potassium carbonate was added to a solution of 112 mg of 2-hydroxy-1-methylthiocarbazole, as obtained in Example 2, in 4 ml of acetone. 956 mg of tert-butyl bromoacetate was added to the reaction mixture which was then stirred for 2 hours at room temperature. After this time, the reaction mixture was poured into ice water, and concentrated by evaporation under reduced pressure. The aqueous layer was extracted with ethyl acetate. The organic extract was washed with a saturated aqueous solution of sodium chloride, dried over anhydrous magnesium sulfate, and concentrated by evaporation under reduced pressure. The resulting residue was subjected to column chromatography using 3 g of silica gel with a 9:1 v/v mixture of hexane and ethyl acetate as the eluent, to yield 140 mg of the title compound as an oil.

EXAMPLE 44

(1-Methylthiocarbazol-2-yloxy)acetic acid

Following a procedure and using relative proportions of starting materials similar to those described in Example 3, but using tert-butyl (1-methylthiocarbazol-2-yloxy)acetate, as obtained in Example 43, as starting material, the title compound was obtained in quantitative yield, melting at 179°–180° C.

Nuclear Magnetic Resonance Spectrum (CDCl$_3$, 270 MHz), δ ppm: 2.50 (3H, singlet); 4.82 (2H, singlet); 6.79 (1H, doublet, J=8.6 Hz); 7.20 (1H, triplet, J=7.9 Hz); 7.37 (1H, triplet, J=7.9 Hz); 7.47 (1H, doublet, J=7.9 Hz); 7.92 (1H, doublet, J=8.6 Hz); 7.96 (1H, doublet, J=7.9 Hz); 8.89 (1H, broad singlet).

EXAMPLE 45 tert-Butyl (9-benzyl-1-methylthiocarbazol-2-yloxy) acetate

Following a procedure and using relative proportions of starting materials similar to those described in Example 28, but using tert-butyl (1-methylthiocarbazol-2-yloxy)acetate, as obtained in Example 43, as starting material, the title compound was obtained as an oil in a yield of 94%.

EXAMPLE 46

(9-Benzyl-1-methylthiocarbazol-2-yloxy)acetic acid

Following a procedure and using relative proportions of starting materials similar to those described in Example 3, but using tert-butyl (9-benzyl-1-methylthiocarbazol-2-yloxy)acetate, as obtained in Example 45, as starting material, the title compound was obtained in quantitative yield, melting at 188°–189° C.

Nuclear Magnetic Resonance Spectrum (CDCl$_3$, 270 MHz), δ ppm: 2.04 (3H, singlet); 4.85 (2H, singlet); 6.25 (2H, singlet); 6.89 (1H, doublet, J=8.2 Hz); 7.01 (2H, doublet, J=6.7 Hz); 7.1–7.5 (6H, multiplet); 8.05 (1H, doublet, J=7.9 Hz); 8.10 (1H, doublet, J=8.4 Hz).

EXAMPLE 47

(2-Hydroxy-1-oxo-1,2,3,4-tetrahydrocarbazol-2-yl) acetic acid

Following a procedure and using relative proportions of starting materials similar to those described in Example 3, but using tert-butyl 2-hydroxy-1-oxo-1,2,3,4-tetrahydrocarbazol-2-yl)acetate, as obtained in Example 2, as starting material, the title compound was obtained in a yield of 98%, melting at 156°–157° C.

Nuclear Magnetic Resonance Spectrum (hexadeuterated dimethyl sulfoxide, 270 MHz), δ ppm: 2.34 (1H, doubled doublet of doublets, J=5.2, 8.3, 13.5 Hz); 2.55 (1H, triplet of doublets, J=5.2, 13.5 Hz); 2.72 (2H, singlet); 3.03 (1H, doubled doublet of doublets, J=5.2, 8.3, 17.3 Hz); 3.20 (1H, triplet of doublets, J=5.2, 17.3 Hz); 7.10 (1H, triplet, J=7.8 Hz); 7.32 (1H, triplet, J=7.8 Hz); 7.46 (1H, doublet, J=7.8 Hz); 7.62 (1H, doublet, J=7.8 Hz); 11.1 (1H, broad singlet).

EXAMPLE 48

Ethyl 1,2,3,4-tetrahydrocarbazole-3-carboxylate

A solution of 1.08 g of phenylhydrazine and 1.84 g of ethyl 4-oxocyclohexanecarboxylate in 25 ml of acetic acid was refluxed for 30 minutes and then poured into ice water. The aqueous layer was extracted with ethyl acetate. The organic extract was washed thoroughly with a saturated aqueous solution of sodium hydrogencarbonate, dried over anhydrous magnesium sulfate, and concentrated by evaporation under reduced pressure. The resulting residue was subjected to column chromatography using 50 g of silica gel with a 4:1 v/v mixture of hexane and ethyl acetate as the eluent and then recrystallized from ethyl acetate and hexane, to yield 2.28 g of the title compound, melting at 95°–96° C.

Nuclear Magnetic Resonance Spectrum (CDCl$_3$, 270 MHz), δ ppm: 1.30 (3H, triplet, J=7.1 Hz); 1.9–2.1 (1H, multiplet); 2.2–2.4 (1H, multiplet); 2.7–3.0 (4H, multiplet); 3.08 (1H, doublet of doublets, J=5.1, 15.1 Hz); 4.20 (2H, quartet, J=7.1 Hz); 7.08 (1H, triplet, J=7.1 Hz); 7.13 (1H, triplet, J=7.1 Hz); 7.27 (1H, doublet, J=7.1 Hz); 7.47 (1H, doublet, J=7.1 Hz); 7.72 (1H, broad singlet).

EXAMPLE 49

1,2,3,4-Tetrahydrocarbazole-3-carboxylic acid

Following a procedure and using relative proportions of starting materials similar to those described in Example 26, but using ethyl 1,2,3,4-tetrahydrocarbazole-3-carboxylate, as obtained in Example 48, as starting material, the title compound was obtained in a yield of 95%, melting at 198°–199° C.

Nuclear Magnetic Resonance Spectrum (CDCl$_3$, 270 MHz), δ ppm: 2.0–2.2 (1H, multiplet); 2.2–2.4 (1H, multiplet); 2.7–3.2 (5H, multiplet); 7.09 (1H, triplet, J=6.8 Hz); 7.14 (1H, triplet, J=6.8 Hz); 7.29 (1H, doublet, J=6.8 Hz); 7.48 (1H, doublet, J=6.8 Hz); 7.73 (1H, broad singlet).

EXAMPLE 50

Benzyl 1,2,3,4-tetrahydrocarbazole-3-carboxylate 5.53 g of powdered potassium carbonate was added to a solution of 4.34 g of 1,2,3,4-tetrahydrocarbazole-3- carboxylic acid, as obtained in Example 49, in 100 ml of N,N-dimethylformamide. 3.76 g of benzyl bromide were added to the reaction mixture, which was then stirred for 1.5 hours at room temperature, after which the mixture was neutralized by the addition of a 0.5N aqueous solution of hydrochloric acid. The aqueous layer was extracted with ethyl acetate. The organic extract was washed with water, dried over anhydrous magnesium sulfate, and concentrated by evaporation under reduced pressure. The resulting residue was subjected to column chromatography using 150 g of silica gel with a 4:1 v/v mixture of hexane and ethyl acetate as the eluent, and recrystallized from ethyl acetate and hexane, to yield 6.04 g of the title compound, melting at 104°–105° C.

EXAMPLE 51

Benzyl 9-benzoyl-1,2,3,4-tetrahydrocarbazole-3-carboxylate

A solution of 291 mg of benzyl 1,2,3,4-tetrahydrocarbazole-3-carboxylate, as obtained in Example 50, in 2 ml of N,N-dimethylformamide was added, with ice-cooling, to a suspension of 87 mg of sodium hydride (55% w/w dispersion in mineral oil) in 4 ml of N,N-dimethylformamide. 0.12 ml of benzoyl chloride was added to the reaction mixture which was then stirred for 1 hour. After this time, a saturated aqueous solution of ammonium chloride was added to the reaction mixture. The aqueous layer was extracted with ethyl acetate, and the organic extract was washed with water, dried over anhydrous magnesium sulfate and concentrated by evaporation under reduced pressure. The resulting residue was subjected to column chromatography using 10 g of silica gel with a 5:1 v/v mixture of hexane and ethyl acetate as the eluent, to yield 384 mg of the title compound as an oil.

EXAMPLE 52

9-Benzoyl-1,2,3,4-tetrahydrocarbazole-3-carboxylic acid 20 mg of 10% w/w palladium on charcoal was added to a solution of 100 mg of benzyl 9-benzoyl-1,2,3,4-tetrahydrocarbazole-3-carboxylate, as obtained in Example 51, in 5 ml each of methanol and of tetrahydrofuran. The reaction mixture was stirred for 3 hours under a stream of hydrogen gas at room temperature, filtered to remove the catalyst, and concentrated by evaporation under reduced pressure. The resulting residue was recrystallized from ethyl acetate and hexane, to yield 75 mg of the title compound, melting at 189°–190° C.

Nuclear Magnetic Resonance Spectrum (CDCl$_3$, 270 MHz), δ ppm: 1.9–2.0 (1H, multiplet); 2.2–2.4 (1H, multiplet); 2.8–3.2 (5H, multiplet); 7.07 (2H, doublet, J=3.8 Hz); 7.20 (1H, triplet of doublets, J=4.0, 7.9 Hz); 7.4–7.8 (6H, multiplet).

EXAMPLE 53

Benzyl 9-i-butyryl-1,2,3,4-tetrahydrocarbazole-3-carboxylate

Following a procedure and using relative proportions of starting materials similar to those described in Example 51, but using i-butyryl chloride as starting material, the title compound was obtained as an oil in a yield of 83%.

EXAMPLE 54

9-i-Butyryl-1,2,3,4-tetrahydrocarbazole-3-carboxylic acid

Following a procedure and using relative proportions of starting materials similar to those described in Example 52, but using benzyl 9-i-butyryl-1,2,3,4-tetrahydrocarbazole-3-carboxylate, as obtained in Example 53, as starting material, the title compound was obtained in a yield of 98% as an amorphous solid.

Nuclear Magnetic Resonance Spectrum (CDCl$_3$, 270 MHz), δ ppm: 1.34 (3H, doublet, J=6.6 Hz); 1.36 (3H, doublet, J=6.6 Hz); 1.9–2.1 (1H, multiplet); 2.3–2.4 (1H, multiplet); 2.8–3.3 (5H, multiplet); 3.50 (1H, septet, J=6.6 Hz); 7.2–7.4 (2H, multiplet); 7.44 (1H, doublet of doublets, J=1.8, 7.2 Hz); 7.88 (1H, doublet of doublets, J=2.1, 6.8 Hz).

EXAMPLE 55

Ethyl 9-benzyl-1,2,3,4-tetrahydrocarbazole-3-carboxylate

Following a procedure and using relative proportions of starting materials similar to those described in Example 48, but using benzylphenylhydrazine as starting material, the title compound was obtained as an oil in a yield of 89%.

Nuclear Magnetic Resonance Spectrum (CDCl$_3$, 270 MHz), δ ppm: 1.28 (3H, triplet, J=7.1 Hz); 1.9–2.1 (1H, multiplet); 2.2–2.4 (1H, multiplet); 2.6–3.0 (4H, multiplet); 3.12 (1H, doublet of doublets, J=5.3, 15.3 Hz); 4.19 (2H, quartet, J=7.1 Hz); 5.20 (1H, doublet, J=17.0 Hz); 5.27 (1H, doublet, J=17.0 Hz); 6.9–7.0 (2H, multiplet); 7.0–7.4 (6H, multiplet); 7.5–7.6 (1H, multiplet).

EXAMPLE 56

9-Benzyl-1,2,3,4-tetrahydrocarbazole-3-carboxylic acid

Following a procedure and using relative proportions of starting materials similar to those described in Example 26, but using ethyl 9-benzyl-1,2,3,4-tetrahydrocarbazole-3-carboxylate, as obtained in Example 55, as starting material, the title compound was obtained in a yield of 93%, melting at 195°–196° C.

Nuclear Magnetic Resonance Spectrum (CDCl$_3$, 270 MHz), δ ppm: 1.9–2.2 (1H, multiplet); 2.3–2.4 (1H, multiplet); 2.6–3.1 (4H, multiplet); 3.17 (1H, doublet of doublets, J=5.1, 10.1 Hz); 5.22 (1H, doublet, J=16.9 Hz); 5.29 (1H, doublet, J=16.9 Hz); 6.9–7.0 (2H, multiplet); 7.0–7.3 (6H, multiplet); 7.52 (1H, doublet of doublets, J=3.1, 5.8 Hz).

EXAMPLE 57

Ethyl 4-oxocyclohexylideneacetate ethylene acetal

Following a procedure and using relative proportions of starting materials similar to those described in Example 35, but using cyclohexane-1,4-dione monoethylene acetal as starting material, the title compound was obtained in a yield of 87% as an oil.

EXAMPLE 58

Ethyl 4-oxocyclohexylacetate ethylene acetal

Following a procedure and using relative proportions of starting materials similar to those described in Example 36, but using ethyl 4-oxocyclohexylideneacetate ethylene acetal, as obtained in Example 57, as starting material, the title compound was obtained as an oil in a yield of 95%.

EXAMPLE 59

Ethyl 4-oxocyclohexylacetate 50 ml of a 1N aqueous solution of hydrochloric acid was added to a solution of 5.0 g of ethyl 4-oxocyclohexylacetate ethylene acetal, as obtained in Example 58, in 50 ml of acetone. The reaction mixture was stirred for 10 minutes at room temperature, neutralized by the addition of a saturated aqueous solution of sodium hydrogencarbonate, and then concentrated by evaporation under reduced pressure. The resulting residue was extracted with ethyl acetate. The organic extract was washed with a saturated aqueous solution of sodium chloride, dried over anhydrous magnesium sulfate and concentrated by evaporation under reduced pressure. The resulting residue was subjected to column chromatography using 100 g of silica gel with a 4:1 v/v mixture of hexane and ethyl acetate as the eluent, to yield 3.9 g of the title compound as an oil.

EXAMPLE 60

Ethyl (1,2,3,4-tetrahydrocarbazol-3-yl)acetate

Following a procedure and using relative proportions of starting materials similar to those described in Example 48, but using ethyl 4-oxocyclohexylacetate, as obtained in Example 59, as starting material, the title compound was obtained in a yield of 90%, melting at 122°–123° C.

Nuclear Magnetic Resonance Spectrum ($CDCl_3$, 270 MHz), δ ppm: 1.29 (3H, triplet, J=7.1 Hz); 1.6–1.8 (1H, multiplet); 2.0–2.2 (1H, multiplet); 2.3–2.5 (4H, multiplet); 2.7–3.0 (3H, multiplet); 4.18 (2H, quartet, J=7.1 Hz); 7.07 (1H, triplet, J=7.0 Hz); 7.12 (1H, triplet, J=7.0 Hz); 7.27 (1H, doublet, J=7.0 Hz); 7.44 (1H, doublet, J=7.0 Hz): 7.70 (1H, broad singlet).

EXAMPLE 61

(1,2,3,4-Tetrahydrocarbazol-3-yl)acetic acid

Following a procedure and using relative proportions of starting materials similar to those described in Example 26, but using ethyl (1,2,3,4-tetrahydrocarbazol-3-yl)acetate, as obtained in Example 60, as starting material, the title compound was obtained in a yield of 95%, melting at 209°–210° C.

Nuclear Magnetic Resonance Spectrum ($CDCl_3$, 270 MHz), δ ppm: 1.6–1.8 (1H, multiplet); 2.0–2.3 (1H, multiplet); 2.3–3.0 (7H, multiplet); 7.01 (1H, triplet, J=7.5 Hz); 7.07 (1H, triplet, J=7.5 Hz); 7.29 (1H, doublet, J=7.5 Hz); 7.41 (1H, doublet, J=7.5 Hz); 8.98 (1H, broad singlet).

EXAMPLE 62

Ethyl (9-benzyl-1,2,3,4-tetrahydrocarbazol-3-yl) acetate

Following a procedure and-using relative proportions of starting materials similar to those described in Examples 55 and 56, but using ethyl 4-oxocyclohexylacetate, as obtained in Example 59, as starting material, the title compound was obtained as an oil in a yield of 91%.

Nuclear Magnetic Resonance Spectrum ($CDCl_3$, 270 MHz), δ ppm: 1.28 (3H, triplet, J=7.1 Hz); 1.5–1.7 (1H, multiplet); 2.0–2.1 (1H, multiplet); 2.3–2.5 (4H, multiplet); 2.6–2.7 (2H, multiplet); 2.9–3.0 (1H, multiplet); 4.17 (2H, quartet, J=7.1 Hz); 5.21 (1H, doublet, J=17.7 Hz); 5.28 (1H, doublet, J=17.7 Hz); 6.9–7.3 (8H, multiplet); 7.49 (1H, doublet, J=6.5 Hz).

EXAMPLE 63

(9-Benzyl-1,2,3,4-tetrahydrocarbazol-3-yl)acetic acid

Following a procedure and using relative proportions of starting materials similar to those described in Example 26, but using ethyl (9-benzyl-1,2,3,4-tetrahydrocarbazol-3-yl) acetate, as obtained in Example 61, as starting material, the title compound was obtained in a yield of 97%, melting at 156°–158° C.

Nuclear Magnetic Resonance Spectrum ($CDCl_3$, 270 MHz), δ ppm: 1.6–1.8 (1H, multiplet); 2.0–2.1 (1H, multiplet); 2.3–2.8 (6H, multiplet); 3.01 (1H, doublet of doublets, J=4.1, 14.9 Hz); 5.20 (1H, doublet, J=17.9 Hz); 5.27 (1H, doublet, J=17.9 Hz); 6.9–7.3 (8H, multiplet); 7.50 (1H, doublet, J=6.3 Hz).

EXAMPLE 64

Allyl 2-(indol-6-yl)acetate 750 mg of 1-ethyl-3-(3-dimethylaminopropyl) carbodiimide hydrochloride were added to a solution of 450 mg of 2-(indol-6-yl)acetic acid [synthesized according to the procedures described in Chem. Pharm. Bull., 20, 2163 (1972)], 0.27 ml of allyl alcohol and 480 mg of 4-dimethylaminopyridine in 20 ml of methylene chloride, at room temperature, and the resulting mixture was stirred overnight. After completion of the reaction, the reaction mixture was acidified by the addition of a 3% aqueous solution of hydrochloric acid, followed by extraction with ethyl acetate. The extract was washed with water and dried over anhydrous sodium sulfate, and then the solvent was removed by evaporation under reduced pressure. The resulting residue was subjected to column chromatography using 10 g of silica gel with a 4:1 v/v mixture of hexane and ethyl acetate as the eluent, to yield 480 mg of the title compound as an oil.

Nuclear Magnetic Resonance Spectrum ($CDCl_3$, 270 MHz), δ ppm: 8.10 (1H, broad singlet); 7.58 (1H, doublet, J=8.0 Hz); 7.34 (1H, singlet); 7.18 (1H, multiplet); 7.05 (1H, doublet, J=8.0 Hz); 6.52 (1H, multiplet); 5.80–6.00 (1H, multiplet); 5.15–5.35 (2H, multiplet); 4.55–4.65 (2H, multiplet); 3.75 (2H, singlet).

EXAMPLE 65

Allyl 2-benzyl-2-(1-benzylindol-6-yl)acetate and Allyl 2-(1-benzylindol-6-yl)acetate A solution of 100 mg of allyl 2-(indol-6-yl)acetate, as obtained in Example 64, in 1 ml of N,N-dimethylformamide was added, with ice-cooling, to a suspension of 20 mg of sodium hydride (55% w/w dispersion in mineral oil) in 1 ml of N,N-dimethylformamide, and the reaction mixture was stirred at this temperature for 15 minutes. 0.06 ml of benzyl bromide was added to the reaction mixture, with ice-cooling, and the resulting mixture was stirred for a further 30 minutes. After completion of the reaction, water was added to the reaction mixture, followed by extraction with ethyl acetate. The extract was washed with water and dried over anhydrous sodium sulfate, and then the solvent was removed by evaporation under reduced pressure. The residue was purified over column chromatography using 10 g of silica gel with, successively, a 5% v/v solution of ethyl acetate in hexane, and a 10% solution of ethyl acetate in hexane.

44 mg of allyl 2-benzyl-2-(1-benzylindol-6-yl)acetate were obtained from the first fraction (5% eluent), and 70 mg of allyl 2-(1-benzylindol-6-yl)acetate were obtained from the second fraction (10% eluent).

The Nuclear Magnetic Resonance Spectrum [($CDCl_3$, 270 MHz), δ ppm] results for each of the above compounds are as follows:

Allyl 2-benzyl-2-(1-benzylindol-6-yl)acetate 7.61 (1H, doublet, J=8.2 Hz); 7.05–7.40 (13H, multiplet); 6.54 (1H, doublet, J=3.0 Hz); 5.65–5.85 (1H, multiplet);

5.33 (2H, singlet); 5.05–5.20 (2H, multiplet); 4.50–4.60 (2H, multiplet); 3.99 (1H, doublet of doublets, J=8.8, 6.6 Hz); 3.46 (1H, doublet of doublets, J=13.6, 8.8 Hz); 3.09 (1H, doublet of doublets, J=13.6, 6.6 Hz).

Allyl 2-(1-benzylindol-6-yl)acetate 7.59 (1H, doublet, J=8.2 Hz); 7.00–7.30 (8H, multiplet); 6.51 (1H, doublet, J=3.4 Hz); 5.75–5.95 (1H, multiplet); 5.29 (2H, singlet); 5.10–5.30 (2H, multiplet); 4.50–4.60 (2H, multiplet); 3.71 (2H, singlet).

EXAMPLE 66

2-Benzyl-2-(1-benzylindol-6-yl)acetic acid 6 mg of tetrakistriphenylphosphine palladium, 7 mg of triphenylphosphine and 65 mg of sodium 2-ethylhexanoate were added to a solution of 104 mg of allyl 2-benzyl-2-(1-benzylindol-6-yl)acetate, as obtained in Example 65, in 5 ml of methylene chloride, and the resulting mixture was stirred at room temperature overnight. After completion of the reaction, the reaction mixture was acidified by the addition of a 3% aqueous solution of hydrochloric acid, followed by extraction with ethyl acetate. The extract was washed with water and dried over anhydrous sodium sulfate, and then the solvent was removed by evaporation under reduced pressure. The resulting residue was subjected to column chromatography using 5 g of silica gel with a 1:1 v/v mixture of hexane and ethyl acetate as the eluent, to yield 61 mg of the title compound as a solid material, melting at 148°–150° C.

Nuclear Magnetic Resonance Spectrum (CDCl$_3$, 270 MHz), δ ppm: 7.58 (1H, doublet, J=8.0 Hz); 7.00–7.30 (13H, multiplet); 6.50 (1H, doublet, J=8.0 Hz); 5.28 (2H, singlet); 3.93 (1H, triplet, J=8.0 Hz); 3.42 (1H, doublet of doublets, J=13.8, 8.0 Hz); 3.05 (1H, doublet of doublets, J=13.8, 8.0 Hz).

EXAMPLE 67

2-(1-Benzylindol-6-yl)acetic acid

Following a procedure and using relative proportions of starting materials similar to those described in Example 66, but using 16 mg of allyl 2-(1-benzylindol-6-yl)acetate, as obtained in Example 65, as starting material, 6 mg of the title compound was obtained as a solid material, melting at 109°–111° C.

Nuclear Magnetic Resonance Spectrum (CDCl$_3$, 270 MHz), δ ppm: 7.60 (1H, doublet, J=8.0 Hz); 7.00–7.35 (8H, multiplet); 6.51 (1H, doublet, J=4.0 Hz); 5.30 (2H, singlet); 3.72 (2H, singlet).

EXAMPLE 68

Allyl 2-(1-benzoylindol-6-yl)acetate

Following a procedure and using relative proportions of starting materials similar to those described in Example 65, but using 100 mg of allyl 2-(indol-6-yl)acetate, as obtained in Example 64, and 0.05 ml of benzoyl chloride as starting materials, 65 mg of the title compound was obtained as an oil.

Nuclear Magnetic Resonance Spectrum (CDCl$_3$, 270 MHz), δ ppm: 8.41 (1H, singlet); 7.20–7.80 (8H, multiplet); 6.61 (1H, doublet, J=4.0 Hz); 5.80–6.00 (1H, multiplet); 5.20–5.40 (2H, multiplet); 4.55–4.70 (2H, multiplet); 3.84 (2H, singlet).

EXAMPLE 69

2-(1-Benzoylindol-6-yl)acetic acid

Following a procedure and using relative proportions of starting materials similar to those described in Example 66, but using 65 mg of allyl 2-(1-benzoylindol-6-yl)acetate, as obtained in Example 68, as starting material, 26 mg of the title compound was obtained as a solid material, melting at 113°–115° C.

Nuclear Magnetic Resonance Spectrum (CDCl$_3$, 270 MHz), δ ppm: 8.38 (1H, singlet); 7.20–7.80 (8H, multiplet); 6.59 (1H, doublet, J=4.0 Hz); 3.82 (2H, singlet).

EXAMPLE 70

1-Phenyl-1,2,3,4-tetrahydro-β-carboline

A mixture of 1.0 g (6.24 mmol) of tryptamine and 0.73 g (0.87 mmol) of benzaldehyde in 10 ml of acetic acid was refluxed for 3 hours. After completion of the reaction, the solvent was distilled off, and the residue was made alkaline by the addition of a saturated aqueous solution of sodium hydrogencarbonate, followed by extraction with ethyl acetate. The extract was washed with a saturated aqueous solution of sodium chloride and dried over anhydrous sodium sulfate, and then the solvent was removed by evaporation under reduced pressure to give 1.82 g of a crude mixture. The resulting residue was subjected to column chromatography using 35 g of silica gel with a 9:1 by volume mixture of methylene chloride and methanol as the eluent, to yield 1.43 g (92%) of the title compound. The product was subsequently recrystallized from dichloroethane and hexane to yield 0.72 g of pale yellowish brown crystals.

EXAMPLE 71

Benzyl (1-phenyl-1,2,3,4-tetrahydro-β-carbolin-2-yl)acetate 147 mg (1.45 mmol) of triethylamine and 277 mg (1.21 mmol) of benzyl bromoacetate were added successively to a solution of 300 mg (1.21 mmol) of 1-phenyl-1,2,3,4-tetrahydro-β-carboline, as obtained in Example 70, in 10 ml of methylene chloride, with ice-cooling, and the resulting mixture was stirred at room temperature for 3 hours. After this time, 277 mg of benzyl bromoacetate and 183 mg of triethylamine were added to the reaction mixture, and the resulting mixture was allowed to stand for 2 days. At the end of this time, first a saturated aqueous solution of sodium hydrogencarbonate and then water were added successively to the reaction mixture, which was then extracted with ethyl acetate. The resulting extract was washed with a saturated aqueous solution of sodium chloride and dried over anhydrous sodium sulfate, and the ethyl acetate was removed by evaporation under reduced pressure to give 0.61 g of a crude mixture. The resulting residue was subjected to column chromatography using 13 g of silica gel with a 9:1 by volume mixture of hexane and ethyl acetate as the eluent, to yield 0.49 g of the title compound as yellow crystals in quantitative yield. The product was subsequently recrystallized from ethyl acetate to yield 0.37 g of the title compound as yellow crystals, melting at 130.8°–132.0° C.

Nuclear Magnetic Resonance Spectrum (CDCl$_3$, 270 MHz), δ ppm: 2.80–3.30 (4H, multiplet); 3.36 (1H, doublet, J=16 Hz); 3.50 (1H, doublet, J=16 Hz); 5.07 (1H, singlet); 5.12 (1H, doublet, J=16 Hz); 5.18 (1H, doublet, J=16 Hz); 7.05–7.57 (15H, multiplet).

EXAMPLE 72

(1-Phenyl-1,2,3,4-tetrahydro-β-carbolin-2-yl)acetic acid

A catalytic amount of 10% w/w palladium on charcoal was added under a stream of hydrogen to a solution of 260.2 mg (0.656 mmol) of benzyl (1-phenyl-1,2,3,4-tetrahydro-β-carbolin-2-yl)acetate, as obtained in Example 71, in 2 ml each of methanol and of tetrahydrofuran, and hydrogenation was allowed to proceed for 3 hours. The palladium on charcoal catalyst was removed from the reaction mixture by filtration, and the solvent was removed by evaporation under reduced pressure to give 0.32 g of a crude mixture. The resulting residue was subjected to column chromatography using 5 g of silica gel with a 19:1 by volume mixture of methylene chloride and methanol as the eluent, to yield 0.05 g of the title compound as a pale yellow powder, melting at 157°–164° C. (with decomposition).

Nuclear Magnetic Resonance Spectrum (CDCl$_3$, 270 MHz), δ ppm: 3.20–4.13 (6H, multiplet); 6.11 (1H, singlet); 7.15–7.65 (10H, multiplet); 8.07 (1H, singlet).

EXAMPLE 73 tert-Butyl [9-(4-methoxybenzyl)-1-methylthiocarbazol-2-yl]acetate

Following a procedure and using relative proportions of starting materials similar to those described in Example 4, but using 4-methoxybenzyl bromide as starting material, the title compound was obtained as an oil in a yield of 98%.

EXAMPLE 74

[9-(4-Methoxybenzyl)-1-methylthiocarbazol-2-yl] acetic acid

Following a procedure and using relative proportions of starting materials similar to those described in Example 3, but using tert-butyl [9-(4-methoxybenzyl)-1-methylthiocarbazol-2-yl]acetate, as obtained in Example 73, as starting material, the title compound was obtained in quantitative yield as an amorphous solid.

Nuclear Magnetic Resonance Spectrum (CDCl$_3$, 270 MHz), δ ppm: 2.01 (3H, singlet); 3.71 (3H, singlet); 4.22 (2H, singlet); 6.28 (2H, singlet); 6.75 (2H, doublet, J=8.7 Hz); 6.96 (2H, doublet, J=8.7 Hz); 7.2–7.5 (4H, multiplet); 8.07 (1H, doublet, J=7.6 Hz); 8.09 (1H, doublet, J=7.9 Hz).

EXAMPLE 75

9-Benzyl-1-methylthiocarbazole-2-acetamide

An excess of a solution of diazomethane in diethyl ether was added to a solution of 150 mg of 9-benzyl-1-methylthiocarbazol-2-acetic acid, as obtained in Example 5, in 3 ml of diethyl ether. The resulting reaction mixture was stirred for 10 minutes at room temperature and then glacial acetic acid was added. The reaction mixture was next concentrated by evaporation under reduced pressure. 10 ml of saturated methanolic ammonia was added to a solution of the resulting residue in 5 ml of methanol, and the reaction mixture was stirred for 7 days at room temperature. After this time, the reaction mixture was concentrated by evaporation under reduced pressure and the resulting residue was subjected to column chromatography using 400 mg of silica gel using, as eluent, a 4:1 by volume mixture of hexane and ethyl acetate to yield 131 mg of the title compound as an amorphous solid.

EXAMPLE 76

9-Benzyl-1-methylthiocarbazol-2-acetonitrile 32 mg of p-toluene sulfonyl chloride was added to a solution of 20 mg of 9-benzyl-1-methylthiocarbazole-2-acetamide, as obtained in Example 75, in 0.6 ml of pyridine at room temperature. The reaction mixture was then heated to 60° C. and stirred for 2 hours. The reaction mixture was then cooled to room temperature and water was added. The aqueous layer was extracted with ethyl acetate, and the organic extract was washed with a 0.5N aqueous solution of hydrochloric acid, dried over anhydrous magnesium sulfate and concentrated by evaporation under reduced pressure. The resulting residue was subjected to column chromatography using 50 mg of silica gel using, as eluent, a 4:1 by volume mixture of hexane and ethyl acetate to yield 18 mg of the title compound as an oil.

EXAMPLE 77

5-[(9-Benzyl-1-methylthiocarbazol)-2-ylmethyl]-1H-tetrazole 64 mg of ammonium chloride and 78 mg of sodium azide were added to a solution of 13 mg of 9-benzyl-1-methylthiocarbazol-2-acetonitrile, as obtained in Example 76, in 3 ml of N,N-dimethylformamide, at room temperature. The reaction mixture was then heated to 130° C. and stirred for 1 day. After this time, the reaction mixture was cooled to room temperature and water was added. The aqueous layer was extracted with ethyl acetate, and the organic extract was washed with a saturated aqueous solution of sodium chloride, dried over anhydrous magnesium sulfate and concentrated by evaporation under reduced pressure. The resulting residue was subjected to column chromatography using 40 mg of silica gel using, as eluent, a 1:5 by volume mixture of hexane and ethyl acetate to yield 14 mg of the title compound as an amorphous solid.

Nuclear Magnetic Resonance Spectrum (CDCl$_3$, 270 MHz), δ ppm: 1.91 (3H, singlet); 4.81 (2H, singlet); 6.30 (2H, singlet); 6.9–7.1 (2H, multiplet); 7.1–7.5 (7H, multiplet); 8.1–8.2 (2H, multiplet).

EXAMPLE 78

2-[4-tert-Butyldiphenylsilyloxy-2-(indol-2-ylthio) butyl]-4,4-dimethyl-2-oxazoline a) 2-(4-tert-Butyldiphenylsilyloxy-2-hydroxybutyl)-4,4-dimethyl-2-oxazoline 5.2 ml of a solution of 1.6M n-butyllithium in hexane was added dropwise to a solution of 940 mg of 2,4,4-trimethyl-2-oxazoline in 20 ml of tetrahydrofuran with stirring, at −78° C. The resulting mixture was stirred at −78° C. for 1 hour. After this time, 2.00 g of 3-tert-butyldiphenylsilyloxy-1-propanal [prepared as described in Can. J. Chem., 71, 695 (1993)] in 10 ml of tetrahydrofuran was added to the reaction mixture whilst stirring, maintaining the temperature at −78° C. Stirring was continued at −78° C. for 15 minutes, then the reaction mixture was brought to room temperature and stirred for 30 minutes. At the end of this time, the reaction mixture was diluted with water and extracted with ethyl acetate. The ethyl acetate fraction was washed with water, dried over anhydrous sodium sulfate and the solvent removed by evaporation under reduced pressure. The resulting residue was purified by silica gel column chromatography, using a mixture of 50% v/v ethyl acetate and hexane as the eluent, to afford 2.18 g of the title compound as an oil.

Nuclear Magnetic Resonance Spectrum (CDCl$_3$) δ ppm: 1.05 (9H, singlet), 1.26 (6H, singlet), 1.70–1.80 (2H, multiplet), 2.35–2.45 (2H, multiplet), 3.75–3.90 (2H, multiplet), 3.90 (2H, singlet), 4.15–4.20 (1H, multiplet), 4.25 (1H, broad singlet), 7.30–7.70 (10H, multiplet).

b) 2-[4-tert-Butyldiphenylsilyloxy-2-(indol-2-ylthio)butyl]-4,4-dimethyl-2-oxazoline 960 mg of carbon tetrabromide was added to a mixture of 800 mg of 2-(4-tert-butyldiphenylsilyloxy-2-hydroxybutyl)-4,4-dimethyl-2-oxazoline [prepared as described in a) above] and 760 mg of triphenylphosphine in 20 ml of dichloromethane, with stirring, at room temperature, and stirring was continued at this temperature for 30 minutes. After this time, the solvent was removed by evaporation under reduced pressure and the residue was dissolved in 10 ml of acetone. The resulting solution was added to a suspension of 280 mg of indoline-2-thione [prepared as described in Chem. Pharm. Bull., 32, 877, (1984)] and 400 mg of potassium carbonate in 20 ml of acetone, and this mixture was stirred at room temperature for 1 hour. At the end of this time, the solvent was removed by evaporation under reduced pressure, and the resulting residue was diluted with water and then extracted with ethyl acetate. The ethyl acetate fraction was then washed with water and dried over anhydrous sodium sulfate. The solvent was then removed by evaporation under reduced pressure, and the resulting residue was purified by silica gel column chromatography, using a mixture of 20% v/v ethyl acetate in hexane as the eluent, to afford 460 mg of the title compound as an oil.

Nuclear Magnetic Resonance Spectrum (CDCl$_3$) δ ppm: 1.05 (9H, singlet), 1.38 (3H, singlet), 1.42 (3H, singlet), 1.70–1.80 (2H, multiplet), 2.30–2.60 (2H, multiplet), 3.35–3.45 (1H, multiplet), 3.70–3.85 (2H, multiplet), 4.02 (2H, singlet), 6.58 (1H, singlet), 7.05–7.70 (14H, multiplet).

EXAMPLE 79

2-[4-Hydroxy-2-(indol-2-ylthio)butyl]-4,4-dimethyl-2-oxazoline 1 ml of a 1M solution of tetra-n-butyl ammonium fluoride in tetrahydrofuran was added to a solution of 460 mg of 2-[4-tert-butyldiphenylsilyloxy-2-(indol-2-ylthio)butyl]-4,4-dimethyl-2-oxazoline [prepared as described in Example 78b)] in 20 ml of tetrahydrofuran, with stirring, at room temperature, and stirring was continued at this temperature for 30 minutes. After this time, the reaction mixture was diluted with water and then extracted with ethyl acetate. The ethyl acetate fraction was then washed with water and dried over anhydrous sodium sulfate. The solvent was then removed by evaporation under reduced pressure and the resulting residue was purified by silica gel column chromatography, using a mixture of 60% v/v ethyl acetate in hexane as the eluent, to afford 165 mg of the title compound as an oil.

Nuclear Magnetic Resonance Spectrum (CDCl$_3$) δ ppm: 1.36 (3H, singlet), 1.40 (3H, singlet), 1.70–1.85 (2H, multiplet), 2.45–2.55 (2H, multiplet), 3.30–3.45 (1H, multiplet), 3.70–4.00 (2H, multiplet), 4.02 (2H, singlet), 6.67 (1H, singlet), 7.05–7.60 (4H, multiplet).

EXAMPLE 80

2-(2,3,4,9-Tetrahydrothiopyrano[2,3-b]indol-2-yl)methyl-4,4-dimethyl-2-oxazoline 0.05 ml of methanesulfonyl chloride was added to a mixture of 165 mg of 2-[4-hydroxy-2-(indol-2-ylthio)butyl]-4,4-dimethyl-2-oxazoline (prepared as described in Example 79) and 0.10 ml of triethylamine in 5 ml of dichloromethane, with stirring and ice-cooling, and stirring was continued for 30 minutes. At the end of this time, the reaction mixture was diluted with water and then extracted with ethyl acetate. The ethyl acetate fraction was then washed with water and dried over anhydrous sodium sulfate. The solvent was then removed by evaporation under reduced pressure and the resulting residue was dissolved in a mixture of 5 ml of dichloromethane and 5 ml of benzene. 0.26 ml of a solution of 3M ethylmagnesium bromide in diethyl ether was then added to this mixture, with stirring, at room temperature, and stirring was continued at this temperature for 30 minutes. At the end of this time, the reaction mixture was diluted with a saturated aqueous solution of ammonium chloride and then extracted with ethyl acetate. The ethyl acetate fraction was then washed with water and dried over anhydrous sodium sulfate. The solvent was then removed by evaporation under reduced pressure, and the resulting residue was purified by silica gel column chromatography, using a mixture of 30% v/v ethyl acetate in hexane as the eluent, to afford 73 mg of the title compound as a solid.

Nuclear Magnetic Resonance Spectrum (CDCl$_3$) δ ppm: 1.38 (6H, singlet), 2.05–2.40 (2H, multiplet), 2.68 (2H, doublet, J=7.0 Hz), 2.88 (2H, triplet, J=7.0 Hz), 3.75–3.85 (1H, multiplet), 3.95 (2H, singlet), 7.05–7.40 (4H, multiplet), 7.73 (1H, broad singlet).

EXAMPLE 81

2-(9-Benzyl-2,3,4,9-tetrahydrothiopyrano[2,3-b]indol-2-yl)methyl-4,4-dimethyl-2-oxazoline 71 mg of 2-(2,3,4,9-tetrahydrothiopyrano[2,3-b]indol-2-yl)methyl-4,4-dimethyl-2-oxazoline (prepared as described in Example 80) in 1 ml of dimethylformamide was added to a suspension of 11 mg of sodium hydride (55% w/w dispersion in mineral oil) in 1 ml of dimethylformamide, with stirring and ice-cooling. Stirring was continued at this temperature for 30 minutes and then 0.03 ml of benzyl bromide was added to the reaction mixture, with stirring and ice-cooling. Stirring was continued for a further hour. At the end of this time, the reaction mixture was diluted with water and then extracted with ethyl acetate. The ethyl acetate fraction was then washed with water and dried over anhydrous sodium sulfate. The solvent was then removed by evaporation under reduced pressure and the resulting residue was purified by silica gel column chromatography, using a mixture of 20% v/v ethyl acetate in hexane as the eluent, to afford 71 mg of the title compound as an oil.

Nuclear Magnetic Resonance Spectrum (CDCl$_3$) δ ppm: 1.28 (6H, singlet), 2.05–2.40 (2H, multiplet), 2.68 (2H, doublet, J=7.0 Hz), 2.94 (2H, triplet, J=7.0 Hz), 3.75–3.85 (1H, multiplet), 3.93 (2H, singlet), 5.19 (2H, singlet), 7.05–7.45 (9H, multiplet).

EXAMPLE 82

Ethyl 2-(9-benzyl-2,3,4,9-tetrahydrothiopyrano[2,3-b]indol-2-yl)acetate 60 mg of 2-(9-benzyl-2,3,4,9-tetrahydrothiopyrano[2,3-b]indol-2-yl)methyl-4,4-dimethyl-2-oxazoline (prepared as described in Example 81) was dissolved in 5% v/v sulfuric acid in ethanol, and the mixture was refluxed for 6 hours. After this time, the reaction mixture was neutralized by the addition of a saturated aqueous solution of sodium hydrogencarbonate and then extracted with ethyl acetate. The ethyl acetate fraction was then washed with water and dried over anhydrous sodium sulfate. The solvent was then removed by evaporation under reduced pressure, and the resulting residue was purified by silica gel column chromatography, using a mixture of 20% v/v ethyl acetate in hexane as the eluent, to afford 46 mg of the title compound as an oil.

Nuclear Magnetic Resonance Spectrum (CDCl$_3$) δ ppm: 1.25 (3H, triplet, J=7.0 Hz), 2.05–2.35 (2H, multiplet), 2.65–2.80 (2H, multiplet), 2.80–2.95 (2H, multiplet), 3.80–3.90 (1H, multiplet), 4.16 (2H, quartet, J=7.0 Hz), 5.20 (2H, singlet), 7.05–7.45 (9H, multiplet).

EXAMPLE 83

2-(9-Benzyl-2,3,4,9-tetrahydrothiopyrano[2,3-b]indol-2-yl) acetic acid 0.5 ml of a 3% w/v aqueous solution of potassium hydroxide was added to a mixture of 44 mg of ethyl 2-(9-benzyl-2,3,4,9-tetrahydrothiopyrano[2,3-b]indol-2-yl) acetate (prepared as described in Example 82) in 2 ml of ethanol. The reaction mixture was then stirred at room temperature for 2 hours. At the end of this time, the reaction mixture was made acidic by the addition of a 3% w/v aqueous solution of hydrochloric acid and extracted with ethyl acetate. The ethyl acetate fraction was then washed with water and dried over anhydrous sodium sulfate. The solvent was then removed by evaporation under reduced pressure and the resulting residue was recrystallized from hexane and ethyl acetate to afford 37 mg of the title compound as a solid which melted at 164°–167° C.

Nuclear Magnetic Resonance Spectrum (CDCl$_3$) δ ppm: 2.18–2.40 (2H, multiplet), 2.70–2.85 (2H, multiplet), 2.85–3.05 (2H, multiplet), 3.80–3.90 (1H, multiplet), 5.20 (2H, singlet), 7.05–7.50 (9H, multiplet).

EXAMPLE 84

5-(9-Benzyl-2,3,4,9-tetrahydrothiopyrano[2,3-b]indol-2-yl)methyltetrazole (a) 0.015 ml of ethyl chloroformate was added to a mixture of 45 mg of 2-(9-benzyl-2,3,4,9-tetrahydrothiopyrano[2,3-b]indol-2-yl) acetic acid (prepared as described in Example 83) and 0.02 ml triethylamine in 2 ml of tetrahydrofuran, with stirring and ice-cooling, and stirring was continued for 15 minutes. After this time, an excess of methanolic ammonia was added to the reaction mixture which was then stirred for a further 15 minutes. At the end of this time, the resulting mixture was diluted with water and extracted with ethyl acetate. The ethyl acetate fraction was then washed with water and dried over anhydrous sodium sulfate. The solvent was then removed by evaporation under reduced pressure to afford 21 mg of the amide as a solid.

Nuclear Magnetic Resonance Spectrum (CDCl$_3$) δ ppm: 2.05–2.35 (2H, multiplet), 2.55 (2H, doublet, J=7.0 Hz), 2.80–3.00 (2H, multiplet), 3.85–3.95 (1H, multiplet), 5.19 (2H, singlet), 5.42 (1H, broad singlet), 5.67 (1H, broad singlet), 7.05–7.45 (9H, multiplet).

(b) 0.017 ml of trifluoroacetic anhydride was added to a mixture of 20 mg of the compound prepared in (a) and 0.02 ml of pyridine in 1 ml of dichloromethane, with stirring and ice-cooling, and stirring was continued for 30 minutes with ice-cooling. At the end of this time, the reaction mixture was diluted with water and extracted with ethyl acetate. The ethyl acetate fraction was then washed with a 3% w/v aqueous solution of hydrochloric acid, a saturated aqueous solution of sodium hydrogencarbonate and then water in that order, before being dried over anhydrous sodium sulfate. The solvent was then removed by evaporation under reduced pressure to afford 20 mg of the nitrile as an oil.

Nuclear Magnetic Resonance Spectrum (CDCl$_3$) δ ppm: 2.20–2.40 (2H, multiplet), 2.75 (2H, doublet, J=7.0 Hz), 2.80–3.05 (2H, multiplet), 3.60–3.70 (1H, multiplet), 5.18 (2H, singlet), 7.05–7.45 (9H, multiplet).

(c) 30 mg of sodium azide and 30 mg of ammonium chloride were added to a mixture of 20 mg of the compound prepared in (b) in 2 ml of dimethylformamide. The reaction mixture was stirred at 130° C. for 12 hours. At the end of this time, the reaction mixture was made acidic by the addition of a 3% w/v aqueous solution of hydrochloric acid. The mixture was then extracted with ethyl acetate and the ethyl acetate fraction was washed with water and dried over anhydrous sodium sulfate. The solvent was then removed by evaporation under reduced pressure, and the resulting residue was purified by silica gel column chromatography, using ethyl acetate as the eluent, to afford 14 mg of the title compound as a solid which melted at 160°–165° C.

Nuclear Magnetic Resonance Spectrum (CDCl$_3$) δ ppm: 2.10–2.35 (2H, multiplet), 2.85–3.00 (2H, multiplet), 3.15–3.35 (2H, multiplet), 3.70–3.80 (1H, multiplet), 5.20 (2H, singlet), 7.00–7.45 (10H, multiplet).

EXAMPLE 85

Diphenylmethyl 2-(9-benzyl-2,3,4,9-tetrahydrothiopyrano[2,3-b]indol-2-yl)acetate An excess of diphenyldiazomethane was added to a mixture of 100 mg of 2-(9-benzyl-2,3,4,9-tetrahydrothiopyrano[2,3-b]indol-2-yl)acetic acid (prepared as described in Example 83) in 5 ml of ethyl acetate, with stirring, at room temperature, and stirring was continued at this temperature overnight. At the end of this time, the solvent was removed by evaporation under reduced pressure, and the resulting residue was purified by silica gel column chromatography, using a mixture of 6% v/v ethyl acetate in hexane as the eluent, to afford 139 mg of the title compound as an oil.

Nuclear Magnetic Resonance Spectrum (CDCl$_3$) δ ppm: 2.00–2.30 (2H, multiplet), 2.70–3.00 (4H, multiplet), 3.80–3.90 (1H, multiplet), 5.15 (2H, singlet), 6.92 (1H, singlet), 7.00–7.50 (19H, multiplet).

EXAMPLE 86

2-(9-Benzyl-1-oxy-2,3,4,9-tetrahydrothiopyrano[2,3-b]indol-2-yl)acetic acid 40 mg of m-chloroperbenzoic acid was added to a mixture of 100 mg of diphenylmethyl 2-(9-benzyl-2,3,4,9-tetrahydrothiopyrano[2,3-b]indol-2-yl)acetate (prepared as described in Example 85) in 5 ml of dichloromethane, with stirring and ice-cooling, and stirring was continued for 30 minutes. At the end of this time, the reaction mixture was diluted with dichloromethane and then washed first with a saturated aqueous solution of sodium hydrogencarbonate and then with water, before drying over anhydrous sodium sulfate. The solvent was then removed by evaporation under reduced pressure. 2.5 ml of anisole and 2.5 ml of trifluoroacetic acid were added to 101 mg of the resulting residue, with stirring and ice-cooling, and stirring was continued for 15 minutes. At the end of this time, the reaction mixture was diluted with water and extracted with ethyl acetate. The ethyl acetate fraction was then washed with water and dried over anhydrous sodium sulfate. The solvent was then removed by evaporation under reduced pressure and the resulting residue was purified by silica gel column chromatography, using ethyl acetate as the eluent, to afford 38 mg of the title compound as a powder.

Nuclear Magnetic Resonance Spectrum (CDCl$_3$) δ ppm: 2.30–2.70 (2H, multiplet), 3.05–3.15 (2H, multiplet), 3.20–3.35 (2H, multiplet), 4.05–4.15 (1H, multiplet), 5.55 (2H, singlet), 7.05–7.60 (9H, multiplet).

EXAMPLE 87

2-(9-Benzyl-1,1-dioxy-2,3,4,9-tetrahydrothiopyrano[2,3-b]indol-2-yl)acetic acid 40 mg of m-chloroperbenzoic acid was added to a solution of 50 mg of diphenylmethyl 2-(9-benzyl-2,3,4,9-tetrahydrothiopyrano[2,3-b]indol-2-yl)acetate (prepared as described in Example 35) in 5 ml of dichloromethane, with stirring and ice-cooling, and stirring was continued at room temperature for 1 hour. At the end of this time, the reaction mixture was diluted with dichloromethane and then washed first with a saturated aqueous solution of sodium hydrogencarbonate and then water, before drying over anhydrous sodium sulfate. The solvent was then removed by evaporation under reduced pressure. 1 ml of anisole and 1 ml of trifluoroacetic acid were added to 48 mg of the resulting residue, with stirring and ice-cooling, and stirring was continued for 30 minutes. At the end of this time, the reaction mixture was diluted with water and extracted with ethyl acetate. The ethyl acetate fraction was then washed with water and dried over anhydrous sodium sulfate. The solvent was then removed by evaporation under reduced pressure, and the resulting residue was purified by silica gel column chromatography, using ethyl acetate as the eluent, to afford 22 mg of the title compound as a powder.

Nuclear Magnetic Resonance Spectrum (CDCl$_3$) δ ppm: 2.40–2.80 (2H, multiplet), 3.05–3.15 (2H, multiplet), 3.20–3.35 (2H, multiplet), 4.10–4.20 (1H, multiplet), 5.55 (2H, singlet), 7.05–7.60 (9H, multiplet).

EXAMPLE 88

1-Benzyl-4-cyanoindole

Following a procedure and using relative proportions of starting materials similar to those described in Example 65, but using 4-cyanoindole as starting material, the title compound was obtained in a yield of 94%.

Nuclear Magnetic Resonance Spectrum (CDCl$_3$, 270 MHz), δ ppm: 5.37 (2H, singlet), 6.77 (1H, doublet, J=3.4 Hz), 7.05–7.50 (9H, multiplet).

EXAMPLE 89

4-Acetyl-1-benzylindole 3.3 ml of a 2M solution of methylmagnesium iodide in diethyl ether was added to a mixture of 1.00 g of 1-benzyl-4-cyanoindole (prepared as described in Example 88) in 50 ml of tetrahydrofuran, with ice-cooling, and the reaction mixture was stirred for 1 hour. After this time, a saturated aqueous solution of ammonium chloride was added to the reaction mixture. The aqueous layer was extracted with diethyl ether, and the resulting organic fraction was washed with water, dried over anhydrous magnesium sulfate and concentrated by evaporation under reduced pressure. The resulting residue was purified by silica gel column chromatography, using 50 g of silica gel and a 4:1 v/v mixture of hexane and ethyl acetate as the eluent, to yield 1.00 g of the title compound as an oil.

Nuclear Magnetic Resonance Spectrum (CDCl$_3$, 270 MHz), δ ppm: 2.57 (3H, singlet), 5.45 (2H, singlet), 7.00–7.50 (10H, multiplet).

EXAMPLE 90

(1-Benzylindol-4-yl)thioacetomorpholide

Following a procedure and using relative proportions of starting materials similar to those described in Example 38, but using 4-acetyl-1-benzylindole (prepared as described in Example 89) as starting material, the title compound was obtained in a yield of 53% as an oil.

Nuclear Magnetic Resonance Spectrum (CDCl$_3$, 270 MHz), δ ppm: 3.29 (2H, triplet, J=5.2 Hz), 3.56 (2H, triplet, J=5.2 Hz), 3.76 (2H, triplet, J=5.2 Hz), 4.41 (2H, triplet, J=5.2 Hz), 4.63 (2H, singlet), 5.33 (2H, singlet), 6.60 (1H, doublet, J=3.2 Hz), 7.00–7.35 (9H, multiplet).

EXAMPLE 91

(1-Benzylindol-4-yl)acetic acid

Following a procedure and using relative proportions of starting materials similar to those described in Example 39, but using (1-benzylindol-4-yl)thioacetomorpholide (prepared as described in Example 90) as starting material, the title compound was obtained in a yield of 42%, melting at 138°–140° C.

Nuclear Magnetic Resonance Spectrum (CDCl$_3$, 270 MHz), δ ppm: 3.93 (2H, singlet) 5.31 (2H, singlet), 6.59 (1H, doublet, J=3.4 Hz), 7.00–7.35 (9H, multiplet).

EXAMPLE 92

5-(1-Benzylindol-4-yl)methyl-1H-tetrazole

Following a procedure and using relative proportions of starting materials similar to those described in Example 84, but using 50 mg of (1-benzylindol-4-yl)acetic acid (prepared as described in Example 91) as starting material, 12 mg of the title compound was obtained as a colorless solid, melting at 201°–205° C. (with decomposition)

Nuclear Magnetic Resonance Spectrum (CDCl$_3$ and tetradeuterated methanol, 270 MHz), δ ppm: 4.57 (2H, singlet), 5.33 (2H, singlet), 6.47 (1H, doublet, J=3.2 Hz), 7.00–7.55 (9H, multiplet).

EXAMPLE 93

5-(1-Benzylindol-4-yl)-1H-tetrazole

Following a procedure and using relative proportions of starting materials similar to those described in Example 77, but using 1-benzyl-4-cyanoindole (prepared as described in Example 88) as starting material, the title compound was obtained in a yield of 84%, melting at 224°–228° C. (with decomposition)

Nuclear Magnetic Resonance Spectrum (CDCl$_3$ and tetradeuterated methanol, 270 MHz), δ ppm: 5.41 (2H, singlet), 7.00–7.55 (10H, multiplet).

EXAMPLE 94

N-Methanesulfonyl(9-benzylcarbazol-2-yl)acetamide 0.055 ml (0.63 nmol) of oxalyl chloride was added, with ice-cooling, to a mixture of 100 mg (0.32 mmol) of (9-benzylcarbazol-2-yl)acetic acid (prepared as described in Example 42) in 3 ml of methylene chloride, and the whole was stirred for 30 minutes at room temperature. After this time, the solvent was removed by evaporation under reduced pressure. 5 ml of methylene chloride, 0.08 ml (0.99 mmol)

of pyridine and 60 mg (0.63 mmol) of methanesulfonamide were added to the residue thus obtained, with ice-cooling. The reaction mixture was then stirred for 12 hours at room temperature. After the reaction had been allowed to go to completion, water was added to the reaction mixture, which was then extracted with ethyl acetate. The organic fraction was then washed with water and dried over anhydrous sodium sulfate, and the solvent was removed by evaporation under reduced pressure. The residue was purified by silica gel column chromatography, using 30 g of silica gel with a 50% v/v solution of methanol in ethyl acetate as eluent, to yield 46 mg of the title compound as an amorphous solid.

Nuclear Magnetic Resonance Spectrum (CDCl$_3$, 270 MHz), δ ppm: 3.01 (3H, singlet), 3.83 (2H, singlet), 5.51 (2H, singlet), 7.10–7.95 (12H, multiplet).

EXAMPLE 95

N-Methanesulfonyl-(9-benzyl-1-methylcarbazol-2-yl)formamide

Following a procedure and using relative proportions of starting materials similar to those described in Example 94, but using (9-benzyl-1-methylcarbazol-2-yl)- carboxylic acid (prepared as described in Example 29) as starting material, the title compound was obtained in a yield of 44%, as an amorphous solid.

Nuclear Magnetic Resonance Spectrum (CDCl$_3$, 270 MHz), δ ppm: 2.85 (3H, singlet), 3.03 (3H, singlet), 5.72 (2H, singlet), 7.10–7.65 (10H, multiplet), 8.10 (1H, doublet, J=7.0 Hz).

EXAMPLE 96

N-Acetyl-(9-benzyl-1-methylcarbazol-2-yl) methanesulfonamide a) A solution so 400 mg (1.21 mmol) of ethyl (9-benzyl-1-methylcarbazol-2-yl)carboxylate (prepared as described in Example 28) in 10 ml of tetrahydrofuran was added, with ice-cooling, to a suspension of 92 mg (2.42 mmol) of lithium aluminum hydride in 10 ml of tetrahydrofuran, and the resulting mixture was stirred for 30 minutes. After this time, 0.4 ml of 4% w/v aqueous sodium hydroxide was added to the reaction mixture. Precipitated material was filtered off and the filtrate was concentrated by evaporation under reduced pressure to afford 320 mg (1.11 mmol) of the alcohol as an oil.

b) 350 mg (1.68 mmol) of phosphorus pentachloride was added, with ice-cooling, to a solution of 320 mg of the compound obtained in a) and 0.18 ml (2.23 mmol) of pyridine in 15 ml of dichloromethane. The reaction mixture was stirred for 30 minutes. After this time, water was added and the aqueous layer was extracted with diethyl ether. The organic fraction was then washed with water, dried over anhydrous sodium sulfate and concentrated by evaporation under reduced pressure to afford the chloride as an oil.

c) The whole of the compound obtained in b) above and 140 mg (1.11 mmol) of sodium sulfite were added to a mixture of 5 ml of water and 2 ml of dimethyl sulfoxide, and the resulting mixture was heated to 130° C. and maintained at this temperature for 14 hours. The solvents were removed by evaporation under reduced pressure, the residue was extracted with methanol, and the filtrate was concentrated to afford the sodium salt of the sulfonic acid as an amorphous solid.

d) 450 mg (2.16 mmol) of phosphorus pentachloride and one drop of POCl$_3$ were added to the powdered compound obtained in c) above, and the mixture was heated at 70° C. for 2 hours. After this time, a large excess of concentrated, aqueous ammonia was added, with ice-cooling, to the reaction mixture. The whole was then stirred overnight at room temperature. The reaction mixture was extracted with methylene chloride, and the organic fraction was washed with water and dried over anhydrous sodium sulfate. The solvent was then removed by evaporation under reduced pressure and the residue was purified by silica gel column chromatography, using 30 g of silica gel and a 10% v/v solution of methanol in ethyl acetate as eluent, to yield 98 mg of the sulfonamide as an amorphous solid.

Nuclear Magnetic Resonance Spectrum (CDCl$_3$ and tetradeuterated methanol, 270 MHz), δ ppm: 2.90 (3H, singlet), 3.87 (2H, singlet), 5.51 (2H, singlet), 7.10–7.85 (11H, multiplet).

e) 0.04 ml (0.56 mmol) of acetyl chloride was added to a solution of 96 mg (0.27 mmol) of the sulfonamide obtained in d) above in a mixture of 0.15 ml (1.85 mmol) of pyridine and 2 ml of methylene chloride, and the whole was stirred overnight at room temperature. After the reaction had been allowed to go to completion, water was added to the reaction mixture which was then extracted with ethyl acetate. The extract was washed with water and dried over anhydrous sodium sulfate, and then the solvent was removed by evaporation under reduced pressure. The residue was purified by silica gel column chromatography, using 10 g of silica gel with ethyl acetate as the eluent, to yield 32 mg of the title compound as an amorphous solid.

Nuclear Magnetic Resonance Spectrum (CDCl$_3$, 270 MHz), δ ppm: 2.48 (3H, singlet), 3.08 (3H, singlet), 3.84 (2H, singlet), 5.51 (2H, singlet), 7.10–7.85 (11H, multiplet).

EXAMPLE 97

5-[(9-Benzyl-4-methyl-1-methylthiocarbazol)-2-yl-methyl]-1H-tetrazole

The title compound was prepared following a similar procedure to that of Examples 75–77, but starting with 9-benzyl-4-methylthiocarbazol-2-acetic acid. The title compound was obtained as an amorphous solid.

Nuclear Magnetic Resonance Spectrum (CDCl$_3$, 270 MHz), δ ppm: 1.91 (3H, singlet), 2.87 (3H, singlet), 4.76 (2H, singlet), 6.34 (2H, doublet, J=17 Hz), 6.9–7.0 (2H, multiplet), 7.08 (1H, singlet), 7.2–7.5 (6H, multiplet),. 8.21 (1H, doublet, J=8 Hz).

EXAMPLE 98

Methyl 4-(indol-1-yl)methylbenzoate

Following a procedure and using relative proportions of starting materials similar to those described in Example 65, but using indole and methyl 4-(bromomethyl)benzoate as starting material, the title compound was obtained as a solid.

Nuclear Magnetic Resonance Spectrum (CDCl$_3$, 270 MHz), δ ppm: 3.88 (3H, singlet), 5.37 (2H, singlet), 6.57 (1H, doublet, J=3.2 Hz), 7.10–7.30 (7H, multiplet), 7.68 (1H, doublet, J=6.2 Hz), 8.05 (2H, doublet, J=8.2 Hz).

EXAMPLE 99

4-(Indol-1-yl)methylbenzoic Acid

Following a procedure and using relative proportions of starting materials similar to those described in Example 83, but using methyl 4-(indol-1-yl)methyl benzoate as starting material, the title compound was obtained as a solid melting at 163°–165° C.

Nuclear Magnetic Resonance Spectrum (CDCl$_3$, 270 MHz), δ ppm: 5.41 (2H, singlet), 6.60 (1H, doublet, J=3.3 Hz), 7.05–7.30 (6H, multiplet), 7.68 (1H, doublet, J=6.2 Hz), 8.03 (2H, doublet, J=8.2 Hz).

EXAMPLE 100

5-[4-(Indol-1-yl)methyl]phenyl-1H-tetrazole

Following a procedure and using relative proportions of starting materials similar to those described in Examples 75–77, but using 4-(indol-1-yl)methylbenzoic acid as starting material, the title compound was obtained as a solid melting at 181°–184° C. (with decomposition).

Nuclear Magnetic Resonance Spectrum (CDCl$_3$ and tetradeuterated methanol, 270 Mz), δ ppm: 5.40 (2H, singlet), 6.59 (1H, doublet, J=3.2 Hz), 7.05–7.30 (6H, multiplet), 7.68 (1H, doublet, J=6.2 Hz), 7.98 (2H, doublet, J=8.2 Hz).

EXAMPLE 101

1-(4-Phenylbenzyl)-4-cyanoindole

Following a procedure and using relative proportions of starting materials similar to those described in Example 65, but using 4-cyanoindole and 4-phenylbenzylchloride as starting materials, the title compound was obtained as a solid.

Nuclear Magnetic Resonance Spectrum (CDCl$_3$, 270 MHz), δ ppm: 5.40 (2H, singlet), 6.78 (1H, doublet, J=3.0 Hz), 7.10–7.60 (13H, multiplet).

EXAMPLE 102

2-[1-(4-Phenylbenzyl)indol-4-yl]acetic Acid

Following procedures and using relative proportions of starting materials similar to those described in Examples 89, 90 and 91, but using 1-(4-phenylbenzyl)-4-cyanoindole as starting material, the title compound was obtained as a solid melting at 159°–160° C.

Nuclear Magnetic Resonance Spectrum (CDCl$_3$, 270 MHz), δ ppm: 3.94 (2H, singlet), 5.36 (2H, singlet), 6.62 (1H, doublet, J=3.2 Hz), 7.04 (1H, doublet, J=7.1 Hz), 7.10–7.60 (12H, multiplet).

EXAMPLE 103

2-(9-Benzyl-4-methyl-2,3,4,9-tetrahydrothiopyrano[2,3-b]indol-2-yl acetic Acid

Following procedures and using relative proportions of starting materials similar to those described in Examples 78, 79, 80, 81, 82 and 83, but using 3-tert-butyldiphenylsilyloxy-1-butanol as starting material, the title compound was obtained as a solid melting at 158°–162° C.

Nuclear Magnetic Resonance Spectrum (CDCl$_3$, 270 MHz), δ ppm: 1.44 (3H, doublet, J=6.8 Hz), 2.10–2.20 (2H, multiplet), 2.76 (2H, doublet, J=7.0 Hz), 3.25–3.40 (1H, multiplet), 3.80–3.95 (1H, multiplet), 5.20 (2H, singlet), 7.05–7.60 (9H, multiplet)

EXAMPLE 104

5-(9-Benzyl-4-methyl-2,3,4,9-tetrahydrothiopyrano[2,3-b]indol-2-yl)methyl-1H-tetrazole Following a procedure and using relative proportions of starting materials similar to those described in Example 84, but using 2-(9-benzyl-4-methyl-2,3,4,9-tetrahydrothiopyrano[2,3-b]indol-2-yl)acetic acid as starting material, the title compound was obtained as a solid melting at 176°–178° C.

Nuclear Magnetic Resonance Spectrum (CDCl$_3$ and tetradeuterated methanol, 270 MHz), δ ppm: 1.41 (3H, doublet, J=6.9 Hz), 2.03–2.25 (2H, multiplet), 3.25–3.45 (3H, multiplet), 3.90–4.05 (1H, multiplet), 5.18 (2H, singlet), 7.05–7.60 (9H, multiplet).

EXAMPLE 105

1-Benzyl-2,3-dimethyl-6-acetylindole

Following a procedure and using relative proportions of starting materials similar to those described in Examples 40 and 65 but using 2,3-dimethylindole as starting material, the title compound was obtained as a solid.

Nuclear Magnetic Resonance Spectrum (CDCl$_3$, 270 MHz), δ ppm: 2.30 (6H, singlet), 2.62 (3H, singlet), 5.37 (2H, singlet), 6.95 (1H, doublet, J=2.0 Hz), 7.20–7.30 (4H, multiplet), 7.53 (1H, doublet, J=8.4 Hz), 7.71 (1H, doublet, J=8.4 Hz), 7.92 (1H, singlet).

EXAMPLE 106

2-(1-Benzyl-2,3-dimethylindol-6-yl)acetic Acid

Following procedures and using relative proportions of starting materials similar to those described in Example 89, 90 and 91, but using 1-benzyl-2,3-dimethyl- 6-acetylindole as starting material, the title compound was obtained as a solid melting at 137° C. (with decomposition).

Nuclear Magnetic Resonance Spectrum (CDCl$_3$, 270 MHz), δ ppm: 2.25 (6H, singlet), 3.69 (2H, singlet), 5.27 (2H, singlet), 6.90–7.50 (8H, multiplet).

EXAMPLE 107

5-(1-Benzyl-2,3-dimethylindol-6-yl)methyl-1H-tetrazole

Following a procedure and using relative proportions of starting materials similar to those described in Examples 75, 76 and 77, but using (1-benzyl-2,3-dimethylindol-6-yl) acetic acid as starting material, the title compound was obtained as a solid melting at 160°–163° C. (with decomposition).

Nuclear Magnetic Resonance Spectrum (CDCl$_3$ and tetradeuterated methanol, 270 MHz), δ ppm: 2.26 (3H, singlet), 2.27 (3H, singlet), 4.33 (2H, singlet), 5.26 (2H, singlet), 6.90–7.30 (7H, multiplet), 7.46 (1H, doublet, J=8.0 Hz).

EXAMPLE 108

5-(9-Benzylcarbazol-2-yl)methyl-1H-tetrazole

Following a procedure and using relative proportions of starting materials similar to those described in Examples 75, 76 and 77, but using 2-(9-benzylcarbazole-2-yl)acetic acid as starting material, the title compound was obtained as a solid melting at 175°–184° C. (with decomposition).

Nuclear Magnetic Resonance Spectrum (CDCl$_3$ and tetradeuterated methanol, 270 MHz), δ ppm: 4.44 (2H, singlet), 5.50 (2H, singlet), 7.05–7.45 (10H, multiplet), 8.08 (2H, triplet, J=7.8 Hz).

EXAMPLE 109

Diethyl (9-Benzyl-1,2,3,4-tetrahydrocarbazol-2-yl)malonate

The title compound was obtained by following a procedure and using relative proportions of starting materials similar to those described in Example 48, but using N,N-benzylphenylhydrazine and diethyl 3-oxocyclohexylmalonate as starting materials.

EXAMPLE 110

(9-Benzyl-1,2,3,4-tetrahydrocarbazol-2-yl)malonic acid

The title compound was obtained by following a procedure and using relative proportions of starting materials similar to those described in Example 26, but using diethyl (9-benzyl-1,2,3,4-tetrahydrocarbazol-2-yl)malonate as starting material.

Nuclear Magnetic Resonance Spectrum (CDCl$_3$, 270 MHz), δ ppm: 1.6–1.9 (1H, multiplet), 2.1–2.4 (1H, multiplet), 2.5–3.0 (5H, multiplet), 3.39 (1H, doublet, J=8.4 Hz), 5.23 (2H, singlet), 6.9–7.6 (9H, multiplet).

EXAMPLE 111

(9-Benzyl-1,2,3,4-tetrahydrocarbazol-2-yl)acetic Acid

A solution of 200 mg of (9-benzyl-1,2,3,4-tetrahydrocarbazol-2-yl)malonic acid, obtained as described in Example 110, in 5 ml of N,N-dimethylformamide was refluxed for 2 hours. The solvent was evaporated under reduced pressure. The resulting residue was subjected to column chromatography using 5 g of silica gel with a 1:2 v/v mixture of ethyl acetate and hexane as the eluent, then recrystallized from ethyl acetate and hexane, to yield 162 mg of the title compound.

Nuclear Magnetic Resonance Spectrum (CDCl$_3$, 270 MHz), δ ppm: 1.5–1.8 (1H, multiplet), 2.0–2.2 (1H, multiplet), 2.3–2.6 (4H, multiplet), 2.7–3.0 (3H, multiplet), 5.24 (2H, singlet), 6.9–7.3 (8H, multiplet), 7.4–7.6 (1H, multiplet).

EXAMPLE 112

(Ethyl 9-Benzyl-4-oxo-1,2,3,4-tetrahydrocarbazol-3-yl)acetate 227 mg of 2,3-dichloro-5,6-dicyano-p-benzoquinone (DDQ) in 2 ml of tetrahydrofuran was added dropwise, with ice-cooling, to a solution of 174 mg of ethyl (9-benzyl-1,2,3,4-tetrahydrocarbazol-3-yl)acetate, obtained as described in Example 62, in 4.5 ml of tetrahydrofuran and 0.5 ml of water. The reaction mixture was stirred for 10 minutes. A saturated aqueous solution of sodium chloride was then added to the reaction mixture, the aqueous layer was extracted with ethyl acetate, and the organic extract was washed with a saturated aqueous solution of sodium chloride, dried over anhydrous magnesium sulfate and concentrated by evaporation under reduced pressure. The resulting residue was subjected to column chromatography using 8 g of silica gel using a 2:3 v/v mixture of ethyl acetate and hexane as the eluent, then recrystallized from ethyl acetate and hexane, to yield 169 mg of the title compound.

EXAMPLE 113

(9-Benzyl-4-oxo-1,2,3,4-tetrahydrocarbazol-3-yl) acetic Acid

The title compound was obtained by following a procedure and using relative proportions of starting materials similar to those described in Example 26, but using ethyl (9-benzyl-4-oxo-1,2,3,4-tetra-hydrocarbazol-3-yl)acetate as starting material.

Nuclear Magnetic Resonance Spectrum (CDCl$_3$, 270 MHz), δ ppm 2.0–2.2 (1H, multiplet), 2.3–2.5 (1H, multiplet), 2.45 (1H, doublet, J=11.3 Hz), 2.9–3.2 (4H, multiplet), 5.35 (2H, singlet), 7.0–7.1 (2H, multiplet), 7.2–7.4 (6H, multiplet), 8.26 (1H, doublet, J=6.6 Hz).

EXAMPLE 114

Isopropyl (1-Methylthio-4-propylcarbazol-2-yl) acetate

The title compound was obtained by following procedures and using relative proportions of starting materials similar to those described in Examples 1 and 2, but using 1,1-bismethylthio-2-oxo-4-propyl-1,2,3,4-tetrahydrocarbazole as starting material.

EXAMPLE 115

Isopropyl (9-Benzyl-1-methylthio-4-propylcarbazol-2-yl)acetate

The title compound was obtained by following a procedure and using relative proportions of starting materials similar to those described in Example 13, but using isopropyl (1-methylthio-4-propylcarbazol-2-yl)acetate as starting material.

EXAMPLE 116

(9-Benzyl-1-methylthio-4-propylcarbazol-2-yl)acetic Acid

The title compound was obtained by following a procedure and using relative proportions of starting materials similar to those described in Example 26, but using isopropyl (9-benzyl-1-methylthio-4-propylcarbazol-2-yl)acetate as starting material.

Nuclear Magnetic Resonance Spectrum (CDCl$_3$, 270 MHz), δ ppm 1.13 (3H, triplet, J=7.4 Hz), 1.8–2.0 (1H, multiplet), 1.97 (3H, singlet), 3.20 (3H, triplet, J=7.8 Hz), 4.15 (2H, singlet), 6.40 (2H, singlet), 7.0–7.5 (8H, multiplet), 8.0–8.2 (2H, multiplet).

EXAMPLE 117

Isopropyl 2-(9-Benzyl-1-methylthio-4-propylcarbazol-2-yl)-3-phenylpropionate

The title compound was obtained by following a procedure and using relative proportions of starting materials similar to those described in Example 13, but using isopropyl (1-methylthio-4-propylcarbazol-2-yl)acetate as starting material.

EXAMPLE 118

2-(9-Benzyl-1-methylthio-4-propylcarbazol-2-yl)-3-phenylpropionic Acid

The title compound was obtained by following a procedure and using relative proportions of starting materials similar to those described in Example 26, but using isopropyl 2-(9-benzyl-1-methylthio-4-propylcarbazol-2-yl)-3-phenylpropionate as starting material.

Nuclear Magnetic Resonance Spectrum (CDCl$_3$, 270 MHz), δ ppm 1.12 (3H, triplet, J=7.3 Hz), 1.84 (3H, singlet), 1.8–2.0 (1H, multiplet), 3.05 (1H, doublet of doublets, J=13.7 Hz, J=7.2 Hz), 3.1–3.4 (2H, multiplet), 3.47 (1H, doublet of doublets, J=13.7 Hz, J=7.8 Hz), 5.37 (1H, triplet, J=7.5 Hz), 6.35 (2H, singlet), 6.9–7.5 (14H, multiplet), 8.11 (1H, doublet, J=7.9 Hz).

EXAMPLE 119 tert-Butyl (1-Methylthio-4-propylcarbazol-2-yl)oxyacetate

The title compound was obtained by following a procedure and using relative proportions of starting materials similar to those described in Example 43, but using 2-hydroxy-1-methylthio-4-propylcarbazole as starting material.

EXAMPLE 120

(1-Methylthio-4-propylcarbazol-2-yl)oxyacetic Acid

The title compound was obtained by following a procedure and using relative proportions of starting materials similar to those described in Example 26, but using tert-butyl (1-methylthio-4-propylcarbazol-2-yl)oxyacetate as starting material.

Nuclear Magnetic Resonance Spectrum (CDCl$_3$, 270 MHz), δ ppm 1.10 (3H, triplet, J=7.4 Hz), 1.8–2.0 (1H, multiplet), 2.43 (3H, singlet), 3.15 (2H, triplet, J=7.7 Hz), 4.86 (2H, singlet), 6.63 (1H, singlet), 7.26 (1H, triplet, J=7.6 Hz), 7.41 (1H, triplet, 7.6 Hz), 7.49 (1H, doublet, J=7.6 Hz), 8.00 (1H, doublet, J=7.6 Hz), 8.62 (1H, broad singlet).

EXAMPLE 121

Methyl (9-Benzyl-1,2,3,4-tetrahydrocarbazol-2-yl)acetate

The title compound was obtained by following a procedure and using relative proportions of starting materials similar to those described in Example 85, but using (9-benzyl-1,2,3,4-tetrahydrocarbazol-2-yl)acetic acid and diazomethane as starting materials.

EXAMPLE 122

Methyl (9-Benzyl-4-oxo-1,2,3,4-tetrahydrocarbazol-2-yl)acetate

The title compound was obtained by following a procedure and using relative proportions of starting materials similar to those described in Example 112, but using methyl (9-benzyl-1,2,3,4-tetrahydrocarbazol-2-yl)acetate and diazomethane as starting materials.

EXAMPLE 123

(9-Benzyl-4-oxo-1,2,3,4-tetrahydrocarbazol-2-yl)acetic Acid

The title compound was obtained by following a procedure and using relative proportions of starting materials similar to those described in Example 26, but using methyl (9-benzyl-4-oxo-1,2,3,4-tetrahydrocarbazol-2-yl)acetate as starting material.

Nuclear Magnetic Resonance Spectrum (CDCl$_3$, 270 MHz), δ ppm 2.3–3.0 (6H, multiplet), 3.17 (1H, doublet of doublets, J=16.4 Hz, J=4.4 Hz), 5.35 (2H, singlet), 6.9–7.1 (2H, multiplet), 7.2–7.4 (6H, multiplet), 8.27 (1H, doublet, J=8.0 Hz).

EXAMPLE 124

[1-(3-Benzyloxybenzyl)indol-4-yl]thioacetomorpholide

Following procedures and using relative proportions of starting materials similar to those described in Examples 88, 89 and 90, but using 3-benzyloxybenzyl chloride as a starting material, the title compound was obtained as an amorphous solid.

EXAMPLE 125

[1-(3-Benzyloxybenzyl)indol-4-yl]acetic Acid

Following a procedure and using relative proportions of starting materials similar to those described in Example 39, but using [1-(3-benzyloxybenzyl)indol-4-yl]thioacetomorpholide, as obtained in Example 124, as a starting material, the title compound was obtained as a solid melting at 130°–133° C. and in a yield of 80%.

Nuclear Magnetic Resonance Spectrum (CDCl$_3$, 270 MHz), δ ppm: 3.93 (2H, singlet); 4.97 (2H, singlet); 5.27 (2H, singlet); 6.57–7.40 (14H, multiplet).

EXAMPLE 126

[1-(4-Pyridylmethyl)indol-4-yl]thioacetomorpholide

Following procedures and using relative proportions of starting materials similar to those described in Examples 88, 89 and 90, but using 4-pyridylmethyl chloride as a starting material, the title compound was obtained as an amorphous solid.

EXAMPLE 127

[1-(4-Pyridylmethyl)indol-4-yl]acetic Acid

Following a procedure and using relative proportions of starting materials similar to those described in Example 39, but using [1-(4-pyridylmethyl)indol-4-yl]thioacetomorpholide, as obtained in Example 126, as a starting material, the title compound was obtained in a yield of 79% as an amorphous solid.

Nuclear Magnetic Resonance Spectrum (CDCl$_3$+tetradeuterated methanol, 270 MHz), δ ppm: 3.81 (2H, singlet); 5.32 (2H, singlet); 6.68 (1H, doublet, J=3.5 Hz); 6.92–7.13 (6H, multiplet); 8.41 (2H, doublet, J=6.4 Hz).

EXAMPLE 128

5-[1-(3-Benzyloxybenzyl)indol-4-yl]methyl-1H-tetrazole

Following procedures and using relative proportions of starting materials similar to those described in Examples 75, 76 and 77, but using [1-(3-benzyloxybenzyl)indol-4-yl]acetic acid, as obtained in Example 125, as a starting material, the title compound was obtained as a solid melting at 172°–174° C.

Nuclear Magnetic Resonance Spectrum (CDCl$_3$+tetradeuterated methanol, 270 MHz), δ ppm: 4.58 (2H, singlet); 4.98 (2H, singlet); 5.29 (2H, singlet); 6.46 (1H, doublet, J=3.2 Hz); 6.70 (1H, singlet); 6.71 (1H, doublet, J=7.1 Hz); 6.87 (1H, doublet of doublets, J=8.7,1.9 Hz); 7.00 (1H, doublet, J=7.3 Hz); 7.1–7.4 (9H, multiplet).

EXAMPLE 129

(1-Diphenylmethylindol-4-yl)thioacetomorpholide

Following procedures and using relative proportions of starting materials similar to those described in Examples 88, 89 and 90, but using diphenylmethyl bromide as a starting material, the title compound was obtained, as an oil.

EXAMPLE 130

(1-Diphenylmethylindol-4-yl)acetic Acid

Following a procedure and using relative proportions of starting materials similar to those described in Example 39, but using (1-diphenylmethylindol-4-yl) thioacetomorpholide, as obtained in Example 129, as a starting material, the title compound was obtained in a quantitative yield as a solid melting at 170°–175° C.

Nuclear Magnetic Resonance Spectrum (CDCl$_3$, 270 MHz), δ ppm: 3.92 (2H, singlet); 6.53 (2H, doublet, J=3.3 Hz); 6.81 (1H, singlet); 6.84 (1H, doublet, J=3.3 Hz); 7.0–7.4 (13H, multiplet).

EXAMPLE 131

Methyl (9-Benzyl-4-methyl-1-propoxycarbazol-2-yl) acetate

Following a procedure and using relative proportions of starting materials similar to those described in Example 220, but using iodopropane as a starting material, the title compound was obtained in a yield of 90% as an oil.

EXAMPLE 132

(9-Benzyl-4-methyl-1-propoxycarbazol-2-yl)acetic Acid

Following a procedure and using relative proportions of starting materials similar to those described in Example 14, but using methyl (9-benzyl-4-methyl-1-propoxycarbazol-2-yl)acetate, as obtained in Example 131, as a starting material, the title compound was obtained in a yield of 88% as a solid melting at 175°–177° C.

Nuclear Magnetic Resonance Spectrum (CDCl$_3$, 270 MHz), δ ppm: 0.82 (3H, triplet, J=7.5 Hz); 1.67 (2H, sixted, J=7.2 Hz); 2.84 (3H, singlet); 3.67 (2H, triplet, J=6.9 Hz); 3.84 (2H, singlet); 5.89 (2H, singlet); 6.92 (1H, singlet); 7.02–7.42 (8H, multiplet); 8.17 (1H, doublet, J=7.4 Hz).

EXAMPLE 133

Methyl (9-Benzyl-1-benzyloxy-4-methylcarbazol-2-yl)acetate

Following a procedure and using relative proportions of starting materials similar to those described in Example 220, but using benzyl bromide as a starting material, the title compound was obtained in a yield of 93% as an oil.

EXAMPLE 134

(9-Benzyl-1-benzyloxy-4-methylcarbazol-2-yl)acetic Acid

Following a procedure and using relative proportions of starting materials similar to those described in Example 14, but using methyl (9-benzyl-1-benzyloxy-4-methylcarbazol-2-yl)acetate, as obtained in Example 133, as a starting material, the title compound was obtained in a yield of 86% as a solid melting at 187°–191° C.

Nuclear Magnetic Resonance Spectrum (CDCl$_3$, 270 MHz), δ ppm: 2.86 (3H, singlet); 3.86 (2H, singlet); 4.81 (2H, singlet); 5.86 (2H, singlet); 6.90–7.42 (14H, multiplet); 8.19 (1H, doublet, J=7.9 Hz).

EXAMPLE 135 tert-Butyl [9-(3-Benzyloxybenzyl)-4-methyl-1-methylthiocarbazol-2-yl]acetate

Following a procedure and using relative proportions of starting materials similar to those described in Example 4, but using tert-butyl (4-methyl-1-methylthiocarbazol-2-yl) acetate and 3-benzyloxybenzyl chloride as starting materials, the title compound was obtained in a yield of 78% as an oil.

EXAMPLE 136

[9-(3-Benzyloxybenzyl)-4-methyl-1-methylthiocarbazol-2-yl]acetic Acid

Following a procedure and using relative proportions of starting materials similar to those described in Example 3, but using tert-butyl [9-(3-benzyloxybenzyl)-4-methyl-1-methylthiocarbazol-2-yl]acetate, as obtained in Example 135, as a starting material, the title compound was obtained in a yield of 85% as a solid melting at 178°–180° C.

Nuclear Magnetic Resonance Spectrum (CDCl$_3$, 270 MHz), δ ppm: 1.92 (3H, singlet); 2.89 (3H, singlet); 4.19 (2H, singlet); 4.90 (2H, singlet); 6.33 (2H, singlet); 6.6–7.5 (13H, multiplet); 8.18 (1H, doublet, J=7.8 Hz).

EXAMPLE 137

5-[9-(3-Benzyloxybenzyl)-4-methyl-1-methylthiocarbazol-2-yl]methyl-1H-tetrazole

Following procedures and using relative proportions of starting materials similar to those described in Examples 75, 76 and 77, but using [9-(3-benzyloxybenzyl)-4-methyl-1-methylthiocarbazol-2-yl]acetic acid, as obtained in Example 136, as a starting material, the title compound was obtained as a solid melting at 205°–207° C.

Nuclear Magnetic Resonance Spectrum (CDCl$_3$, 270 MHz), δ ppm: 1.86 (3H, singlet); 2.87 (3H, singlet); 4.78 (2H, singlet); 4.92 (2H, singlet); 6.34 (2H, singlet); 6.60–7.50 (13H, multiplet); 8.20 (1H, doublet, J=7.8 Hz).

EXAMPLE 138 tert-Butyl [4-Methyl-1-methylthio-9-(3-nitrobenzyl) carbazol-2-yl]acetate

Following a procedure and using relative proportions of starting materials similar to those described in Example 4, but using tert-butyl (4-methyl-1-methylthiocarbazol-2-yl) acetate and 3-nitrobenzyl bromide as starting materials, the title compound was obtained in a yield of 83% as an oil.

EXAMPLE 139

[4-Methyl-1-methylthio-9-(3-nitrobenzyl)carbazol-2-yl]acetic Acid

Following a procedure and using relative proportions of starting materials similar to those described in Example 3, but using tert-butyl [4-methyl-1-methyl-9-(3-nitrobenzyl) thiocarbazol-2-yl]acetate, as obtained in Example 138, as a starting material, the title compound was obtained in a yield of 98% as a solid melting at 196°–201° C.

Nuclear Magnetic Resonance Spectrum (CDCl$_3$, 270 MHz), δ ppm: 2.02 (3H, singlet); 2.90 (3H, singlet); 4.19 (2H, singlet); 6.42 (2H, singlet); 7.09 (1H, singlet); 7.15–7.50 (5H, multiplet); 8.06 (1H, doublet, J=6.6 Hz); 8.07 (1H, singlet); 8.21 (1H, doublet, J=7.7 Hz).

EXAMPLE 140 tert-Butyl [9-(3-Fluorobenzyl)-4-methyl-1-methylthiocarbazol-2-yl]acetate

Following a procedure and using relative proportions of starting materials similar to those described in Example 4, but using tert-butyl (4-methyl-1-methylthiocarbazol-2-yl) acetate and 3-fluorobenzyl bromide as starting materials, the title compound was obtained in a yield of 90% as an oil.

EXAMPLE 141

[9-(3-Fluorobenzyl)-4-methyl-1-methylthiocarbazol-2-yl]acetic Acid

Following a procedure and using relative proportions of starting materials similar to those described in Example 3, but using tert-butyl [9-(3-fluorobenzyl)-4-methyl-1-methylthiocarbazol-2-yl]acetate, as obtained in Example 140, as a starting material, the title compound was obtained in a yield of 97% as a solid melting at 195°–202° C.

Nuclear Magnetic Resonance Spectrum (CDCl$_3$, 270 MHz), δ ppm: 1.98 (3H, singlet); 2.89 (3H, singlet); 4.20 (2H, singlet); 6.36 (2H, singlet); 6.70–6.90 (3H, multiplet); 7.07 (1H, singlet); 7.15–7.50 (4H, multiplet); 8.20 (1H, doublet, J=7.9 Hz).

EXAMPLE 142 tert-Butyl [9-(4-Fluorobenzyl)-4-methyl-1-methylthiocarbazol-2-yl]acetate

Following a procedure and using relative proportions of starting materials similar to those described in Example 4, but using tert-butyl (4-methyl-1-methylthiocarbazol-2-yl) acetate and 4-fluorobenzyl bromide as starting materials, the title compound was obtained in a yield of 91% as an oil.

EXAMPLE 143

[9-(4-Fluorobenzyl)-4-methyl-1-methylthiocarbazol-2-yl]acetic Acid

Following a procedure and using relative proportions of starting materials similar to those described in Example 3, but using tert-butyl [9-(4-fluorobenzyl)-4-methyl-1-methylthiocarbazol-2-yl]acetate, as obtained in Example 142, as a starting material, the title compound was obtained in a yield of 97% as a solid melting at 189°–194° C.

Nuclear Magnetic Resonance Spectrum (CDCl$_3$, 270 MHz), δ ppm: 1.98 (3H, singlet); 2.89 (3H, singlet); 4.20 (2H, singlet); 6.33 (2H, singlet); 6.85–7.03 (4H, multiplet); 7.06 (1H, singlet); 7.25–7.50 (3H, multiplet); 8.19 (1H, doublet, J=8.0 Hz).

EXAMPLE 144 tert-Butyl [9-(3-Chlorobenzyl)-4-methyl-1-methylthiocarbazol-2-yl]acetate

Following a procedure and using relative proportions of starting materials similar to those described in Example 4, but using tert-butyl (4-methyl-1-methylthiocarbazol-2-yl) acetate and 3-chlorobenzyl bromide as starting materials, the title compound was obtained in a yield of 86% as an oil.

EXAMPLE 145

[9-(3-Chlorobenzyl)-4-methyl-1-methylthiocarbazol-2-yl]acetic Acid

Following a procedure and using relative proportions of starting materials similar to those described in Example 3, but using tert-butyl [9-(3-chlorobenzyl)-4-methyl-1-methylthiocarbazol-2-yl]acetate, as obtained in Example 144, as a starting material, the title compound was obtained in a quantitative yield as a solid melting at 205°–210° C.

Nuclear Magnetic Resonance Spectrum (CDCl$_3$, 270 MHz), δ ppm: 1.97 (3H, singlet); 2.89 (3H, singlet); 4.19 (2H, singlet); 6.33 (2H, singlet); 6.85 (1H, doublet, J=6.5 Hz); 7.06 (1H, singlet); 7.10–7.50 (6H, multiplet); 8.19 (1H, doublet, J=7.8 Hz).

EXAMPLE 146 tert-Butyl {9-[(1-Methyl-2-pyridon-4-yl)methyl]-4-methyl-1-methylthiocarbazol-2-yl}acetate Following a procedure and using relative proportions of starting materials similar to those described in Example 4, but using tert-butyl (4-methyl-1-methylthiocarbazol-2-yl) acetate and chloro(1-methyl-2-pyridon-4-yl)methane as starting materials, the title compound was obtained in a yield of 87% as an oil.

EXAMPLE 147

{9-((1-Methyl-2-pyridon-4-yl)methylbenzyl)-4-methyl-1-methylthiocarbazol-2-yl}acetic Acid Following a procedure and using relative proportions of starting materials similar to those described in Example 3, but using tert-butyl {9-[(1-methyl-2-pyridon-4-yl) methylbenzyl]-4-methyl-1-methylthiocarbazol-2-yl}acetate, as obtained in Example 146, as a starting material, the title compound was obtained in a quantitative yield as a solid melting at 188°–197° C.

Nuclear Magnetic Resonance Spectrum (CDCl$_3$+ tetradeuterated methanol, 270 MHz), δ ppm: 2.16 (3H, singlet); 2.88 (3H, singlet); 3.46 (3H, singlet); 4.14 (2H, singlet); 5.91 (1H, doublet of doublets, J=7.1,1.9 Hz); 6.17 (1H, singlet); 6.22 (2H, singlet); 7.08 (1H, singlet); 7.18 (1H, doublet, J=7.0 Hz); 7.20–7.54 (3H, multiplet); 8.18 (1H, doublet, J=8.1 Hz).

EXAMPLE 148 tert-Butyl [9-(3,4-Dichlorobenzyl)-4-methyl-1-methylthiocarbazol-2-yl]acetate

Following a procedure and using relative proportions of starting materials similar to those described in Example 4, but using tert-butyl (4-methyl-1-methylthiocarbazol-2-yl) acetate and 3,4-dichlorobenzyl chloride as starting materials, the title compound was obtained in a yield of 82% as an oil.

EXAMPLE 149

[9-(3,4-Dichlorobenzyl)-4-methyl-1-methylthiocarbazol-2-yl]acetic Acid

Following a procedure and using relative proportions of starting materials similar to those described in Example 3, but using tert-butyl [9-(3,4-dichlorobenzyl)-4-methyl-1-methylthiocarbazol-2-yl]acetate, as obtained in Example 148, as a starting material, the title compound was obtained in a quantitative yield, as a solid melting at 110°–120° C.

Nuclear Magnetic Resonance Spectrum (CDCl$_3$, 270 MHz), δ ppm: 2.02 (3H, singlet); 2.89 (3H, singlet); 4.20 (2H, singlet); 6.30 (2H, singlet); 6.80 (1H, doublet of doublets, J=8.5, 1.9 Hz); 7.07 (1H, singlet); 7.21 (1H, doublet, J=1.9 Hz); 7.26–7.50 (4H, multiplet); 8.19 (1H, doublet, J=7.4 Hz).

EXAMPLE 150 tert-Butyl [9-Methylsulfonyl-4-methyl-1-methylthiocarbazol-2-yl]acetate

Following a procedure and using relative proportions of starting materials similar to those described in Example 4, but using tert-butyl (4-methyl-1-methylthiocarbazol-2-yl)acetate and methylsulfonyl chloride as starting materials, the title compound was obtained in a yield of 95% as an oil.

EXAMPLE 151

(9-Methylsulfonyl-4-methyl-1-methylthiocarbazol-2-yl)acetic Acid

Following a procedure and using relative proportions of starting materials similar to those described in Example 3, but using tert-butyl (9-methylsulfonyl-4-methyl-1-methylthiocarbazol-2-yl)acetate, as obtained in Example 150, as a starting material, the title compound was obtained in a quantitative yield as a solid melting at 217°–218° C.

Nuclear Magnetic Resonance Spectrum (CDCl$_3$+ tetradeuterated methanol, 270 MHz), δ ppm: 2.22 (3H, singlet); 2.78 (3H, singlet); 3.53 (3H, singlet); 4.15 (2H, singlet); 7.30 (1H, singlet); 7.37–7.50 (2H, multiplet); 7.90 (1H, doublet, J=7.6 Hz); 8.00 (1H, doublet, J=8.1 Hz).

EXAMPLE 152

5-[9-(3,4-Dichlorobenzyl)-4-methyl-1-methylthiocarbazol-2-yl]methyl-1H-tetrazole Following procedures and-using relative proportions of starting materials similar to those described in Examples 75, 76 and 77, but using [9-(3,4-dichlorobenzyl)-4-methyl-1-methylthiocarbazol-2-yl]acetic acid, as obtained in Example 149, as a starting material, the title compound was obtained as a solid melting at 242°–245° C.

Nuclear Magnetic Resonance Spectrum (CDCl$_3$+ tetradeuterated methanol, 270 MHz), δ ppm: 1.97 (3H, singlet); 2.87 (3H, singlet); 4.79 (2H, singlet); 6.30 (2H, singlet); 6.81 (1H, doublet of doublets, J=8.6, 1.9 Hz); 7.05 (1H, singlet); 7.18 (1H, doublet, J=1.7 Hz); 7.28–7.35 (5H, multiplet).

EXAMPLE 153

Isopropyl (1-Methylthio-4-propylcarbazol-2-yl) acetate a) Ethyl 3-(indol-3-yl)hexanoate 10.7 g (148 mmol) of butanal was added gradually to 300 ml of a solution of 11.6 g of indole (98.6 mmol) and 14.2 g of Meldrum's acid (98.6 mmol) in acetonitrile at room temperature. 500 mg of proline was added to the reaction mixture which was then stirred overnight. The solvent was removed by evaporation under reduced pressure. The residue was dissolved in 200 ml of pyridine, and 15 ml of ethanol and 2.5 g of copper powder were added to the resulting solution. The reaction mixture was then refluxed for 4 hours and the copper powder was filtered off after this time. The solvent was removed by evaporation under reduced pressure. The residue was subjected to column chromatography (eluent: a 15% v/v solution of ethyl acetate in hexane) to yield 20.1 g (78%) of the title compound as an oil.

b) 1,1-Bismethylthio-4-propyl-1,2,3,4-tetrahydrocarbazol-2-one

Following procedures and using relative proportions of starting materials similar to those described in Examples 1a) and 1b), but using ethyl 3-(indol-3-yl)hexanoate, as obtained in a) above, as a starting material, the title compound was obtained as an amorphous solid.

c) Isopropyl (2-hydroxy-1,1-bismethylthio-4-propyl-1,2,3,4-tetrahydrocarbazol-2-yl) acetate Following a procedure and using relative proportions of starting materials similar to those described in Example 1d), but using 1,1-bismethylthio-4-propyl-1,2,3,4-tetrahydrocarbazol-2-one, as obtained in b) above, and isopropyl acetate as starting materials, the title compound was obtained in a yield of 81% as an oil.

d) Isopropyl (1-methylthio-4-propylcarbazol-2-yl)acetate

Following a procedure and using relative proportions of starting materials similar to those described in Example 2, but using isopropyl (2-hydroxy-1,1-bismethylthio-4-propyl-1,2,3,4-tetrahydrocarbazol-2-yl)acetate, as obtained in c) above, as a starting material, the title compound was obtained in a yield of 89% as an amorphous solid.

EXAMPLE 154

(1-Methylcarbazol-2-yl)thioacetomorpholide a) 2-Acetyl-1-methylcarbazole 15 ml of a 1.5M solution of methyllithium (22 mmol) in diethyl ether was added to 30 ml of a solution of 1.25 g of 1-methylcarbazol-2-ylcarboxylic acid (5.5 mmol—as obtained in Example 26) in diethyl ether, at a temperature of −78° C. The reaction mixture was then warmed to room temperature and stirred for 1 hour. After this time, the mixture was poured into a 0.5N aqueous solution of hydrogenchloride. The aqueous layer was extracted with ethyl acetate and the resulting organic layer was washed successively with a saturated aqueous solution of sodium hydrogencarbonate and a saturated aqueous solution of sodium chloride, in that order, dried over anhydrous magnesium sulfate, and the solvent was then removed by evaporation under reduced pressure. The residue was subjected to column chromatography (eluent: a 25% v/v solution of ethyl acetate in hexane) to yield 1.08 g (88%) of the title compound as an amorphous solid.

b) (1-Methylcarbazol-2-yl)thioacetomorpholide

Following a procedure and using relative proportions of starting materials similar to those described in Example 38, but using 2-acetyl-1-methylcarbazole, as obtained in a) above, as a starting material, the title compound was obtained in a yield of 75% as an oil.

EXAMPLE 155

(1-Methylcarbazol-2-yl)acetic Acid

Following a procedure and using relative proportions of starting materials similar to those described in Example 39, but using (1-methylcarbazol-2-yl)thioacetomorpholide, as obtained in Example 154, as a starting material, the title compound was obtained in a yield of 85% as a solid melting at 121° C. (with decomposition).

Nuclear Magnetic Resonance Spectrum (CDCl$_3$, 270 MHz), δ ppm: 2.51 (3H, singlet); 3.86 (2H, singlet); 7.11 (1H, doublet, J=7.9 Hz); 7.22 (1H, triplet, J=7.9 Hz); 7.3–7.5 (2H, multiplet); 7.88 (1H, doublet, J=7.9 Hz); 8.01 (1H, broad singlet); 8.03 (1H, doublet, J=7.9 Hz).

EXAMPLE 156

[9-(3-Nitrobenzyl)carbazol-2-yl]acetomorpholide a) Carbazol-2-ylacetomorpholide

An excess of a 1N aqueous solution of potassium hydroxide was added to 50 ml of an ethanolic solution of 3.10 g of (carbazol-2-yl)thioacetomorpholide (10 mmol), as obtained in Example 38, and the reaction mixture was stirred overnight at room temperature. The aqueous layer was then acidified by adding a 0.5N aqueous solution of hydrogen chloride to the mixture, and the reaction mixture was then extracted with ethyl acetate. The resulting organic layer was washed successively with a saturated aqueous solution of sodium hydrogencarbonate and a saturated aqueous solution of sodium chloride, in that order, dried over anhydrous magnesium sulfate, and the solvent was then removed by evaporation under reduced pressure. The residue was subjected to column chromatography (eluent: an 80% v/v solution of ethyl acetate in hexane) to yield 2.54 g (86%) of the title compound as an amorphous solid.

b) [9-(3-Nitrobenzyl)carbazol-2-yl]acetomorpholide

Following a procedure and using relative proportions of starting materials similar to those described in Example 4, but using (carbazol-2-yl)acetomorpholide, as obtained in a) above, and 3-nitrobenzyl bromide as starting materials, the title compound was obtained in a yield of 83% as an amorphous solid.

EXAMPLE 157

[9-(3-Nitrobenzyl)carbazol-2-yl]acetic Acid

Following a procedure and using relative proportions of starting materials similar to those described in Example 39, but using [9-(3-nitrobenzyl)carbazol-2-yl]acetomorpholide, as obtained in Example 156, as a starting material, the title compound was obtained in a yield of 81% as an amorphous solid.

Nuclear Magnetic Resonance Spectrum (CDCl$_3$, 270 MHz), δ ppm: 3.55 (2H, singlet); 5.17 (2H, singlet); 6.9–7.4 (7H, multiplet); 7.6–7.9 (4H, multiplet).

EXAMPLE 158

Methyl [9-(3-Acetamidobenzyl)carbazol-2-yl] acetate a) Methyl [9-(3-Nitrobenzyl)carbazol-2-yl]acetate Following a procedure and using relative proportions of starting materials similar to those described in Example 1a), but using [9-(3-nitrobenzyl)carbazol-2-yl]acetic acid, as obtained in Example 157, as a starting material, the title compound was obtained in a quantitative yield as an oil.

b) Methyl [9-(3-Acetamidobenzyl)carbazol-2-yl]acetate 20 mg of a 10% w/w preparation of palladium-on-carbon were added to 2 ml of a 1:1 v/v mixture of ethanol and tetrahydrofuran in which were dissolved 114 mg of methyl [9-(3-nitrobenzyl)carbazol-2-yl]acetate (0.30 mmol), as obtained in a) above. The reaction mixture was then stirred for 3 hours at room temperature under a stream of hydrogen. After this time, the catalyst was filtered off, and the solvent was removed by evaporation under reduced pressure to yield an amine compound. The thus obtained compound was dissolved in 0.5 ml of pyridine and then 0.5 ml of anhydrous acetic acid was added to the resulting solution. The reaction mixture was stirred for 30 min at room temperature and then an excess of water was added. The aqueous layer was extracted with ethyl acetate and the resulting organic layer was washed successively with a diluted aqueous solution of hydrogen chloride and a saturated aqueous solution of sodium chloride, in that order, dried over anhydrous magnesium sulfate, and then the solvent was removed by evaporation under reduced pressure. The residue was subjected to column chromatography (eluent: a 40% v/v solution of ethyl acetate in hexane) to yield 110 mg (93%) of the title compound as an oil.

EXAMPLE 159

[9-(3-Acetamidobenzyl)carbazol-2-yl]acetic Acid

Following a procedure and using relative proportions of starting materials similar to those described in Example 14, but using methyl [9-(3-acetamidobenzyl)carbazol-2-yl] acetate, as obtained in Example 158, as a starting material, the title compound was obtained in a yield of 98% as a solid melting at 138°–140° C. (with decomposition).

Nuclear Magnetic Resonance Spectrum (CDCl$_3$, 270 MHz), δ ppm: 2.06 (3H, singlet); 3.76 (2H, singlet); 5.49 (2H, singlet); 6.94 (1H, doublet, J=7.3 Hz); 7.06 (1H, singlet); 7.1–7.4 (6H, multiplet); 7.67 (1H, doublet, J=7.9 Hz); 8.0–8.1 (2H, multiplet).

EXAMPLE 160

[9-(4-Benzyloxybenzyl)-carbazol-2-yl] acetomorpholide

Following a procedure and using relative proportions of starting materials similar to those described in Example 156b), but using 4-benzyloxybenzyl chloride, as a starting material, the title compound was obtained in a yield of 77% as an amorphous solid.

EXAMPLE 161

[9-(4-Benzyloxybenzyl)carbazol-2-yl]acetic Acid

Following a procedure and using relative proportions of starting materials similar to those described in Example 39, but using [9-(4-benzyloxybenzyl)carbazol-2-yl] acetomorpholide, as obtained in Example 160, as a starting material, the title compound was obtained in a yield of 90% as a solid melting at 169°–171° C.

Nuclear Magnetic Resonance Spectrum (CDCl$_3$, 270 MHz), δ ppm: 3.81 (2H, singlet); 4.98 (2H, singlet); 5.44 (2H, singlet); 6.85 (2H, doublet, J=8.7 Hz); 7.07 (2H, doublet, J=8.7 Hz); 7.1–7.5 (10H, multiplet); 8.0–8.1 (2H, multiplet).

EXAMPLE 162

Methyl [9-(4-Hydroxybenzyl)carbazol-2-yl]acetate a) Methyl [9-(4-benzyloxybenzyl)carbazol-2-yl]acetate Following a procedure and using relative proportions of starting materials similar to those described in Example 1a), but using [9-(4-benzyloxybenzyl)carbazol-2-yl]acetic acid, as obtained in Example 161, as a starting material, the title compound was obtained in a quantitative yield as an oil.

b) Methyl [9-(4-hydroxybenzyl)carbazol-2-yl]acetate

Following a procedure and using relative proportions of starting materials similar to those described in Example 52, but using methyl [9-(4-benzyloxybenzyl)carbazol-2-yl] acetate, as obtained in a) above, as a starting material, the title compound was obtained in a yield of 75% as an oil.

EXAMPLE 163

[9-(4-Hydroxybenzyl)carbazol-2-yl]acetic Acid

Following a procedure and using relative proportions of starting materials similar to those described in Example 14, but using methyl [9-(4-hydroxybenzyl)carbazol-2-yl] acetate, as obtained in Example 162, as a starting material, the title compound was obtained in a quantitative yield as a solid melting at 216° C. (with decomposition).

Nuclear Magnetic Resonance Spectrum (CDCl$_3$, 270 MHz), δ ppm: 3.80 (2H, singlet); 5.44 (2H, singlet); 6.75 (2H, doublet, J=8.5 Hz); 7.02 (2H, doublet, J=8.5 Hz); 7.1–7.3 (2H, multiplet); 7.3–7.4 (3H, multiplet); 7.47 (1H, singlet); 8.0–8.1 (2H, multiplet).

EXAMPLE 164

[9-(3-Benzyloxybenzyl)carbazol-2-yl] acetomorpholide

Following a procedure and using relative proportions of starting materials similar to those described in Example 156b), but using 3-benzyloxybenzyl chloride, as a starting material, the title compound was obtained in a yield of 79% as an amorphous solid.

EXAMPLE 165

[9-(3-Benzyloxybenzyl)carbazol-2-yl]acetic Acid

Following a procedure and using relative proportions of starting materials similar to those described in Example 39, but using [9-(3-benzyloxybenzyl)carbazol-2-yl] acetomorpholide, as obtained in Example 164, as a starting material, the title compound was obtained in a yield of 89% as a solid melting at 154°–156° C.

Nuclear Magnetic Resonance Spectrum (CDCl$_3$, 270 MHz), δ ppm: 3.79 (2H, singlet); 4.91 (2H, singlet); 5.45 (2H, singlet); 6.7–6.8 (2H, multiplet); 6.82 (1H, doublet of doublets, J=8.2,2.0 Hz); 7.1–7.4 (10H, multiplet); 7.41 (1H, triplet, J=7.5 Hz); 8.0–8.1 (2H, multiplet).

EXAMPLE 166

Methyl [9-(3-Hydroxybenzyl)carbazol-2-yl]acetate

Following a procedure and using relative proportions of starting materials similar to those described in Example 162, but using [9-(3-benzyloxybenzyl)carbazol-2-yl]acetic acid, as obtained in Example 165, as a starting material, the title compound was obtained as an oil.

EXAMPLE 167

[9-(3-Hydroxybenzyl)carbazol-2-yl]acetic Acid

Following a procedure and using relative proportions of starting materials similar to those described in Example 14, but using methyl [9-(3-hydroxybenzyl)carbazol-2-yl] acetate, as obtained in Example 166, as a starting material, the title compound was obtained in a quantitative yield as a solid melting at 186°–187° C.

Nuclear Magnetic Resonance Spectrum (CDCl$_3$, 270 MHz), δ ppm: 3.79 (2H, singlet); 5.47 (2H, singlet); 6.54 (1H, singlet); 6.7–6.8 (2H, multiplet); 7.12 (1H, triplet, J=7.8 Hz); 7.1–7.5 (5H, multiplet); 8.0–8.1 (2H, multiplet).

EXAMPLE 168

(1-Methylthio-4-propylcarbazol-2-yl)acetic Acid

Following a procedure and using relative proportions of starting materials similar to those described in Example 26, but using isopropyl (1-methylthio-4-propylcarbazol-2-yl) acetate, as obtained in Example 114, as a starting material, the title compound was obtained in a yield of 95% as a solid melting at 160°–161° C.

Nuclear Magnetic Resonance Spectrum (CDCl$_3$, 270 MHz), δ ppm: 1.10 (3H, triplet, J=7.3 Hz); 1.8–1.9 (2H, multiplet); 2.34 (3H, singlet); 3.16 (2H, triplet, J=7.7 Hz); 4.17 (2H, singlet); 7.01 (1H, singlet); 7.26 (1H, triplet, J=7.7 Hz); 7.43 (1H, triplet, J=7.7 Hz); 7.51 (1H, doublet, J=7.7 Hz); 8.05 (1H, doublet, J=7.7 Hz); 8.70 (1H, broad singlet).

EXAMPLE 169

Isopropyl [1-Methylthio-9-(3-nitrobenzyl)-4-propylcarbazol-2-yl]acetate

Following a procedure and using relative proportions of starting materials similar to those described in Example 4, but using isopropyl (1-methylthio-4-propylcarbazol-2-yl) acetate, as obtained in Example 114, and 3-nitrobenzyl chloride as starting materials, the title compound was obtained in a yield of 80% as an oil.

EXAMPLE 170

[1-Methylthio-9-(3-nitrobenzyl)-4-propylcarbazol-2-yl]acetic Acid

Following a procedure and using relative proportions of starting materials similar to those described in Example 26, but using isopropyl [1-methylthio-9-(3-nitrobenzyl)-4-propylcarbazol-2-yl]acetate, as obtained in Example 169, as a starting material, the title compound was obtained in a quantitative yield as a solid melting at 150° C. (with decomposition).

Nuclear Magnetic Resonance Spectrum [CDCl$_3$+(CD$_3$)$_2$CO, 270 MHz], δ ppm: 1.13 (3H, triplet, J=7.3 Hz); 1.8–2.0 (2H, multiplet); 2.02 (3H, singlet); 3.21 (2H, triplet, J=7.8 Hz); 4.20 (2H, singlet); 6.42 (2H, singlet); 7.09 (1H, singlet); 7.2–7.5 (5H, multiplet); 8.0–8.2 (3H, multiplet).

EXAMPLE 171

Isopropyl 2-[1-Methylthio-9-(3-nitrobenzyl)-4-propylcarbazol-2-yl]-3-(3-nitrophenyl)propionate Following a procedure and using relative proportions of starting materials similar to those described in Example 16, but using isopropyl (1-methylthio-4-propylcarbazol-2-yl) acetate, as obtained in Example 114, and 3-nitrobenzyl chloride as starting materials, the title compound was obtained in a yield of 88% as an oil.

EXAMPLE 172

2-[1-Methylthio-9-(3-nitrobenzyl)-4-propylcarbazol-2-yl]-3-(3-nitrophenyl)propionic Acid Following a procedure and using relative proportions of starting materials similar to those described in Example 26, but using isopropyl 2-[1-methylthio-9-(3-nitrobenzyl)-4-propylcarbazol-2-yl]-3-(3-nitrophenyl)propionate, as obtained in Example 171, as a starting material, the title compound was obtained in a quantitative yield as an amorphous solid.

Nuclear Magnetic Resonance Spectrum (CDCl$_3$, 270 MHz), δ ppm: 1.12 (3H, triplet, J=7.4 Hz); 1.8–2.0 (2H, multiplet); 2.00 (3H, singlet); 3.1–3.3 (3H, multiplet); 3.56 (1H, doublet of doublets, J=13.9,7.5 Hz); 5.38 (1H, triplet, J=7.5 Hz); 6.31 (1H, doublet, J=17.4 Hz); 6.40 (1H, doublet, J=17.4 Hz); 7.1–7.5 (7H, multiplet); 7.18 (1H, singlet); 7.9–8.2 (5H, multiplet).

EXAMPLE 173

Isopropyl [9-(3-acetamidobenzyl)-1-methylthio-4-propylcarbazol-2-yl]acetate

Following a procedure and using relative proportions of starting materials similar to those described in Example 158, but using isopropyl [1-methylthio-9-(3-nitrobenzyl)-4-propylcarbazol-2-yl]acetate, as obtained in Example 169, as a starting material, the title compound was obtained as an oil.

EXAMPLE 174

[9-(3-Acetamidobenzyl)-1-methylthio-4-propylcarbazol-2-yl]acetic Acid

Following a procedure and using relative proportions of starting materials similar to those described in Example 26, but using isopropyl [9-(3-acetamidobenzyl)-1-methylthio-4-propylcarbazol-2-yl]acetate, as obtained in Example 173, as a starting material, the title compound was obtained in a quantitative yield as a solid melting at 130°–134° C. (with decomposition).

Nuclear Magnetic Resonance Spectrum (CDCl$_3$, 270 MHz), δ ppm: 1.14 (3H, triplet, J=7.4 Hz); 1.8–2.0 (2H, multiplet); 2.02 (3H, singlet); 2.07 (3H, singlet); 3.20 (2H, triplet, J=7.8 Hz); 4.20 (2H, singlet); 6.36 (2H, singlet); 6.76 (1H, doublet, J=7.3 Hz); 7.0–7.5 (6H, multiplet); 7.60 (1H, doublet, J=8.0 Hz); 8.10 (1H, doublet, J=8.0 Hz); 8.40 (1H, broad singlet).

EXAMPLE 175

Isopropyl [1-Methylthio-9-(4-nitrobenzyl)-4-propylcarbazol-2-yl]acetate

Following a procedure and using relative proportions of starting materials similar to those described in Example 4, but using isopropyl (1-methylthio-4-propylcarbazol-2-yl) acetate, as obtained in Example 114, and 4-nitrobenzyl bromide as starting materials, the title compound was obtained in a yield of 76% as an oil.

EXAMPLE 176

[1-Methylthio-9-(4-nitrobenzyl)-4-propylcarbazol-2-yl]acetic Acid

Following a procedure and using relative proportions of starting materials similar to those described in Example 26, but using isopropyl [1-methylthio-9-(4-nitrobenzyl)-4-propylcarbazol-2-yl]acetate, as obtained in Example 175, as a starting material, the title compound was obtained in a quantitative yield as an amorphous solid.

Nuclear Magnetic Resonance Spectrum [CDCl$_3$+(CD$_3$)$_2$CO, 270 MHz], δ ppm: 1.13 (3H, triplet, J=7.3 Hz); 1.8–2.0 (2H, multiplet); 1.99 (3H, singlet); 3.20 (2H, doublet of doublets, J=8.8,6.9 Hz); 4.18 (2H, singlet); 6.43 (2H, singlet); 7.08 (1H, singlet); 7.18 (2H, doublet, J=8.9 Hz); 7.2–7.4 (1H, multiplet); 7.43 (1H, triplet, J=7.5 Hz); 8.0–8.2 (4H, multiplet).

EXAMPLE 177

Isopropyl [9-(4-Acetamidobenzyl)-1-methylthio-4-propylcarbazol-2-yl]acetate

Following a procedure and using relative proportions of starting materials similar to those described in Example 158b), but using isopropyl [1-methylthio-9-(4-nitrobenzyl)-4-propylcarbazol-2-yl]acetate, as obtained in Example 175, as a starting material, the title compound was obtained as an oil.

EXAMPLE 178

[9-(4-Acetamidobenzyl)-1-methylthio-4-propylcarbazol-2-yl]acetic Acid

Following a procedure and using relative proportions of starting materials similar to those described in Example 26, but using isopropyl [9-(4-acetamidobenzyl)-1-methylthio-4-propylcarbazol-2-yl]acetate, as obtained in Example 177, as a starting material, the title compound was obtained in a quantitative yield as a solid melting at 219°–221° C.

Nuclear Magnetic Resonance Spectrum (CDCl$_3$, 270 MHz), δ ppm: 1.13 (3H, triplet, J=7.3 Hz); 1.8–2.0 (2H, multiplet); 2.12 (3H, singlet); 2.15 (3H, singlet); 3.20 (2H, triplet, J=7.8 Hz); 4.19 (2H, singlet); 6.35 (2H, singlet); 6.99 (2H, doublet, J=8.5 Hz); 7.08 (1H, singlet); 7.26 (1H, triplet, J=7.5 Hz); 7.3–7.5 (4H, multiplet); 7.88 (1H, broad singlet); 8.10 (1H, doublet, J=7.5 Hz).

EXAMPLE 179 tert-Butyl [9-(4-Chlorobenzyl)-4-methyl-1-methylthiocarbazol-2-yl]acetate

Following a procedure and using relative proportions of starting materials similar to those described in Example 4, but using tert-butyl (4-methyl-1-methylthiocarbazol-2-yl) acetate and 4-chlorobenzyl chloride as starting materials, the title compound was obtained in a yield of 92% as an oil.

EXAMPLE 180

[9-(4-Chlorobenzyl)-4-methyl-1-methylthiocarbazol-2-yl]acetic Acid

Following a procedure and using relative proportions of starting materials similar to those described in Example 3, but using tert-butyl [9-(4-chlorobenzyl)-4-methyl-1-methylthiocarbazol-2-yl]acetate, as obtained in Example 179, as a starting material, the title compound was obtained in a quantitative yield as a solid melting at 198°–199° C.

Nuclear Magnetic Resonance Spectrum (CDCl$_3$, 270 MHz), δ ppm: 1.99 (3H, singlet); 2.89 (3H, singlet); 4.19 (2H, singlet); 6.33 (2H, singlet); 6.95 (2H, doublet, J=8.4 Hz); 7.06 (1H, singlet); 7.19 (2H, doublet, J=8.4 Hz); 7.2–7.4 (2H, multiplet); 7.43 (1H, triplet, J=7.6 Hz); 8.19 (1H, doublet, J=7.6 Hz).

EXAMPLE 181

Isopropyl (9-Benzyl-6-methoxy-4-methyl-1-methylthiocarbazol-2-yl)acetate

Following a procedure and using relative proportions of starting materials similar to those described in Example 114, but using 5-methoxyindole and acetaldehyde as starting materials, the title compound was obtained as an oil.

EXAMPLE 182

(9-Benzyl-6-methoxy-4-methyl-1-methylthiocarbazol-2-yl)acetic Acid

Following a procedure and using relative proportions of starting materials similar to those described in Example 26, but using isopropyl (9-benzyl-6-methoxy-4-methyl-1-methylthiocarbazol-2-yl)acetate, as obtained in Example 181, as a starting material, the title compound was obtained in a yield of 97% as a solid melting at 205°–206° C.

Nuclear Magnetic Resonance Spectrum (CDCl$_3$, 270 MHz), δ ppm: 1.95 (3H, singlet); 2.87 (3H, singlet); 3.92 (3H, singlet); 4.18 (2H, singlet); 6.34 (2H, singlet); 7.0–7.3 (8H, multiplet); 7.70 (1H, doublet, J=2.5 Hz).

EXAMPLE 183

Isopropyl (9-Benzyl-5-methoxy-4-methyl-1-methylthiocarbazol-2-yl)acetate

Following a procedure and using relative proportions of starting materials similar to those described in Example 114, but using 4-methoxyindole and acetaldehyde as starting materials, the title compound was obtained as an oil.

EXAMPLE 184

(9-Benzyl-5-methoxy-4-methyl-1-methylthiocarbazol-2-yl)acetic Acid

Following a procedure and using relative proportions of starting materials similar to those described in Example 26, but using isopropyl (9-benzyl-5-methoxy-4-methyl-1-methylthiocarbazol-2-yl)acetate, as obtained in Example 183, as a starting material, the title compound was obtained in a quantitative yield as a solid melting at 214°–216° C.

Nuclear Magnetic Resonance Spectrum (CDCl$_3$, 270 MHz), δ ppm: 1.91 (3H, singlet); 2.99 (3H, singlet); 3.99 (3H, singlet); 4.15 (2H, singlet); 6.37 (2H, singlet); 6.69 (1H, doublet, J=8.1 Hz); 6.9–7.1 (4H, multiplet); 7.1–7.3 (3H, multiplet); 7.32 (1H, triplet, J=8.1 Hz).

EXAMPLE 185

Isopropyl (9-Benzyl-6-hydroxy-4-methyl-1-methylthiocarbazol-2-ylacetate 0.48 ml of a 1.0M solution of boron tribromide (0.48 mmol) in methylene chloride was added to 1 ml of a solution of 106 mg isopropyl (9-benzyl-6-methoxy-4-methyl-1-methylthiocarbazol-2-yl)acetate (0.24 mmol), as obtained in Example 181, in methylene chloride, at a temperature of −78° C. The reaction mixture was then warmed to at 0° C. and stirred for 3 hours. After this time, the reaction mixture was poured into a saturated aqueous solution of sodium hydrogencarbonate, and the aqueous layer was extracted with methylene chloride. The resulting organic layer was washed with a saturated aqueous solution of sodium chloride, dried over anhydrous magnesium sulfate, and then the solvent was removed by evaporation under reduced pressure. The residue was subjected to column chromatography (eluent: a 15% v/v solution of ethyl acetate in hexane) to yield 81 mg (79%) of the title compound as an oil.

EXAMPLE 186

(9-Benzyl-6-hydroxy-4-methyl-1-methylthiocarbazol-2-yl)acetic Acid

Following a procedure and using relative proportions of starting materials similar to those described in Example 26, but using isopropyl (9-benzyl-6-hydroxy-4-methyl-1-methylthiocarbazol-2-yl)acetate, as obtained in Example 185, as a starting material, the title compound was obtained in a yield of 94% as a solid melting at 219°–222° C.

Nuclear Magnetic Resonance Spectrum (CDCl$_3$, 270 MHz), δ ppm: 1.99 (3H, singlet); 2.84 (3H, singlet); 4.17 (2H, singlet); 6.35 (2H, singlet); 7.0–7.4 (9H, multiplet); 7.69 (1H, singlet).

EXAMPLE 187

Isopropyl (4-Isopropyl-1-methylthiocarbazol-2-yl)acetate

Following a procedure and using relative proportions of starting materials similar to those described in Example 114, but using isobutyraldehyde as a starting material, the title compound was obtained as an oil.

EXAMPLE 188

(4-Isopropyl-1-methylthiocarbazol-2-yl)acetic Acid

Following a procedure and using relative proportions of starting materials similar to those described in Example 26, but using isopropyl (4-isopropyl-1-methylthiocarbazol-2-yl)acetate, as obtained in Example 187, as a starting material, the title compound was obtained in a quantitative yield as a solid melting at 171°–173° C.

Nuclear Magnetic Resonance Spectrum (CDCl$_3$, 270 MHz), δ ppm: 1.47 (6H, doublet, J=6.8 Hz); 2.35 (3H. singlet); 3.91 (1H, sep, J=6.8 Hz); 4.19 (2H, singlet); 7.11 (1H, singlet); 7.25 (1H, triplet, J=7.7 Hz); 7.43 (1H, triplet, J=7.7 Hz); 7.51 (1H, doublet, J=7.7 Hz); 8.14 (1H, doublet, J=7.7 Hz); 8.72 (1H, broad singlet).

EXAMPLE 189

Isopropyl (9-Benzyl-4-isopropyl-1-methylthiocarbazol-2-yl)acetate

Following a procedure and using relative proportions of starting materials similar to those described in Example 4, but using isopropyl (4-isopropyl-1-methylthiocarbazol-2-yl)acetate, as obtained in Example 187, as a starting material, the title compound was obtained in a yield of 83% as an oil.

EXAMPLE 190

(9-Benzyl-4-isopropyl-1-methylthiocarbazol-2-yl)acetic Acid

Following a procedure and using relative proportions of starting materials similar to those described in Example 26, but using isopropyl (9-benzyl-4-isopropyl-1-methylthiocarbazol-2-yl)acetate, as obtained in Example 189, as a starting material, the title compound was obtained in a quantitative yield as a solid melting at 170°–171° C.

Nuclear Magnetic Resonance Spectrum (CDCl$_3$, 270 MHz), δ ppm: 1.49 (6H, doublet, J=6.8 Hz); 1.94 (3H, singlet); 4.00 (1H, sep, J=6.8 Hz); 4.22 (2H, singlet); 6.39 (2H, singlet); 7.0–7.1 (2H, multiplet); 7.1–7.5 (7H, multiplet); 8.21 (1H, doublet, J=7.9 Hz).

EXAMPLE 191

3-(1-Benzylindol-3-yl)propionic Acid 8 ml of a solution of 1.00 g of indol-3-ylpropionic acid in dimethyl formamide were added gradually to 4 ml of a suspension of 460 mg (10.6 mmol) of sodium hydride (55% w/v dispersion in mineral oil) in dimethyl formamide at a temperature of −5° C., and the resulting mixture was stirred for 30 minutes at this temperature. After this time, 1.8 g (10.6 mmol) of benzyl bromide was added to the mixture which was then warmed to room temperature, stirred for 10 min, poured into ice-water, and acidified with a 1N aqueous solution of hydrogen chloride. The resulting aqueous layer was extracted with methylene chloride, and the extract was dried over anhydrous magnesium sulfate and then the solvent was removed by evaporation under reduced pressure. The residue was recrystallized from a 1:1 v/v mixture of ethyl acetate and hexane to yield 1.15 g (79%) of the title compound melting at 121°–122° C.

EXAMPLE 192

(1-Benzylindol-3-yl)thioacetomorpholide

Following procedures and using relative proportions of starting materials similar to those described in Examples 4 and 90, but using 3-acetylindole as a starting material, the title compound was obtained as an oil.

EXAMPLE 193

(1-Benzylindol-3-yl)acetic Acid

Following a procedure and using relative proportions of starting materials similar to those described in Example 39, but using (1-benzylindol-3-yl)thioacetomorpholide, as obtained in Example 192, as a starting material, the title compound was obtained in a yield of 76% as a solid melting at 155°–156° C.

Nuclear Magnetic Resonance Spectrum (CDCl$_3$, 270 MHz), δ ppm: 3.82 (2H, singlet); 5.30 (2H, singlet); 7.11–7.67 (10H, multiplet).

EXAMPLE 194

Methyl (1-Benzyl-3-formylindol-6-yl)acetate a) Methyl (1-benzylindol-6-yl)acetate Following a procedure and using relative proportions of starting materials similar to those described in Example 1a), but using (1-benzylindol-6-yl)acetic acid, as obtained in Example 67, as a starting material, the title compound was obtained in a yield of 98% as an oil.

b) Methyl (1-benzyl-3-formylindol-6-yl)acetate 18 mg (0.12 mmol) of phosphoryl oxychloride was added gradually to 4 ml of a solution of 25 mg (0.09 mmol) of methyl (1-benzylindol-6-yl)acetate, as obtained in a) above, in dimethyl formamide, at room temperature, and the resulting mixture was stirred for 30 minutes. After this time, an excess of a 2N aqueous solution of sodium hydroxide was added to the mixture, which was then stirred for 10 minutes. The aqueous layer was extracted with methylene chloride and the extract was washed with a saturated aqueous solution of sodium chloride, dried over anhydrous magnesium sulfate and then the solvent was removed by evaporation under reduced pressure. The residue was subjected to column chromatography (eluent: a 25% v/v solution of ethyl acetate in hexane) to yield 23 mg (83%) of the title compound as an oil.

EXAMPLE 195

(1-Benzyl-3-formylindol-6-yl)acetic Acid

Following a procedure and using relative proportions of starting materials similar to those described in Example 14, but using methyl (1-benzyl-3-formylindol-6-yl)acetate, as obtained in Example 194, as a starting material, the title compound was obtained in a yield of 92% as a solid melting at 162°–163° C.

Nuclear Magnetic Resonance Spectrum (CDCl$_3$, 270 MHz), δ ppm: 3.74 (2H, singlet); 5.33 (2H, singlet); 7.17–8.28 (9H, multiplet); 9.96 (1H, singlet).

EXAMPLE 196

Methyl (3-Benzoyl-1-benzylindol-6-yl)acetate

Following a procedure and using relative proportions of starting materials similar to those described in Example 194b), but using N,N-dimethylbenzamide as a starting material, the title compound was obtained in a yield of 70% as an oil.

EXAMPLE 197

(3-Benzoyl-1-benzylindol-6-yl)acetic Acid

Following a procedure and using relative proportions of starting materials similar to those described in Example 14, but using methyl (3-benzoyl-1-benzylindol-6-yl)acetate, as obtained in Example 196, as a starting material, the title compound was obtained in a yield of 90% as a solid melting at 195°–196° C.

Nuclear Magnetic Resonance Spectrum (CDCl$_3$, 270 MHz), δ ppm: 3.75 (2H, singlet); 5.35 (2H, singlet); 7.24–8.39 (14H, multiplet).

EXAMPLE 198

Methyl (3-Acetyl-1-benzylindol-6-yl)acetate

Following a procedure and using relative proportions of starting materials similar to those described in Example 194b), but using N,N-dimethylacetamide as a starting material, the title compound was obtained in a yield of 75% as an oil.

EXAMPLE 199

(3-Acetyl-1-benzylindol-6-yl)acetic Acid

Following a procedure and using relative proportions of starting materials similar to those described in Example 14, but using methyl (3-acetyl-1-benzylindol-6-yl)acetate, as obtained in Example 198, as a starting material, the title compound was obtained in a yield of 88% as a solid melting at 211°–212° C.

Nuclear Magnetic Resonance Spectrum (CDCl$_3$, 270 MHz), δ ppm: 2.50 (3H, singlet); 3.73 (2H, singlet); 5.33 (2H, singlet); 7.14–7.35 (7H, multiplet); 7.72 (1H, singlet); 8.34 (1H, doublet, J=8.0 Hz).

EXAMPLE 200

(9-Benzyl-1-methylsulfinyl-4-methylcarbazol-2-yl) acetic Acid

Following a procedure and using relative proportions of starting materials similar to those described in Example 26, but using isopropyl (9-benzyl-1-methanesulfinyl-4-methylcarbazol-2-yl)acetate, as obtained in Example 215 below, as a starting material, the title compound was obtained in a yield of 96% as a solid melting at 210° C. (with decomposition).

Nuclear Magnetic Resonance Spectrum (d$_6$-DMSO, 270 MHz), δ ppm: 2.74 (3H, singlet); 2.83 (3H, singlet); 3.94 (1H, doublet, J=16.0 Hz); 4.30 (1H, doublet, J=16.0 Hz) 6.18 (2H, singlet); 6.86 (2H, doublet, J=7.26 Hz); 7.01 (1H, singlet); 7.17–7.53 (6H, multiplet); 8.20 (1H, doublet, J=7.88 Hz).

EXAMPLE 201

Isopropyl (9-Benzyl-1-methylsulfonyl-4-methylcarbazol-2-yl)acetate 44 mg (0.25 mmol) of m-chloroperbenzoic acid was added to 6 ml of a solution of 100 mg (0.23 mmol) of isopropyl (9-benzyl-1-methylsulfinyl-4-methylcarbazol-2-yl)acetate, as obtained in Example 215 below, in methylene chloride at room temperature, and the mixture was stirred for 30 minutes. After this time, a saturated aqueous solution of sodium hydrogencarbonate was added to the mixture, the aqueous layer was extracted with methylene chloride, the extract was dried over anhydrous magnesium sulfate and then the solvent was removed by evaporation under reduced pressure. The residue was subjected to column chromatography (eluent: a 50% v/v solution of ethyl acetate in hexane) to yield 90 mg (87%) of the title compound as an amorphous solid.

EXAMPLE 202

(9-Benzyl-1-methylsulfonyl-4-methylcarbazol-2-yl) acetic Acid

Following a procedure and using relative proportions of starting materials similar to those described in Example 26, but using isopropyl (9-benzyl-1-methanesulfonyl-4-methylcarbazol-2-yl)acetate, as obtained in Example 201, as a starting material, the title compound was obtained in a yield of 95% as a solid melting at 167°–168° C.

Nuclear Magnetic Resonance Spectrum (CDCl$_3$, 270 MHz), δ ppm: 2.94 (3H, singlet); 3.06 (3H, singlet); 4.31 (2H, singlet); 6.25 (2H, singlet); 6.77 (2H, doublet, J=7.7 Hz); 7.03 (1H, singlet); 7.14–7.46 (6H, multiplet); 8.20 (1H, doublet, J=7.7 Hz).

EXAMPLE 203

Isopropyl (4,9-Dimethyl-1-methylsulfinylcarbazol-2-yl)acetate a) Isopropyl (4,9-dimethyl-1-methylthiocarbazol-2-yl)acetate Following a procedure and using relative proportions of starting materials similar to those described in Example 4, but using isopropyl (4-methyl-1-methylthiocarbazol-2-yl)acetate and methyl iodide as starting materials, the title compound was obtained in a yield of 80% as an oil.

b) Isopropyl (4,9-dimethyl-1-methylsulfinylcarbazol-2-yl)acetate

Following a procedure and using relative proportions of starting materials similar to those described in Example 215 below, but using isopropyl (4,9-dimethyl-1-methylthiocarbazol-2-yl)acetate, as obtained in a) above, as a starting material, the title compound was obtained in a yield of 89% as an oil.

EXAMPLE 204

(4,9-Dimethyl-1-methylsulfinylcarbazol-2-yl)acetic Acid

Following a procedure and using relative proportions of starting materials similar to those described in Example 26, but using isopropyl (4,9-dimethyl-1-methylsulfinylcarbazol-2-yl)acetate, as obtained in Example 203, as a starting material, the title compound was obtained in a yield of 84% as a solid melting at 219°–220° C.

Nuclear Magnetic Resonance Spectrum (d$_6$-DMSO, 270 MHz), δ ppm: 2.79 (3H, singlet); 3.13 (3H, singlet); 3.85 (2H, broad singlet); 4.41 (3H, singlet); 6.89 (1H, singlet); 7.28 (1H, triplet, J=7.4 Hz); 7.51 (1H, triplet, J=7.4 Hz); 7.63 (1H, doublet, J=7.6 Hz); 8.14 (1H, doublet, J=7.8 Hz).

EXAMPLE 205

Isopropyl (1-Benzylthio-4,9-dimethylcarbazol-2-yl)acetate

Following a procedure and using relative proportions of starting materials similar to those described in Example 216 below, but using isopropyl (4,9-dimethyl-1-methylsulfinylcarbazol-2-yl)acetate, as obtained in Example 203, and benzyl bromide as starting materials, the title compound was obtained in a yield of 72% as an oil.

EXAMPLE 206

(1-Benzylthio-4,9-dimethylcarbazol-2-yl)acetic Acid

Following a procedure and using relative proportions of starting materials similar to those described in Example 26, but using isopropyl (1-benzylthio-4,9-dimethylcarbazol-2-yl)acetate, as obtained in Example 205, as a starting material, the title compound was obtained in a yield of 82% as a solid melting at 187°–188° C.

Nuclear Magnetic Resonance Spectrum (CDCl$_3$, 270 MHz), δ ppm: 2.85 (3H, singlet); 3.23 (2H, singlet); 3.90 (2H, singlet); 4.32 (3H, singlet); 6.93–7.57 (9H, multiplet); 8.16 (1H, doublet, J=7.9 Hz).

EXAMPLE 207

Isopropyl (4,9-Dimethyl-1-isopropylthiocarbazol-2-yl)acetate

Following a procedure and using relative proportions of starting materials similar to those described in Example 216 below, but using isopropyl (4,9-dimethyl-1-methylsulfinylcarbazol-2-yl)acetate, as obtained in Example 203, and isopropyl iodide as starting materials, the title compound was obtained in a yield of 65% as an oil.

EXAMPLE 208

(4,9-Dimethyl-1-isopropylthiocarbazol-2-yl)acetic Acid

Following a procedure and using relative proportions of starting materials similar to those described in Example 26, but using isopropyl (4,9-dimethyl-1-isopropylthiocarbazol-2-yl)acetate, as obtained in Example 207, as a starting material, the title compound was obtained in a yield of 90% as a solid melting at 205°–206° C.

Nuclear Magnetic Resonance Spectrum (CDCl$_3$, 270 MHz), δ ppm: 1.17 (6H, doublet, J=6.73 Hz); 2.85 (3H, singlet); 3.06 (1H, hepted, J=6.7 Hz); 4.23 (2H, broad singlet); 4.41 (3H, singlet); 7.01 (1H, singlet); 7.25–7.54 (3H, multiplet); 8.15 (1H, doublet, J=7.8 Hz).

EXAMPLE 209

Isopropyl (4,9-Dimethyl-1-propylthiocarbazol-2-yl)acetate

Following a procedure and using relative proportions of starting materials similar to those described in Example 216 below, but using isopropyl (4,9-dimethyl-1-methylsulfinylcarbazol-2-yl)acetate, as obtained in Example 203 and propyl iodide as starting materials, the title compound was obtained in a yield of 69% as an oil.

EXAMPLE 210

(4,9-Dimethyl-1-propylthiocarbazol-2-yl)acetic Acid

Following a procedure and using relative proportions of starting materials similar to those described in Example 26, but using isopropyl (4,9-dimethyl-1-propylthiocarbazol-2-yl)acetate, as obtained in Example 209, as a starting material, the title compound was obtained in a yield of 84% as a solid melting at 187°–188° C.

Nuclear Magnetic Resonance Spectrum (CDCl$_3$, 270 MHz), δ ppm: 0.94 (3H, triplet, J=7.3 Hz); 1.56 (2H, sixted, J=7.4 Hz); 2.66 (2H, triplet, J=7.54 Hz); 2.85 (3H, singlet); 4.22 (2H, singlet); 4.44 (3H, singlet); 7.00 (1H, singlet); 7.24–7.47 (3H, multiplet); 8.15 (1H, doublet, J=7.9 Hz).

EXAMPLE 211 tert-Butyl [4-Methyl-1-methylthio-9-(2-phenethyl)carbazol-2-yl]acetate

Following a procedure and using relative proportions of starting materials similar to those described in Example 4, but using tert-butyl (4-methyl-1-methylthiocarbazol-2-yl)

acetate and 2-phenylethyl bromide as starting materials, the title compound was obtained in a yield of 77% as an oil.

EXAMPLE 212

[4-Methyl-1-methylthio-9-(2-phenethyl)carbazol-2-yl]acetic Acid

Following a procedure and using relative proportions of starting materials similar to those described in Example 3, but using tert-butyl [4-methyl-1-methylthio-9-(2-phenethyl) carbazol-2-yl]acetate, as obtained in Example 211, as a starting material, the title compound was obtained in a quantitative yield as a solid melting at 181°–182° C.

Nuclear Magnetic Resonance Spectrum (CDCl$_3$, 270 MHz), δ ppm: 2.29 (3H, singlet); 2.86 (3H, singlet); 3.04 (2H, triplet, J=8.1 Hz); 4.25 (2H, singlet); 5.17 (2H, triplet, J=8.1 Hz); 7.04 (1H, singlet); 7.25–7.36 (6H, multiplet); 7.51 (2H, doublet, J=3.3 Hz); 8.17 (1H, doublet, J=7.9 Hz).

EXAMPLE 213 tert-Butyl [4-Methyl-1-methylthio-9-(3-phenylpropyl)carbazol-2-yl]acetate

Following a procedure and using relative proportions of starting materials similar to those described in Example 4, but using tert-butyl (4-methyl-1-methylthiocarbazol-2-yl) acetate and 3-phenylpropyl bromide as starting materials, the title compound was obtained in a yield of 74% as an oil.

EXAMPLE 214

[4-Methyl-1-methylthio-9-(3-phenylpropyl)carbazol-2-yl]acetic Acid

Following a procedure and using relative proportions of starting materials similar to those described in Example 3, but using tert-butyl [4-methyl-1-methylthio-9-(3-phenylpropyl)carbazol-2-yl]acetate, as obtained in Example 213, as a starting material, the title compound was obtained in a quantitative yield as a solid melting at 155°–156° C.

Nuclear Magnetic Resonance Spectrum (CDCl$_3$, 270 MHz), δ ppm: 2.13 (2H, triplet, J=7.6 Hz); 2.2 (3H, singlet); 2.73 (2H, triplet, J=7.6 Hz); 2.84 (3H, singlet); 4.22 (2H, singlet); 4.94 (2H, triplet, J=7.6 Hz); 7.00 (1H, singlet); 7.17–7.48 (8H, multiplet); 8.14 (1H, doublet, J=7.8 Hz).

EXAMPLE 215

Isopropyl (9-Benzyl-4-methyl-1-methylsulfinylcarbazol-2-yl)acetate 750 mg of 80% v/v m-chloroperbenzoic acid in water was added gradually to 40 ml of a solution of isopropyl (9-benzyl-1-methylthio-4-methylcarbazol-2-yl)acetate (1.00 g), obtained in a manner similar to that of the title compound of Example 115, in methylene chloride, and the reaction mixture was stirred for 1 hour, with ice-cooling. After this time, the reaction mixture was diluted with an excess of ethyl acetate and washed with a saturated aqueous solution of sodium hydrogen-carbonate. The resulting organic layer was dried over anhydrous sodium sulfate and then the solvent was removed by evaporation under reduced pressure. The residue was subjected to column chromatography (eluent: a 50–60% v/v solution of ethyl acetate in hexane) to yield 719 mg of the title compound as a solid.

Nuclear Magnetic Resonance Spectrum (CDCl$_3$, 270 MHz), δ ppm: 1.23 (3H, doublet, J=6.6 Hz); 1.27 (3H, doublet, J=6.6 Hz); 2.51 (3H, singlet); 2.91 (3H, singlet); 4.18 (1H, doublet, J=16.7 Hz); 4.70 (1H, broad singlet); 5.03 (1H, multiplet); 6.06 (2H, broad singlet); 6.90–7.50 (9H, multiplet); 8.22 (1H, doublet, J=7.8 Hz).

EXAMPLE 216

Isopropyl (9-Benzyl-4-methyl-1-n-propylthiocarbazol-2-yl)acetate 0.1 ml of anhydrous trifluoroacetic acid was added to 5 ml of a solution of 100 mg isopropyl (9-benzyl-4-methyl-1-methylsulfinylcarbazol-2-yl)acetate, as obtained in Example 215, in methylene chloride, and the reaction mixture was refluxed for 30 minutes. The solvent was then removed by evaporation under reduced pressure and the residue was dissolved in 2 ml of methylene chloride. 0.5 ml of n-propyl iodide, 1 ml of triethylamine and 1 ml of methanol were then all added to the resulting solution at room temperature and the reaction mixture was stirred for 30 minutes. After this time, the reaction mixture was diluted with an excess of ethyl acetate, and washed with a dilute aqueous solution of hydrogen chloride, a saturated aqueous solution of sodium hydrogencarbonate and a saturated aqueous solution of sodium chloride, in that order. The resulting organic layer was dried over anhydrous sodium sulfate and then the solvent was removed by evaporation under reduced pressure. The residue was subjected to column chromatography (eluent: a 4–6% v/v solution of ethyl acetate in hexane) to yield 86 mg of the title compound as a solid.

Nuclear Magnetic Resonance Spectrum (CDCl$_3$, 270 MHz), δ ppm: 0.78 (3H, triplet, J=7.4 Hz); 1.22 (6H, doublet, J=6.6 Hz); 1.33 (2H, multiplet); 2.38 (2M, triplet, J=7.4 Hz); 2.89 (3H, singlet); 4.12 (2H, singlet); 5.04 (1H, multiplet); 6.42 (2H, singlet); 6.95–7.45 (9H, multiplet); 8.19 (1H, doublet, J=7.8 Hz).

EXAMPLE 217

(9-Benzyl-4-methyl-1-n-propylthiocarbazol-2-yl) acetic Acid

Following a procedure and using relative proportions of starting materials similar to those described in Example 26, but using 96 mg of isopropyl (9-benzyl-1-n-propylthio-4-methylcarbazol-2-yl)acetate, as obtained in Example 216, 64 mg of the title compound was obtained as a solid melting at 190°–193° C.

Nuclear Magnetic Resonance Spectrum (CDCl$_3$, 270 MHz), δ ppm: 0.81 (3H, triplet, J=7.4 Hz); 1.38 (2H, multiplet); 2.41 (2H, triplet, J=7.4 Hz); 2.94 (3H, singlet); 4.25 (2H, singlet); 6.46 (2H, singlet); 7.00–7.50 (9H, multiplet); 8.24 (1H, doublet, J=7.8 Hz).

EXAMPLE 218

(9-Benzyl-4-methyl-1-i-propylthiocarbazol-2-yl) acetic Acid

Following procedures and using relative proportions of starting materials similar to those described in Examples 216 and 217, but using isopropyl iodide as a starting material, the title compound was obtained as a solid melting at 207°–210° C.

Nuclear Magnetic Resonance Spectrum (CDCl$_3$, 270 MHz), δ ppm: 0.99 (6H, doublet, J=6.6 Hz); 2.89 (3H, singlet); 2.90 (1H, multiplet); 4.23 (2H, singlet); 6.41 (2H, singlet); 7.00–7.45 (9H, multiplet); 8.28 (1H, doublet, J=7.8 Hz).

EXAMPLE 219

Methyl (9-Benzyl-1-hydroxy-4-methylcarbazol-2-yl) acetate a) 10-Benzyl-5-methyl-2,3-dihydrofuro[2,3-a]carbazol-2-one Following a procedure and using relative proportions of starting materials similar to those described in Example 4, but using 5-methyl-2,3-dihydrofuro[2,3-a]carbazol-2-one [obtained as described by Y. Oikawa, M. Tanaka, H. Hirasawa and O. Yonemitsu in Chem. Pharm. Bull., 29, 1606 (1981)], the title compound was obtained as an amorphous solid in a yield of 88%.

b) Methyl (9-benzyl-1-hydroxy-4-methylcarbazol-2-yl) acetate 0.5 ml of a 1M methanolic solution of sodium methoxide was added to 5 ml of a methanolic solution of 10-benzyl-5-methyl-2,3-dihydrofuro[2,3-a]carbazol-2-one (80 mg), as obtained in Example 219a) above, with ice-cooling, and the reaction mixture was stirred for 30 minutes at room temperature. After this time, the reaction mixture was diluted with an excess of an aqueous solution of ammonium chloride and then extracted with ethyl acetate. The resulting organic layer was washed with water, dried over anhydrous sodium sulfate and then the solvent was removed by evaporation under reduced pressure. The residue was subjected to column chromatography (eluent: a 15–20% v/v solution of ethyl acetate in hexane) to yield 83 mg of the title compound as a solid.

Nuclear Magnetic Resonance Spectrum (CDCl$_3$, 270 MHz), δ ppm: 2.80 (3H, singlet); 3.75 (3H, singlet); 3.82 (2H, singlet); 6.00 (2H, singlet); 6.72 (1H, singlet); 7.10–7.50 (8H, multiplet); 8.09 (1H, singlet); 8.16 (1H, doublet, J=7.8 Hz).

EXAMPLE 220

Methyl (9-Benzyl-1-methoxy-4-methylcarbazol-2-yl)acetate 120 mg of anhydrous pottasium carbonate and 0.14 ml of methyl iodide were added to 4 ml of a solution of 80 mg of methyl (9-benzyl-1-hydroxy-4-methylcarbazol-2-yl)acetate, as obtained in Example 219, in dimethyl formamide, at room temperature, and the reaction mixture was stirred for 1 hour. After this time, the reaction mixture was diluted with an excess of ethyl acetate, and then washed with a saturated aqueous solution of sodium chloride. The resulting organic layer was dried over anhydrous sodium sulfate and then the solvent was removed by evaporation under reduced pressure. The residue was subjected to column chromatography (eluent: a 15–20% v/v solution of ethyl acetate in hexane) to yield 84 mg of the title compound as a solid.

Nuclear Magnetic Resonance Spectrum (CDCl$_3$, 270 MHz), δ ppm: 2.84 (3H, singlet); 3.62 (3H, singlet); 3.71 (3H, singlet); 3.82 (2H, singlet); 5.88 (2H, singlet); 6.91 (1H, singlet); 7.05–7.45 (8H, multiplet); 8.17 (1H, doublet, J=7.8 Hz).

EXAMPLE 221

(9-Benzyl-1-methoxy-4-methylcarbazol-2-yl)acetic Acid

Following a procedure and using relative proportions of starting materials similar to those described in Example 26, but using 80 mg of methyl (9-benzyl-1-methoxy-4-methylcarbazol-2-yl)acetate, as obtained in Example 220, 61 mg of the title compound was obtained as a solid melting at 200°–202° C.

Nuclear Magnetic Resonance Spectrum (CDCl$_3$, 270 MHz), δ ppm: 2.84 (3H, singlet); 3.63 (3H, singlet); 3.85 (2H, singlet); 5.87 (2H, singlet); 6.91 (1H, singlet); 7.05–7.45 (8H, multiplet); 8.17 (1H, doublet, J=7.8 Hz).

EXAMPLE 222

[9-(4-Methoxycarbonylbenzyl)-1-methylcarbazol-2-yl]acetic Acid a) Methyl [9-(4-methoxycarbonylbenzyl)-1-methylcarbazol-2-yl]-acetate Following a procedure and using relative proportions of starting materials similar to those described in Example 4, but using methyl (1-methylcarbazol-2-yl)acetate and 4-methoxycarbonylbenzyl bromide as starting materials, the title compound was obtained as an oil.

b) [9-(4-Methoxycarbonylbenzyl)-1-methylcarbazol-2-yl] acetic acid

Following a procedure and using relative proportions of starting materials similar to those described in Example 14, but using methyl [9-(4-methoxycarbonylbenzyl)-1-methylcarbazol-2-yl]-acetate, as obtained in a) above, as a starting material, the title compound was obtained as a solid melting at 200°–202° C.

Nuclear Magnetic Resonance Spectrum (CDCl$_3$, 270 MHz), δ ppm: 2.50 (3H, singlet); 3.83 (2H, singlet); 3.88 (3H, singlet); 5.77 (2H, singlet); 7.10–7.45 (7H, multiplet); 7.98 (2H, doublet, J=8.0 Hz); 8.10 (1H, doublet, J=8.2 Hz).

EXAMPLE 223

[9-(4-Carboxylbenzyl)-1-methylcarbazol-2-yl]acetic Acid

Following a procedure and using relative proportions of starting materials similar to those described in Example 26, but using [9-(4-methoxycarbonylbenzyl)-1-methylcarbazol-2-yl]acetic acid, as obtained in Example 222, as a starting material, the title compound was obtained as a solid melting at 220°–225° C. (with decomposition).

Nuclear Magnetic Resonance Spectrum (CDCl$_3$+ tetradeuterated methanol, 270 MHz), δ ppm: 2.52 (3H, singlet); 3.82 (2H, singlet); 5.80 (2H, singlet); 7.10–7.50 (7H, multiplet); 7.93 (2H, doublet, J=8.0 Hz); 8.10 (1H, doublet, J=8.2 Hz).

EXAMPLE 224

[9-(4-Carbamoylbenzyl)-1-methylcarbazol-2-yl] acetic Acid

[9-(4-Methoxycarbonylbenzyl)-1-methylcarbazol-2-yl] acetic acid, as obtained in Example 222, was treated with methanolic ammonia at room temperature to afford the title compound as a solid melting at 255°–260° C. (with decomposition).

Nuclear Magnetic Resonance Spectrum (CDCl$_3$+ tetradeuterated methanol, 270 MHz), δ ppm: 2.50 (3H, singlet); 3.86 (2H, singlet); 5.78 (2H, singlet); 7.10–7.40 (7H, multiplet); 7.92 (2H, doublet, J=8.0 Hz); 8.06 (1H, doublet, J=8.2 Hz).

EXAMPLE 225

Methyl (1-Benzylindol-6-yl)acrylate

Following procedures and using relative proportions of starting materials similar to those described in Examples 35 and 4, but using indol-6-ylcarbaldehyde, the title compound was obtained as an oily material.

Nuclear Magnetic Resonance Spectrum (CDCl$_3$, 270 MHz), δ ppm: 3.79 (3H, singlet); 5.33 (2H, singlet); 6.40 (1H, doublet, J=18.0 Hz); 6.58 (1H, doublet, J=3.2 Hz); 7.10–7.40 (8H, multiplet); 7.61 (1H, doublet, J=8.0 Hz); 7.88 (1H, doublet, J=18.0 Hz).

EXAMPLE 226

(1-Benzylindol-6-yl)acrylic Acid

Following a procedure and using relative proportions of starting materials similar to those described in Example 26, but using methyl (1-benzylindol-6-yl)acrylate, as obtained in Example 225, the title compound was obtained as a solid melting at 202°–204° C.

Nuclear Magnetic Resonance Spectrum (CDCl$_3$, 270 MHz), δ ppm: 5.33 (2H, singlet); 6.40 (1H, doublet, J=18.0 Hz); 6.57 (1H, doublet, J=3.2 Hz); 7.10–7.50 (9H, multiplet); 7.86 (1H, doublet, J=18.0 Hz).

EXAMPLE 227

(1-Benzylindol-6-yl)propionic Acid

Following procedures and using relative proportions of starting materials similar to those described in Examples 36 and 26, but using methyl (1-benzylindol-6-yl)acrylate, as obtained in Example 225, the title compound was obtained as a solid melting at 104°–106° C.

Nuclear Magnetic Resonance Spectrum (CDCl$_3$, 270 MHz), δ ppm: 2.68 (2H, triplet, J=8.0 Hz); 3.02 (2H, triplet, J=8.0 Hz); 5.31 (2H, singlet); 6.50 (2H, doublet, J=3.2 Hz); 6.89 (1H, doublet, J=8.4 Hz); 7.10–7.40 (7H, multiplet); 7.58 (1H, doublet, J=8.4 Hz).

EXAMPLE 228

N-(9-Benzyl-4-methyl-1-methylthiocarbazol-2-ylacetyl)methylsulfonamide 74.6 mg (0.26 mmol) of carbonyldiimidazole was added to 1 ml of a solution of 50 mg (0.13 mmol) of (9-benzyl-4-methyl-1-methylthiocarbazol-2-yl)acetic acid, as obtained in Example 14, in tetrahydrofuran, and the reaction mixture was stirred for 1 hour at room temperature. After this time, 43.8 mg (0.26 mmol) of methanesulfonamide and 70.0 mg (0.26 mmol) of 1,8-diazabicyclo[5.4.0]undec-7-ene were added to the mixture which was first stirred overnight at room temperature and then refluxed for 2 hours. After this time, an excess of water was added to the mixture, and the resulting aqueous layer was extracted with ethyl acetate. The extracted organic layer was first washed with water and then with a saturated aqueous solution of sodium chloride, dried over anhydrous sodium sulfate and the solvent was then removed by evaporation under reduced pressure. The residue was subjected to column chromotography (eluent: a 50% v/v solution of ethyl acetate in hexane) to yield 48 mg (80%) of the title compound.

Nuclear Magnetic Resonance Spectrum (CDCl$_3$, 270 MHz), δ ppm: 1.93 (3H, singlet); 2.91 (3H, singlet); 3.22 (3H, singlet); 4.10 (2H, singlet); 6.35 (2H, singlet); 6.97–7.53 (9H, multiplet); 8.00 (1H, singlet); 8.22 (1H, doublet, J=7.9 Hz).

EXAMPLE 229

{9-[2-(3-Chlorophenyl)ethyl]-4-methyl-1-methylthiocarbazol-2-yl}acetic Acid a) tert-Butyl {9-[2-(3-Chlorophenyl)ethyl]-4-methyl-1-methylthio-carbazol-2-yl}acetate Following a procedure and using relative proportions of starting materials similar to those described in Example 4, but using tert-butyl (4-methyl-1-methylthiocarbazol-2-yl) acetate and 2-(3-chlorophenyl)ethyl bromide as starting materials, the title compound was obtained in a yield of 73% as an oil.

b) {9-[2-(3-Chlorophenyl)ethyl]-4-methyl-1-methylthiocarbazol-2-yl}acetic acid

Following a procedure and using relative porportions of starting materials similar to those described in Example 3, but using tert-butyl {9-[2-(3-chlorophenyl)ethyl]-4-methyl-1-methylthiocarbazol-2-yl}acetate, as obtained in a), as a starting material, the title compound was obtained in a quantative yield, as a solid melting 171°–178° C.

Nuclear Magnetic Resonance Spectrum (CDCl$_3$, 270 MHz), δ ppm: 2.29 (3H, singlet); 2.86 (3H, singlet); 2.95–3.05 (2H, multiplet); 4.24 (2H, singlet); 5.10–5.20 (2H, multiplet); 7.05 (1H, singlet); 7.13–7.53 (7H, multiplet); 8.17 (1H, doublet, J=7.9 Hz).

EXAMPLE 230

(1-Methylthio-4-trifluoromethylcarbazol-2-yl)acetic Acid a) Diethyl 1-(indol-3-yl)-2,2,2-trifluoroethylmalonate 400 mg (17.4 mmol) of sodium was added to 10 ml of a solution of 2.23 g (13.9 mmol) of diethyl malonate in toluene under a stream of nitrogen gas, and the reaction mixture was refluxed for 2 hours. After this time, the reaction mixture was cooled to room temperature, and 6 ml of 2 toluene solution of 1.00 g (4.6 mmol) of 1-(indol-3-yl) -2,2,2-trifluoroethanol were added. The resulting mixture was then refluxed for 30 minutes. After this time, the mixture was added to 100 ml of ethanol, acidified with a dilute aqueous solution of hydrogen chloride, and the solvent was removed by evaporation under reduced pressure. The resulting aqueous layer was extracted with ethyl acetate and the extracted organic layer was washed with a saturated aqueous solution of sodium chloride, dried over anhydrous sodium sulfate and the solvent removed by evaporation under reduced pressure. The residue was subjected to column chromotography (eluent: a 20% v/v solution of ethyl acetate in hexane) to yield 1.49 g (91%) of the title compound.

b) 3-(Indol-3-yl)-4,4,4-trifluorobutyric acid

Following procedures and using relative proportions of starting materials similar to those described in Examples 109 and 110, but using diethyl 1-(indol-3-yl)-2,2,2-trifluoroethylmalonate, as obtained in a) above, as a starting material, the title compound was obtained as an amorphous solid.

c) isopropyl (1-methylthio-4-trifluoromethylcarbazol-2-yl) acetate

Following procedures and using relative proportions of starting materials similar to those described in Examples 1 and 2, but using 3-(indol-3-yl)-4,4,4-trifluorobutyric acid, as obtained in b) above, as a starting material, the title compound was obtained as an oil.

d) (1-Methylthio-4-trifluoromethylcarbazol-2-yl)acetic acid

Following a procedure and using relative proportions of starting materials similar to those described in Example 26, but using isopropyl (1-methylthio-4-trifluoromethylcarbazol-2-yl)acetate, as obtained in c) above, as a starting material, the title compound was obtained in a quantative yield as a solid melting at 115°–120° C.

Nuclear Magnetic Resonance Spectrum (CDCl$_3$, 270 MHz), δ ppm: 2.39 (3H, singlet); 4.22 (2H, singlet); 7.28–7.56 (4H, multiplet); 8.28 (1H, doublet, J=8.2 Hz); 8.88 (1H, singlet);

EXAMPLE 231

(9-Benzyl-1-methylthio-4-trifluoromethyl carbazol-2-yl)acetic Acid a) Isopropyl (9-benzyl-1-methylthio-4-trifluoromethylcarbazol-2-yl)acetate Following a procedure and using relative proportions of starting materials similar to those described in Example 4, but using isopropyl (1-methylthio-4-trifluoromethylcarbazol-2-yl)acetate, as obtained in Example 230 c), as starting material, the title compound was obtained in a yield of 88% as an oil.

b) (9-Benzyl-1-methylthio-4-trifluoromethylcarbazol-2-yl) acetic acid

Following a procedure and using relative proportions of starting materials similar to those described in Example 26, but using isopropyl (9-benzyl-1-methylthio-4-trifluoromethylcarbazol-2-yl)acetate, as obtained in a) above, as a starting material, the title compound was obtained in a quantative yield as a solid melting at 166°–167° C.

Nuclear Magnetic Resonance Spectrum (CDCl$_3$, 270 MHz), δ ppm: 1.97 (3H, singlet); 4.24 (2H, singlet); 6.40 (2H, singlet); 7.03–7.56 (9H, multiplet); 8.36 (1F, doublet, J=8.1 Hz).

EXAMPLE 232

(4-Methylthiocarbazol-3-yl)acetic Acid a) Isopropyl (4-methylthiocarbazol-3-yl)acetane Following procedures and using relative proportions of starting materials similar to those described in Examples 1a), 34, 35, 36, 1b), 1c), 1d) and 2, but using indol-2-ylcarboxylic acid as starting material, the title compound was obtained as an oil.

b) (4-Methylthiocarbazol-3-yl) acetic acid

Following a procedure and using relative proportions of starting materials similar to those described in Example 26, but using isopropyl (4-methylthiocarbazol-3-yl)acetate, as obtained in a) above, as a starting material, the title compound was obtained in a quantative yield as a solid melting at 200°–210° C. (with decomposition).

Nuclear Magnetic Resonance Spectrum (CDCl$_3$+ tetradeuterated methanol, 270 MHz), δ ppm: 2.40 (3H, singlet); 4.18 (2H, singlet); 7.20–7.50 (5H, multiplet) 8.87 (1H, doublet, J=8.0 Hz).

EXAMPLE 233

(9-Benzyl-4-methylthiocarbazol-3-yl)acetic Acid a) Isopropyl (9-benzyl-4-methylthiocarbazol-3-yl)acetate Following a procedure and using relative proportions of starting materials similar to those described in Example 4, but using isopropyl (4-methylthiocarbazol-3-yl)acetate, as obtained in Example 232a), as a starting material, the title compound was obtained in a yield of 91% as an oil.

b) (9-Benzyl-4-methylthiocarbazol-3-yl)acetic acid

Following a procedure and using relative proportions of starting materials similar to those described in Example 26, but using isopropyl (9-benzyl-4-methylthiocarbazol-3-yl) acetate, as obtained in a) above, as a starting material, the title compound was obtained in a quantative yield as a solid melting 181°–189° C.

Nuclear Magnetic Resonance Spectrum (CDCl$_3$, 270 MHz), δ ppm: 2.42 (3H, singlet); 4.22 (2H, singlet); 5.51 (2H, singlet); 7.10–7.50 (10H, multiplet); 8.94 (1H, doublet, J=7.9 Hz).

EXAMPLE 234

(9-Benzyl-1-isopropylthiocarbazol-4-methyl-2-yl) methyl-1H-tetrazole

Following procedures and using relative proportions of starting materials similar to those described in Examples 75, 76 and 77, but using (9-benzyl-1-isopropylthio-4-methylcarbazol-2-yl)acetic acid, as obtained in Example 218, as a starting material, the title compound was obtained as a solid melting at 231°–232° C.

Nuclear Magnetic Resonance Spectrum (tetradeuterated methanol, 270 MHz), δ ppm: 1.03 (6H, doublet, J=6.7 Hz); 2.94 (4H, multiplet); 4.83 (2H, broad singlet); 6.43 (2H, broad singlet); 6.98–7.47 (9H, multiplet); 8.21 (1H, doublet, J=7.9 Hz).

EXAMPLE 235

(9-Benzyl-4-isopropyl-1-isopropylthiocarbazol-2-yl) acetic Acid a) Isopropyl (9-benzyl-4-isopropyl-1-isopropylthiocarbazol-2-yl)acetate Following a procedure and using relative proportions of starting materials similar to those described in Example 216, but using isopropyl (4-isopropyl-1-methylthiocarbazol-2-yl) acetate, as obtained in Example 189, as a starting material, the title compound was obtained in a yield of 77% as an oil.

b) (9-Benzyl-4-isopropyl-1-isopropylthiocarbazol-2-yl) acetic acid

Following a procedure and using relative proportions of starting materials similar to those described in Example 26, but using isopropyl (9-benzyl-4-isopropyl-1-isopropylthiocarbazol-2-yl)acetate, as obtained in a) above, as a starting material, the title compound was obtained in a quantative yield as a solid melting at 217°–218° C.

Nuclear Magnetic Resonance Spectrum (CDCl$_3$+ tetradeuterated methanol in a ratio of 20:1 v/v. 270 MHz), δ ppm: 0.98 (6H, doublet, J=6.8 Hz) 1.50 (6H, doublet, J=6.8 Hz); 2.80 (1H, quintuplet, J=6.8 Hz); 3.99 (1H, quintuplet, J=6.8 Hz); 4.23 (2H, singlet); 6.42 (2H, singlet); 7.04–7.42 (9H, multiplet); 8.20 (1H, doublet, J=7.9 Hz).

The compounds of the present invention may be administered in any suitable fashion for the desired treatment. For example, the compounds of the present invention can be administered orally in the form of tablets, capsules, granules, powders or syrups, or parenterally by intravenous injection, or as suppositories or the Like. These pharmaceutical formulations can be prepared by mixing the compounds of the present invention with one or more adjuvants, such as excipients (e.g. organic excipients including sugar derivatives, such as lactose, sucrose, glucose, mannitol or sorbitol; starch derivatives, such as corn starch, mashed potato, α-starch, dextrine or carboxymethyl starch; cellulose derivatives, such as crystalline cellulose, low hydroxypropyl-substituted cellulose, hydroxypropylmethyl cellulose, carboxymethyl cellulose, carboxymethyl cellulose calcium or internally bridged carboxymethyl cellulose sodium; gum arabic; dextran; and Pullulan; inorganic excipients including silicates, such as light silicic acid anhydride, synthetic aluminium silicate or magnesium meta-silicic acid aluminate; phosphates, such as calcium phosphate; carbonates, such as calcium carbonate; and sulphates, such as calcium sulphate); lubricants (e.g. metal stearates, such as stearic acid, calcium stearate or magnesium stearate; talc; colloidal silica; waxes, such as beeswax or spermaceti; boric acid; adipic acid; sulphates, such as sodium sulphate; glycol; fumaric acid; sodium benzoate; DL-leucine; sodium salts of aliphatic acids; lauryl sulphates, such as sodium laurylsulphate or magnesium laurylsulphate; silicates, such as silicic acid anhydride or silicic acid hydrate; and the foregoing starch derivatives); binders (e.g. polyvinyl pyrrolidone, Macrogol; and similar compounds to the excipients described above); disintegrating agents (e.g. similar compounds to the excipients described above; and chemically modified starch-celluloses, such as Crosscarmelose sodium, sodium carboxymethyl starch or bridged polyvinyl pyrrolidone); stabilisers (e.g. p-hydroxybenzoates, such as methylparaben or propylparaben; alcohols, such as chlorobutanol, benzyl alcohol or phenylethyl alcohol; benzalkonium chloride; phenols, such as phenol or cresol; thimerosal; dehydroacetic acid; and sorbic acid); corrigents (e.g. sweeteners, vinegar or perfumes, such as those conventionally used); diluents and the like.

The compounds of the present invention may also be administered by any other suitable route, such as: parenterally, intravenously, eye-drops, suppositories, dermal patch and sustained release formulations, using any suitable excipients, preservatives, flavourings, colourings and other ingredients as appropriate and/or desired.

The dose varies depending upon the condition and age of the patient and upon the route and type of administration but, for example, the compounds of the present invention can be administered orally in a daily dose of from 0.01 to 1000 mg/kg body weight (preferably 0.05 to 200 mg/kg body weight), either as a single dose or as divided doses.

Biological Activity

The compounds of the present invention may be assayed for allosteric activity at m1 muscarinic receptors as described below, although the assays we describe are not necessarily exhaustive, and other assays may be employed, as desired, to establish allosterism.

It will be understood that the present invention also envisages any of the accompanying assays, as described below, as well as any compounds, and the use of any compounds, which exhibit an allosteric effect by any one or more of such assays.

In the following assays, it is necessary, or at least desirable, to use a cell line which expresses only one type of muscarinic receptor, such as m1, and which does not exhibit a high level of acetylcholinesterase activity.

A suitable cell line is CHO (Chinese Hamster Ovary), which are readily engineered to express only one receptor sub-type.

Preparation of CHO cell membranes

To obtain the large amount of cell membranes required, plates of 530 cm$^2$ culture area were used. CHO cells which express m1, m2, m3 and m4 receptors were grown separately in MEM alpha medium containing 10% newborn calf serum and antibiotics. When cells reached confluence, they were washed twice with 10 ml of 20 mM HEPES containing 10 mM EDTA (pH 7.4), scraped into the same buffer and homogenized using a Polytron (trademark) homogenizer (setting 5-6 for 5 sec×2). Membrane pellets were obtained by centrifugation (40000×g, 10 min, 4° C.) and resuspended in 20 mM HEPES–0.1 mM EDTA (pH 7.4). Centrifugation and resuspension were repeated twice to wash the cell membranes. After measurement of membrane protein, the membranes (1 or 2 mg protein/ml) were stored at −70° C.

ACh inhibition of $^3$H-NMS binding

While the direct assay measures ACh (=acetylcholine) binding only to the high affinity state, the indirect assay measures effects only at the low affinity state. This is achieved by including 0.2 mM GTP in the assay. In this assay a fixed concentration of $^3$H-NMS (roughly the Kd value) is incubated in the absence and presence of a fixed concentration of ACh (at about the IC$_{50}$ value) and the effects of three concentrations of test agent are measured, again in the absence and presence of ACh.

Calculating the effects on $^3$H-NMS binding alone is as follows: binding in the presence of the agent is expressed as a percentage of binding in its absence and, if the effect is inhibitory, an IC$_{50}$ is estimated graphically. The assay also contains a single high concentration of $^3$H-NMS (4 nM, about 30 times the Kd) which provides an estimate of B$_{max}$ (i.e. maximum binding). Assuming that the agent acts only allosterically, and to modify only the affinity of $^3$H-NMS with no effect on B$_{max}$, the affinity of $^3$H-NMS in the presence of the agent can be estimated and hence the allosterism.

Figures 1, 1B, 2, 3:
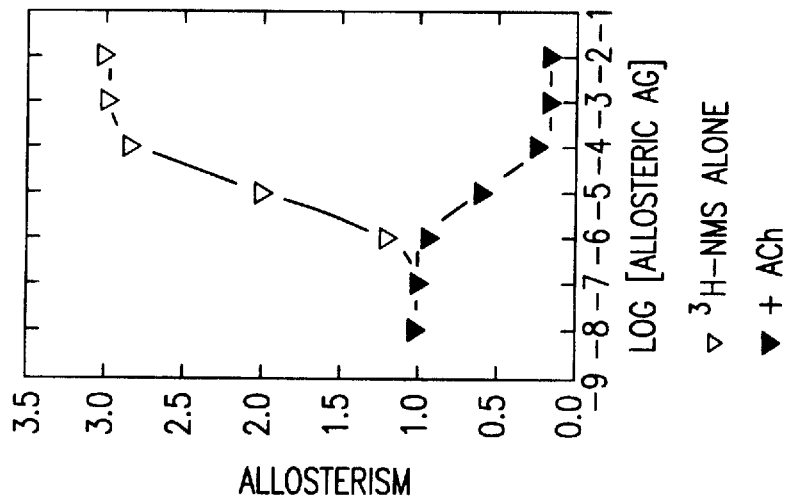
Figures 1, 1B, 2:
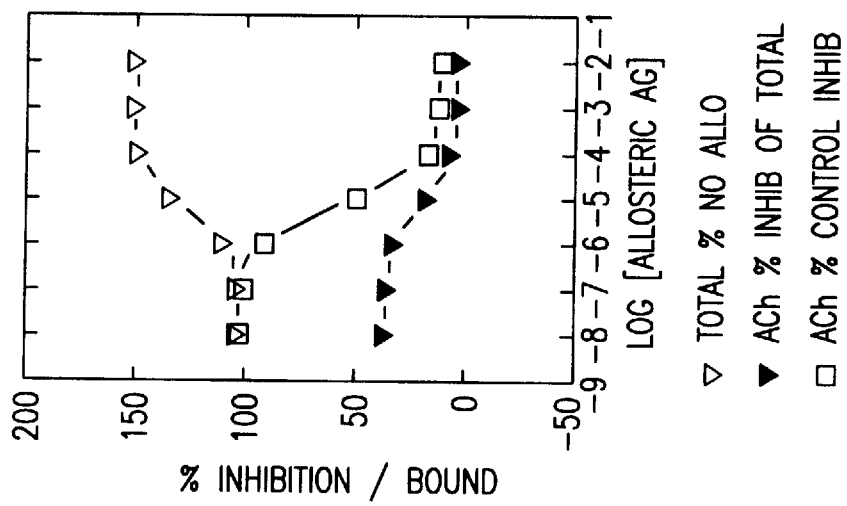
Figures 1, 1B:
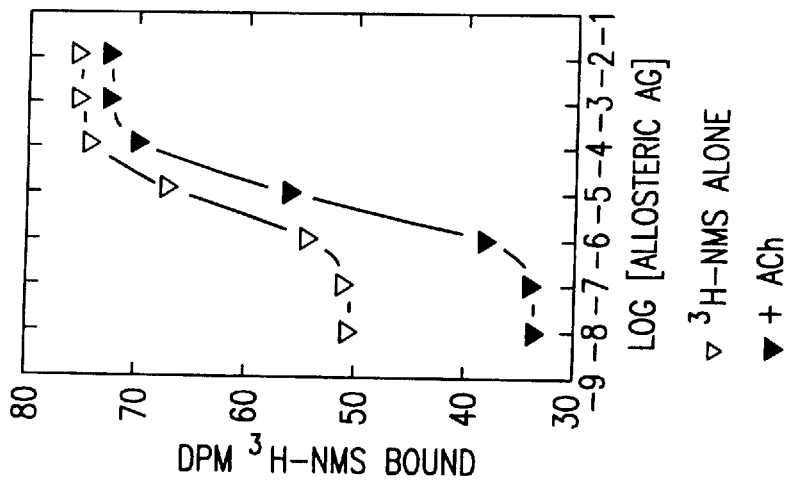
Figures 1, 1B, 2, 3, 4, 5, 6:
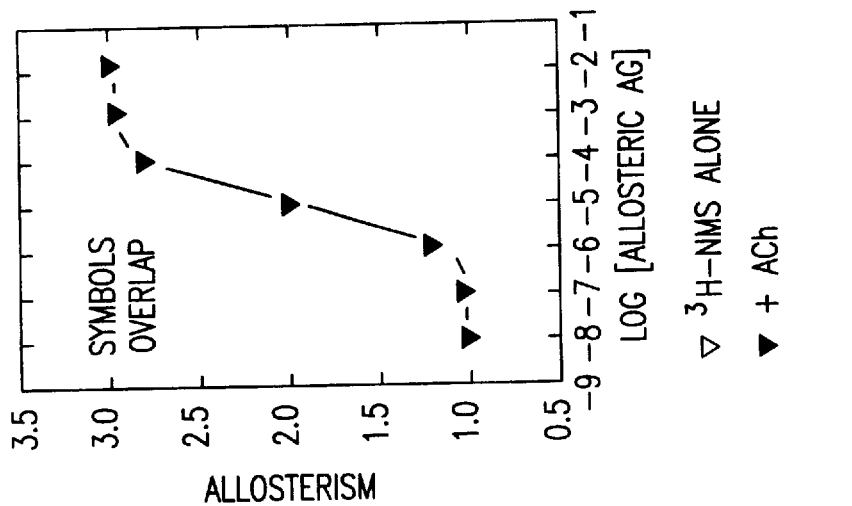
Figures 1, 1B, 2, 3, 4, 5:
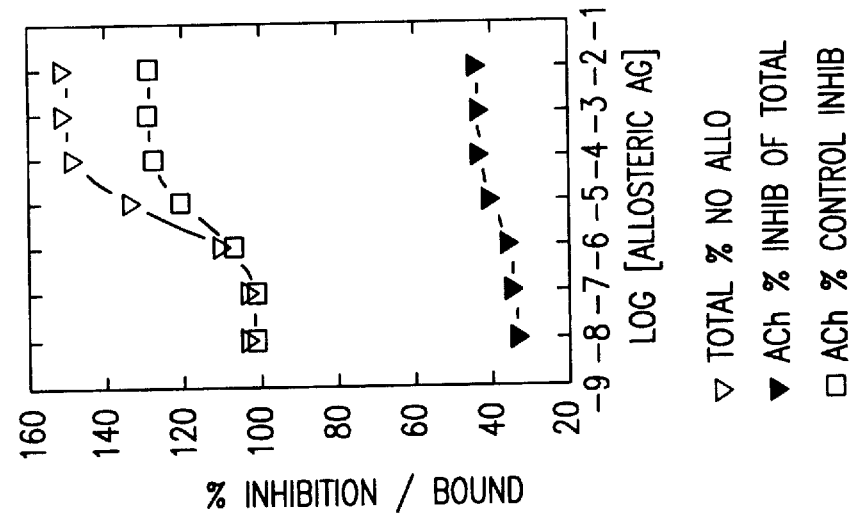
Figures 1, 1B, 2, 3, 4:
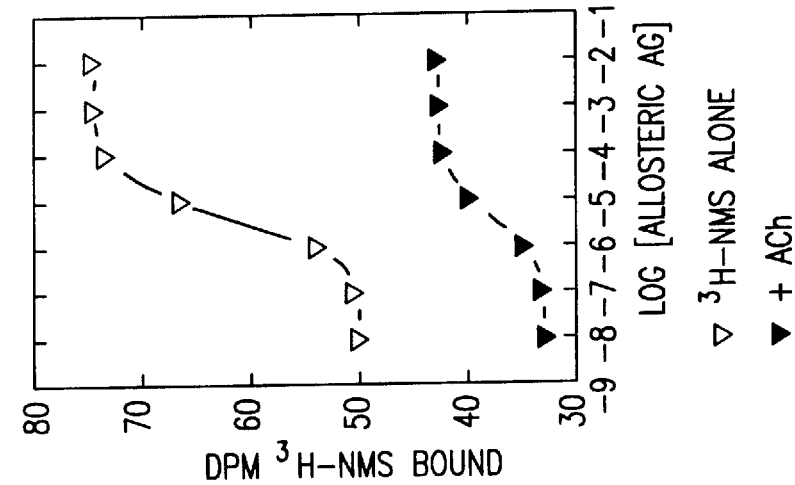

Expressing the effect on cold ACh binding will be explained with reference to FIGS. 1a, b and c. These figures show theoretical data and the effects of the transformations described below. In FIGS. 1a and 1b $^3$H-NMS and cold ACh are present at their Kd concentrations; in FIG. 1a the agent has a negative allosteric effect on $^3$H-NMS, while in FIG. 1b it has a positive allosteric effect on $^3$H-NMS. The left panels show the amount of $^3$H-NMS specifically bound in the assay. If the affinity of ACh is reduced by the test agent, as shown in the top panels of FIGS. 1a and 1b, the inhibition by ACh will decrease, but the counts recovered will also depend on the effect of the agent on $^3$H-NMS binding alone. To calculate the effect on ACh binding the inhibitory effect of ACh is first calculated as a percent of its own control in the absence of ACh. Next it is assumed that fractional inhibition is the same as tractional occupancy, and inhibition in the presence of agent is expressed as a percentage of inhibition in the absence of agent. The effects of these transformations are shown in the centre panels. Expressing inhibition by ACh in the presence of agent as a percentage of inhibition in the absence of agent allows the effect of the agent on cold ACh binding to be seen on the same scale as the effect on $^3$H-NMS and $^3$H-ACh binding and is generally preferred.

Figures 1, 1C, 2, 3:
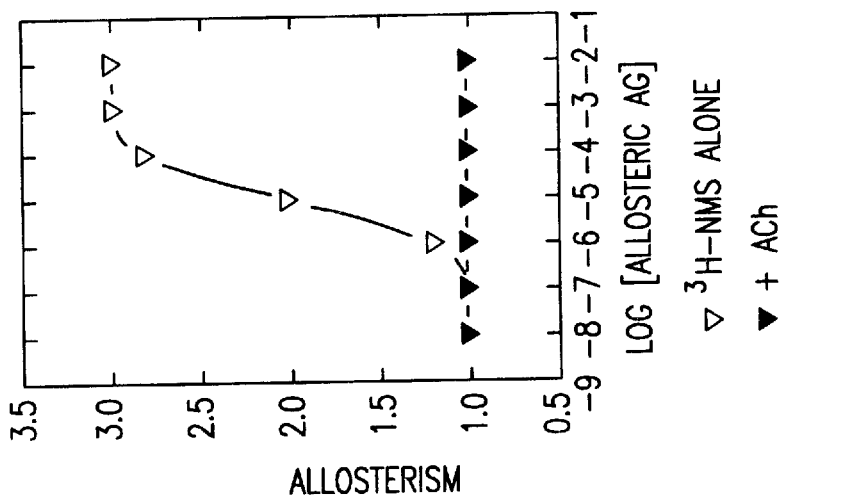
Figures 1, 1C, 2:
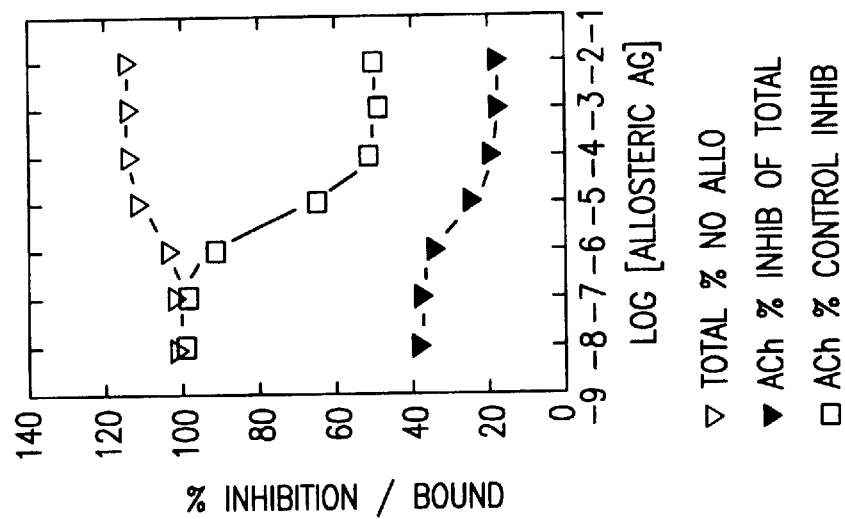
Figures 1, 1C:
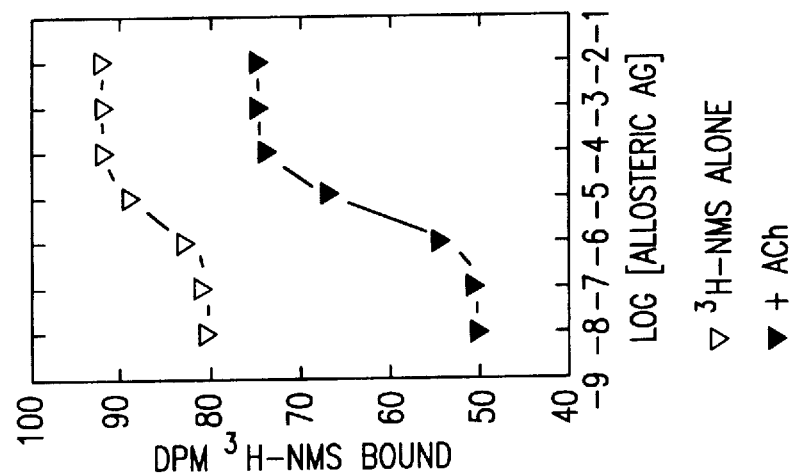

If the concentration of $^3$H-NMS used in the indirect assay is around the Kd value or less, the transformation described above provides a qualitative and semi-quantitative measure of the agent's effect. If a higher concentration of $^3$H-NMS is used, or if the agent has a positive allosteric effect on $^3$H-NMS, then the results of this transformation may be misleading. This is demonstrated in FIG. 1c, where a high $^3$H-NMS concentration and positive allosterism on $^3$H-NMS make the agent have an inhibitory effect on ACh binding expressed as percentage of control inhibition, even though the agent actually has a positive effect on ACh affinity. This problem is reduced or eliminated by estimating the affinity of ACh and hence the allosterism. It is assumed that ACh binds to a single affinity state i.e. that its inhibition curve has a slope of 1, and so an IC$_{50}$ is calculated from the percentage inhibition of control binding. This value is used with the estimate of $^3$H-NMS affinity described above to calculate the ACh affinity. The allosterism of the agent on both $^3$H-NMS and cold ACh is shown in the right panels of FIGS. 1a–1c.

Estimation of affinity constants (pKi)

If the three concentrations of agent used in the assay are appropriate, and the agent has an inhibitory effect, it is possible to estimate the apparent affinity (pKi) of the agent in competition with $^3$H-NMS and hot and cold ACh The allosterism transformation shows the potency of the agent independently of the concentrations of $^3$H-NMS and cold ACh in the assay and, in the case of cold ACh, independently of effects on $^3$H-NMS binding, but involves some assumptions. We prefer to read the data off the graph as pIC$_{50}$ values and then convert them to pKi values using correction factors derived from the theory of competitive antagonism—this correction also works with negative allosteric agents [Ehlert, Mol. Pharmacol. 33, 187, (1988)]. In order to allow for the influence of ³H-NMS concentration, the PIC$_{50}$ values with ³H-NMS are converted to pKi values using the Cheng-Prussof equation $$Ki=IC_{50}/([^3H\text{-}NMS]/Kd+1)$$

The equivalent correction factor in the presence of cold ACh is $$Ki=IC_{50}/([^3H\text{-}NMS]/Kd+[ACh]/Ka+1)$$

It is often not possible to read pIC$_{50}$ values off the graph because 50% inhibition is not reached (a frequent occurrence with weak agents) but 50% inhibition may have been obtained with the allosterism measure, in which case this value is read off the graph as the pKi value, without further transformation.

The use of non-linear regression analysis to estimate pKi values and weak allosterism While the estimation of pKi values from visual inspection of graphs is quick and usually adequate, there are two circumstances which justify the use of more time-consuming curve-fitting procedures. Firstly, there may be a clear and quantifiable inhibitory trend in the data even though 50% inhibition was not attained. Secondly, aspects of the data may suggest that the agent is acting as a weakly allosteric agent. If the agent is a strong allosteric, or competitive, inhibitor then it should cause maximally 100% inhibition and its pKi against ³H-NMS should be approximately equal to its pKi against hot or cold ACh. A weak allosteric agent, however, will maximally inhibit less than 100% of the binding, and pKi values simply read off the graph will underestimate its 'true' pKi. It is necessary, given the paucity of data under normal test conditions, to constrain the slope of the inhibition curve to unity, and the fitted estimates are only accepted if their standard errors are suitably low (about 0.3 log units for pIC$_{50}$ and 15% of the estimate for maximal inhibition). If % inhibition data are fitted then the correction factor is applied to convert pIC$_{50}$ to pKi values.

Procedure

Membranes (10 μg of protein) are incubated in 1.12 ml (³H-NMS) or 0.25 ml (³H-ACh) of buffer containing 20 mM HEPES+100 mM NaCl+10 mM MgCl2 (+0.2 mM GTP in ³H-NMS assays), pH 7.4, at 30° C. for two hours. The bound radioligand is collected by filtration through Whatman GF/B glass-fibre filters soaked in 0.1% polyethylenimine using a 30-place Brandel cell harvester, and the radioactivity measured with liquid scintillation counting. Nonspecific binding is measured in the presence of 1 μM QNB.

Design and analysis

The ³H-NMS assay contains 0.2 mM GTP and uses ³H-NMS concentrations of about 4 and 0.15 nM. The fixed ACh concentration is 30 μM. Total and nonspecific binding are measured with 4 nM ³H-NMS to provide an estimate of B$_{max}$. Using 0.15 nM ³H-NMS, binding in the absence and presence of ACh is measured alone and in the presence of three concentrations of each of four agents, and nonspecific binding is measured with QNB alone. Each point is measured in duplicate (quadruplicate for 0.15 nm ³H-NMS alone).

The data are analyzed as described above, and graphs produced, using the Minitab program. Where possible, IC$_{50}$ values are estimated visually from the graphs.

Results for some of the compounds of the present invention are presented in the Activity Table below. Each compound was tested at 3 μg/ml.

ACTIVITY TABLE

| Compound of Example | Effect on ACh Binding |
| --- | --- |
| 5 | 2.62 |
| 7 | 3.55 |
| 8 | 3.46 |
| 14 | 3.89 |
| 15 | 2.42 |
| 17 | 2.50 |
| 23 | 2.72 |
| 37 | 2.09 |
| 46 | 2.21 |
| 61 | 2.11 |
| 77 | 3.69 |
| 83 | 2.08 |
| 84 | 3.30 |
| 91 | 2.76 |
| 97 | 4.97 |
| 116 | 3.99 |
| 132 | 2.68 |
| 134 | 3.40 |
| 136 | 2.36 |
| 141 | 3.81 |
| 143 | 5.36 |
| 145 | 5.27 |
| 149 | 6.49 |
| 152 | 2.02 |
| 165 | 2.24 |
| 172 | 2.59 |
| 176 | 2.08 |
| 180 | 5.02 |
| 182 | 2.57 |
| 190 | 4.78 |
| 200 | 3.59 |
| 202 | 2.66 |
| 206 | 2.13 |
| 210 | 2.03 |
| 212 | 4.93 |
| 214 | 4.34 |
| 217 | 3.99 |
| 218 | 4.91 |
| 229 | 5.79 |
| 231 | 3.78 |
| 233 | 2.26 |
| 235 | 2.82 |

What is claimed is:

1. A compound selected from the group consisting of (9-benzyl-4-methyl-1-i-propylthiocarbazol-2-yl)acetic acid; (9-benzyl-4-methyl-1-n-propylthiocarbazol-2-yl)acetic acid; (9-benzyl-4-methyl-1-i-butylthiocarbazol-2-yl)acetic acid; (9-benzyl-4-methyl-1-methylthiocarbazol-2-yl)acetic acid; (9-benzyl-4-methyl-1-benzylthiocarbazol-2-yl)acetic acid; (9-benzyl-4-methyl-1-i-propoxycarbazol-2-yl)acetic acid; (9-benzyl-4-methyl-1-n-propoxycarbazol-2-yl)acetic acid; (9-benzyl-4-methyl-1-i-butoxycarbazol-2-yl)acetic acid; (9-benzyl-4-methyl-1-methoxycarbazol-2-yl)acetic acid; and (9-benzyl-4-methyl-1-benzyloxycarbazol-2-yl)acetic acid.

2. The compound of claim 1, which is (9-benzyl-4-methyl-1-i-propylthiocarbazol-2-yl)acetic acid.

3. The compound of claim 1, which is (9-benzyl-4-methyl-1-n-propylthiocarbazol-2-yl)acetic acid.

4. The compound of claim 1, which is (9-benzyl-4-methyl-1-i-butylthiocarbazol-2-yl)acetic acid.

5. The compound of claim 1, which is (9-benzyl-4-methyl-1-methylthiocarbazol-2-yl)acetic acid.

6. The compound of claim 1, which is (9-benzyl-4-methyl-1-benzylthiocarbazol-2-yl)acetic acid.

7. The compound of claim 1, which is (9-benzyl-4-methyl-1-i-propoxycarbazol-2-yl)acetic acid.

8. The compound of claim 1, which is (9-benzyl-4-methyl-1-n-propoxycarbazol-2-yl)acetic acid.

9. The compound of claim 1, which is (9-benzyl-4-methyl-1-i-butoxycarbazol-2-yl)acetic acid.

10. The compound of claim 1, which is (9-benzyl-4-methyl-1-methoxycarbazol-2-yl)acetic acid.

11. The compound of claim 1, which is (9-benzyl-4-methyl-1-benzyloxycarbazol-2-yl)acetic acid.

12. A composition for treating dementia, Alzheimer's disease or delirium comprising a pharmaceutically effective amount of a compound or a pharmaceutically acceptable salt or ester thereof, in combination with a pharmaceutically acceptable carrier, wherein the compound is selected from the group consisting of
(9-benzyl-4-methyl-1-i-propylthiocarbazol-2-yl)acetic acid,
(9-benzyl-4-methyl-1-n-propylthiocarbazol-2-yl)acetic acid,
(9-benzyl-4-methyl-1-i-butylthiocarbazol-2-yl)acetic acid,
(9-benzyl-4-methyl-1-methylthiocarbazol-2-yl)acetic acid,
(9-benzyl-4-methyl-1-benzylthiocarbazol-2-yl)acetic acid,
(9-benzyl-4-methyl-1-i-propoxycarbazol-2-yl)acetic acid,
(9-benzyl-4-methyl-1-n-propoxycarbazol-2-yl)acetic acid,
(9-benzyl-4-methyl-1-i-butoxycarbazol-2-yl)acetic acid,
(9-benzyl-4-methyl-1-methoxycarbazol-2-yl)acetic acid and
(9-benzyl-4-methyl-1-benzyloxycarbazol-2-yl)acetic acid.

13. A method of regulating m1 receptor response in vivo in a mammalian subject, comprising administering to said subject an effective amount of a selective allosteric effector to regulate said receptor, wherein said selective allosteric effector is a compound of formula (I):

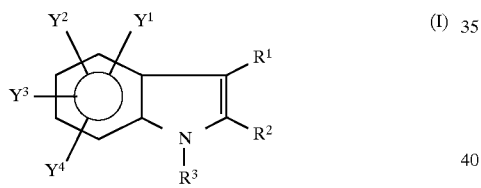

wherein:

$Y^1$, $Y^2$, $Y^3$ and $Y^4$ are the same or different and each represents a hydrogen a hydrogen atom, a halogen atom, a nitro group, a cyano group, a hydroxyl group, a thiol group, an amino group, an unsubstituted alkyl group having from 1 to 6 carbon atoms, an alkyl group having from 1 to 6 carbon atoms and substituted with a keto group or at least one substituent α defined below, a haloalkyl group having from 1 to 6 carbon atoms, an alkylthio group having from 1 to 6 carbon atoms, a carboxyl group, a protected carboxyl group, a sulfonamide group, a protected sulfonamide group or a group of formula

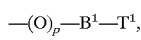

wherein $T^1$ represents a carboxyl group, a thiocarboxy group, a dithiocarboxy group, a protected carboxyl group, a protected thiocarboxy group, a protected dithiocarboxy group, a sulfonamide group, a protected sulfonamide group or a tetrazolyl group, $B^1$ represents a direct bond or an alkylene group which has from 1 to 4 carbon atoms and which is unsubstituted or is substituted by at least one of substituents α, defined below, and p is 0 or 1;

$R^1$ and $R^2$ together represent a group of formula (Ia):

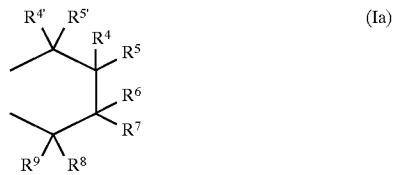

in which $R^4$ and $R^{4'}$ are the same or different and each represents a hydrogen atom or an alkyl group having from 1 to 6 carbon atoms;

$R^5$ and $R^{5'}$ are the same or different and each represents a hydrogen atom or a group of formula —(O)$_p$—(CH$_2$)$_n$—T$^3$ in which T$^3$ represents a carboxyl group, a sulfonamide group, a protected sulfonamide group, or a tetrazolyl group and n=0, 1 or 2, and p is as defined above;

$R^6$ represents a hydrogen atom or a hydroxyl group;

$R^7$ represents a hydrogen atom, a carboxyl group, a protected carboxyl group, a sulfonamide group, a protected sulfonamide group, or a group of formula —(O)$_p$—B$^3$—T$^4$ in which T$^4$ represents a carboxyl group, a protected carboxyl group, a sulfonamide group, a protected sulfonamide group, or a tetrazolyl group and B$^3$ represents an alkylene group which has from 1 to 4 carbon atoms and which is unsubstituted or is substituted by at least one of substituents α, and p is as defined above;

$R^8$ represents a hydrogen atom; or
when $R^9$ represents an alkylthio group having from 1 to 6 carbon atoms, $R^7$ and $R^8$ together represent a lactone group;

$R^9$ represents a hydrogen atom or an alkylthio group having from 1 to 6 carbon atoms; or $R^8$ and $R^9$ together represent an oxo group;

$R^1$ and $R^2$ together represent a group of formula (Ib):

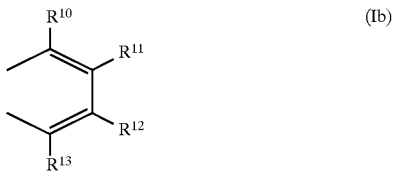

in which $R^{10}$, $R^{11}$, $R^{12}$ and $R^{13}$ are the same or different and each represents a hydrogen atom, an alkyl group having from 1 to 6 carbon atom, an hydroxyalkyl group having from 1 to 6 carbon atoms, an alkylthio group having from 1 to 6 carbon atoms, a hydroxyl group, a carboxyl group, a protected carboxyl group, a sulfonamide group, a protected sulfonamide group, or a group of formula
—(O)$_p$—B$^4$—T$^5$, in which T$^5$ represts a carboxyl group, a protected carboxyl group, a sulfonamide group, a protected sulfonamide group or a tetrazolyl group, B$^4$ represents an alkylene group which has from 1 to 4 carbon atoms and which is unsubstituted or is substituted by at least one of substituents α, and, and p is as defined above;

$R^3$ represents a hydrogen atom or an amino protecting group; and said substituents α are hydroxyl groups, aryl groups, aralkyl groups and substituted aralkyl groups;

or a pharmaceutically acceptable salt or ester thereof.

14. A method of regulating m1 receptor response in vivo in a mammalian subject comprising administering to said subject an effective amount of a selective allosteric effect to regulate said receptor, wherein said selective effect is a compound selected from the group consisting of
(9-benzyl-4-methyl-1-i-propylthiocarbazol-2-yl)acetic acid,
(9-benzyl-4-methyl-1-n-propylthiocarbazol-2-yl)acetic acid,
(9-benzyl-4-methyl-1-i-butylthiocarbazol-2-yl)acetic acid,
(9-benzyl-4-methyl-1-methylthiocarbazol-2-yl)acetic acid,
(9-benzyl-4-methyl-1-benzylthiocarbazol-2-yl)acetic acid,
(9-benzyl-4-methyl-1-i-propoxycarbazol-2-yl)acetic acid,
(9-benzyl-4-methyl-1-n-propoxycarbazol-2-yl)acetic acid,
(9-benzyl-4-methyl-1-i-butoxycarbazol-2-yl)acetic acid,
(9-benzyl-4-methyl-1-methoxycarbazol-2-yl)acetic acid,
(9-benzyl-4-methyl-1-benzyloxycarbazol-2-yl)acetic acid,
pharmaceutically acceptable salts thereof and pharmaceutically acceptable esters thereof.

15. A method for treating dementia, Alzheimer's disease or delirium comprising administering to a patient in need thereof a pharmaceutically effective amount of a compound of a formula (I) or a pharmaceutically acceptable salt or ester thereof, either alone or in combination with a pharmaceutically acceptable carrier, the compound of the formula (I) being

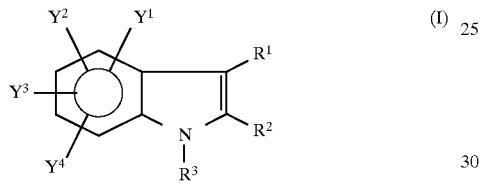

wherein:

$Y^1$, $Y^2$, $Y^3$ and $Y^4$ are the same or different and each represents a hydrogen atom, a halogen atom, a nitro group, a cyano group, a hydroxyl group, a thiol group, an amino group, an alkyl group having from 1 to 6 carbon atoms, an alkyl group having from 1 to 6 carbon atoms and substituted with a keto group or at least one substituent α defined below, a haloalkyl group having from 1 to 6 carbon atoms, an alkylthio group having from 1 to 6 carbon atoms, a carboxyl group, a protected carboxyl group, a sulfonamide group, a protected sulfonamide group or a group of formula

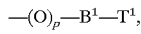

wherein $T^1$ represents a carboxyl group, a thiocarboxyl group, a dithiocarboxy group, a protected carboxyl group, a protected thiocarboxy group, a protected dithiocarboxy group, a sulfonamide group, a protected sulfonamide group or a tetrazolyl group, $B^1$ represents a direct bond or an alkylene group which has from 1 to 4 carbon atoms and which is unsubstituted or is substituted by at least one of substituents α, defined below, and p is 0 or 1;

$R^1$ and $R^2$ together represent a group of formula (Ia):

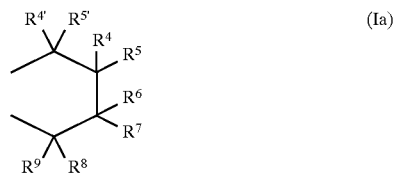

in which $R^4$ and $R^{4'}$ are the same or different and each represents a hydrogen atom or an alkyl group having from 1 to 6 carbon atoms;

$R^5$ and $R^{5'}$ are the same or different and each represents a hydrogen atom or a group of formula $—(O)_p—(CH_2)_n—T^3$ in which $T^3$ represents a carboxyl group, a protected carboxyl group, a sulfonamide group, a protected sulfonamide group, or a tetrazolyl group and n=0, 1 or 2, and p is as defined above;

$R^6$ represents a hydrogen atom or a hydroxyl group;

$R^7$ represents a hydrogen atom, a carboxyl group, a protected carboxyl group, a sulfonamide group, a protected sulfonamide group, or a group of formula $—(O)_p—B^3—T^4$ in which $T^4$ represents a carboxyl group, a protected carboxyl group, a sulfonamide group, a protected sulfonamide group, or a tetrazolyl group and $B^3$ represents an alkylene group which has from 1 to 4 carbon atoms and which is unsubstituted or is substituted by at least one of substituents α, and p is as defined above;

$R^8$ represents a hydrogen atom; or
when $R^9$ represents an alkylthio group having from 1 to 6 carbon atoms, $R^7$ and $R^8$ together represent a lactone group;

$R^9$ represents a hydrogen atom or an alkylthio group having from 1 to 6 carbon atoms; or $R^8$ and $R^9$ together represent an oxo group; or $R^1$ and $R^2$ together represent a group of formula (Ib):

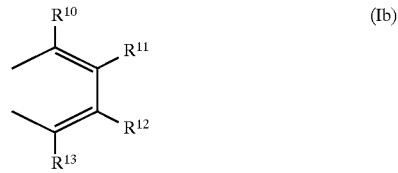

in which $R^{10}$, $R^{11}$, $R^{12}$ and $R^{13}$ are the same or different and each represents a hydrogen atom, an alkyl group having from 1 to 6 carbon atoms, a hydroxyalkyl group having from 1 to 6 carbon atoms, an alkylthio group having from 1 to 6 carbon atoms, a hydroxyl group, a carboxyl group, a protected carboxyl group, a sulfonamide group, a protected sulfonamide group, or a group of formula

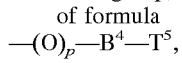

in which $T^5$ represents a carboxyl group, a protected carboxyl group, a sulfonamide group, a protected sulfonamide group or a tetrazolyl group, $B^4$ represents an alkylene group which has from 1 to 4 carbon atoms and which is unsubstituted or is substituted by at least one of substituents α, and, and p is as defined above;

$R^3$ represents a hydrogen atom or an amino protecting group; and said substituents α are hydroxyl groups, aryl groups, aralkyl groups and substituted aralkyl groups.

16. A method for treating dementia, Alzheimer's disease or delirium comprising administering to a patient in need thereof a pharmaceutically effective amount of a compound or a pharmaceutically acceptable salt or ester thereof, either alone or in combination with a pharmaceutically acceptable carrier, wherein the compound is selected from the group consisting of
(9-benzyl-4-methyl-1-i-propylthiocarbazol-2-yl)acetic acid,
(9-benzyl-4-methyl-1-n-propylthiocarbazol-2-yl)acetic acid,
(9-benzyl-4-methyl-1-i-butylthiocarbazol-2-yl)acetic acid,
(9-benzyl-4-methyl-1-methylthiocarbazol-2-yl)acetic acid,
(9-benzyl-4-methyl-1-benzylthiocarbazol-2-yl)acetic acid, (9-benzyl-4-methyl-1-i-propoxycarbazol-2-yl)acetic acid,
(9-benzyl-4-methyl-1-n-propoxycarbazol-2-yl)acetic acid,
(9-benzyl-4-methyl-1-i-butoxycarbazol-2-yl)acetic acid
(9-benzyl-4-methyl-1-methoxycarbazol-2-yl)acetic acid and
(9-benzyl-4-methyl-1-benzyloxycarbazol-2-yl)acetic acid.

17. A method of sedating a patient comprising administering to a patient in need thereof a pharmaceutically effective amount of a compound of a formula (I) or a pharmaceutically acceptable salt or ester thereof, either alone or in combination with a pharmaceutically acceptable carrier, the compound of the formula (I) being

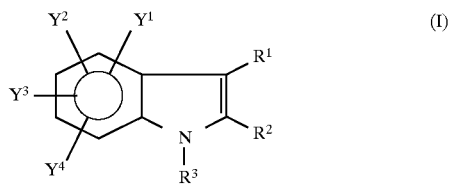

wherein $Y^1$, $Y^2$, $Y^3$ and $Y^4$ are the same or different and each represents a hydrogen atom, a halogen atom, a nitro group, a cyano group, a hydroxyl group, a thiol group, an amino group, an unsubstituted alkyl group having from 1 to 6 carbon atoms, an alkyl group having from 1 to 6 carbon atoms and substituted with a keto group or at least one substituent α defined below, a haloalkyl group having from 1 to 6 carbon atoms, an alkylthio group having from 1 to 6 carbon atoms, a carboxyl group, a protected carboxyl group, a sulfonamide group, a protected sulfonamide group or a group of formula

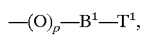

wherein $T^1$ represents a carboxyl group, a thiocarboxy group, a dithiocarboxy group, a protected carboxyl group, a protected thiocarboxy group, a protected dithiocarboxy group, a sulfonamide group, a protected sulfonamide group or a tetrazolyl group, $B^1$ represents a direct bond or an alkylene group which has from 1 to 4 carbon atoms and which is unsubstituted or is substituted by at least one of substituents α, defined below, and p is 0 or 1;

$R^1$ and $R^2$ together represent a group of formula (Ia):

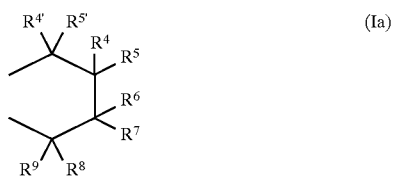

in which $R^4$ and $R^{4'}$ are the same or different and each represents a hydrogen atom or an alkyl group having from 1 to 6 carbon atoms;

$R^5$ and $R^{5'}$ are the same or different and each represents a hydrogen atom or a group of formula $—(O)_p$ $—(CH_2)_n—T^3$ in which $T^3$ represents a carboxyl group, a protected carboxyl group, a sulfonamide group, a protected sulfonamide group, or a tetrazolyl group and n=0, 1 or 2, and p is as defined above;

$R^6$ represents a hydrogen atom or a hydroxyl group;

$R^7$ represents a hydrogen atom, a carboxyl group, a protected carboxyl group, a sulfonamide group, a protected sulfonamide group, or a group of formula $—(O)_p—B^3—T^4$ in which $T^4$ represents a carboxyl group, a protected carboxyl group, a sulfonamide group, a protected sulfonamide group, or a tetrazolyl group and $B^3$ represents an alkylene group which has from 1 to 4 carbon atoms and which is unsubstituted or is substituted by at least one of substituents α, and p is as defined above;

$R^8$ represents a hydrogen atom; or
when $R^9$ represents an alkylthio group having from 1 to 6 carbon atoms, $R^7$ and $R^8$ together represent a lactone group;

$R^9$ represents a hydrogen atom or an alkylthio group having from 1 to 6 carbon atoms; or $R^8$ and $R^9$ together represent an oxo group; or $R^1$ and $R^2$ together represent a group of formula (Ib):

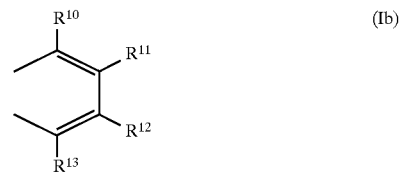

in which $R^{10}$, $R^{11}$, $R^{12}$ and $R^{13}$ are the same or different and each represents a hydrogen atom, an alkyl group having from 1 to 6 carbon atoms, a hydroxyalkyl group having from 1 to 6 carbon atoms, an alkylthio group having from 1 to 6 carbon atoms, a hydroxyl group, a carboxyl group, a protected carboxyl group, a sulfonamide group, a protected sulfonamide group, or a group of formula

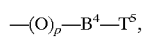

in which $T^5$ represents a carboxyl group, a protected carboxyl group, a sulfonamide group, a protected sulfonamide group or a tetrazolyl group, $B^4$ represents an alkylene group which has from 1 to 4 carbon atoms and which is unsubstituted or is substituted by at least one of substituents α, and, and p is as defined above;

$R^3$ represents a hydrogen atom or an amino protecting group; and said substituents α are hydroxyl groups, aryl groups, aralkyl groups and substituted aralkyl groups.

18. A method of sedating a patient comprising administering to a patient in need thereof a pharmaceutically effective amount of a compound or a pharmaceutically acceptable salt or ester thereof, either alone or in combination with a pharmaceutically acceptable carrier, wherein the compound is selected from the group consisting of
(9-benzyl-4-methyl-1-i-propylthiocarbazol-2-yl)acetic acid,
(9-benzyl-4-methyl-1-n-propylthiocarbazol-2-yl)acetic acid,
(9-benzyl-4-methyl-1-i-butylthiocarbazol-2-yl)acetic acid,
(9-benzyl-4-methyl-1-methylthiocarbazol-2-yl)acetic acid,
(9-benzyl-4-methyl-1-benzylthiocarbazol-2-yl)acetic acid,
(9-benzyl-4-methyl-1-i-propoxycarbazol-2-yl)acetic acid,
(9-benzyl-4-methyl-1-n-propoxycarbazol-2-yl)acetic acid,
(9-benzyl-4-methyl-1-i-butoxycarbazol-2-yl)acetic acid,
(9-benzyl-4-methyl-1-methoxycarbazol-2-yl)acetic acid and
(9-benzyl-4-methyl-1-benzyloxycarbazol-2-yl)acetic acid.

* * * * *

UNITED STATES PATENT AND TRADEMARK OFFICE
CERTIFICATE OF CORRECTION

PATENT NO. : 5,877,199
DATED : March 2, 1999
INVENTOR(S) : Birdsall et al

It is certified that error appears in the above-identified patent and that said Letters Patent is hereby corrected as shown below:

Column 62,
Line 63: delete "Hi" and insert -- H1 --.

Column 69,
Line 54: delete "From" and insert -- from --.

Column 140,
Line 36 (Claim 13): after "group;" insert -- or --.

Signed and Sealed this

Thirty-first Day of July, 2001

*Attest:*

NICHOLAS P. GODICI
*Attesting Officer*     *Acting Director of the United States Patent and Trademark Office*